United States Patent
Grice et al.

(10) Patent No.: US 10,093,635 B2
(45) Date of Patent: Oct. 9, 2018

(54) MAGL INHIBITORS

(71) Applicant: ABIDE THERAPEUTICS, INC., San Diego, CA (US)

(72) Inventors: Cheryl A. Grice, Encinitas, CA (US); Daniel J. Buzard, San Diego, CA (US); Michael B. Shaghafi, San Diego, CA (US)

(73) Assignee: ABIDE THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 15/814,322

(22) Filed: Nov. 15, 2017

(65) Prior Publication Data

US 2018/0134674 A1    May 17, 2018

Related U.S. Application Data

(60) Provisional application No. 62/423,099, filed on Nov. 16, 2016.

(51) Int. Cl.
    *C07D 295/195* (2006.01)
(52) U.S. Cl.
    CPC ................ *C07D 295/195* (2013.01)
(58) Field of Classification Search
    CPC .................................... C07D 295/195
    See application file for complete search history.

(56) References Cited

U.S. PATENT DOCUMENTS

| | | | |
|---|---|---|---|
| 9,133,148 B2 | 9/2015 | Cisar et al. | |
| 9,487,495 B2 | 11/2016 | Cisar et al. | |
| 9,771,341 B2 | 9/2017 | Cisar et al. | |
| 2011/0275650 A1 | 11/2011 | Cravatt et al. | |
| 2014/0357693 A1 | 12/2014 | Shaul et al. | |
| 2015/0148330 A1 | 5/2015 | Cisar et al. | |
| 2016/0137649 A1 | 5/2016 | Jones et al. | |
| 2017/0073320 A1 | 3/2017 | Cisar et al. | |
| 2017/0334874 A1 | 11/2017 | Cisar et al. | |

FOREIGN PATENT DOCUMENTS

| | | |
|---|---|---|
| DE | 1802739 A1 | 6/1969 |
| JP | S6183073 A | 4/1986 |
| JP | 2000500448 A | 1/2000 |
| JP | 2008500270 A | 1/2008 |
| JP | 2008521768 A | 6/2008 |
| JP | 2009523729 A | 6/2009 |
| JP | 2010513447 A | 4/2010 |
| RU | 2167150 C2 | 5/2001 |
| WO | WO-8911794 A1 | 12/1989 |
| WO | WO-9311097 A1 | 6/1993 |
| WO | WO-9517439 A2 | 6/1995 |
| WO | WO-9800408 A1 | 1/1998 |
| WO | WO-0125188 A1 | 4/2001 |
| WO | WO-0234382 A1 | 5/2002 |
| WO | WO-2005063698 A1 | 7/2005 |
| WO | WO-2005070910 A2 | 8/2005 |
| WO | WO-2005080363 A1 | 9/2005 |
| WO | WO-2006074025 A1 | 7/2006 |
| WO | WO-2008106047 A2 | 9/2008 |
| WO | WO-2009141238 A1 | 11/2009 |
| WO | WO-2010009207 A1 | 1/2010 |
| WO | WO-2010111050 A1 | 9/2010 |
| WO | WO-2010129497 A1 | 11/2010 |
| WO | WO-2011054795 A1 | 5/2011 |
| WO | WO-2011151808 A1 | 12/2011 |
| WO | WO-2013102431 A1 | 7/2013 |
| WO | WO-2013103973 A1 | 7/2013 |
| WO | WO-2013142307 A1 | 9/2013 |
| WO | WO-2016014975 A2 | 1/2016 |
| WO | WO-2016149401 A2 | 9/2016 |

OTHER PUBLICATIONS

Berge et al. Pharmaceutical Salts. Journal of Pharmaceutical Sciences 66(1):1-19 (Jan. 1977).
Blankman et al. A comprehensive profile of brain enzymes that hydrolyze the endocannabinoid 2-arachidonoylglycerol. Chem. Biol. 14:1347-1356 (2007).
Chang et al. Highly Selective Inhibitors of Monoacylglycerol Lipase Bearing a Reactive Group that is Bioisosteric with Endocannabinoid Substrates. ChemBiol 19(5):579-588 (2012).
Chang et al. Proteome-wide reactivity profiling identifies diverse carbamate chemotypes tuned for serine hydrolase inhibition. ACS Chem Biol 8:1590-1599 (2013).
Co-pending U.S. Appl. No. 15/814,318, filed Nov. 15, 2017.
Fleisher et al. Improved oral drug delivery: solubility limitations overcome by the use of prodrugs. Advanced Drug Delivery Reviews 19:115-130 (1996).
Foster et al. Deuterium isotope effects in the metabolism of drugs and xenobiotics: implications for drug design. Adv Drug Res 14:1-36 (1985).
Fowler. Monoacylglycerol lipase—a target for drug development? Br Pharmacol. 166:1568-1585 (2012).
Gately et al. Deuterioglucose: alteration of biodistribution by an isotope effect. J Nucl Med 27:388-394 (1986).
Gordon et al. The metabolism of the abortifacient terpene, (R)-(+)-pulegone, to a proximate toxin, menthofuran. Drug Metab Dispos 15:589-594 (1987).
King et al. URB602 inhibits monoacylglycerol lipase and selectively blocks 2-arachidonoylglycerol degradation in intact brain slices. Chem Biol 14(12):1357-1365 (2007).
Korhonen et al. Piperazine and piperidine carboxamides and carbamates as inhibitors of fatty acid amide hydrolase (FAAH) and monoacylglycerol lipase (MAGL). Bioorg Med Chem 22(23):6694-6705 (2014).
Kushner et al. Pharmacological uses and perspectives of heavy water and deuterated compounds. Can J Physiol Pharmacol 77:79-88 (1999).

(Continued)

*Primary Examiner* — Paul V Ward
(74) *Attorney, Agent, or Firm* — Wilson, Sonsini, Goodrich & Rosati

(57) ABSTRACT

Provided herein are piperazine carbamates and pharmaceutical compositions comprising said compounds. The subject compounds and compositions are useful as modulators of MAGL. Furthermore, the subject compounds and compositions are useful for the treatment of pain.

18 Claims, No Drawings

(56) References Cited

OTHER PUBLICATIONS

Lijinsky et al. Dose-response studies in carcinogenesis by nitroso-N-methyl-N-(2-phenyl)ethylamine in rats and the effects of deuterium substitution. Food Chem Toxicol 20:393-399 (1982).

Lijinsky et al. Dose-response studies with nitrosoheptamethyleneimine and its alpha-deuterium-labeled derivative in F344 rats. J Nat Cancer Inst 69:1127-1133 (1982).

Long et al. Characterization of tunable piperidine and piperazine carbamates as inhibitors of endocannabinoid hydrolases. J Med chem 53(4):1830-1842 (2010).

Long et al. Selective blockade of 2-arachidonoylglycerol hydrolysis produces cannabinoid behavioral effects. Nat Chem Biol. 5(1):37-44 (2009).

Mangold et al. Effects of deuterium labeling on azido amino acid mutagenicity in *Salmonella typhimurium*. Mutat Res 308:33-42 (1994).

Meanwell et al. Synopsis of some recent tactical application of bioisosteres in drug design. J Med Chem 54(8):2529-2591 (2011).

Mukhamadieva et al. Search for New Drugs Synthesis and Biological Activity of O-Carbamoylated 1,1,1,3,3,3-Hexafluoroisopropanols As New Specific Inhibitors of Carboxylesterase. Pharmaceutical Chemistry Journal 46(8):461-464 (2012).

Niphakis et al.O-Hydroxyacetamide Carbamates as a Highly Potent and Selective Class of Endocannabinoid Hydrolase Inhibitors. ACS Chem. Neurosci. 3(5):418-426 (2012/Web2011).

Patani et al. Bioisosterism: A Rational Approach in Drug Design. Chem. Rev. 96:3147-3176 (1996).

PCT/US2013/020551 International Preliminary Report on Patentability dated Jul. 17, 2014.

PCT/US2013/020551 International Search Report dated May 21, 2013.

PCT/US2016/022690 International Preliminary Report on Patentability dated Sep. 28, 2017.

PCT/US2016/022690 International Search Report and Written Opinion dated Aug. 30, 2016.

PubChem CID 17217128 http://pubchem.ncbi.nlm.nih.gov/summary/summary.cgi?cid=17217128 Retrieved Apr. 30, 2013 Create Date: Nov. 13, 2007 (3 pgs.).

PubChem CID 3469875. http://pubchem.ncbi.nlm.nih.gov/summary/summary.cgi?cid=3469875Retrieved Mar. 4, 2013 Create Date: Sep. 8, 2005 (11 pgs.).

PubChem CID 669902 http://pubchem.ncbi.nlm.nih.gov/summary/summary.cgi?cid=669902 Retrieved May 1, 2013 Create Date: Jul. 8, 2005 (4 pgs.).

Rautio et al. Prodrugs: design and clinical applications. Nat Rev Drug Discov 7(3):255-270 (2008).

Science IP Report dated Dec. 11, 2014 (126 pgs.).

Silverman. The Organic Chemistry of Drug Design and Drug Action. Academic Press (pp. 15-22) (1992).

South. Synthesis and Reactions of Halogenated Thiazole Isocyanates. Journal of Heterocyclic Chemistry 28:1003-1011 (1991).

Studnev et al. Synthesis, Antibacterial and Immunotropic Activity of Poly(fluoroalkyl-N-arylcarbamates. Pharmaceutical Chemistry Journal 36(12):654-657 (2002).

Thornber. Isosterism and molecular modification in drug design. Chem Soc Rev 8:563-580 (1979).

Urry et al. Free-radical chain addition reactions of aldehydes with perfluoro ketones and chloro perfluoro ketones. J Org Chem 32(2):347-352 (1967).

U.S. Appl. No. 14/369,982 Office Action dated Mar. 8, 2016.

U.S. Appl. No. 14/369,982 Office Action dated Oct. 22, 2015.

U.S. Appl. No. 14/599,105 Office Action dated Apr. 8, 2015.

U.S. Appl. No. 15/072,229 First Action Interview dated Sep. 19, 2016.

U.S. Appl. No. 15/072,229 Office Action dated Jan. 10, 2017.

U.S. Appl. No. 15/272,313 Office Action dated Apr. 10, 2017.

U.S. Appl. No. 15/272,313 Office Action dated Aug. 25, 2017.

Wade. Deuterium isotope effects on noncovalent interactions between molecules. Chem Biol Interact 117:191-217 (1999).

Zello et al. Plasma and urine enrichments following infusion of L-[1-13C]phenylalanine and L-[ring-2H5]phenylalanine in humans: evidence for an isotope effect in renal tubular reabsorption. Metabolism 43:487-491 (1994).

Co-pending U.S. Appl. No. 15/925,517, filed Mar. 19, 2018.

PCT/US2017/061868 International Search Report and Written Opinion dated Mar. 20, 2018.

PCT/US2017/061868 Invitation to Pay Additional Fees dated Jan. 22, 2018.

MAGL INHIBITORS

CROSS-REFERENCE

This application claims benefit of U.S. Provisional Application No. 62/423,099, filed on Nov. 16, 2016, which is herein incorporated by reference in its entirety.

BACKGROUND

Monoacylglycerol lipase (MAGL) is an enzyme responsible for hydrolyzing endocannabinoids such as 2-AG (2-arachidonoylglycerol), an arachidonate based lipid, in the nervous system.

BRIEF SUMMARY OF THE INVENTION

This disclosure provides, for example, compounds and compositions which are modulators of MAGL, and their use as medicinal agents, processes for their preparation, and pharmaceutical compositions that include disclosed compounds as at least one active ingredient. The disclosure also provides for the use of disclosed compounds as medicaments and/or in the manufacture of medicaments for the inhibition of MAGL activity in warm-blooded animals such as humans.

In one aspect is a compound of Formula (I):

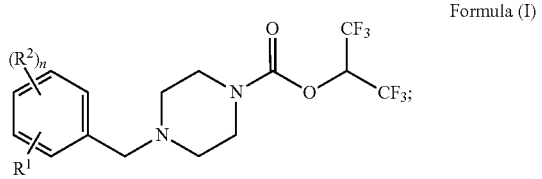

Formula (I)

wherein:
$R^1$ is $-R^{14}$, $-OR^3$, $-SR^4$, $-S(O)_2R^4$, $-N(R^4)(R^5)$, $-NH(R^4)$, or $-C\equiv C-(CR^6R^7)-R^8$;
each $R^2$ is independently selected from $C_{1-6}$alkyl, halogen, $-CN$, $C_{1-6}$haloalkyl, $-C_{1-6}$alkyl(heterocycloalkyl), $-OR^{17}$, and $-C(O)NR^{18}R^{19}$;
$R^3$ is $-(CR^6R^7)_m-R^8$, $-(CR^6R^7)_p-Y-(CR^6R^7)_q-R^8$, or $-(CR^6R^7)_t-C_{3-6}$cycloalkyl-$R^8$;
$R^4$ is $-(CR^6R^7)_m-R^8$, $-(CR^6R^7)_v-C(O)OH$, or $-(CR^6R^7)_p-Y-(CR^6R^7)_q-R^8$;
$R^{4'}$ is $-(CR^6R^7)_m-R^8$, $-(CR^6R^7)_p-Y-(CR^6R^7)_q-R^8$, $-C_{4-6}$alkyl-$C(O)OH$, $-C_{3-6}$cycloalkyl-$C(O)OH$, or $-C_{1-6}$alkyl-$C_{3-6}$cycloalkyl-$C(O)OH$;
Y is $-O-$ or $-N(R^{22})-$;
$R^5$ is $C_{1-6}$alkyl or $-CH_2$-phenyl optionally substituted with one, two, or three groups independently selected from halogen, $C_{1-6}$alkyl, $C_{1-6}$haloalkyl, and $C_{1-6}$alkoxy;
each $R^6$ and $R^7$ is each independently selected from H, F, and $C_{1-6}$alkyl; or $R^6$ and $R^7$, together with the carbon to which they are attached, form a $C_{3-6}$cycloalkyl ring;
$R^8$ is $-C(O)OR^9$, $-C(O)R^{10}$, or $-C(O)O-(CR^{12}R^{13})-OC(O)R^{11}$;
$R^{8'}$ is $-C(O)OR^{9'}$, $-C(O)R^{10'}$, or $-C(O)O-(CR^{12}R^{13})-OC(O)R^{11}$;
$R^9$ is H or $C_{1-6}$alkyl;
$R^{9'}$ is $C_{1-6}$alkyl;
$R^{10}$ is $C_{1-6}$alkyl or $-NHSO_2R^{21}$;
$R^{10'}$ is $C_{2-6}$alkyl or $-NHSO_2R^{21}$;
$R^{11}$ is $C_{1-6}$alkyl or $C_{1-6}$alkoxy;
$R^{12}$ and $R^{13}$ is each independently H or $C_{1-6}$alkyl;
$R^{14}$ is $-(CR^{15}R^{16})_m-R^8$ or $-(CR^6R^7)_p-Y-(CR^6R^7)_q-R^8$;
each $R^{15}$ and $R^{16}$ is each independently selected from H, F, and $C_{1-6}$alkyl;
each $R^{17}$ is independently selected from H, $C_{1-6}$alkyl, $C_{1-6}$haloalkyl, and $C_{3-6}$cycloalkyl;
each $R^{18}$ and $R^{19}$ is each independently selected from H, $C_{1-6}$alkyl, $C_{3-6}$cycloalkyl, aryl, and heteroaryl; or $R^{18}$ and $R^{19}$, together with the nitrogen to which they are attached, form a heterocycloalkyl ring optionally substituted with one, two, or three $R^{20}$;
each $R^{20}$ is independently selected from halogen, $C_{1-6}$alkyl, $C_{1-6}$haloalkyl, oxo, $-CN$, and $C_{3-6}$cycloalkyl;
$R^{21}$ is $C_{1-6}$alkyl or $C_{3-6}$cycloalkyl;
$R^{22}$ is H, $C_{1-6}$alkyl, or $-SO_2R^{23}$;
$R^{23}$ is $C_{1-6}$alkyl;
m is 1, 2, 3 or 4;
n is 0, 1, 2, 3, or 4;
p is 2, 3, or 4;
q is 1, 2, or 3;
t is 0, 1, or 2; and
v is 3 or 4;
or a pharmaceutically acceptable salt or solvate thereof.

In some embodiments is a compound of Formula (I), or a pharmaceutically acceptable salt or solvate thereof, wherein $R^1$ is $-OR^3$. In some embodiments is a compound of Formula (I), or a pharmaceutically acceptable salt or solvate thereof, wherein $R^3$ is $-(CR^6R^7)_m-R^8$. In some embodiments is a compound of Formula (I), or a pharmaceutically acceptable salt or solvate thereof, wherein m is 1, 2, or 3. In some embodiments is a compound of Formula (I), or a pharmaceutically acceptable salt or solvate thereof, wherein m is 1. In some embodiments is a compound of Formula (I), or a pharmaceutically acceptable salt or solvate thereof, wherein m is 2. In some embodiments is a compound of Formula (I), or a pharmaceutically acceptable salt or solvate thereof, wherein m is 3. In some embodiments is a compound of Formula (I), or a pharmaceutically acceptable salt or solvate thereof, wherein $R^3$ is $-(CR^6R^7)_p-Y-(CR^6R^7)_q-R^8$. In some embodiments is a compound of Formula (I), or a pharmaceutically acceptable salt or solvate thereof, wherein Y is $-O-$. In some embodiments is a compound of Formula (I), or a pharmaceutically acceptable salt or solvate thereof, wherein Y is $-N(R^{22})-$. In some embodiments is a compound of Formula (I), or a pharmaceutically acceptable salt or solvate thereof, wherein $R^{22}$ is $-SO_2R^{23}$. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein $R^1$ is $-C\equiv C-(CR^6R^7)-R^8$. In some embodiments is a compound of Formula (I), or a pharmaceutically acceptable salt or solvate thereof, wherein $R^3$ is $-(CR^6R^7)_t-C_{3-6}$cycloalkyl-$R^8$. In some embodiments is a compound of Formula (I), or a pharmaceutically acceptable salt or solvate thereof, wherein t is 1. In some embodiments is a compound of Formula (I), or a pharmaceutically acceptable salt or solvate thereof, wherein t is 0. In some embodiments is a compound of Formula (I), or a pharmaceutically acceptable salt or solvate thereof, wherein each $R^6$ and $R^7$ is each independently selected from H and $C_{1-6}$alkyl. In some embodiments is a compound of Formula (I), or a pharmaceutically acceptable salt or solvate thereof, wherein each $R^6$ and $R^7$ is H. In some embodiments is a compound of Formula (I), or a pharmaceutically acceptable salt or solvate thereof, wherein $R^6$ and $R^7$, together with the carbon to which they are attached, form a $C_{3-6}$cycloalkyl ring. In some embodiments is a compound of Formula (I), or a pharmaceutically acceptable salt or solvate thereof, wherein $R^8$ is —C(O)OR$^9$. In some embodiments is a compound of Formula (I), or a pharmaceutically acceptable salt or solvate thereof, wherein $R^9$ is H. In some embodiments is a compound of Formula (I), or a pharmaceutically acceptable salt or solvate thereof, wherein $R^9$ is $C_{1-6}$alkyl. In some embodiments is a compound of Formula (I), or a pharmaceutically acceptable salt or solvate thereof, wherein $R^8$ is —C(O)R$^{10}$. In some embodiments is a compound of Formula (I), or a pharmaceutically acceptable salt or solvate thereof, wherein $R^{10}$ is —NHSO$_2$R$^{21}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^{11}$ is $C_{1-6}$alkyl. In some embodiments is a compound of Formula (I), or a pharmaceutically acceptable salt or solvate thereof, wherein $R^{11}$ is $C_{1-6}$alkoxy. In some embodiments is a compound of Formula (I), or a pharmaceutically acceptable salt or solvate thereof, wherein $R^1$ is —N(R$^4$)(R$^5$). In some embodiments is a compound of Formula (I), or a pharmaceutically acceptable salt or solvate thereof, wherein $R^5$ is —CH$_3$. In some embodiments is a compound of Formula (I), or a pharmaceutically acceptable salt or solvate thereof, wherein $R^5$ is —CH$_2$-phenyl optionally substituted with one, two, or three groups independently selected from halogen, $C_{1-6}$alkyl, $C_{1-6}$haloalkyl, and $C_{1-6}$alkoxy. In some embodiments is a compound of Formula (I), or a pharmaceutically acceptable salt or solvate thereof, wherein $R^1$ is —SR$^4$. In some embodiments is a compound of Formula (I), or a pharmaceutically acceptable salt or solvate thereof, wherein $R^1$ is —S(O)$_2$R$^4$. In some embodiments is a compound of Formula (I), or a pharmaceutically acceptable salt or solvate thereof, wherein $R^4$ is —(CR$^6$R$^7$)$_v$—C(O)OH. In some embodiments is a compound of Formula (I), or a pharmaceutically acceptable salt or solvate thereof, wherein v is 3. In some embodiments is a compound of Formula (I), or a pharmaceutically acceptable salt or solvate thereof, wherein v is 4. In some embodiments is a compound of Formula (I), or a pharmaceutically acceptable salt or solvate thereof, wherein $R^4$ is —(CR$^6$R$^7$)$_m$—R$^8$. In some embodiments is a compound of Formula (I), or a pharmaceutically acceptable salt or solvate thereof, wherein m is 1, 2, or 3. In some embodiments is a compound of Formula (I), or a pharmaceutically acceptable salt or solvate thereof, wherein m is 1. In some embodiments is a compound of Formula (I), or a pharmaceutically acceptable salt or solvate thereof, wherein m is 2. In some embodiments is a compound of Formula (I), or a pharmaceutically acceptable salt or solvate thereof, wherein m is 3. In some embodiments is a compound of Formula (I), or a pharmaceutically acceptable salt or solvate thereof, wherein $R^{11}$ is —C(O)OR$^{9'}$. In some embodiments is a compound of Formula (I), or a pharmaceutically acceptable salt or solvate thereof, wherein $R^{8'}$ is —C(O)R$^{10}$. In some embodiments is a compound of Formula (I), or a pharmaceutically acceptable salt or solvate thereof, wherein $R^{10'}$ is —NHSO$_2$R$^{21}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^{11}$ is $C_{1-6}$alkyl. In some embodiments is a compound of Formula (I), or a pharmaceutically acceptable salt or solvate thereof, wherein $R^{11}$ is $C_{1-6}$alkoxy. In some embodiments is a compound of Formula (I), or a pharmaceutically acceptable salt or solvate thereof, wherein each $R^4$ is —(CR$^6$R$^7$)$_p$—Y—(CR$^6$R$^7$)$_q$—R$^8$. In some embodiments is a compound of Formula (I), or a pharmaceutically acceptable salt or solvate thereof, wherein Y is —O—. In some embodiments is a compound of Formula (I), or a pharmaceutically acceptable salt or solvate thereof, wherein Y is —N(R$^{22}$)—. In some embodiments is a compound of Formula (I), or a pharmaceutically acceptable salt or solvate thereof, wherein $R^{22}$ is —SO$_2$R$^{23}$. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein $R^8$ is —C(O)OR$^9$. In some embodiments is a compound of Formula (I), or a pharmaceutically acceptable salt or solvate thereof, wherein $R^9$ is H. In some embodiments is a compound of Formula (I), or a pharmaceutically acceptable salt or solvate thereof, wherein $R^9$ is $C_{1-6}$alkyl. In some embodiments is a compound of Formula (I), or a pharmaceutically acceptable salt or solvate thereof, wherein $R^8$ is —C(O)R$^{10}$. In some embodiments is a compound of Formula (I), or a pharmaceutically acceptable salt or solvate thereof, wherein $R^{10}$ is —NHSO$_2$R$^{21}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^{11}$ is $C_{1-6}$alkyl. In some embodiments is a compound of Formula (I), or a pharmaceutically acceptable salt or solvate thereof, wherein $R^{11}$ is $C_{1-6}$alkoxy. In some embodiments is a compound of Formula (I), or a pharmaceutically acceptable salt or solvate thereof, wherein $R^1$ is —NH(R$^{4'}$). In some embodiments is a compound of Formula (I), or a pharmaceutically acceptable salt or solvate thereof, wherein $R^{4'}$ is —(CR$^6$R$^7$)$_m$—R$^{8'}$. In some embodiments is a compound of Formula (I), or a pharmaceutically acceptable salt or solvate thereof, wherein m is 1, 2, or 3. In some embodiments is a compound of Formula (I), or a pharmaceutically acceptable salt or solvate thereof, wherein m is 1. In some embodiments is a compound of Formula (I), or a pharmaceutically acceptable salt or solvate thereof, wherein m is 2. In some embodiments is a compound of Formula (I), or a pharmaceutically acceptable salt or solvate thereof, wherein m is 3. In some embodiments is a compound of Formula (I), or a pharmaceutically acceptable salt or solvate thereof, wherein $R^{8'}$ is —C(O)OR$^{9'}$. In some embodiments is a compound of Formula (I), or a pharmaceutically acceptable salt or solvate thereof, wherein $R^{8'}$ is —C(O)R$^{10'}$. In some embodiments is a compound of Formula (I), or a pharmaceutically acceptable salt or solvate thereof, wherein $R^{10'}$ is —NHSO$_2$R$^{21}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^{11}$ is $C_{1-6}$alkyl. In some embodiments is a compound of Formula (I), or a pharmaceutically acceptable salt or solvate thereof, wherein $R^{11}$ is $C_{1-6}$alkoxy. In some embodiments is a compound of Formula (I), or a pharmaceutically acceptable salt or solvate thereof, wherein each $R^{4'}$ is —(CR$^6$R$^7$)$_p$—Y—(CR$^6$R$^7$)$_q$—

R[8]. In some embodiments is a compound of Formula (I), or a pharmaceutically acceptable salt or solvate thereof, wherein Y is —O—. In some embodiments is a compound of Formula (I), or a pharmaceutically acceptable salt or solvate thereof, wherein Y is —N(R[22])—. In some embodiments is a compound of Formula (I), or a pharmaceutically acceptable salt or solvate thereof, wherein R[22] is —SO$_2$R[23]. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein R[8] is —C(O)OR[9]. In some embodiments is a compound of Formula (I), or a pharmaceutically acceptable salt or solvate thereof, wherein R[9] is H. In some embodiments is a compound of Formula (I), or a pharmaceutically acceptable salt or solvate thereof, wherein R[9] is C$_{1-6}$alkyl. In some embodiments is a compound of Formula (I), or a pharmaceutically acceptable salt or solvate thereof, wherein R[8] is —C(O)R[10]. In some embodiments is a compound of Formula (I), or a pharmaceutically acceptable salt or solvate thereof, wherein R[10] is —NHSO$_2$R[21]. In some embodiments is a compound of Formula (I), or a pharmaceutically acceptable salt or solvate thereof, wherein R[8] is —C(O)O—(CR[12]R[13])—OC(O)R[11]. In some embodiments is a compound of Formula (I), or a pharmaceutically acceptable salt or solvate thereof, wherein R[11] is C$_{1-6}$alkyl. In some embodiments is a compound of Formula (I), or a pharmaceutically acceptable salt or solvate thereof, wherein R[11] is C$_{1-6}$alkoxy. In some embodiments is a compound of Formula (I), or a pharmaceutically acceptable salt or solvate thereof, wherein each R[6] and R[7] is each independently selected from H and C$_{1-6}$alkyl. In some embodiments is a compound of Formula (I), or a pharmaceutically acceptable salt or solvate thereof, wherein each R[6] and R[7] is H. In some embodiments is a compound of Formula (I), or a pharmaceutically acceptable salt or solvate thereof, wherein R[6] and R[7], together with the carbon to which they are attached, form a C$_{3-6}$cycloalkyl ring. In some embodiments is a compound of Formula (I), or a pharmaceutically acceptable salt or solvate thereof, wherein R[4'] is —C$_{4-6}$alkyl-C(O)OH. In some embodiments is a compound of Formula (I), or a pharmaceutically acceptable salt or solvate thereof, wherein R[4'] is —C$_{3-6}$cycloalkyl-C(O)OH. In some embodiments is a compound of Formula (I), or a pharmaceutically acceptable salt or solvate thereof, wherein R[4'] is —C$_{1-6}$alkyl-C$_{3-6}$cycloalkyl-C(O)OH. In some embodiments is a compound of Formula (I), or a pharmaceutically acceptable salt or solvate thereof, wherein R[1] is —R[14]. In some embodiments is a compound of Formula (I), or a pharmaceutically acceptable salt or solvate thereof, wherein R[14] is —(CR[15]R[16])$_m$—R[8]. In some embodiments is a compound of Formula (I), or a pharmaceutically acceptable salt or solvate thereof, wherein R[14] is —(CR[15]R[16])$_m$—R[8] and m is 1. In some embodiments is a compound of Formula (I), or a pharmaceutically acceptable salt or solvate thereof, wherein R[14] is —(CR[15]R[16])$_m$—R[8] and m is 2. In some embodiments is a compound of Formula (I), or a pharmaceutically acceptable salt or solvate thereof, wherein R[14] is —(CR[15]R[16])$_m$—R[8] and m is 3. In some embodiments is a compound of Formula (I), or a pharmaceutically acceptable salt or solvate thereof, wherein R[14] is —(CR[15]R[16])$_m$—R[8] and m is 4. In some embodiments is a compound of Formula (I), or a pharmaceutically acceptable salt or solvate thereof, wherein R[14] is —(CR[15]R[16])$_m$—R[8] and R[8] is —C(O)OR[9]. In some embodiments is a compound of Formula (I), or a pharmaceutically acceptable salt or solvate thereof, wherein R[14] is —(CR[15]R[16])$_m$—R[8], R[8] is —C(O)OR[9], and R[9] is H. In some embodiments is a compound of Formula (I), or a pharmaceutically acceptable salt or solvate thereof, wherein R[14] is —(CR[15]R[16])$_m$—R[8], R[8] is —C(O)OR[9], and R[9] is C$_{1-6}$alkyl. In some embodiments is a compound of Formula (I), or a pharmaceutically acceptable salt or solvate thereof, wherein each R[2] is independently selected from C$_{1-6}$alkyl, halogen, —CN, and C$_{1-6}$haloalkyl. In some embodiments is a compound of Formula (I), or a pharmaceutically acceptable salt or solvate thereof, wherein each R[2] is independently selected from C$_{1-6}$alkyl, halogen, and C$_{1-6}$haloalkyl. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein each R[2] is —C$_1$. In some embodiments is a compound of Formula (I), or a pharmaceutically acceptable salt or solvate thereof, wherein each R[2] is —CF$_3$.

In another aspect is a compound selected from:

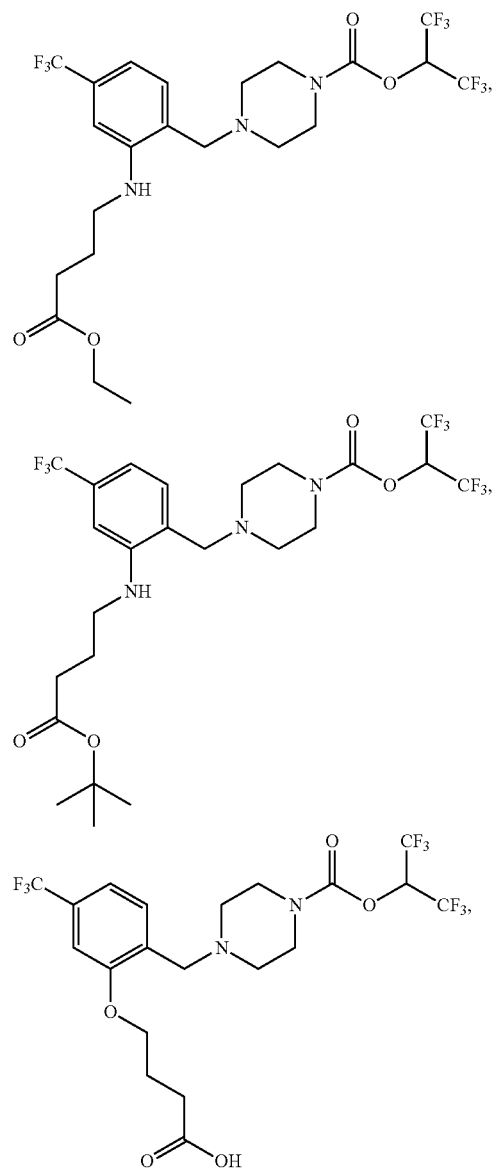

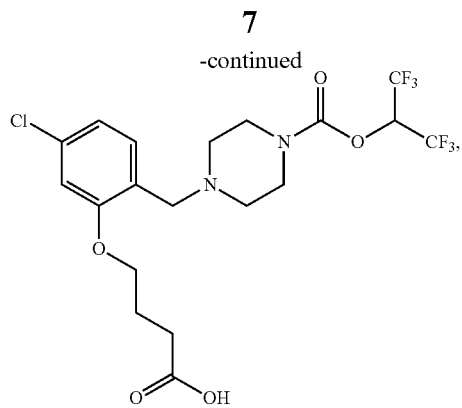
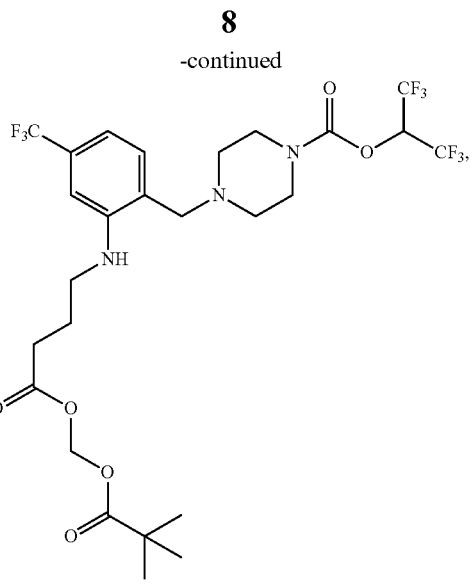
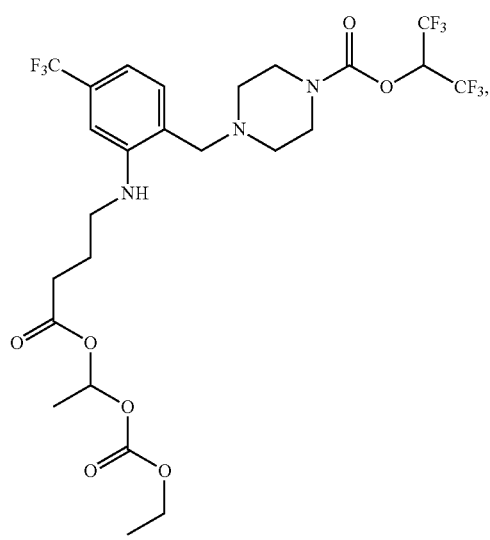
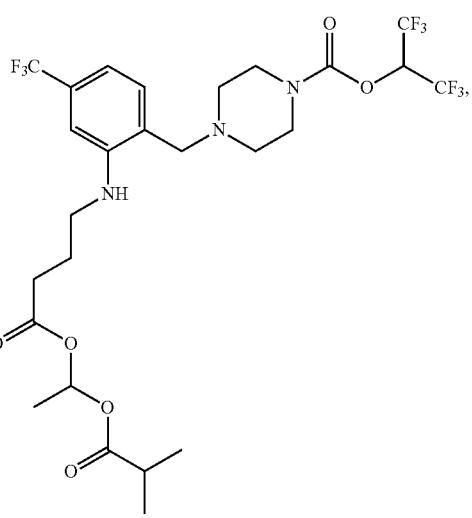
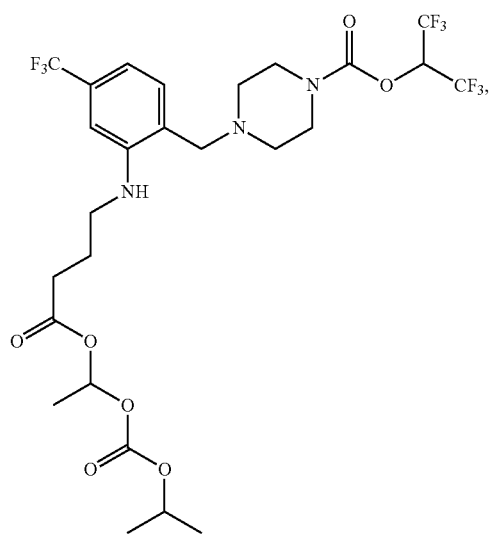
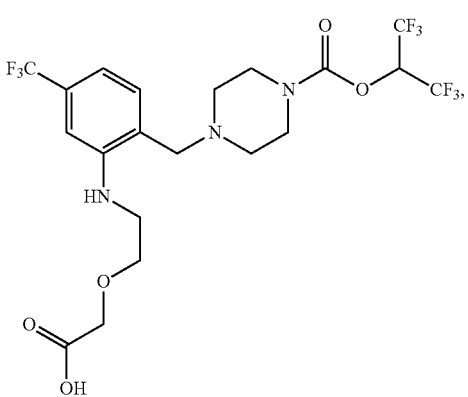

-continued
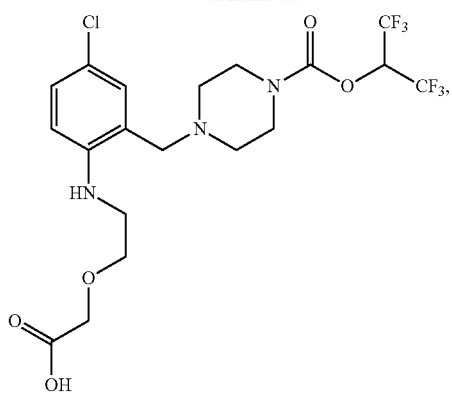
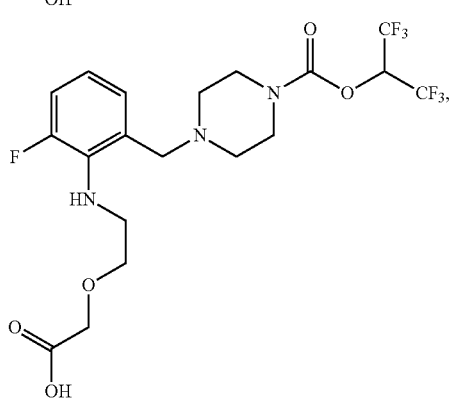
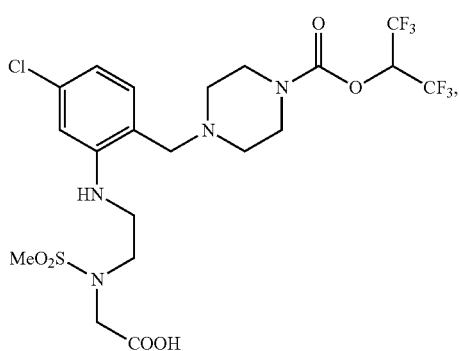
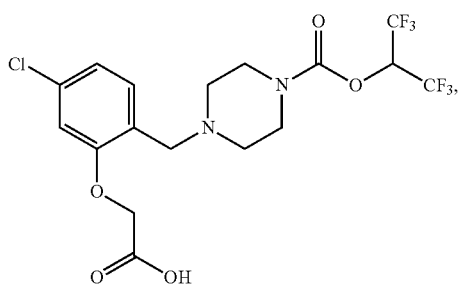
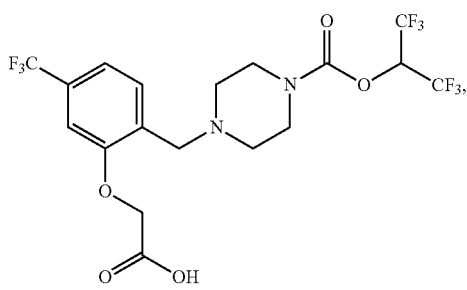
-continued
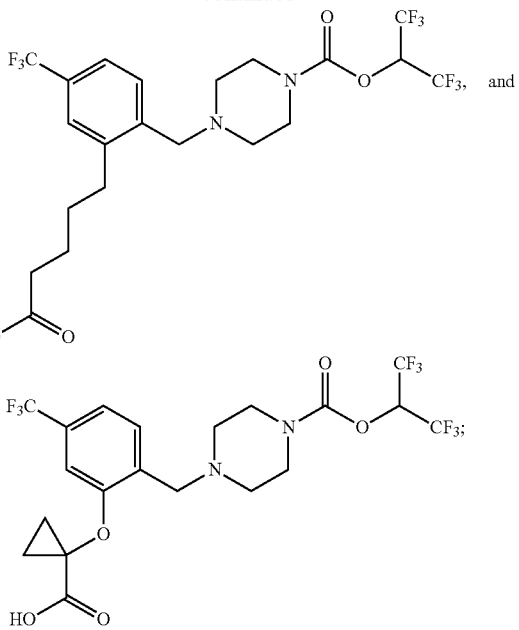
or a pharmaceutically acceptable salt or solvate thereof.
In another aspect is a compound selected from:
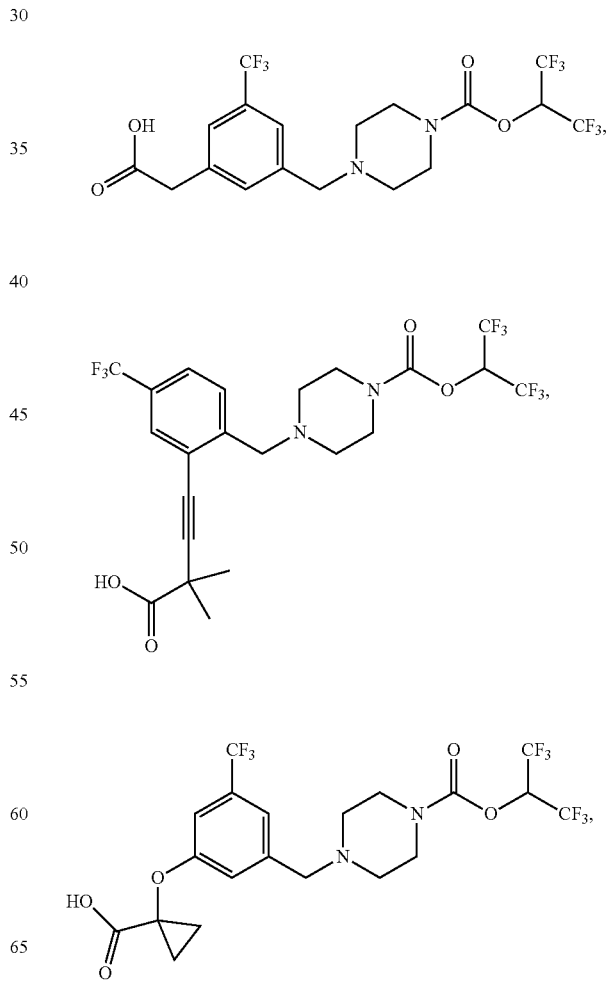

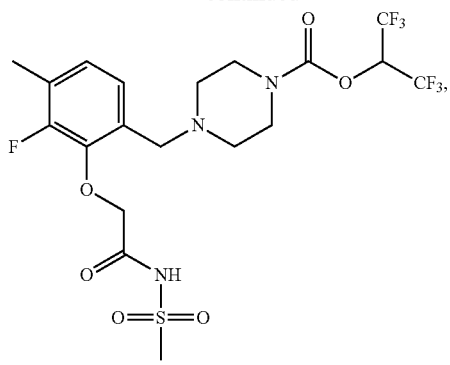
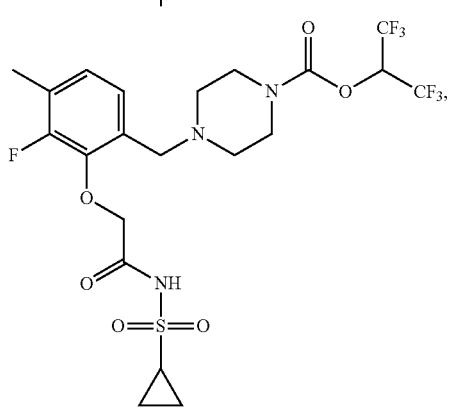
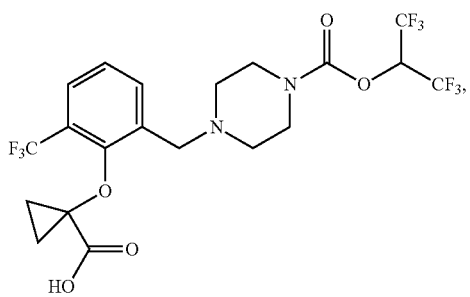
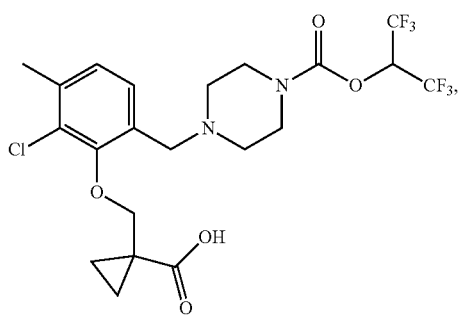
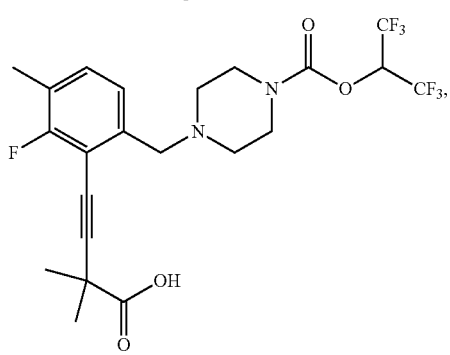
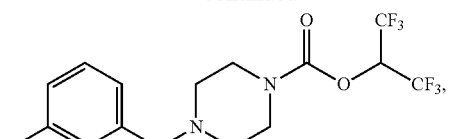
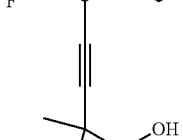
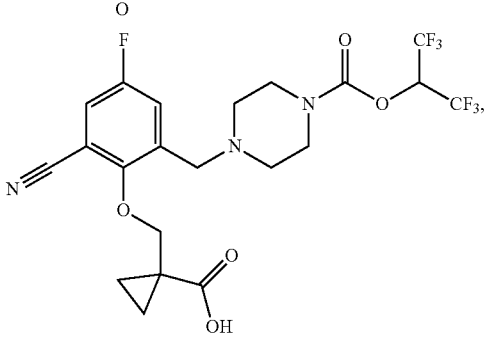
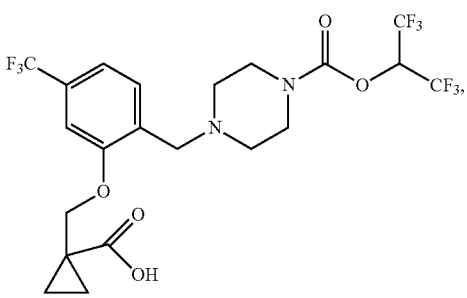
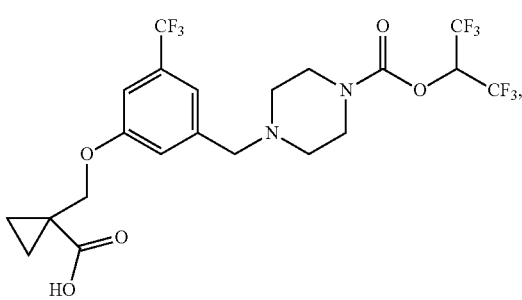
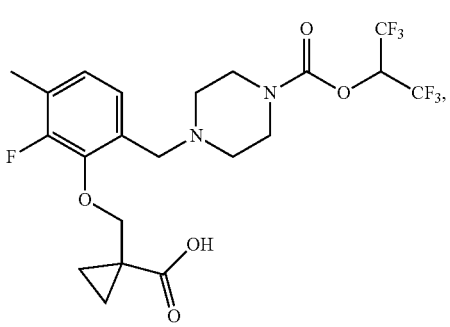

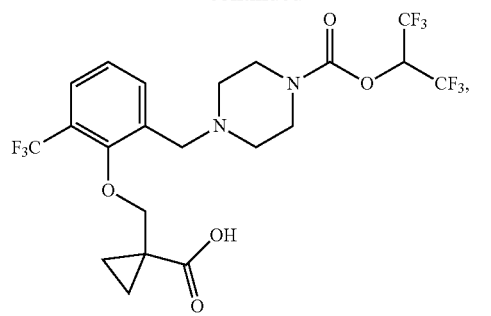
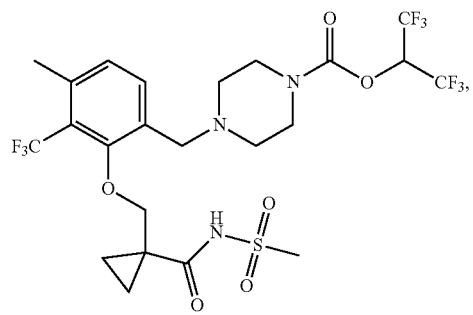
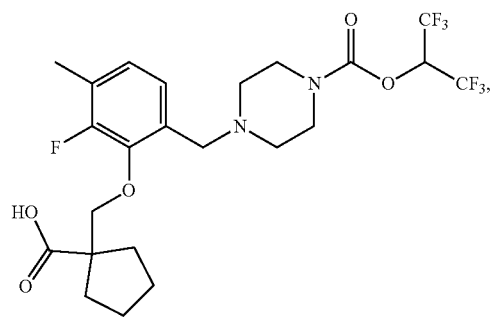
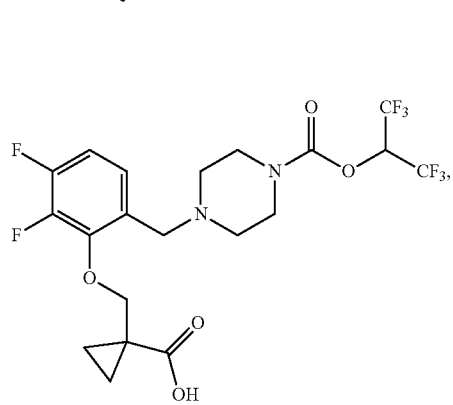
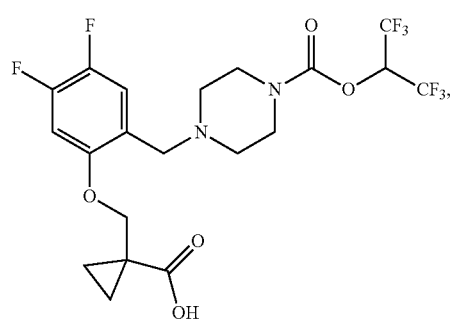
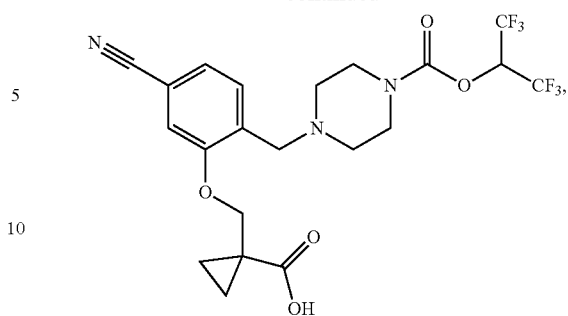
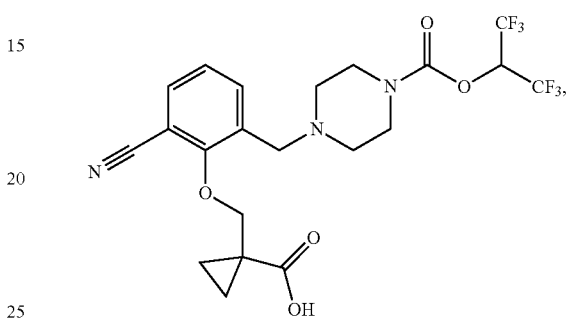
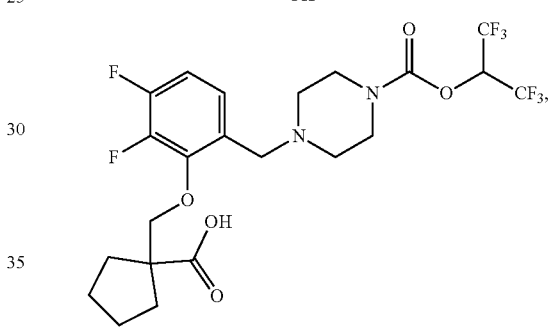
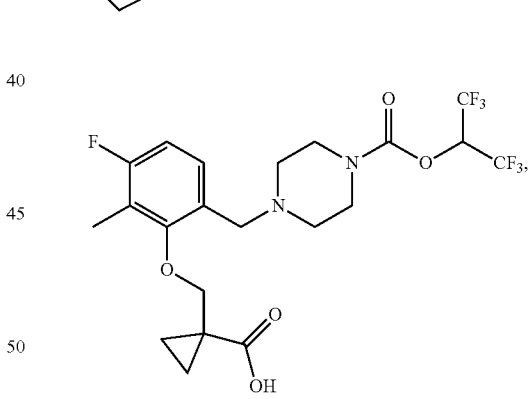
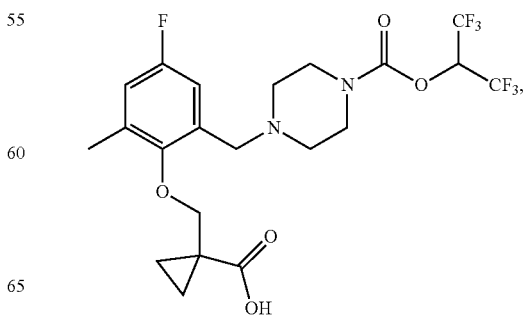

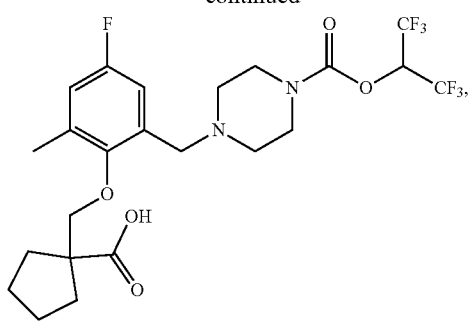
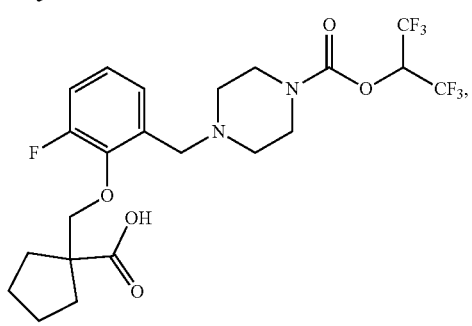
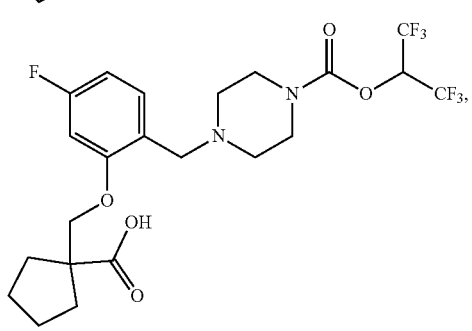
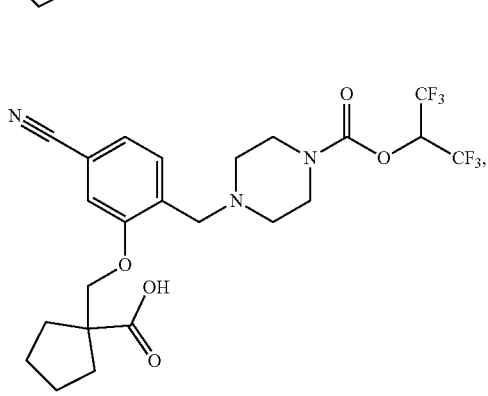
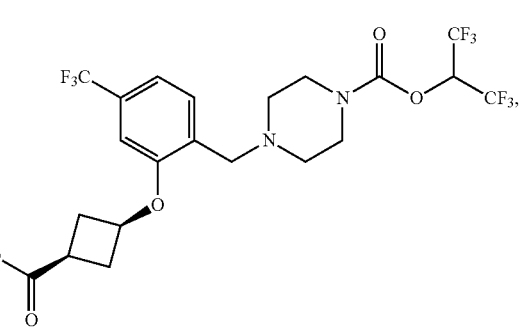
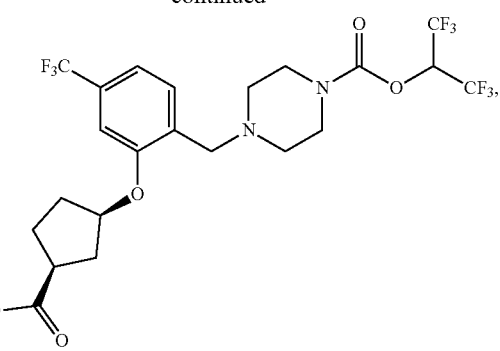
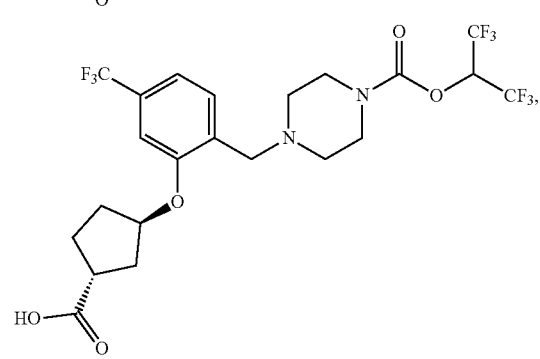
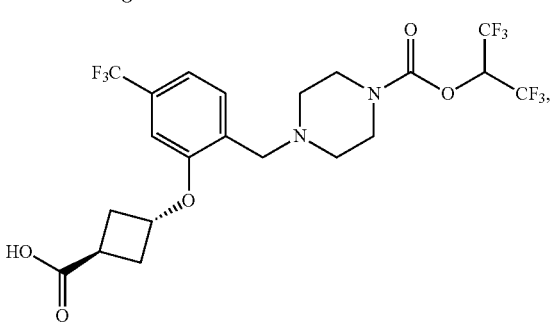
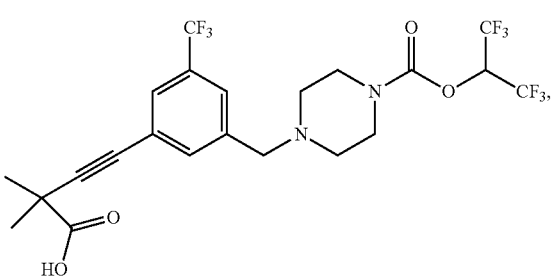
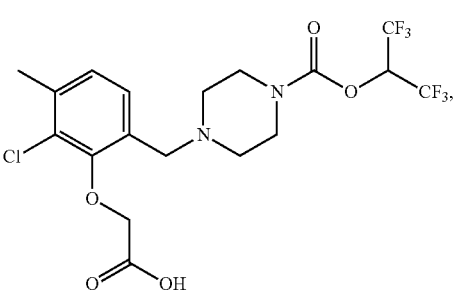

-continued

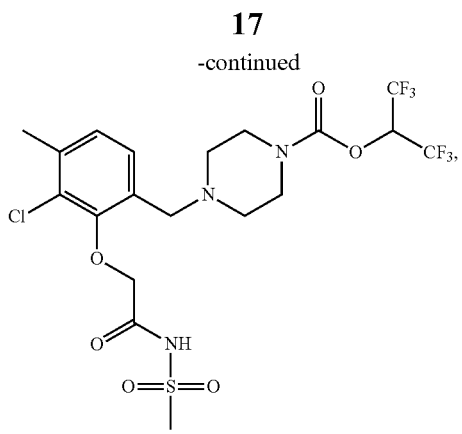

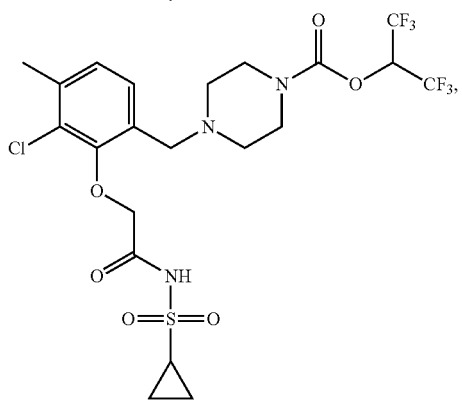

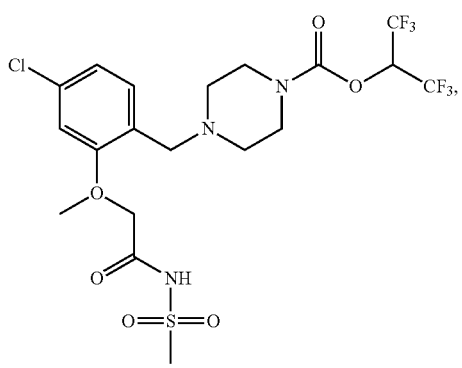

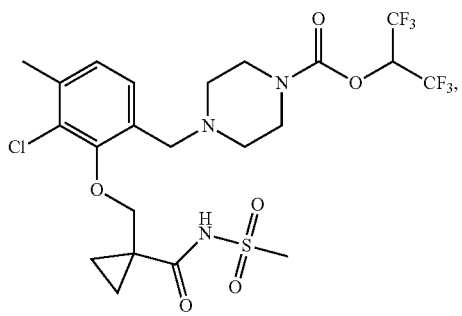

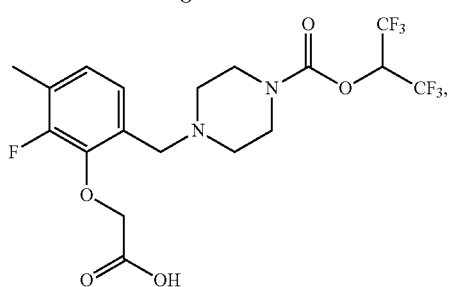

-continued

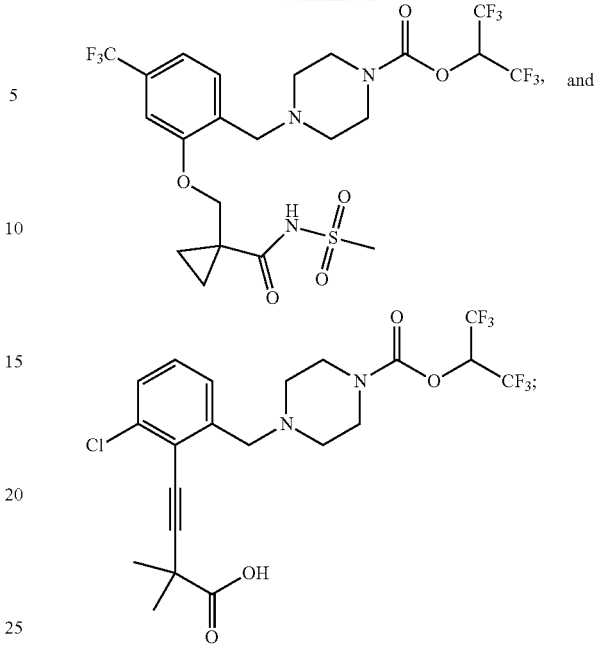

or a pharmaceutically acceptable salt or solvate thereof.

In another embodiment is a pharmaceutical composition comprising a compound of Formula (I) described herein, or a pharmaceutically acceptable salt or solvate thereof, and at least one pharmaceutically acceptable excipient.

In another embodiment is a method of treating pain in a patient in need thereof comprising administering to the patient a therapeutically effective amount of a compound of Formula (I) described herein, or a pharmaceutically acceptable salt or solvate thereof. In some embodiments, the pain is neuropathic pain. In some embodiments, the pain is inflammatory pain.

In another embodiment is a method of treating a disease or disorder in a patient in need thereof comprising administering to the patient a therapeutically effective amount of a compound of Formula (I) described herein, or a pharmaceutically acceptable salt or solvate thereof, wherein the disease or disorder is selected from the group consisting of epilepsy/seizure disorder, multiple sclerosis, neuromyelitis optica (NMO), Tourette syndrome, Alzheimer's disease, and abdominal pain associated with irritable bowel syndrome. In some embodiments, the disease or disorder is epilepsy/seizure disorder. In some embodiments, the disease or disorder is multiple sclerosis. In some embodiments, the disease or disorder is neuromyelitis optica (NMO). In some embodiments, the disease or disorder is Tourette syndrome. In some embodiments, the disease or disorder is Alzheimer's disease. In some embodiments, the disease or disorder is abdominal pain associated with irritable bowel syndrome.

In another embodiment is a method of treating attention deficit and hyperactivity disorder (ADHD) in a patient in need thereof comprising administering to the patient a therapeutically effective amount of a compound of Formula (I) described herein, or a pharmaceutically acceptable salt or solvate thereof.

DETAILED DESCRIPTION OF THE INVENTION

This disclosure is directed, at least in part, to compounds capable of inhibiting MAGL.

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range varies between 1% and 15% of the stated number or numerical range. The term "comprising" (and related terms such as "comprise" or "comprises" or "having" or "including") is not intended to exclude that which in other certain embodiments, for example, an embodiment of any composition of matter, composition, method, or process, or the like, described herein, may "consist of" or "consist essentially of" the described features.

Definitions

As used in the specification and appended claims, unless specified to the contrary, the following terms have the meaning indicated below.

As used herein, $C_1$-$C_x$ includes $C_1$-$C_2$, $C_1$-$C_3$ ... $C_1$-$C_x$. $C_1$-$C_x$ refers to the number of carbon atoms that make up the moiety to which it designates (excluding optional substituents).

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.

"Alkyl" or "alkylene" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to six carbon atoms (e.g., $C_1$-$C_6$ alkyl). In other embodiments, an alkyl comprises one to five carbon atoms (e.g., $C_1$-$C_8$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_8$ alkyl). In other embodiments, an alkyl comprises three to five carbon atoms (e.g., $C_3$-$C_8$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)$R^a$, —N($R^a$)$_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, $SR^a$, —OC(O)—$R^f$, —N($R^a$)$_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)$R^a$, —N($R^a$)$_2$, —C(O)$R^a$, —C(O)O$R^a$, —C(O)N($R^a$)$_2$, —N($R^a$)C(O)O$R^f$, —OC(O)—NR$^a$R$^f$, —N($R^a$)C(O)$R^f$, —N($R^a$)S(O)$_t$$R^f$ (where t is 1 or 2), —S(O)$_t$O$R^a$ (where t is 1 or 2), —S(O)$_t$$R^f$ (where t is 1 or 2) and —S(O)$_t$N($R^a$)$_2$ (where t is 1 or 2) where each $R^a$ is independently hydrogen, alkyl, fluoroalkyl, cycloalkyl, aryl, aralkyl, heterocycloalkyl, heteroaryl or heteroarylalkyl, and each $R^f$ is independently alkyl, fluoroalkyl, cycloalkyl, aryl, aralkyl, heterocycloalkyl, heteroaryl or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from six to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O) $R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkyloxy" refers to a radical bonded through an oxygen atom of the formula —O-aralkyl, where aralkyl is as defined above.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Cycloalkyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a cycloalkyl comprises three to ten carbon atoms. In other embodiments, a cycloalkyl comprises five to seven carbon atoms. The cycloalkyl is attached to the rest of the molecule by a single bond. Cycloalkyls are saturated, (i.e., containing single C—C bonds only) or partially unsaturated (i.e., containing one or more double bonds or triple bonds.) Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). A partially unsaturated cycloalkyl is also referred to as "cycloalkenyl." Examples of monocyclic cycloalkenyls include, e.g., cyclopentenyl, cyclohexenyl, cycloheptenyl, and cyclooctenyl. Polycyclic cycloalkyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "cycloalkyl" is meant to include cycloalkyl radicals optionally substituted by one or more substituents independently selected from alkyl, alkenyl, alkynyl, halo, fluoroalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O) $R^a$, —$R^b$—C(O)$OR^a$, —$R^b$—C(O)N($R^a$)$_2$, —$R^b$—O—$R^e$—C(O)N($R^a$)$_2$, —$R^b$—N($R^a$)C(O)$OR^a$, —$R^b$—N($R^a$)C(O)$R^a$, —$R^b$—N($R^a$)S(O)$_t R^a$ (where t is 1 or 2), —$R^b$—S(O)$_t OR^a$ (where t is 1 or 2), —$R^b$—S(O)$_t R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Halo" or "halogen" refers to bromo, chloro, fluoro or iodo substituents.

"Haloalkyl" refers to an alkyl radical, as defined above, that is substituted by one or more halo radicals, as defined above.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl radical are optionally substituted as defined above for an alkyl group.

"Haloalkoxy" refers to an alkoxy radical, as defined above, that is substituted by one or more halo radicals, as defined above.

"Heterocycloalkyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocycloalkyl radical is a monocyclic, bicyclic, tricyclic or tetracyclic ring system, which include fused, spiro, or bridged ring systems. The heteroatoms in the heterocycloalkyl radical are optionally oxidized. One or more nitrogen atoms, if present, are optionally quaternized. The heterocycloalkyl radical is partially or fully saturated. In some embodiments, the heterocycloalkyl is attached to the rest of the molecule through any atom of the ring(s). Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O) $R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—R—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$ (where t is 1 or 2), —$R^b$—S(O)$_t$$OR^a$ (where t is 1 or 2), —$R^b$—S(O)$_t$$R^a$ (where t is 1 or 2) and —$R^b$—S(O)$_t$N($R^a$)$_2$ (where t is 1 or 2), where each $R^a$ is independently hydrogen, alkyl, fluoroalkyl, cycloalkyl, cycloalkylalkyl, aryl, aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O— heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

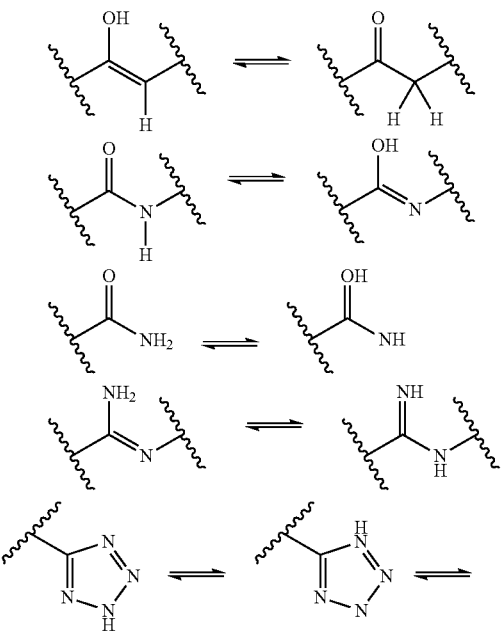

-continued

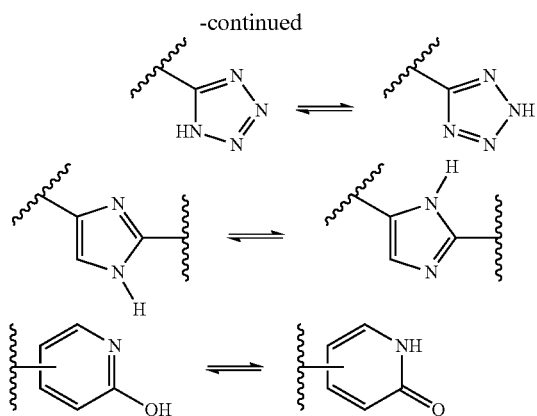

"Optional" or "optionally" means that a subsequently described event or circumstance may or may not occur and that the description includes instances when the event or circumstance occurs and instances in which it does not. For example, "optionally substituted aryl" means that the aryl radical are or are not substituted and that the description includes both substituted aryl radicals and aryl radicals having no substitution.

"Pharmaceutically acceptable salt" includes both acid and base addition salts. A pharmaceutically acceptable salt of any one of the pyrazole compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating" or "palliating" or "ameliorating" are used interchangeably herein. These terms refers to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are administered to a patient at risk of developing a particular disease, or to a patient reporting one or more of the physiological symptoms of a disease, even though a diagnosis of this disease has not been made.

Compounds

The compounds of Formula (I), (Ia), or (Ib) described herein which are modulators of MAGL. These compounds, and compositions comprising these compounds, are useful for the treatment of pain. In some embodiments, the compounds of Formula (I), (Ia), or (Ib) described herein are useful for treating epilepsy/seizure disorder, multiple sclerosis, neuromyelitis optica (NMO), Tourette syndrome, Alzheimer's disease, or abdominal pain associated with irritable bowel syndrome.

In some embodiments is a compound of Formula (I):

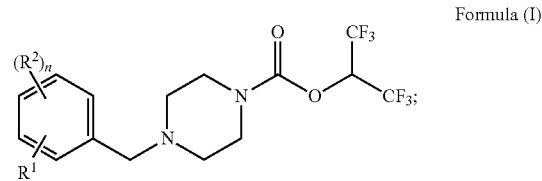

Formula (I)

wherein:
$R^1$ is —$R^{14}$, —$OR^3$, —$SR^4$, —$S(O)_2R^4$, —$N(R^4)(R^5)$, —$NH(R^4)$, or —C≡C—$(CR^6R^7)$—$R^8$;
each $R^2$ is independently selected from $C_{1-6}$alkyl, halogen, —CN, $C_{1-6}$haloalkyl, —$C_{1-6}$alkyl(heterocycloalkyl), —$OR^{17}$, and —$C(O)NR^{18}R^{19}$;

$R^3$ is $-(CR^6R^7)_m-R^8$, $-(CR^6R^7)_p-Y-(CR^6R^7)_q-R^8$, or $-(CR^6R^7)_t-C_{3-6}$cycloalkyl-$R^8$;

$R^4$ is $-(CR^6R^7)_m-R^{8'}$, $-(CR^6R^7)_v-C(O)OH$, or $-(CR^6R^7)_p-Y-(CR^6R^7)_q-R^8$;

$R^{4'}$ is $-(CR^6R^7)_m-R^{8'}$, $-(CR^6R^7)_p-Y-(CR^6R^7)_q-R^8$, $-C_{4-6}$alkyl-$C(O)OH$, $-C_{3-6}$cycloalkyl-$C(O)OH$, or $-C_{1-6}$alkyl-$C_{3-6}$cycloalkyl-$C(O)OH$;

Y is $-O-$ or $-N(R^{22})-$;

$R^5$ is $C_{1-6}$alkyl or $-CH_2$-phenyl optionally substituted with one, two, or three groups independently selected from halogen, $C_{1-6}$alkyl, $C_{1-6}$haloalkyl, and $C_{1-6}$alkoxy;

each $R^6$ and $R^7$ is each independently selected from H, F, and $C_{1-6}$alkyl; or $R^6$ and $R^7$, together with the carbon to which they are attached, form a $C_{3-6}$cycloalkyl ring;

$R^8$ is $-C(O)OR^9$, $-C(O)R^{10}$, or $-C(O)O-(CR^{12}R^{13})-OC(O)R^{11}$;

$R^{8'}$ is $-C(O)OR^{9'}$, $-C(O)R^{10'}$, or $-C(O)O-(CR^{12}R^{13})-OC(O)R^{11}$;

$R^9$ is H or $C_{1-6}$alkyl;

$R^{9'}$ is $C_{1-6}$alkyl;

$R^{10}$ is $C_{1-6}$alkyl or $-NHSO_2R^{21}$;

$R^{10'}$ is $C_{2-6}$alkyl or $-NHSO_2R^{21}$;

$R^{11}$ is $C_{1-6}$alkyl or $C_{1-6}$alkoxy;

$R^{12}$ and $R^{13}$ is each independently H or $C_{1-6}$alkyl;

$R^{14}$ is $-(CR^{15}R^{16})_m-R^8$ or $-(CR^6R^7)_p-Y-(CR^6R^7)_q-R^8$;

each $R^{15}$ and $R^{16}$ is each independently selected from H, F, and $C_{1-6}$alkyl;

each $R^{17}$ is independently selected from H, $C_{1-6}$alkyl, $C_{1-6}$haloalkyl, and $C_{3-6}$cycloalkyl;

each $R^{18}$ and $R^{19}$ is each independently selected from H, $C_{1-6}$alkyl, $C_{3-6}$cycloalkyl, aryl, and heteroaryl; or $R^{18}$ and $R^{19}$, together with the nitrogen to which they are attached, form a heterocycloalkyl ring optionally substituted with one, two, or three $R^{20}$;

each $R^{20}$ is independently selected from halogen, $C_{1-6}$alkyl, $C_{1-6}$haloalkyl, oxo, $-CN$, and $C_{3-6}$cycloalkyl;

$R^{21}$ is $C_{1-6}$alkyl or $C_{3-6}$cycloalkyl;

$R^{22}$ is H, $C_{1-6}$alkyl, or $-SO_2R^{23}$;

$R^{23}$ is $C_{1-6}$alkyl;

m is 1, 2, 3 or 4;

n is 0, 1, 2, 3, or 4;

p is 2, 3, or 4;

q is 1, 2, or 3;

t is 0, 1, or 2; and v is 3 or 4;

or a pharmaceutically acceptable salt or solvate thereof.

In some embodiments is a compound of Formula (I), or a pharmaceutically acceptable salt or solvate thereof, wherein $R^1$ is $-NH(R^{4'})$. In some embodiments is a compound of Formula (I), or a pharmaceutically acceptable salt or solvate thereof, wherein $R^1$ is $-NH(R^{4'})$ and $R^{4'}$ is $-(CR^6R^7)_m-R^{8'}$. In some embodiments is a compound of Formula (I), or a pharmaceutically acceptable salt or solvate thereof, wherein $R^1$ is $-NH(R^{4'})$, $R^{4'}$ is $-(CR^6R^7)_m-R^{8'}$, and each $R^6$ and $R^7$ is each independently selected from H and $C_{1-6}$alkyl. In some embodiments is a compound of Formula (I), or a pharmaceutically acceptable salt or solvate thereof, wherein $R^1$ is $-NH(R^{4'})$, $R^{4'}$ is $-(CR^6R^7)_m-R^{8'}$, and each $R^6$ and $R^7$ is H. In some embodiments is a compound of Formula (I), or a pharmaceutically acceptable salt or solvate thereof, wherein m is 1, 2, or 3. In some embodiments is a compound of Formula (I), or a pharmaceutically acceptable salt or solvate thereof, wherein m is 1. In some embodiments is a compound of Formula (I), or a pharmaceutically acceptable salt or solvate thereof, wherein m is 2. In some embodiments is a compound of Formula (I), or a pharmaceutically acceptable salt or solvate thereof, wherein m is 3. In some embodiments is a compound of Formula (I), or a pharmaceutically acceptable salt or solvate thereof, wherein m is 4. In some embodiments is a compound of Formula (I), or a pharmaceutically acceptable salt or solvate thereof, wherein $R^{8'}$ is $-C(O)OR^{9'}$. In some embodiments is a compound of Formula (I), or a pharmaceutically acceptable salt or solvate thereof, wherein $R^{8'}$ is $-C(O)OR^{9'}$ and $R^{9'}$ is $-CH_3$. In some embodiments is a compound of Formula (I), or a pharmaceutically acceptable salt or solvate thereof, wherein $R^{8'}$ is $-C(O)OR^{9'}$ and $R^{9'}$ is $-CH_2CH_3$. In some embodiments is a compound of Formula (I), or a pharmaceutically acceptable salt or solvate thereof, wherein $R^{8'}$ is $-C(O)R^{10'}$. In some embodiments is a compound of Formula (I), or a pharmaceutically acceptable salt or solvate thereof, wherein $R^{8'}$ is $-C(O)R^{10'}$, and $R^{10'}$ is $-NHSO_2R^{21}$. In some embodiments is a compound of Formula (I), or a pharmaceutically acceptable salt or solvate thereof, wherein $R^{8'}$ is $-C(O)R^{10'}$, $R^{10'}$ is $-NHSO_2R^{21}$, and $R^{21}$ is $C_{1-6}$alkyl. In some embodiments is a compound of Formula (I), or a pharmaceutically acceptable salt or solvate thereof, wherein $R^{8'}$ is $-C(O)R^{10'}$, $R^{10'}$ is $-NHSO_2R^{21}$, and $R^{21}$ is $C_{3-6}$cycloalkyl. In some embodiments is a compound of Formula (I), or a pharmaceutically acceptable salt or solvate thereof, wherein $R^{8'}$ is $-C(O)O-(CR^{12}R^{13})-OC(O)R^{11}$. In some embodiments is a compound of Formula (I), or a pharmaceutically acceptable salt or solvate thereof, wherein $R^{8'}$ is $-C(O)O-(CR^{12}R^{13})-OC(O)R^{11}$ and $R^{11}$ is $C_{1-6}$alkyl. In some embodiments is a compound of Formula (I), or a pharmaceutically acceptable salt or solvate thereof, wherein $R^{8'}$ is $-C(O)O-(CR^{12}R^{13})-OC(O)R^{11}$ and $R^{11}$ is $C_{1-6}$alkoxy. In some embodiments is a compound of Formula (I), or a pharmaceutically acceptable salt or solvate thereof, wherein $R^1$ is $-NH(R^{4'})$ and $R^{4'}$ is $-CH_2CH_2C(O)OCH_3$. In some embodiments is a compound of Formula (I), or a pharmaceutically acceptable salt or solvate thereof, wherein $R^1$ is $-NH(R^{4'})$ and $R^{4'}$ is $-CH_2CH_2C(O)OCH_2CH_3$. In some embodiments is a compound of Formula (I), or a pharmaceutically acceptable salt or solvate thereof, wherein $R^1$ is $-NH(R^{4'})$ and $R^{4'}$ is $-CH_2CH_2C(O)OC(CH_3)_3$. In some embodiments is a compound of Formula (I), or a pharmaceutically acceptable salt or solvate thereof, wherein $R^1$ is $-NH(R^{4'})$ and $R^{4'}$ is $-CH_2CH_2CH_2C(O)OCH_3$. In some embodiments is a compound of Formula (I), or a pharmaceutically acceptable salt or solvate thereof, wherein $R^1$ is $-NH(R^{4'})$ and $R^{4'}$ is $-CH_2CH_2CH_2C(O)OCH_2CH_3$. In some embodiments is a compound of Formula (I), or a pharmaceutically acceptable salt or solvate thereof, wherein $R^1$ is $-NH(R^{4'})$ and $R^{4'}$ is $-CH_2CH_2CH_2C(O)OC(CH_3)_3$.

In some embodiments is a compound of Formula (I), or a pharmaceutically acceptable salt or solvate thereof, wherein $R^1$ is $-NH(R^{4'})$ and $R^{4'}$ is $-(CR^6R^7)_p-Y-(CR^6R^7)_q-R^8$. In some embodiments is a compound of Formula (I), or a pharmaceutically acceptable salt or solvate thereof, wherein $R^1$ is $-NH(R^{4'})$, $R^{4'}$ is $-(CR^6R^7)_p-Y-(CR^6R^7)_q-R^8$, and each $R^6$ and $R^7$ is each independently selected from H and $C_{1-6}$alkyl. In some embodiments is a compound of Formula (I), or a pharmaceutically acceptable salt or solvate thereof, wherein $R^1$ is $-NH(R^{4'})$, $R^{4'}$ is $-(CR^6R^7)_p-Y-(CR^6R^7)_q-R^8$, and each $R^6$ and $R^7$ is H. In some embodiments is a compound of Formula (I), or a pharmaceutically acceptable salt or solvate thereof, wherein $R^1$ is $-NH(R^{4'})$, $R^{4'}$ is $-(CR^6R^7)_p-Y-(CR^6R^7)_q-R^8$, and Y is $-O-$. In some embodiments is a compound of Formula (I), or a pharmaceutically acceptable salt or solvate thereof, wherein $R^1$ is —NH($R^{4'}$), $R^{4'}$ is —($CR^6R^7$)$_p$—Y—($CR^6R^7$)$_q$—$R^8$, and Y is —N($R^{22}$)—. In some embodiments is a compound of Formula (I), or a pharmaceutically acceptable salt or solvate thereof, wherein $R^1$ is —NH($R^{4'}$), $R^{4'}$ is —($CR^6R^7$)$_p$—Y—($CR^6R^7$)$_q$—$R^8$, Y is —N($R^{22}$)—, and $R^{22}$ is —$SO_2R^{23}$. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein $R^8$ is —C(O)O$R^9$. In some embodiments is a compound of Formula (I), or a pharmaceutically acceptable salt or solvate thereof, wherein $R^8$ is —C(O)O$R^9$ and $R^9$ is H. In some embodiments is a compound of Formula (I), or a pharmaceutically acceptable salt or solvate thereof, wherein $R^8$ is —C(O)O$R^9$ and $R^9$ is $C_{1-6}$alkyl. In some embodiments is a compound of Formula (I), or a pharmaceutically acceptable salt or solvate thereof, wherein $R^8$ is —C(O)O$R^9$ and $R^9$ is —$CH_3$. In some embodiments is a compound of Formula (I), or a pharmaceutically acceptable salt or solvate thereof, wherein $R^8$ is —C(O)O$R^9$ and $R^9$ is —$CH_2CH_3$. In some embodiments is a compound of Formula (I), or a pharmaceutically acceptable salt or solvate thereof, wherein $R^8$ is —C(O)$R^{10}$. In some embodiments is a compound of Formula (I), or a pharmaceutically acceptable salt or solvate thereof, wherein $R^8$ is —C(O)$R^{10}$ and $R^{10}$ is —NHSO$_2R^{21}$. In some embodiments is a compound of Formula (I), or a pharmaceutically acceptable salt or solvate thereof, wherein $R^8$ is —C(O)$R^{10}$, $R^{10}$ is —NHSO$_2R^{21}$, and $R^{21}$ is $C_{1-6}$alkyl. In some embodiments is a compound of Formula (I), or a pharmaceutically acceptable salt or solvate thereof, wherein $R^8$ is —C(O)$R^{10}$, $R^{10}$ is —NHSO$_2R^{21}$, and $R^{21}$ is $C_{3-6}$cycloalkyl. In some embodiments is a compound of Formula (I), or a pharmaceutically acceptable salt or solvate thereof, wherein $R^8$ is —C(O)O—($CR^{12}R^{13}$)—OC(O)$R^{11}$. In some embodiments is a compound of Formula (I), or a pharmaceutically acceptable salt or solvate thereof, wherein $R^8$ is —C(O)O—($CR^{12}R^{13}$)—OC(O)$R^{11}$ and $R^{11}$ is $C_{1-6}$alkyl. In some embodiments is a compound of Formula (I), or a pharmaceutically acceptable salt or solvate thereof, wherein $R^8$ is —C(O)O—($CR^{12}R^{13}$)—OC(O)$R^{11}$ and $R^{11}$ is $C_{1-6}$alkoxy. In some embodiments is a compound of Formula (I), or a pharmaceutically acceptable salt or solvate thereof, wherein $R^1$ is —NH($R^{4'}$) and $R^{4'}$ is —$CH_2CH_2OCH_2C(O)OH$. In some embodiments is a compound of Formula (I), or a pharmaceutically acceptable salt or solvate thereof, wherein $R^1$ is —NH($R^{4'}$) and $R^{4'}$ is —$CH_2CH_2N(SO_2CH_3)CH_2C(O)OH$. In some embodiments is a compound of Formula (I), or a pharmaceutically acceptable salt or solvate thereof, wherein $R^1$ is —NH($R^{4'}$) and $R^{4'}$ is —$CH_2CH_2CH_2C(O)OCH(CH_3)OC(O)OCH_2CH_3$. In some embodiments is a compound of Formula (I), or a pharmaceutically acceptable salt or solvate thereof, wherein $R^1$ is —NH($R^{4'}$) and $R^{4'}$ is —$CH_2CH_2CH_2C(O)OCH(CH_3)OC(O)OCH(CH_3)_2$. In some embodiments is a compound of Formula (I), or a pharmaceutically acceptable salt or solvate thereof, wherein $R^1$ is —NH($R^{4'}$) and $R^{4'}$ is —$CH_2CH_2CH_2C(O)OCH_2OC(O)OC(CH_3)_3$. In some embodiments is a compound of Formula (I), or a pharmaceutically acceptable salt or solvate thereof, wherein $R^1$ is —NH($R^{4'}$) and $R^{4'}$ is —$CH_2CH_2CH_2C(O)OCH(CH_3)OC(O)CH(CH_3)_2$.

In some embodiments is a compound of Formula (I), or a pharmaceutically acceptable salt or solvate thereof, wherein $R^1$ is —NH($R^{4'}$) and $R^{4'}$ is —$C_{4-6}$alkyl-C(O)OH. In some embodiments is a compound of Formula (I), or a pharmaceutically acceptable salt or solvate thereof, wherein $R^1$ is —NH($R^{4'}$) and $R^{4'}$ is —$CH_2CH_2CH_2CH_2C(O)OH$. In some embodiments is a compound of Formula (I), or a pharmaceutically acceptable salt or solvate thereof, wherein $R^1$ is —NH($R^{4'}$) and $R^{4'}$ is —$CH_2CH(CH_3)CH_2C(O)OH$.

In some embodiments is a compound of Formula (I), or a pharmaceutically acceptable salt or solvate thereof, wherein $R^1$ is —NH($R^{4'}$) and $R^{4'}$ is —$C_{3-6}$cycloalkyl-C(O)OH. In some embodiments is a compound of Formula (I), or a pharmaceutically acceptable salt or solvate thereof, wherein $R^1$ is —NH($R^{4'}$) and $R^{4'}$ is —$C_{1-6}$alkyl-$C_{3-6}$cycloalkyl-C(O)OH.

In some embodiments is a compound of Formula (I), or a pharmaceutically acceptable salt or solvate thereof, wherein $R^1$ is —N($R^4$)($R^5$). In some embodiments is a compound of Formula (I), or a pharmaceutically acceptable salt or solvate thereof, wherein $R^1$ is —N($R^4$)($R^5$) and $R^5$ is $C_{1-6}$alkyl. In some embodiments is a compound of Formula (I), or a pharmaceutically acceptable salt or solvate thereof, wherein $R^1$ is —N($R^4$)($R^5$) and $R^5$ is —$CH_3$. In some embodiments is a compound of Formula (I), or a pharmaceutically acceptable salt or solvate thereof, wherein $R^1$ is —N($R^4$)($R^5$) and $R^5$ is —$CH_2$— phenyl optionally substituted with one, two, or three groups independently selected from halogen, $C_{1-6}$alkyl, $C_{1-6}$haloalkyl, and $C_{1-6}$alkoxy. In some embodiments is a compound of Formula (I), or a pharmaceutically acceptable salt or solvate thereof, wherein $R^1$ is —N($R^4$)($R^5$) and $R^5$ is —$CH_2$-phenyl optionally substituted with one or two groups independently selected from halogen, $C_{1-6}$alkyl, $C_{1-6}$haloalkyl, and $C_{1-6}$alkoxy. In some embodiments is a compound of Formula (I), or a pharmaceutically acceptable salt or solvate thereof, wherein $R^1$ is —N($R^4$)($R^5$) and $R^5$ is —$CH_2$-phenyl optionally substituted with one group selected from halogen, $C_{1-6}$alkyl, $C_{1-6}$haloalkyl, and $C_{1-6}$alkoxy. In some embodiments is a compound of Formula (I), or a pharmaceutically acceptable salt or solvate thereof, wherein $R^1$ is —N($R^4$)($R^5$) and $R^4$ is —($CR^6R^7$)$_m$—$R^8$. In some embodiments is a compound of Formula (I), or a pharmaceutically acceptable salt or solvate thereof, wherein $R^1$ is —N($R^4$)($R^5$), $R^4$ is —($CR^6R^7$)$_m$—$R^8$, and each $R^6$ and $R^7$ is each independently selected from H and $C_{1-6}$alkyl. In some embodiments is a compound of Formula (I), or a pharmaceutically acceptable salt or solvate thereof, wherein $R^1$ is —N($R^4$)($R^5$), $R^4$ is —($CR^6R^7$)$_m$—$R^8$, and each $R^6$ and $R^7$ is H. In some embodiments is a compound of Formula (I), or a pharmaceutically acceptable salt or solvate thereof, wherein m is 1, 2, or 3. In some embodiments is a compound of Formula (I), or a pharmaceutically acceptable salt or solvate thereof, wherein m is 1. In some embodiments is a compound of Formula (I), or a pharmaceutically acceptable salt or solvate thereof, wherein m is 2. In some embodiments is a compound of Formula (I), or a pharmaceutically acceptable salt or solvate thereof, wherein m is 3. In some embodiments is a compound of Formula (I), or a pharmaceutically acceptable salt or solvate thereof, wherein m is 4. In some embodiments is a compound of Formula (I), or a pharmaceutically acceptable salt or solvate thereof, wherein $R^{8'}$ is —C(O)O$R^{9'}$. In some embodiments is a compound of Formula (I), or a pharmaceutically acceptable salt or solvate thereof, wherein $R^{8'}$ is —C(O)O$R^{9'}$ and $R^{9'}$ is —$CH_3$. In some embodiments is a compound of Formula (I), or a pharmaceutically acceptable salt or solvate thereof, wherein $R^{8'}$ is —C(O)O$R^{9'}$ and $R^{9'}$ is —$CH_2CH_3$. In some embodiments is a compound of Formula (I), or a pharmaceutically acceptable salt or solvate thereof, wherein $R^{8'}$ is —C(O)$R^{10'}$. In some embodiments is a compound of Formula (I), or a pharmaceutically acceptable salt or solvate thereof, wherein $R^{8'}$ is —C(O)$R^{10'}$ and $R^{10'}$ is —NHSO$_2$R$^{21}$. In some embodiments is a compound of Formula (I), or a pharmaceutically acceptable salt or solvate thereof, wherein $R^{8'}$ is —C(O)$R^{10'}$, $R^{10'}$ is —NHSO$_2$R$^{21}$, and $R^{21}$ is $C_{1-6}$alkyl. In some embodiments is a compound of Formula (I), or a pharmaceutically acceptable salt or solvate thereof, wherein $R^{8'}$ is —C(O)$R^{10'}$, $R^{10'}$ is —NHSO$_2$R$^{21}$, and $R^{21}$ is $C_{3-6}$cycloalkyl. In some embodiments is a compound of Formula (I), or a pharmaceutically acceptable salt or solvate thereof, wherein $R^{8'}$ is —C(O)O—(CR$^{12}$R$^{13}$)—OC(O)R$^{11}$. In some embodiments is a compound of Formula (I), or a pharmaceutically acceptable salt or solvate thereof, wherein $R^{8'}$ is —C(O)O—(CR$^{12}$R$^{13}$)—OC(O)R$^{11}$ and $R^{11}$ is $C_{1-6}$alkyl. In some embodiments is a compound of Formula (I), or a pharmaceutically acceptable salt or solvate thereof, wherein $R^{8'}$ is —C(O)O—(CR$^{12}$R$^{13}$)—OC(O)R$^{11}$ and $R^{11}$ is $C_{1-6}$alkoxy. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$C(O)OCH$_3$. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$C(O)OCH$_2$CH$_3$. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$C(O)OC(CH$_3$)$_3$. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OCH$_3$. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OCH$_2$CH$_3$. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OC(CH$_3$)$_3$.

In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —(CR$^6$R$^7$)$_p$—Y—(CR$^6$R$^7$)$_q$—R$^8$. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —(CR$^6$R$^7$)$_p$—Y—(CR$^6$R$^7$)$_q$—R$^8$, and each $R^6$ and $R^7$ is each independently selected from H and $C_{1-6}$alkyl. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$— phenyl optionally substituted with one, two, or three groups independently selected from halogen, $C_{1-6}$alkyl, $C_{1-6}$haloalkyl, and $C_{1-6}$alkoxy, and $R^4$ is —(CR$^6$R$^7$)$_p$—Y—(CR$^6$R$^7$)$_q$—R$^8$, and each $R^6$ and $R^7$ is H. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —(CR$^6$R$^7$)$_p$—Y—(CR$^6$R$^7$)$_q$—R$^8$, and Y is —O—. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —(CR$^6$R$^7$)$_p$—Y—(CR$^6$R$^7$)$_q$—R$^8$, and Y is —N(R$^{22}$)—. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —(CR$^6$R$^7$)$_p$—Y—(CR$^6$R$^7$)$_q$—R$^8$, Y is —N(R$^{22}$)—, and $R^{22}$ is —SO$_2$R$^{23}$. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein $R^8$ is —C(O)OR$^9$. In some embodiments is a compound of Formula (I), or a pharmaceutically acceptable salt or solvate thereof, wherein $R^8$ is —C(O)OR$^9$ and $R^9$ is H. In some embodiments is a compound of Formula (I), or a pharmaceutically acceptable salt or solvate thereof, wherein $R^8$ is —C(O)OR$^9$ and $R^9$ is $C_{1-6}$alkyl. In some embodiments is a compound of Formula (I), or a pharmaceutically acceptable salt or solvate thereof, wherein $R^8$ is —C(O)OR$^9$ and $R^9$ is —CH$_3$. In some embodiments is a compound of Formula (I), or a pharmaceutically acceptable salt or solvate thereof, wherein $R^8$ is —C(O)OR$^9$ and $R^9$ is —CH$_2$CH$_3$. In some embodiments is a compound of Formula (I), or a pharmaceutically acceptable salt or solvate thereof, wherein $R^8$ is —C(O)R$^{10}$. In some embodiments is a compound of Formula (I), or a pharmaceutically acceptable salt or solvate thereof, wherein $R^8$ is —C(O)R$^{10}$ and $R^{10}$ is —NHSO$_2$R$^{21}$. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{1-6}$alkyl. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{3-6}$cycloalkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkoxy. In some embodiments is a compound of Formula (I), or a pharmaceutically acceptable salt or solvate thereof, wherein $R^1$ is —N(R$^4$)(R$^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$OCH$_2$C(O)OH. In some embodiments is a compound of Formula (I), or a pharmaceutically acceptable salt or solvate thereof, wherein $R^1$ is —N($R^4$)($R^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$N(SO$_2$CH$_3$)CH$_2$C(O)OH. In some embodiments is a compound of Formula (I), or a pharmaceutically acceptable salt or solvate thereof, wherein $R^1$ is —N($R^4$)($R^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OCH(CH$_3$)OC(O)OCH$_2$CH$_3$. In some embodiments is a compound of Formula (I), or a pharmaceutically acceptable salt or solvate thereof, wherein $R^1$ is —N($R^4$)($R^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OCH(CH$_3$)OC(O)OCH(CH$_3$)$_2$. In some embodiments is a compound of Formula (I), or a pharmaceutically acceptable salt or solvate thereof, wherein $R^1$ is —N($R^4$)($R^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OCH$_2$OC(O)OC(CH$_3$)$_3$. In some embodiments is a compound of Formula (I), or a pharmaceutically acceptable salt or solvate thereof, wherein $R^1$ is —N($R^4$)($R^5$), $R^5$ is —CH$_3$ or —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OCH(CH$_3$)OC(O)CH(CH$_3$)$_2$.

In some embodiments is a compound of Formula (I), or a pharmaceutically acceptable salt or solvate thereof, wherein $R^1$ is —N($R^4$)($R^5$) and $R^4$ is —(CR$^6$R$^7$)$_v$—C(O)OH. In some embodiments is a compound of Formula (I), or a pharmaceutically acceptable salt or solvate thereof, wherein $R^1$ is —N($R^4$)($R^5$), $R^5$ is —CH$_3$, and $R^4$ is —(CR$^6$R$^7$)$_v$—C(O)OH. In some embodiments is a compound of Formula (I), or a pharmaceutically acceptable salt or solvate thereof, wherein $R^1$ is —N($R^4$)($R^5$), $R^5$ is —CH$_3$, $R^4$ is —(CR$^6$R$^7$)$_v$—C(O)OH, and v is 3. In some embodiments is a compound of Formula (I), or a pharmaceutically acceptable salt or solvate thereof, wherein $R^1$ is —N($R^4$)($R^5$), $R^5$ is —CH$_3$, $R^4$ is —(CR$^6$R$^7$)$_v$—C(O)OH, and v is 4. In some embodiments is a compound of Formula (I), or a pharmaceutically acceptable salt or solvate thereof, wherein $R^1$ is —N($R^4$)($R^5$), $R^5$ is —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —(CR$^6$R$^7$)$_v$—C(O)OH. In some embodiments is a compound of Formula (I), or a pharmaceutically acceptable salt or solvate thereof, wherein $R^1$ is —N($R^4$)($R^5$), $R^5$ is —CH$_2$-phenyl optionally substituted with one, two, or three groups independently selected from halogen, $C_{1-6}$alkyl, $C_{1-6}$haloalkyl, and $C_{1-6}$alkoxy, $R^4$ is —(CR$^6$R$^7$)$_v$—C(O)OH, and v is 3. In some embodiments is a compound of Formula (I), or a pharmaceutically acceptable salt or solvate thereof, wherein $R^1$ is —N($R^4$)($R^5$), $R^5$ is —CH$_2$-phenyl optionally substituted with one, two, or three groups independently selected from halogen, $C_{1-6}$alkyl, $C_{1-6}$haloalkyl, and $C_{1-6}$alkoxy, $R^4$ is —(CR$^6$R$^7$)$_v$—C(O)OH, and v is 4. In some embodiments is a compound of Formula (I), or a pharmaceutically acceptable salt or solvate thereof, wherein $R^1$ is —N($R^4$)($R^5$), $R^5$ is —CH$_3$, and $R^4$ is —CH$_2$CH$_2$CH$_2$C(O)OH. In some embodiments is a compound of Formula (I), or a pharmaceutically acceptable salt or solvate thereof, wherein $R^1$ is —N($R^4$)($R^5$), $R^5$ is —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$C(O)OH. In some embodiments is a compound of Formula (I), or a pharmaceutically acceptable salt or solvate thereof, wherein $R^1$ is —N($R^4$)($R^5$), $R^5$ is —CH$_3$, and $R^4$ is —CH$_2$CH$_2$CH$_2$CH$_2$C(O)OH. In some embodiments is a compound of Formula (I), or a pharmaceutically acceptable salt or solvate thereof, wherein $R^1$ is —N($R^4$)($R^5$), $R^5$ is —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH$_2$CH$_2$CH$_2$C(O)OH. In some embodiments is a compound of Formula (I), or a pharmaceutically acceptable salt or solvate thereof, wherein $R^1$ is —N($R^4$)($R^5$), $R^5$ is —CH$_3$, and $R^4$ is —CH$_2$CH(CH$_3$)CH$_2$C(O)OH. In some embodiments is a compound of Formula (I), or a pharmaceutically acceptable salt or solvate thereof, wherein $R^1$ is —N($R^4$)($R^5$), $R^5$ is —CH$_2$-phenyl optionally substituted with one, two, or three groups independently selected from halogen, $C_{1-6}$alkyl, $C_{1-6}$haloalkyl, and $C_{1-6}$alkoxy, and $R^4$ is —CH$_2$CH(CH$_3$)CH$_2$C(O)OH.

In some embodiments is a compound of Formula (I), or a pharmaceutically acceptable salt or solvate thereof, wherein $R^1$ is —OR$^3$. In some embodiments is a compound of Formula (I), or a pharmaceutically acceptable salt or solvate thereof, wherein $R^1$ is —OR$^3$ and $R^3$ is —(CR$^6$R$^7$)$_m$—R$^8$. In some embodiments is a compound of Formula (I), or a pharmaceutically acceptable salt or solvate thereof, wherein $R^8$ is —C(O)OR$^9$. In some embodiments is a compound of Formula (I), or a pharmaceutically acceptable salt or solvate thereof, wherein $R^8$ is —C(O)OR$^9$ and $R^9$ is H. In some embodiments is a compound of Formula (I), or a pharmaceutically acceptable salt or solvate thereof, wherein $R^8$ is —C(O)OR$^9$ and $R^9$ is $C_{1-6}$alkyl. In some embodiments is a compound of Formula (I), or a pharmaceutically acceptable salt or solvate thereof, wherein $R^8$ is —C(O)OR$^9$ and $R^9$ is —CH$_3$. In some embodiments is a compound of Formula (I), or a pharmaceutically acceptable salt or solvate thereof, wherein $R^8$ is —C(O)OR$^9$ and $R^9$ is —CH$_2$CH$_3$. In some embodiments is a compound of Formula (I), or a pharmaceutically acceptable salt or solvate thereof, wherein $R^8$ is —C(O)R$^{10}$. In some embodiments is a compound of Formula (I), or a pharmaceutically acceptable salt or solvate thereof, wherein $R^8$ is —C(O)R$^{10}$ and $R^{10}$ is —NHSO$_2$R$^{21}$. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{1-6}$alkyl. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{3-6}$cycloalkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkoxy. In some embodiments is a compound of Formula (I), or a pharmaceutically acceptable salt or solvate thereof, wherein $R^1$ is —OR$^3$ and $R^3$ is —CH$_2$C(O)OH. In some embodiments is a compound of Formula (I), or a pharmaceutically acceptable salt or solvate thereof, wherein $R^1$ is —$OR^3$ and $R^3$ is —$CH_2CH_2C(O)OH$. In some embodiments is a compound of Formula (I), or a pharmaceutically acceptable salt or solvate thereof, wherein $R^1$ is —$OR^3$ and $R^3$ is

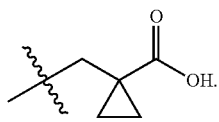 [SMILES: *CC1(C(=O)O)CC1]

In some embodiments is a compound of Formula (I), or a pharmaceutically acceptable salt or solvate thereof, wherein $R^1$ is —$OR^3$ and $R^3$ is

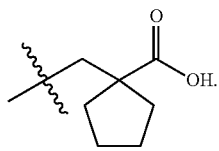 [SMILES: *CC1(C(=O)O)CCCC1]

In some embodiments is a compound of Formula (I), or a pharmaceutically acceptable salt or solvate thereof, wherein $R^1$ is —$OR^3$ and $R^3$ is —$CH_2CH_2CH_2C(O)OH$. In some embodiments is a compound of Formula (I), or a pharmaceutically acceptable salt or solvate thereof, wherein $R^1$ is —$OR^3$ and $R^3$ is —$CH_2CH(CH_3)CH_2C(O)OH$. In some embodiments is a compound of Formula (I), or a pharmaceutically acceptable salt or solvate thereof, wherein $R^1$ is —$OR^3$ and $R^3$ is —$CH_2CH_2C(O)OCH_3$. In some embodiments is a compound of Formula (I), or a pharmaceutically acceptable salt or solvate thereof, wherein $R^1$ is —$OR^3$ and $R^3$ is —$CH_2CH_2C(O)OCH_2CH_3$. In some embodiments is a compound of Formula (I), or a pharmaceutically acceptable salt or solvate thereof, wherein $R^1$ is —$OR^3$ and $R^3$ is —$CH_2CH_2C(O)OC(CH_3)_3$. In some embodiments is a compound of Formula (I), or a pharmaceutically acceptable salt or solvate thereof, wherein $R^1$ is —$OR^3$ and $R^3$ is —$CH_2CH_2CH_2C(O)OCH_3$. In some embodiments is a compound of Formula (I), or a pharmaceutically acceptable salt or solvate thereof, wherein $R^1$ is —$OR^3$ and $R^3$ is —$CH_2CH_2CH_2C(O)OCH_2CH_3$. In some embodiments is a compound of Formula (I), or a pharmaceutically acceptable salt or solvate thereof, wherein $R^1$ is —$OR^3$ and $R^3$ is —$CH_2CH_2CH_2C(O)OC(CH_3)_3$.

In some embodiments is a compound of Formula (I), or a pharmaceutically acceptable salt or solvate thereof, wherein $R^1$ is —$OR^3$ and $R^3$ is —$(CR^6R^7)_p$—Y—$(CR^6R^7)_q$—$R^8$. In some embodiments is a compound of Formula (I), or a pharmaceutically acceptable salt or solvate thereof, wherein $R^1$ is —$OR^3$, $R^3$ is —$(CR^6R^7)_p$—Y—$(CR^6R^7)_q$—$R^8$, and each $R^6$ and $R^7$ is each independently selected from H and $C_{1-6}$alkyl. In some embodiments is a compound of Formula (I), or a pharmaceutically acceptable salt or solvate thereof, wherein $R^1$ is —$OR^3$, $R^3$ is —$(CR^6R^7)_p$—Y—$(CR^6R^7)_q$—$R^8$, and each $R^6$ and $R^7$ is H. In some embodiments is a compound of Formula (I), or a pharmaceutically acceptable salt or solvate thereof, wherein $R^1$ is —$OR^3$, $R^3$ is —$(CR^6R^7)_p$—Y—$(CR^6R^7)_q$—$R^8$, and Y is —O—. In some embodiments is a compound of Formula (I), or a pharmaceutically acceptable salt or solvate thereof, wherein $R^1$ is —$OR^3$, $R^3$ is —$(CR^6R^7)_p$—Y—$(CR^6R^7)_q$—$R^8$, and Y is —$N(R^{22})$—. In some embodiments is a compound of Formula (I), or a pharmaceutically acceptable salt or solvate thereof, wherein $R^1$ is —$OR^3$, $R^3$ is —$(CR^6R^7)_p$—Y—$(CR^6R^7)_q$—$R^8$, Y is —$N(R^{22})$—, and $R^{22}$ is —$SO_2R^{23}$. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein $R^8$ is —$C(O)OR^9$. In some embodiments is a compound of Formula (I), or a pharmaceutically acceptable salt or solvate thereof, wherein $R^8$ is —$C(O)OR^9$ and $R^9$ is H. In some embodiments is a compound of Formula (I), or a pharmaceutically acceptable salt or solvate thereof, wherein $R^8$ is —$C(O)OR^9$ and $R^9$ is $C_{1-6}$alkyl. In some embodiments is a compound of Formula (I), or a pharmaceutically acceptable salt or solvate thereof, wherein $R^8$ is —$C(O)OR^9$ and $R^9$ is —$CH_3$. In some embodiments is a compound of Formula (I), or a pharmaceutically acceptable salt or solvate thereof, wherein $R^8$ is —$C(O)OR^9$ and $R^9$ is —$CH_2CH_3$. In some embodiments is a compound of Formula (I), or a pharmaceutically acceptable salt or solvate thereof, wherein $R^8$ is —$C(O)R^{10}$. In some embodiments is a compound of Formula (I), or a pharmaceutically acceptable salt or solvate thereof, wherein $R^8$ is —$C(O)R^{10}$ and $R^{10}$ is —$NHSO_2R^{21}$. In some embodiments is a compound of Formula (I), or a pharmaceutically acceptable salt or solvate thereof, wherein $R^8$ is —$C(O)R^{10}$, $R^{10}$ is —$NHSO_2R^{21}$, and $R^{21}$ is $C_{1-6}$alkyl. In some embodiments is a compound of Formula (I), or a pharmaceutically acceptable salt or solvate thereof, wherein $R^8$ is —$C(O)R^{10}$, $R^{10}$ is —$NHSO_2R^{21}$, and $R^{21}$ is $C_{3-6}$cycloalkyl. In some embodiments is a compound of Formula (I), or a pharmaceutically acceptable salt or solvate thereof, wherein $R^8$ is —$C(O)O$—$(CR^{12}R^{13})$—$OC(O)R^{11}$. In some embodiments is a compound of Formula (I), or a pharmaceutically acceptable salt or solvate thereof, wherein $R^8$ is —$C(O)O$—$(CR^{12}R^{13})$—$OC(O)R^{11}$ and $R^{11}$ is $C_{1-6}$alkyl. In some embodiments is a compound of Formula (I), or a pharmaceutically acceptable salt or solvate thereof, wherein $R^8$ is —$C(O)O$—$(CR^{12}R^{13})$—$OC(O)R^{11}$ and $R^{11}$ is $C_{1-6}$alkoxy. In some embodiments is a compound of Formula (I), or a pharmaceutically acceptable salt or solvate thereof, wherein $R^1$ is —$OR^3$ and $R^3$ is —$CH_2CH_2OCH_2C(O)OH$. In some embodiments is a compound of Formula (I), or a pharmaceutically acceptable salt or solvate thereof, wherein $R^1$—$OR^3$ and $R^3$ is —$CH_2CH_2N(SO_2CH_3)CH_2C(O)OH$. In some embodiments is a compound of Formula (I), or a pharmaceutically acceptable salt or solvate thereof, wherein $R^1$ is —$OR^3$ and $R^3$ is —$CH_2CH_2CH_2C(O)OCH(CH_3)OC(O)OCH_2CH_3$. In some embodiments is a compound of Formula (I), or a pharmaceutically acceptable salt or solvate thereof, wherein $R^1$ is —$OR^3$ and $R^3$ is —$CH_2CH_2CH_2C(O)OCH(CH_3)OC(O)OCH(CH_3)_2$. In some embodiments is a compound of Formula (I), or a pharmaceutically acceptable salt or solvate thereof, wherein $R^1$ is —$OR^3$ and $R^3$ is —$CH_2CH_2CH_2C(O)OCH_2OC(O)OC(CH_3)_3$. In some embodiments is a compound of Formula (I), or a pharmaceutically acceptable salt or solvate thereof, wherein $R^1$ is —$OR^3$ and $R^3$ is —$CH_2CH_2CH_2C(O)OCH(CH_3)OC(O)CH(CH_3)_2$.

In some embodiments is a compound of Formula (I), or a pharmaceutically acceptable salt or solvate thereof, wherein $R^1$ is —$OR^3$ and $R^3$ is —$(CR^6R^7)_t$—$C_{3-6}$cycloalkyl-$R^8$. In some embodiments is a compound of Formula (I), or a pharmaceutically acceptable salt or solvate thereof, wherein $R^1$ is —$OR^3$, $R^3$ is —$(CR^6R^7)_t$—$C_{3-6}$cycloalkyl-$R^8$, and t is 0. In some embodiments is a compound of Formula (I), or a pharmaceutically acceptable salt or solvate thereof, wherein $R^1$ is —$OR^3$, $R^3$ is —$(CR^6R^7)_t$—$C_{3-6}$cycloalkyl-$R^8$, and t is 1. In some embodiments is a compound of Formula (I), or a pharmaceutically acceptable salt or solvate thereof, wherein $R^1$ is —$OR^3$, $R^3$ is —$(CR^6R^7)_t$—$C_{3-6}$cycloalkyl-$R^8$, and t is 2. In some embodiments is a compound of Formula (I), or a pharmaceutically acceptable salt or solvate thereof, wherein $R^1$ is —$OR^3$ and $R^3$ is -cyclopropyl-C(O)OH. In some embodiments is a compound of Formula (I), or a pharmaceutically acceptable salt or solvate thereof, wherein $R^1$ is —$OR^3$ and $R^3$ is -cyclobutyl-C(O)OH. In some embodiments is a compound of Formula (I), or a pharmaceutically acceptable salt or solvate thereof, wherein $R^1$ is —$OR^3$ and $R^3$ is -cyclopentyl-C(O)OH.

In some embodiments is a compound of Formula (I), or a pharmaceutically acceptable salt or solvate thereof, wherein $R^1$ is —$R^{14}$. In some embodiments is a compound of Formula (I), or a pharmaceutically acceptable salt or solvate thereof, wherein $R^1$ is —$R^{14}$ and $R^{14}$ is —$(CR^{15}R^{16})_m$—$R^8$. In some embodiments is a compound of Formula (I), or a pharmaceutically acceptable salt or solvate thereof, wherein $R^{14}$ is —$(CR^{15}R^{16})_m$—$R^8$ and m is 1. In some embodiments is a compound of Formula (I), or a pharmaceutically acceptable salt or solvate thereof, wherein $R^{14}$ is —$(CR^{15}R^{16})_m$—$R^8$ and m is 2. In some embodiments is a compound of Formula (I), or a pharmaceutically acceptable salt or solvate thereof, wherein $R^{14}$ is —$(CR^{15}R^{16})_m$—$R^8$ and m is 3. In some embodiments is a compound of Formula (I), or a pharmaceutically acceptable salt or solvate thereof, wherein $R^{14}$ is —$(CR^{15}R^{16})_m$—$R^8$ and m is 4. In some embodiments is a compound of Formula (I), or a pharmaceutically acceptable salt or solvate thereof, wherein $R^8$ is —C(O)$OR^9$. In some embodiments is a compound of Formula (I), or a pharmaceutically acceptable salt or solvate thereof, wherein $R^8$ is —C(O)$OR^9$ and $R^9$ is H. In some embodiments is a compound of Formula (I), or a pharmaceutically acceptable salt or solvate thereof, wherein $R^8$ is —C(O)$OR^9$ and $R^9$ is $C_{1-6}$alkyl. In some embodiments is a compound of Formula (I), or a pharmaceutically acceptable salt or solvate thereof, wherein $R^8$ is —C(O)$OR^9$ and $R^9$ is —$CH_3$. In some embodiments is a compound of Formula (I), or a pharmaceutically acceptable salt or solvate thereof, wherein $R^8$ is —C(O)$OR^9$ and $R^9$ is —$CH_2CH_3$. In some embodiments is a compound of Formula (I), or a pharmaceutically acceptable salt or solvate thereof, wherein $R^8$ is —C(O)$R^{10}$. In some embodiments is a compound of Formula (I), or a pharmaceutically acceptable salt or solvate thereof, wherein $R^8$ is —C(O)$R^{10}$ and $R^{10}$ is —$NHSO_2R^{21}$. In some embodiments is a compound of Formula (I), or a pharmaceutically acceptable salt or solvate thereof, wherein $R^8$ is —C(O)$R^{10}$, $R^{10}$ is —$NHSO_2R^{21}$, and $R^{21}$ is $C_{1-6}$alkyl. In some embodiments is a compound of Formula (I), or a pharmaceutically acceptable salt or solvate thereof, wherein $R^8$ is —C(O)$R^{10}$, $R^{10}$ is —$NHSO_2R^{21}$, and $R^{21}$ is $C_{3-6}$cycloalkyl. In some embodiments is a compound of Formula (I), or a pharmaceutically acceptable salt or solvate thereof, wherein $R^8$ is —C(O)O—($CR^{12}R^{13}$)—OC(O)$R^{11}$. In some embodiments is a compound of Formula (I), or a pharmaceutically acceptable salt or solvate thereof, wherein $R^8$ is —C(O)O—($CR^{12}R^{13}$)—OC(O)$R^{11}$ and $R^{11}$ is $C_{1-6}$alkyl. In some embodiments is a compound of Formula (I), or a pharmaceutically acceptable salt or solvate thereof, wherein $R^8$ is —C(O)O—($CR^{12}R^{13}$)—OC(O)$R^{11}$ and $R^{11}$ is $C_{1-6}$alkoxy. In some embodiments is a compound of Formula (I), or a pharmaceutically acceptable salt or solvate thereof, wherein $R^1$ is —$R^{14}$ and $R^{14}$ is —$CH_2C(O)OH$. In some embodiments is a compound of Formula (I), or a pharmaceutically acceptable salt or solvate thereof, wherein $R^1$ is —$R^{14}$ and $R^{14}$ is —$CH_2CH_2C(O)OH$. In some embodiments is a compound of Formula (I), or a pharmaceutically acceptable salt or solvate thereof, wherein $R^1$ is —$R^{14}$ and $R^{14}$ is —$CH_2CH_2CH_2C(O)OH$. In some embodiments is a compound of Formula (I), or a pharmaceutically acceptable salt or solvate thereof, wherein $R^1$ is —$R^{14}$ and $R^{14}$ is —$CH_2CH_2CH_2CH_2C(O)OH$. In some embodiments is a compound of Formula (I), or a pharmaceutically acceptable salt or solvate thereof, wherein $R^1$ is —$R^{14}$ and $R^{14}$ is —$CH_2CH(CH_3)CH_2C(O)OH$. In some embodiments is a compound of Formula (I), or a pharmaceutically acceptable salt or solvate thereof, wherein $R^1$ is —$R^{14}$ and $R^{14}$ is —$CH_2CH_2C(O)OCH_3$. In some embodiments is a compound of Formula (I), or a pharmaceutically acceptable salt or solvate thereof, wherein $R^1$ is —$R^{14}$ and $R^{14}$ is —$CH_2CH_2C(O)OCH_2CH_3$. In some embodiments is a compound of Formula (I), or a pharmaceutically acceptable salt or solvate thereof, wherein $R^1$ is —$R^{14}$ and $R^{14}$ is —$CH_2CH_2C(O)OC(CH_3)_3$. In some embodiments is a compound of Formula (I), or a pharmaceutically acceptable salt or solvate thereof, wherein $R^1$ is —$R^{14}$ and $R^{14}$ is —$CH_2CH_2CH_2C(O)OCH_3$. In some embodiments is a compound of Formula (I), or a pharmaceutically acceptable salt or solvate thereof, wherein $R^1$ is —$R^{14}$ and $R^{14}$ is —$CH_2CH_2CH_2C(O)OCH_2CH_3$. In some embodiments is a compound of Formula (I), or a pharmaceutically acceptable salt or solvate thereof, wherein $R^1$ is —$R^{14}$ and $R^{14}$ is —$CH_2CH_2CH_2C(O)OC(CH_3)_3$. In some embodiments is a compound of Formula (I), or a pharmaceutically acceptable salt or solvate thereof, wherein $R^1$ is —$R^{14}$ and $R^{14}$ is —$CH_2CH_2CH_2CH_2C(O)OCH_3$. In some embodiments is a compound of Formula (I), or a pharmaceutically acceptable salt or solvate thereof, wherein $R^1$ is —$R^{14}$ and $R^{14}$ is —$CH_2CH_2CH_2CH_2C(O)OCH_2CH_3$. In some embodiments is a compound of Formula (I), or a pharmaceutically acceptable salt or solvate thereof, wherein $R^1$ is —$R^{14}$ and $R^{14}$ is —$CH_2CH_2CH_2CH_2C(O)OC(CH_3)_3$.

In some embodiments is a compound of Formula (I), or a pharmaceutically acceptable salt or solvate thereof, wherein $R^1$ is —$R^{14}$ and $R^{14}$ is —$(CR^6R^7)_p$—Y—$(CR^6R^7)_q$—$R^8$. In some embodiments is a compound of Formula (I), or a pharmaceutically acceptable salt or solvate thereof, wherein $R^1$ is —$R^{14}$, $R^{14}$ is —$(CR^6R^7)_p$—Y—$(CR^6R^7)_q$$R^8$, and each $R^6$ and $R^7$ is each independently selected from H and $C_{1-6}$alkyl. In some embodiments is a compound of Formula (I), or a pharmaceutically acceptable salt or solvate thereof, wherein $R^1$ is —$R^{14}$, $R^{14}$ is is —$(CR^6R^7)_p$—Y—$(CR^6R^7)_q$—$R^8$, and each $R^6$ and $R^7$ is H. In some embodiments is a compound of Formula (I), or a pharmaceutically acceptable salt or solvate thereof, wherein $R^1$ is —$R^{14}$, $R^{14}$ is is —$(CR^6R^7)_p$—Y—$(CR^6R^7)_q$—$R^8$, and Y is —O—. In some embodiments is a compound of Formula (I), or a pharmaceutically acceptable salt or solvate thereof, wherein $R^1$ is —$R^{14}$, $R^{14}$ is —$(CR^6R^7)_p$—Y—$(CR^6R^7)_q$—$R^8$, and Y is —N($R^{22}$)—. In some embodiments is a compound of Formula (I), or a pharmaceutically acceptable salt or solvate thereof, wherein $R^1$ is —$R^{14}$, $R^{14}$ is —$(CR^6R^7)_p$—Y—$(CR^6R^7)_q$—$R^8$, Y is —N($R^{22}$)—, and $R^{22}$ is —$SO_2R^{23}$. In some embodiments is a compound of Formula (I), or a pharmaceutically acceptable salt or solvate thereof, wherein q is 1. In some embodiments is a compound of Formula (I), or a pharmaceutically acceptable salt or solvate thereof, wherein p is 2. In some embodiments is a compound of Formula (I), or a pharmaceutically acceptable salt or solvate thereof, wherein $R^8$ is —C(O)$OR^9$. In some embodiments is a compound of Formula (I), or a pharmaceutically acceptable salt or solvate thereof, wherein $R^8$ is —C(O)OR$^9$ and $R^9$ is H. In some embodiments is a compound of Formula (I), or a pharmaceutically acceptable salt or solvate thereof, wherein $R^8$ is —C(O)OR$^9$ and $R^9$ is $C_{1-6}$alkyl. In some embodiments is a compound of Formula (I), or a pharmaceutically acceptable salt or solvate thereof, wherein $R^8$ is —C(O)OR$^9$ and $R^9$ is —CH$_3$. In some embodiments is a compound of Formula (I), or a pharmaceutically acceptable salt or solvate thereof, wherein $R^8$ is —C(O)OR$^9$ and $R^9$ is —CH$_2$CH$_3$. In some embodiments is a compound of Formula (I), or a pharmaceutically acceptable salt or solvate thereof, wherein $R^8$ is —C(O)R$^{10}$. In some embodiments is a compound of Formula (I), or a pharmaceutically acceptable salt or solvate thereof, wherein $R^8$ is —C(O)R$^{10}$ and $R^{10}$ is —NHSO$_2$R$^{21}$. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{1-6}$alkyl. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{3-6}$cycloalkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkoxy. In some embodiments is a compound of Formula (I), or a pharmaceutically acceptable salt or solvate thereof, wherein $R^1$ is —R$^{14}$ and $R^{14}$ is —CH$_2$CH$_2$OCH$_2$C(O)OH. In some embodiments is a compound of Formula (I), or a pharmaceutically acceptable salt or solvate thereof, wherein $R^1$ is —R$^{14}$ and $R^{14}$ is —CH$_2$CH$_2$N(SO$_2$CH$_3$)CH$_2$C(O)OH. In some embodiments is a compound of Formula (I), or a pharmaceutically acceptable salt or solvate thereof, wherein $R^1$ is —R$^{14}$ and $R^{14}$ is —CH$_2$CH$_2$CH$_2$C(O)OCH(CH$_3$)OC(O)OCH$_2$CH$_3$. In some embodiments is a compound of Formula (I), or a pharmaceutically acceptable salt or solvate thereof, wherein $R^1$ is —R$^{14}$ and $R^{14}$ is —CH$_2$CH$_2$CH$_2$C(O)OCH(CH$_3$)OC(O)OCH(CH$_3$)$_2$. In some embodiments is a compound of Formula (I), or a pharmaceutically acceptable salt or solvate thereof, wherein $R^1$ is —R$^{14}$ and $R^{14}$ is —CH$_2$CH$_2$CH$_2$C(O)OCH$_2$OC(O)OC(CH$_3$)$_3$. In some embodiments is a compound of Formula (I), or a pharmaceutically acceptable salt or solvate thereof, wherein $R^1$ is —R$^{14}$ and $R^{14}$ is —CH$_2$CH$_2$CH$_2$C(O)OCH(CH$_3$)OC(O)CH(CH$_3$)$_2$.

In some embodiments is a compound of Formula (I), or a pharmaceutically acceptable salt or solvate thereof, wherein $R^1$ is —C≡C—(CR$^6$R$^7$)—R$^8$. In some embodiments is a compound of Formula (I), or a pharmaceutically acceptable salt or solvate thereof, wherein $R^1$ is —C≡C—(CR$^6$R$^7$)—R$^8$ and $R^6$ and $R^7$ is independently selected from H and $C_{1-6}$alkyl. In some embodiments is a compound of Formula (I), or a pharmaceutically acceptable salt or solvate thereof, wherein $R^1$ is —C≡C—(CR$^6$R$^7$)—R$^8$ and $R^6$ and $R^7$ is each independently $C_{1-6}$alkyl. In some embodiments is a compound of Formula (I), or a pharmaceutically acceptable salt or solvate thereof, wherein $R^1$ is —C≡C—(CR$^6$R$^7$)—R$^8$ and $R^6$ and $R^7$ is —CH$_3$. In some embodiments is a compound of Formula (I), or a pharmaceutically acceptable salt or solvate thereof, wherein $R^8$ is —C(O)OR$^9$. In some embodiments is a compound of Formula (I), or a pharmaceutically acceptable salt or solvate thereof, wherein $R^8$ is —C(O)OR$^9$ and $R^9$ is H. In some embodiments is a compound of Formula (I), or a pharmaceutically acceptable salt or solvate thereof, wherein $R^8$ is —C(O)OR$^9$ and $R^9$ is $C_{1-6}$alkyl. In some embodiments is a compound of Formula (I), or a pharmaceutically acceptable salt or solvate thereof, wherein $R^8$ is —C(O)OR$^9$ and $R^9$ is —CH$_3$. In some embodiments is a compound of Formula (I), or a pharmaceutically acceptable salt or solvate thereof, wherein $R^8$ is —C(O)OR$^9$ and $R^9$ is —CH$_2$CH$_3$. In some embodiments is a compound of Formula (I), or a pharmaceutically acceptable salt or solvate thereof, wherein $R^8$ is —C(O)R$^{10}$. In some embodiments is a compound of Formula (I), or a pharmaceutically acceptable salt or solvate thereof, wherein $R^8$ is —C(O)R$^{10}$ and $R^{10}$ is —NHSO$_2$R$^{21}$. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{1-6}$alkyl. In some embodiments is a compound of Formula (I), or a pharmaceutically acceptable salt or solvate thereof, wherein $R^8$ is —C(O)R$^{10}$, $R^{10}$ is —NHSO$_2$R$^{21}$, and $R^{21}$ is $C_{3-6}$cycloalkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkyl. In some embodiments is a compound of Formula (I), or a pharmaceutically acceptable salt or solvate thereof, wherein $R^8$ is —C(O)O—(CR$^{12}$R$^{13}$)—OC(O)R$^{11}$ and $R^{11}$ is $C_{1-6}$alkoxy. In some embodiments is a compound of Formula (I), or a pharmaceutically acceptable salt or solvate thereof, wherein $R^1$ is In some embodiments is a compound of Formula (I), or a pharmaceutically acceptable salt or solvate thereof, wherein n is 0, 1, 2, or 3. In some embodiments is a compound of Formula (I), or a pharmaceutically acceptable salt or solvate thereof, wherein n is 0, 1, or 2. In some embodiments is a compound of Formula (I), or a pharmaceutically acceptable salt or solvate thereof, wherein n is 1 or 2. In some embodiments is a compound of Formula (I), or a pharmaceutically acceptable salt or solvate thereof, wherein n is 0 or 1. In some embodiments is a compound of Formula (I), or a pharmaceutically acceptable salt or solvate thereof, wherein n is 0. In some embodiments is a compound of Formula (I), or a pharmaceutically acceptable salt or solvate thereof, wherein n is 1. In some embodiments is a compound of Formula (I), or a pharmaceutically acceptable salt or solvate thereof, wherein n is 2. In some embodiments is a compound of Formula (I), or a pharmaceutically acceptable salt or solvate thereof, wherein n is 3. In some embodiments is a compound of Formula (I), or a pharmaceutically acceptable salt or solvate thereof, wherein n is 4.

In some embodiments is a compound of Formula (I), or a pharmaceutically acceptable salt or solvate thereof, wherein n is 1 and $R^2$ is halogen, $C_{1-6}$alkyl, $C_{1-6}$haloalkyl, or —OR$^{17}$. In some embodiments is a compound of Formula (I), or a pharmaceutically acceptable salt or solvate thereof, wherein n is 1 and $R^2$ is independently selected from $C_{1-6}$alkyl, halogen, —CN, or $C_{1-6}$haloalkyl. In some embodiments is a compound of Formula (I), or a pharmaceutically acceptable salt or solvate thereof, wherein n is 1 and $R^2$ is halogen, $C_{1-6}$alkyl, or $C_{1-6}$haloalkyl. In some embodiments is a compound of Formula (I), or a pharmaceutically acceptable salt or solvate thereof, wherein n is 1 and $R^2$ is halogen. In some embodiments is a compound of Formula (I), or a pharmaceutically acceptable salt or solvate thereof, wherein n is 1 and $R^2$ is —Cl. In some embodiments is a compound of Formula (I), or a pharmaceutically acceptable salt or solvate thereof, wherein n is 1 and $R^2$ is —F. In some embodiments is a compound of Formula (I), or a pharmaceutically acceptable salt or solvate thereof, wherein n is 1 and $R^2$ is $C_{1-6}$alkyl. In some embodiments is a compound of Formula (I), or a pharmaceutically acceptable salt or solvate thereof, wherein n is 1 and $R^2$ is —CH$_3$. In some embodiments is a compound of Formula (I), or a pharmaceutically acceptable salt or solvate thereof, wherein n is 1 and $R^2$ is $C_{1-6}$haloalkyl. In some embodiments is a compound of Formula (I), or a pharmaceutically acceptable salt or solvate thereof, wherein n is 1 and $R^2$ is —CF$_3$. In some embodiments is a compound of Formula (I), or a pharmaceutically acceptable salt or solvate thereof, wherein n is 1 and $R^2$ is $C_{1-6}$alkoxy. In some embodiments is a compound of Formula (I), or a pharmaceutically acceptable salt or solvate thereof, wherein n is 1 and $R^2$ is —OCH$_3$. In some embodiments is a compound of Formula (I), or a pharmaceutically acceptable salt or solvate thereof, wherein n is 1 and $R^2$ is $C_{1-6}$haloalkoxy. In some embodiments is a compound of Formula (I), or a pharmaceutically acceptable salt or solvate thereof, wherein n is 1 and $R^2$ is —OCF$_3$. In some embodiments is a compound of Formula (I), or a pharmaceutically acceptable salt or solvate thereof, wherein n is 1 and $R^2$ is —OH. In some embodiments is a compound of Formula (I), or a pharmaceutically acceptable salt or solvate thereof, wherein n is 1 and $R^2$ is —CN.

In some embodiments is a compound of Formula (I), or a pharmaceutically acceptable salt or solvate thereof, wherein n is 2 and each $R^2$ is independently halogen, $C_{1-6}$alkyl, $C_{1-6}$haloalkyl, or —OR$^{17}$. In some embodiments is a compound of Formula (I), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (I), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, or —OCF$_3$. In some embodiments is a compound of Formula (I), or a pharmaceutically acceptable salt or solvate thereof, wherein n is 2 and each $R^2$ is independently halogen, $C_{1-6}$alkyl, $C_{1-6}$haloalkyl, or —OCF$_3$. In some embodiments is a compound of Formula (I), or a pharmaceutically acceptable salt or solvate thereof, wherein n is 2 and each $R^2$ is independently halogen, $C_{1-6}$alkyl, or $C_{1-6}$haloalkyl. In some embodiments is a compound of Formula (I), or a pharmaceutically acceptable salt or solvate thereof, wherein n is 2 and each $R^2$ is independently halogen or $C_{1-6}$haloalkyl. In some embodiments is a compound of Formula (I), or a pharmaceutically acceptable salt or solvate thereof, wherein n is 2 and each $R^2$ is independently halogen or $C_{1-6}$alkyl. In some embodiments is a compound of Formula (I), or a pharmaceutically acceptable salt or solvate thereof, wherein n is 2 and each $R^2$ is independently halogen. In some embodiments is a compound of Formula (I), or a pharmaceutically acceptable salt or solvate thereof, wherein n is 2 and each $R^2$ is independently $C_{1-6}$alkyl. In some embodiments is a compound of Formula (I), or a pharmaceutically acceptable salt or solvate thereof, wherein n is 2 and each $R^2$ is independently $C_{1-6}$haloalkyl.

In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, or —OCF$_3$. In some embodiments is a compound of Formula (I), or a pharmaceutically acceptable salt or solvate thereof, wherein n is 3 and each $R^2$ is independently halogen, $C_{1-6}$alkyl, $C_{1-6}$haloalkyl, or —OCF$_3$. In some embodiments is a compound of Formula (I), or a pharmaceutically acceptable salt or solvate thereof, wherein n is 3 and each $R^2$ is independently halogen, $C_{1-6}$alkyl, or $C_{1-6}$haloalkyl. In some embodiments is a compound of Formula (I), or a pharmaceutically acceptable salt or solvate thereof, wherein n is 3 and each $R^2$ is independently halogen or $C_{1-6}$haloalkyl. In some embodiments is a compound of Formula (I), or a pharmaceutically acceptable salt or solvate thereof, wherein n is 3 and each $R^2$ is independently halogen or $C_{1-6}$alkyl. In some embodiments is a compound of Formula (I), or a pharmaceutically acceptable salt or solvate thereof, wherein n is 3 and each $R^2$ is independently halogen. In some embodiments is a compound of Formula (I), or a pharmaceutically acceptable salt or solvate thereof, wherein n is 3 and each $R^2$ is independently $C_{1-6}$alkyl. In some embodiments is a compound of Formula (I), or a pharmaceutically acceptable salt or solvate thereof, wherein n is 3 and each $R^2$ is independently $C_{1-6}$haloalkyl.

In some embodiments is a compound of Formula (I), or a pharmaceutically acceptable salt or solvate thereof, wherein n is 4 and each $R^2$ is independently halogen, $C_{1-6}$alkyl, $C_{1-6}$haloalkyl, and —OR$^{17}$.

In some embodiments is a compound of Formula (Ia):

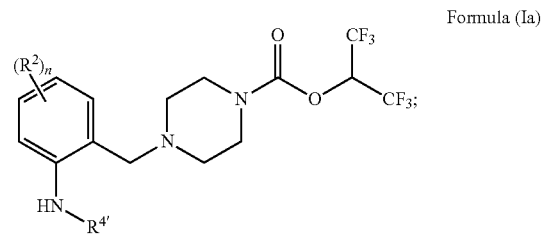

Formula (Ia)

wherein:
  each $R^2$ is independently selected from $C_{1-6}$alkyl, halogen, —CN, $C_{1-6}$haloalkyl, —$C_{1-6}$alkyl(heterocycloalkyl), —OR$^{17}$, and —C(O)NR$^{18}$R$^{19}$;
  $R^{4'}$ is —(CR$^6$R$^7$)$_m$—R$^8$, —(CR$^6$R$^7$)$_p$—Y—(CR$^6$R$^7$)$_q$—R$^8$, —C$_{4-6}$alkyl-C(O)OH, —C$_{3-6}$cycloalkyl-C(O)OH, or —C$_{1-6}$alkyl-C$_{3-6}$cycloalkyl-C(O)OH;
  Y is —O— or —N(R$^{22}$)—;
  each $R^6$ and $R^7$ is each independently selected from H, F, and $C_{1-6}$alkyl; or $R^6$ and $R^7$, together with the carbon to which they are attached, form a $C_{3-6}$cycloalkyl ring;

R⁸ is —C(O)OR⁹, —C(O)R¹⁰, or —C(O)O—(CR¹²R¹³)—OC(O)R¹¹;
R⁸' is —C(O)OR⁹', —C(O)R¹⁰', or —C(O)O—(CR¹²R¹³)—OC(O)R¹¹;
R⁹ is H or $C_{1-6}$alkyl;
R⁹' is $C_{1-6}$alkyl;
R¹⁰ is $C_{1-6}$alkyl or —NHSO₂R²¹;
R¹⁰' is $C_{2-6}$alkyl or —NHSO₂R²¹;
R¹¹ is $C_{1-6}$alkyl or $C_{1-6}$alkoxy;
R¹² and R¹³ is each independently H or $C_{1-6}$alkyl;
each R¹⁷ is independently selected from H, $C_{1-6}$alkyl, $C_{1-6}$haloalkyl, and $C_{3-6}$cycloalkyl;
each R¹⁸ and R¹⁹ is each independently selected from H, $C_{1-6}$alkyl, $C_{3-6}$cycloalkyl, aryl, and heteroaryl; or R¹⁸ and R¹⁹, together with the nitrogen to which they are attached, form a heterocycloalkyl ring optionally substituted with one, two, or three R²⁰;
each R²⁰ is independently selected from halogen, $C_{1-6}$alkyl, $C_{1-6}$haloalkyl, oxo, —CN, and $C_{3-6}$cycloalkyl;
R²¹ is $C_{1-6}$alkyl or $C_{3-6}$cycloalkyl;
R²² is H, $C_{1-6}$alkyl, or —SO₂R²³;
R²³ is $C_{1-6}$alkyl;
m is 1, 2, 3 or 4;
n is 0, 1, 2, 3, or 4;
p is 2, 3, or 4; and
q is 1, 2, or 3;
or a pharmaceutically acceptable salt or solvate thereof.

In some embodiments is a compound of Formula (Ia), or a pharmaceutically acceptable salt or solvate thereof, wherein R⁴' is —(CR⁶R⁷)ₘ—R⁸. In some embodiments is a compound of Formula (Ia), or a pharmaceutically acceptable salt or solvate thereof, wherein R⁴' is —(CR⁶R⁷)ₘ—R⁸' and each R⁶ and R⁷ is each independently selected from H and $C_{1-6}$alkyl. In some embodiments is a compound of Formula (Ia), or a pharmaceutically acceptable salt or solvate thereof, wherein R⁴' is —(CR⁶R⁷)ₘ—R⁸' and each R⁶ and R⁷ is H. In some embodiments is a compound of Formula (Ia), or a pharmaceutically acceptable salt or solvate thereof, wherein m is 1, 2, or 3. In some embodiments is a compound of Formula (Ia), or a pharmaceutically acceptable salt or solvate thereof, wherein m is 1. In some embodiments is a compound of Formula (Ia), or a pharmaceutically acceptable salt or solvate thereof, wherein m is 2. In some embodiments is a compound of Formula (Ia), or a pharmaceutically acceptable salt or solvate thereof, wherein m is 3. In some embodiments is a compound of Formula (Ia), or a pharmaceutically acceptable salt or solvate thereof, wherein m is 4. In some embodiments is a compound of Formula (Ia), or a pharmaceutically acceptable salt or solvate thereof, wherein R⁸' is —C(O)OR⁹'. In some embodiments is a compound of Formula (Ia), or a pharmaceutically acceptable salt or solvate thereof, wherein R⁸' is —C(O)OR⁹' and R⁹' is —CH₃. In some embodiments is a compound of Formula (Ia), or a pharmaceutically acceptable salt or solvate thereof, wherein R⁸' is —C(O)OR⁹' and R⁹' is —CH₂CH₃. In some embodiments is a compound of Formula (Ia), or a pharmaceutically acceptable salt or solvate thereof, wherein R⁸' is —C(O)R¹⁰'. In some embodiments is a compound of Formula (Ia), or a pharmaceutically acceptable salt or solvate thereof, wherein R⁸' is —C(O)R¹⁰' and R¹⁰' is —NHSO₂R²¹. In some embodiments is a compound of Formula (Ia), or a pharmaceutically acceptable salt or solvate thereof, wherein R⁸' is —C(O)R¹⁰', R¹⁰' is —NHSO₂R²¹, and R²¹ is $C_{1-6}$alkyl. In some embodiments is a compound of Formula (Ia), or a pharmaceutically acceptable salt or solvate thereof, wherein R⁸' is —C(O)R¹⁰', R¹⁰' is —NHSO₂R²¹, and R²¹ is $C_{3-6}$cycloalkyl. In some embodiments is a compound of Formula (Ia), or a pharmaceutically acceptable salt or solvate thereof, wherein R⁸' is —C(O)O—(CR¹²R¹³)—OC(O)R¹¹. In some embodiments is a compound of Formula (Ia), or a pharmaceutically acceptable salt or solvate thereof, wherein R⁸' is —C(O)O—(CR¹²R¹³)—OC(O)R¹¹ and R¹¹ is $C_{1-6}$alkyl. In some embodiments is a compound of Formula (Ia), or a pharmaceutically acceptable salt or solvate thereof, wherein R⁸' is —C(O)O—(CR¹²R¹³)—OC(O)R¹¹ and R¹¹ is $C_{1-6}$alkoxy. In some embodiments is a compound of Formula (Ia), or a pharmaceutically acceptable salt or solvate thereof, wherein R⁴' is —CH₂CH₂C(O)OCH₃. In some embodiments is a compound of Formula (Ia), or a pharmaceutically acceptable salt or solvate thereof, wherein R⁴' is —CH₂CH₂C(O)OCH₂CH₃. In some embodiments is a compound of Formula (Ia), or a pharmaceutically acceptable salt or solvate thereof, wherein R⁴' is —CH₂CH₂C(O)OC(CH₃)₃. In some embodiments is a compound of Formula (Ia), or a pharmaceutically acceptable salt or solvate thereof, wherein R⁴' is —CH₂CH₂CH₂C(O)OCH₃. In some embodiments is a compound of Formula (Ia), or a pharmaceutically acceptable salt or solvate thereof, wherein R⁴' is —CH₂CH₂CH₂C(O)OCH₂CH₃. In some embodiments is a compound of Formula (Ia), or a pharmaceutically acceptable salt or solvate thereof, wherein R⁴' is —CH₂CH₂CH₂C(O)OC(CH₃)₃.

In some embodiments is a compound of Formula (Ia), or a pharmaceutically acceptable salt or solvate thereof, wherein R⁴' is —(CR⁶R⁷)ₚ—Y—(CR⁶R⁷)_q—R⁸. In some embodiments is a compound of Formula (Ia), or a pharmaceutically acceptable salt or solvate thereof, wherein R⁴' is —(CR⁶R⁷)ₚ—Y—(CR⁶R⁷)_q—R⁸ and each R⁶ and R⁷ is each independently selected from H and $C_{1-6}$alkyl. In some embodiments is a compound of Formula (Ia), or a pharmaceutically acceptable salt or solvate thereof, wherein R⁴' is —(CR⁶R⁷)ₚ—Y—(CR⁶R⁷)_q—R⁸ and each R⁶ and R⁷ is H. In some embodiments is a compound of Formula (Ia), or a pharmaceutically acceptable salt or solvate thereof, wherein R⁴' is —(CR⁶R⁷)ₚ—Y—(CR⁶R⁷)_q R⁸ and Y is —O—. In some embodiments is a compound of Formula (Ia), or a pharmaceutically acceptable salt or solvate thereof, wherein R⁴' is —(CR⁶R⁷)—Y—(CR⁶R⁷)_q—R⁸ and Y is —N(R²²)—. In some embodiments is a compound of Formula (Ia), or a pharmaceutically acceptable salt or solvate thereof, wherein R⁴' is —(CR⁶R⁷)ₚ—Y—(CR⁶R⁷)_q—R⁸, Y is —N(R²²)—, and R²² is —SO₂R²³. In some embodiments is a compound of Formula (Ia), or a pharmaceutically acceptable salt or solvate thereof, wherein q is 1. In some embodiments is a compound of Formula (Ia), or a pharmaceutically acceptable salt or solvate thereof, wherein p is 2. In some embodiments is a compound of Formula (Ia), or a pharmaceutically acceptable salt or solvate thereof, wherein R⁸ is —C(O)OR⁹. In some embodiments is a compound of Formula (Ia), or a pharmaceutically acceptable salt or solvate thereof, wherein R⁸ is —C(O)OR⁹ and R⁹ is H. In some embodiments is a compound of Formula (Ia), or a pharmaceutically acceptable salt or solvate thereof, wherein R⁸ is —C(O)OR⁹ and R⁹ is $C_{1-6}$alkyl. In some embodiments is a compound of Formula (Ia), or a pharmaceutically acceptable salt or solvate thereof, wherein R⁸ is —C(O)OR⁹ and R⁹ is —CH₃. In some embodiments is a compound of Formula (Ia), or a pharmaceutically acceptable salt or solvate thereof, wherein R⁸ is —C(O)OR⁹ and R⁹ is —CH₂CH₃. In some embodiments is a compound of Formula (Ia), or a pharmaceutically acceptable salt or solvate thereof, wherein R⁸ is —C(O)R¹⁰. In some embodiments is a compound of Formula (Ia), or a pharmaceutically acceptable salt or solvate thereof, wherein $R^8$ is —C(O)$R^{10}$ and $R^{10}$ is —NHSO$_2R^{21}$. In some embodiments is a compound of Formula (Ia), or a pharmaceutically acceptable salt or solvate thereof, wherein $R^8$ is —C(O)$R^{10}$, $R^{10}$ is —NHSO$_2R^{21}$, and $R^{21}$ is $C_{1-6}$alkyl. In some embodiments is a compound of Formula (Ia), or a pharmaceutically acceptable salt or solvate thereof, wherein $R^8$ is —C(O)$R^{10}$, $R^{10}$ is —NHSO$_2R^{21}$, and $R^{21}$ is $C_{3-6}$cycloalkyl. In some embodiments is a compound of Formula (Ia), or a pharmaceutically acceptable salt or solvate thereof, wherein $R^8$ is —C(O)O—(C$R^{12}R^{13}$)—OC(O)$R^{11}$. In some embodiments is a compound of Formula (Ia), or a pharmaceutically acceptable salt or solvate thereof, wherein $R^8$ is —C(O)O—(C$R^{12}R^{13}$)—OC(O)R and $R^1$ is $C_{1-6}$alkyl. In some embodiments is a compound of Formula (Ia), or a pharmaceutically acceptable salt or solvate thereof, wherein $R^8$ is —C(O)O—(C$R^{12}R^{13}$)—OC(O)$R^{11}$ and $R^{11}$ is $C_{1-6}$alkoxy. In some embodiments is a compound of Formula (Ia), or a pharmaceutically acceptable salt or solvate thereof, wherein $R^{4'}$ is —CH$_2$CH$_2$OCH$_2$C(O)OH. In some embodiments is a compound of Formula (Ia), or a pharmaceutically acceptable salt or solvate thereof, wherein $R^{4'}$ is —CH$_2$CH$_2$N(SO$_2$CH$_3$)CH$_2$C(O)OH. In some embodiments is a compound of Formula (Ia), or a pharmaceutically acceptable salt or solvate thereof, wherein $R^{4'}$ is —CH$_2$CH$_2$CH$_2$C(O)OCH(CH$_3$)OC(O)OCH$_2$CH$_3$. In some embodiments is a compound of Formula (Ia), or a pharmaceutically acceptable salt or solvate thereof, wherein $R^{4'}$ is —CH$_2$CH$_2$CH$_2$C(O)OCH(CH$_3$)OC(O)OCH(CH$_3$)$_2$. In some embodiments is a compound of Formula (Ia), or a pharmaceutically acceptable salt or solvate thereof, wherein $R^{4'}$ is —CH$_2$CH$_2$CH$_2$C(O)OCH$_2$OC(O)OC(CH$_3$)$_3$. In some embodiments is a compound of Formula (Ia), or a pharmaceutically acceptable salt or solvate thereof, wherein $R^{4'}$ is —CH$_2$CH$_2$CH$_2$C(O)OCH(CH$_3$)OC(O)CH(CH$_3$)$_2$.

In some embodiments is a compound of Formula (Ia), or a pharmaceutically acceptable salt or solvate thereof, wherein $R^{4'}$ is —C$_{4-6}$alkyl-C(O)OH. In some embodiments is a compound of Formula (Ia), or a pharmaceutically acceptable salt or solvate thereof, wherein $R^{4'}$ is —CH$_2$CH$_2$CH$_2$CH$_2$C(O)OH. In some embodiments is a compound of Formula (Ia), or a pharmaceutically acceptable salt or solvate thereof, wherein $R^{4'}$ is —CH$_2$CH(CH$_3$)CH$_2$C(O)OH.

In some embodiments is a compound of Formula (Ia), or a pharmaceutically acceptable salt or solvate thereof, wherein $R^{4'}$ is —C$_{3-6}$cycloalkyl-C(O)OH. In some embodiments is a compound of Formula (Ia), or a pharmaceutically acceptable salt or solvate thereof, wherein $R^{4'}$ is —C$_{1-6}$alkyl-C$_{3-6}$cycloalkyl-C(O)OH.

In some embodiments of a compound of Formula (Ia), or a pharmaceutically acceptable salt or solvate thereof, wherein n is 0, 1, 2, or 3. In some embodiments of a compound of Formula (Ia), or a pharmaceutically acceptable salt or solvate thereof, wherein n is 0, 1, or 2. In some embodiments of a compound of Formula (Ia), or a pharmaceutically acceptable salt or solvate thereof, wherein n is 1 or 2. In some embodiments of a compound of Formula (Ia), or a pharmaceutically acceptable salt or solvate thereof, wherein n is 0 or 1. In some embodiments of a compound of Formula (Ia), or a pharmaceutically acceptable salt or solvate thereof, wherein n is 0. In some embodiments of a compound of Formula (Ia), or a pharmaceutically acceptable salt or solvate thereof, wherein n is 1. In some embodiments of a compound of Formula (Ia), or a pharmaceutically acceptable salt or solvate thereof, wherein n is 2. In some embodiments of a compound of Formula (Ia), or a pharmaceutically acceptable salt or solvate thereof, wherein n is 3.

In some embodiments of a compound of Formula (Ia), or a pharmaceutically acceptable salt or solvate thereof, wherein n is 4.

In some embodiments is a compound of Formula (Ia), or a pharmaceutically acceptable salt or solvate thereof, wherein n is 1 and $R^2$ is halogen, $C_{1-6}$alkyl, $C_{1-6}$haloalkyl, or —O$R^{17}$. In some embodiments is a compound of Formula (Ia), or a pharmaceutically acceptable salt or solvate thereof, wherein n is 1 and $R^2$ is independently selected from $C_{1-6}$alkyl, halogen, —CN, or $C_{1-6}$haloalkyl. In some embodiments is a compound of Formula (Ia), or a pharmaceutically acceptable salt or solvate thereof, wherein n is 1 and $R^2$ is halogen, $C_{1-6}$alkyl, or $C_{1-6}$haloalkyl. In some embodiments is a compound of Formula (Ia), or a pharmaceutically acceptable salt or solvate thereof, wherein n is 1 and $R^2$ is halogen. In some embodiments is a compound of Formula (Ia), or a pharmaceutically acceptable salt or solvate thereof, wherein n is 1 and $R^2$ is —C$_1$. In some embodiments is a compound of Formula (Ia), or a pharmaceutically acceptable salt or solvate thereof, wherein n is 1 and $R^2$ is —F. In some embodiments is a compound of Formula (Ia), or a pharmaceutically acceptable salt or solvate thereof, wherein n is 1 and $R^2$ is $C_{1-6}$alkyl. In some embodiments is a compound of Formula (Ia), or a pharmaceutically acceptable salt or solvate thereof, wherein n is 1 and $R^2$ is —CH$_3$. In some embodiments is a compound of Formula (Ia), or a pharmaceutically acceptable salt or solvate thereof, wherein n is 1 and $R^2$ is $C_{1-6}$haloalkyl. In some embodiments is a compound of Formula (Ia), or a pharmaceutically acceptable salt or solvate thereof, wherein n is 1 and $R^2$ is —CF$_3$. In some embodiments is a compound of Formula (Ia), or a pharmaceutically acceptable salt or solvate thereof, wherein n is 1 and $R^2$ is $C_{1-6}$alkoxy. In some embodiments is a compound of Formula (Ia), or a pharmaceutically acceptable salt or solvate thereof, wherein n is 1 and $R^2$ is —OCH$_3$. In some embodiments is a compound of Formula (Ia), or a pharmaceutically acceptable salt or solvate thereof, wherein n is 1 and $R^2$ is $C_{1-6}$haloalkoxy. In some embodiments is a compound of Formula (Ia), or a pharmaceutically acceptable salt or solvate thereof, wherein n is 1 and $R^2$ is —OCF$_3$. In some embodiments is a compound of Formula (Ia), or a pharmaceutically acceptable salt or solvate thereof, wherein n is 1 and $R^2$ is —OH. In some embodiments is a compound of Formula (Ia), or a pharmaceutically acceptable salt or solvate thereof, wherein n is 1 and $R^2$ is —CN.

In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, or —O$R^{17}$. In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, or —OCF$_3$. In some embodiments is a compound of Formula (Ia), or a pharmaceutically acceptable salt or solvate thereof, wherein n is 2 and each $R^2$ is independently halogen, $C_{1-6}$alkyl, $C_{1-6}$haloalkyl, or —OCF$_3$. In some embodiments is a compound of Formula (Ia), or a pharmaceutically acceptable salt or solvate thereof, wherein n is 2 and each $R^2$ is independently halogen, $C_{1-6}$alkyl, or $C_{1-6}$haloalkyl. In some embodiments is a compound of Formula (Ia), or a pharmaceutically acceptable salt or solvate thereof, wherein n is 2 and each $R^2$ is independently halogen or $C_{1-6}$haloalkyl. In some embodiments is a compound of Formula (Ia), or a pharmaceutically acceptable salt or solvate thereof, wherein n is 2 and each $R^2$ is independently halogen or $C_{1-6}$alkyl. In some embodiments is a compound of Formula (Ia), or a pharmaceutically acceptable salt or solvate thereof, wherein n is 2 and each $R^2$ is independently halogen. In some embodiments is a compound of Formula (Ia), or a pharmaceutically acceptable salt or solvate thereof, wherein n is 2 and each $R^2$ is independently $C_{1-6}$alkyl. In some embodiments is a compound of Formula (Ia), or a pharmaceutically acceptable salt or solvate thereof, wherein n is 2 and each $R^2$ is independently $C_{1-6}$haloalkyl.

In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, or —OCF$_3$. In some embodiments is a compound of Formula (Ia), or a pharmaceutically acceptable salt or solvate thereof, wherein n is 3 and each $R^2$ is independently halogen, $C_{1-6}$alkyl, $C_{1-6}$haloalkyl, or —OCF$_3$. In some embodiments is a compound of Formula (Ia), or a pharmaceutically acceptable salt or solvate thereof, wherein n is 3 and each $R^2$ is independently halogen, $C_{1-6}$alkyl, or $C_{1-6}$haloalkyl. In some embodiments is a compound of Formula (Ia), or a pharmaceutically acceptable salt or solvate thereof, wherein n is 3 and each $R^2$ is independently halogen or $C_{1-6}$haloalkyl. In some embodiments is a compound of Formula (Ia), or a pharmaceutically acceptable salt or solvate thereof, wherein n is 3 and each $R^2$ is independently halogen or $C_{1-6}$alkyl. In some embodiments is a compound of Formula (Ia), or a pharmaceutically acceptable salt or solvate thereof, wherein n is 3 and each $R^2$ is independently halogen. In some embodiments is a compound of Formula (Ia), or a pharmaceutically acceptable salt or solvate thereof, wherein n is 3 and each $R^2$ is independently $C_{1-6}$alkyl. In some embodiments is a compound of Formula (Ia), or a pharmaceutically acceptable salt or solvate thereof, wherein n is 3 and each $R^2$ is independently $C_{1-6}$haloalkyl.

In some embodiments is a compound of Formula (Ia), or a pharmaceutically acceptable salt or solvate thereof, wherein n is 4 and each $R^2$ is independently halogen, $C_{1-6}$alkyl, $C_{1-6}$haloalkyl, and —OR$^{17}$.

In some embodiments is a compound of Formula (Ib):

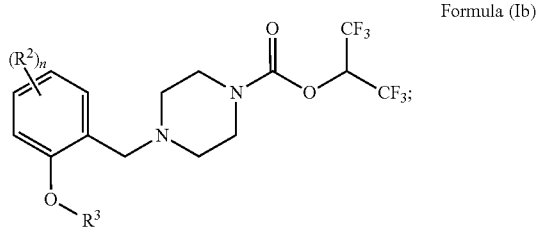

Formula (Ib)

wherein:
each $R^2$ is independently selected from $C_{1-6}$alkyl, halogen, —CN, $C_{1-6}$haloalkyl, —$C_{1-6}$alkyl(heterocycloalkyl), —OR$^{17}$, and —C(O)NR$^{18}$R$^{19}$;
$R^3$ is —(CR$^6$R$^7$)$_m$—R$^8$, —(CR$^6$R$^7$)$_p$—Y—(CR$^6$R$^7$)$_q$—R$^8$, or —(CR$^6$R$^7$)$_t$—C$_{3-6}$cycloalkyl-R$^8$;
Y is —O— or —N(R$^{22}$)—;
each $R^6$ and $R^7$ is each independently selected from H, F, and $C_{1-6}$alkyl; or $R^6$ and $R^7$, together with the carbon to which they are attached, form a $C_{3-6}$cycloalkyl ring;
$R^8$ is —C(O)OR$^9$, —C(O)R$^{10}$, or —C(O)O—(CR$^{12}$R$^{13}$)—OC(O)R$^{11}$;
$R^9$ is H or $C_{1-6}$alkyl;
$R^{10}$ is $C_{1-6}$alkyl or —NHSO$_2$R$^{21}$;
$R^{11}$ is $C_{1-6}$alkyl or $C_{1-6}$alkoxy;
$R^{12}$ and $R^{13}$ is each independently H or $C_{1-6}$alkyl;
each $R^{17}$ is independently selected from H, $C_{1-6}$alkyl, $C_{1-6}$haloalkyl, and $C_{3-6}$cycloalkyl;
each $R^{18}$ and $R^{19}$ is each independently selected from H, $C_{1-6}$alkyl, $C_{3-6}$cycloalkyl, aryl, and heteroaryl; or $R^{18}$ and $R^{19}$, together with the nitrogen to which they are attached, form a heterocycloalkyl ring optionally substituted with one, two, or three $R^{20}$;
each $R^{20}$ is independently selected from halogen, $C_{1-6}$alkyl, $C_{1-6}$haloalkyl, oxo, —CN, and $C_{3-6}$cycloalkyl;
$R^{21}$ is $C_{1-6}$alkyl or $C_{3-6}$cycloalkyl;
$R^{22}$ is H, $C_{1-6}$alkyl, or —SO$_2$R$^{23}$;
$R^{23}$ is $C_{1-6}$alkyl;
m is 1, 2, 3 or 4;
n is 0, 1, 2, 3, or 4;
p is 2, 3, or 4;
q is 1, 2, or 3; and
t is 0, 1, or 2;
or a pharmaceutically acceptable salt or solvate thereof.

In some embodiments is a compound of Formula (Ib), or a pharmaceutically acceptable salt or solvate thereof, wherein $R^3$ is —(CR$^6$R$^7$)$_m$—R$^8$. In some embodiments is a compound of Formula (Ib), or a pharmaceutically acceptable salt or solvate thereof, wherein $R^8$ is —C(O)OR$^9$. In some embodiments is a compound of Formula (Ib), or a pharmaceutically acceptable salt or solvate thereof, wherein $R^8$ is —C(O)OR$^9$ and $R^9$ is H. In some embodiments is a compound of Formula (Ib), or a pharmaceutically acceptable salt or solvate thereof, wherein $R^8$ is —C(O)OR$^9$ and $R^9$ is $C_{1-6}$alkyl. In some embodiments is a compound of Formula (Ib), or a pharmaceutically acceptable salt or solvate thereof, wherein $R^8$ is —C(O)OR$^9$ and $R^9$ is —CH$_3$. In some embodiments is a compound of Formula (Ib), or a pharmaceutically acceptable salt or solvate thereof, wherein $R^8$ is —C(O)OR$^9$ and $R^9$ is —CH$_2$CH$_3$. In some embodiments is a compound of Formula (Ib), or a pharmaceutically acceptable salt or solvate thereof, wherein $R^8$ is —C(O)R$^{10}$. In some embodiments is a compound of Formula (Ib), or a pharmaceutically acceptable salt or solvate thereof, wherein $R^8$ is —C(O)R$^{10}$ and $R^{10}$ is —NHSO$_2$R$^{21}$. In some embodiments is a compound of Formula (Ib), or a pharmaceutically acceptable salt or solvate thereof, wherein $R^8$ is —C(O)R$^{10}$, $R^{10}$ is —NHSO$_2$R$^{21}$, and $R^{21}$ is $C_{1-6}$alkyl. In some embodiments is a compound of Formula (Ib), or a pharmaceutically acceptable salt or solvate thereof, wherein $R^8$ is —C(O)R$^{10}$, $R^{10}$ is —NHSO$_2$R$^{21}$, and $R^{21}$ is $C_{3-6}$cycloalkyl. In some embodiments is a compound of Formula (Ib), or a pharmaceutically acceptable salt or solvate thereof, wherein $R^8$ is —C(O)O—(CR$^{12}$R$^{13}$)—OC(O)R$^{11}$. In some embodiments is a compound of Formula (Ib), or a pharmaceutically acceptable salt or solvate thereof, wherein $R^{8'}$ is —C(O)O—(CR$^{12}$R$^{13}$)—OC(O)R$^{11}$ and $R^{11}$ is $C_{1-6}$alkyl. In some embodiments is a compound of Formula (Ib), or a pharmaceutically acceptable salt or solvate thereof, wherein $R^{8'}$ is —C(O)O—(CR$^{12}$R$^{13}$)—OC(O)R$^{11}$ and R$^{11}$ is $C_{1-6}$alkoxy. In some embodiments is a compound of Formula (Ib), or a pharmaceutically acceptable salt or solvate thereof, wherein $R^3$ is —CH$_2$C(O)OH. In some embodiments is a compound of Formula (Ib), or a pharmaceutically acceptable salt or solvate thereof, wherein $R^3$ is —CH$_2$CH$_2$C(O)OH. In some embodiments is a compound of Formula (Ib), or a pharmaceutically acceptable salt or solvate thereof, wherein $R^1$ is —OR$^3$ and $R^3$ is

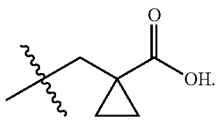 [SMILES: *CC1(C(=O)O)CC1]

In some embodiments is a compound of Formula (Ib), or a pharmaceutically acceptable salt or solvate thereof, wherein $R^1$ is —OR$^3$ and $R^3$ is

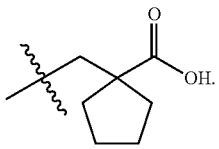 [SMILES: *CC1(C(=O)O)CCCC1]

In some embodiments is a compound of Formula (Ib), or a pharmaceutically acceptable salt or solvate thereof, wherein $R^3$ is —CH$_2$CH$_2$CH$_2$C(O)OH. In some embodiments is a compound of Formula (Ib), or a pharmaceutically acceptable salt or solvate thereof, wherein $R^3$ is —CH$_2$CH(CH$_3$)CH$_2$C(O)OH. In some embodiments is a compound of Formula (Ib), or a pharmaceutically acceptable salt or solvate thereof, wherein $R^3$ is —CH$_2$CH$_2$C(O)OCH$_3$. In some embodiments is a compound of Formula (Ib), or a pharmaceutically acceptable salt or solvate thereof, wherein $R^3$ is —CH$_2$CH$_2$C(O)OCH$_2$CH$_3$. In some embodiments is a compound of Formula (Ib), or a pharmaceutically acceptable salt or solvate thereof, wherein $R^3$ is —CH$_2$CH$_2$C(O)OC(CH$_3$)$_3$. In some embodiments is a compound of Formula (Ib), or a pharmaceutically acceptable salt or solvate thereof, wherein $R^3$ is —CH$_2$CH$_2$CH$_2$C(O)OCH$_3$. In some embodiments is a compound of Formula (Ib), or a pharmaceutically acceptable salt or solvate thereof, wherein $R^3$ is —CH$_2$CH$_2$CH$_2$C(O)OCH$_2$CH$_3$. In some embodiments is a compound of Formula (Ib), or a pharmaceutically acceptable salt or solvate thereof, wherein $R^3$ is —CH$_2$CH$_2$CH$_2$C(O)OC(CH$_3$)$_3$.

In some embodiments is a compound of Formula (Ib), or a pharmaceutically acceptable salt or solvate thereof, wherein $R^3$ is —(CR$^6$R$^7$)$_p$—Y—(CR$^6$R$^7$)$_q$—R$^8$. In some embodiments is a compound of Formula (Ib), or a pharmaceutically acceptable salt or solvate thereof, wherein $R^3$ is —(CR$^6$R$^7$)—Y—(CR$^6$R$^7$)$_q$—R$^8$ and each R$^6$ and R$^7$ is each independently selected from H and $C_{1-6}$alkyl. In some embodiments is a compound of Formula (Ib), or a pharmaceutically acceptable salt or solvate thereof, wherein $R^3$ is —(CR$^6$R$^7$)$_p$—Y—(CR$^6$R$^7$)$_q$—R$^8$ and each R$^6$ and R$^7$ is H. In some embodiments is a compound of Formula (Ib), or a pharmaceutically acceptable salt or solvate thereof, wherein is —(CR$^6$R$^7$)$_p$—Y—(CR$^6$R$^7$)$_q$R$^8$ and Y is —O—. In some embodiments is a compound of Formula (Ib), or a pharmaceutically acceptable salt or solvate thereof, wherein $R^3$ is —(CR$^6$R$^7$)—Y—(CR$^6$R$^7$)$_q$—R$^8$ and Y is —N(R$^{22}$)—. In some embodiments is a compound of Formula (Ib), or a pharmaceutically acceptable salt or solvate thereof, wherein $R^3$ is —(CR$^6$R$^7$)$_p$—Y—(CR$^6$R$^7$)$_q$—R$^8$, Y is —N(R$^{22}$)—, and R$^{22}$ is —SO$_2$R$^{23}$. In some embodiments is a compound of Formula (Ib), or a pharmaceutically acceptable salt or solvate thereof, wherein q is 1. In some embodiments is a compound of Formula (Ib), or a pharmaceutically acceptable salt or solvate thereof, wherein p is 2. In some embodiments is a compound of Formula (Ib), or a pharmaceutically acceptable salt or solvate thereof, wherein R$^8$ is —C(O)OR$^9$. In some embodiments is a compound of Formula (Ib), or a pharmaceutically acceptable salt or solvate thereof, wherein R$^8$ is —C(O)OR$^9$ and R$^9$ is H. In some embodiments is a compound of Formula (Ib), or a pharmaceutically acceptable salt or solvate thereof, wherein R$^8$ is —C(O)OR$^9$ and R$^9$ is $C_{1-6}$alkyl. In some embodiments is a compound of Formula (Ib), or a pharmaceutically acceptable salt or solvate thereof, wherein R$^8$ is —C(O)OR$^9$ and R$^9$ is —CH$_3$. In some embodiments is a compound of Formula (Ib), or a pharmaceutically acceptable salt or solvate thereof, wherein R$^8$ is —C(O)OR$^9$ and R$^9$ is —CH$_2$CH$_3$. In some embodiments is a compound of Formula (Ib), or a pharmaceutically acceptable salt or solvate thereof, wherein R$^8$ is —C(O)R$^{10}$. In some embodiments is a compound of Formula (Ib), or a pharmaceutically acceptable salt or solvate thereof, wherein R$^8$ is —C(O)R$^{10}$ and R$^{10}$ is —NHSO$_2$R$^{21}$. In some embodiments is a compound of Formula (Ib), or a pharmaceutically acceptable salt or solvate thereof, wherein R$^8$ is —C(O)R$^{10}$, R$^{10}$ is —NHSO$_2$R$^{21}$, and R$^{21}$ is $C_{1-6}$alkyl. In some embodiments is a compound of Formula (Ib), or a pharmaceutically acceptable salt or solvate thereof, wherein R$^8$ is —C(O)R$^{10}$, R$^{10}$ is —NHSO$_2$R$^{21}$, and R$^{21}$ is $C_{3-6}$cycloalkyl. In some embodiments is a compound of Formula (Ib), or a pharmaceutically acceptable salt or solvate thereof, wherein R$^8$ is —C(O)O—(CR$^{12}$R$^{13}$)—OC(O)R$^{11}$. In some embodiments is a compound of Formula (Ib), or a pharmaceutically acceptable salt or solvate thereof, wherein R$^8$ is —C(O)O—(CR$^{12}$R$^{13}$)—OC(O)R$^{11}$ and R$^{11}$ is $C_{1-6}$alkyl. In some embodiments is a compound of Formula (Ib), or a pharmaceutically acceptable salt or solvate thereof, wherein R$^8$ is —C(O)O—(CR$^{12}$R$^{13}$)—OC(O)R$^{11}$ and R$^{11}$ is $C_{1-6}$alkoxy. In some embodiments is a compound of Formula (Ib), or a pharmaceutically acceptable salt or solvate thereof, wherein $R^3$ is —CH$_2$CH$_2$OCH$_2$C(O)OH. In some embodiments is a compound of Formula (Ib), or a pharmaceutically acceptable salt or solvate thereof, wherein R$^8$ is —CH$_2$CH$_2$N(SO$_2$CH$_3$)CH$_2$C(O)OH. In some embodiments is a compound of Formula (Ib), or a pharmaceutically acceptable salt or solvate thereof, wherein $R^3$ is —CH$_2$CH$_2$CH$_2$C(O)OCH(CH$_3$)OC(O)OCH$_2$CH$_3$. In some embodiments is a compound of Formula (Ib), or a pharmaceutically acceptable salt or solvate thereof, wherein $R^3$ is —CH$_2$CH$_2$CH$_2$C(O)OCH(CH$_3$)OC(O)OCH(CH$_3$)$_2$. In some embodiments is a compound of Formula (Ib), or a pharmaceutically acceptable salt or solvate thereof, wherein R$^8$ is —CH$_2$CH$_2$CH$_2$C(O)OCH$_2$OC(O)OC(CH$_3$)$_3$. In some embodiments is a compound of Formula (Ib), or a pharmaceutically acceptable salt or solvate thereof, wherein R$^8$ is —CH$_2$CH$_2$CH$_2$C(O)OCH(CH$_3$)OC(O)CH(CH$_3$)$_2$.

In some embodiments is a compound of Formula (Ib), or a pharmaceutically acceptable salt or solvate thereof, wherein $R^3$ is —(CR$^6$R$^7$)$_t$—$C_{3-6}$cycloalkyl-R$^8$. In some embodiments is a compound of Formula (Ib), or a pharmaceutically acceptable salt or solvate thereof, wherein $R^3$ is —(CR$^6$R$^7$)$_t$—$C_{3-6}$cycloalkyl-R$^8$ and t is 0. In some embodiments is a compound of Formula (Ib), or a pharmaceutically acceptable salt or solvate thereof, wherein $R^8$ is —(CR$^6$R$^7$)$_t$—C$_{3-6}$cycloalkyl-R$^8$ and t is 1. In some embodiments is a compound of Formula (Ib), or a pharmaceutically acceptable salt or solvate thereof, wherein $R^3$ is —(CR$^6$R$^7$)$_t$—C$_{3-6}$cycloalkyl-R$^8$ and t is 2. In some embodiments is a compound of Formula (Ib), or a pharmaceutically acceptable salt or solvate thereof, wherein $R^3$ is -cyclopropyl-C(O)OH. In some embodiments is a compound of Formula (Ib), or a pharmaceutically acceptable salt or solvate thereof, wherein $R^3$ is -cyclobutyl-C(O)OH. In some embodiments is a compound of Formula (Ib), or a pharmaceutically acceptable salt or solvate thereof, wherein $R^3$ is -cyclopentyl-C(O)OH.

In some embodiments of a compound of Formula (Ib), or a pharmaceutically acceptable salt or solvate thereof, wherein n is 0, 1, 2, or 3. In some embodiments of a compound of Formula (Ib), or a pharmaceutically acceptable salt or solvate thereof, wherein n is 0, 1, or 2. In some embodiments of a compound of Formula (Ib), or a pharmaceutically acceptable salt or solvate thereof, wherein n is 1 or 2. In some embodiments of a compound of Formula (Ib), or a pharmaceutically acceptable salt or solvate thereof, wherein n is 0 or 1. In some embodiments of a compound of Formula (Ib), or a pharmaceutically acceptable salt or solvate thereof, wherein n is 0. In some embodiments of a compound of Formula (Ib), or a pharmaceutically acceptable salt or solvate thereof, wherein n is 1. In some embodiments of a compound of Formula (Ib), or a pharmaceutically acceptable salt or solvate thereof, wherein n is 2. In some embodiments of a compound of Formula (Ib), or a pharmaceutically acceptable salt or solvate thereof, wherein n is 3. In some embodiments of a compound of Formula (Ib), or a pharmaceutically acceptable salt or solvate thereof, wherein n is 4.

In some embodiments is a compound of Formula (Ib), or a pharmaceutically acceptable salt or solvate thereof, wherein n is 1 and $R^2$ is halogen, $C_{1-6}$alkyl, $C_{1-6}$haloalkyl, or —OR$^{17}$. In some embodiments is a compound of Formula (Ib), or a pharmaceutically acceptable salt or solvate thereof, wherein n is 1 and $R^2$ is independently selected from $C_{1-6}$alkyl, halogen, —CN, or $C_{1-6}$haloalkyl. In some embodiments is a compound of Formula (Ib), or a pharmaceutically acceptable salt or solvate thereof, wherein n is 1 and $R^2$ is halogen, $C_{1-6}$alkyl, or $C_{1-6}$haloalkyl. In some embodiments is a compound of Formula (Ib), or a pharmaceutically acceptable salt or solvate thereof, wherein n is 1 and $R^2$ is halogen. In some embodiments is a compound of Formula (Ib), or a pharmaceutically acceptable salt or solvate thereof, wherein n is 1 and $R^2$ is —C$_1$. In some embodiments is a compound of Formula (Ib), or a pharmaceutically acceptable salt or solvate thereof, wherein n is 1 and $R^2$ is —F. In some embodiments is a compound of Formula (Ib), or a pharmaceutically acceptable salt or solvate thereof, wherein n is 1 and $R^2$ is $C_{1-6}$alkyl. In some embodiments is a compound of Formula (Ib), or a pharmaceutically acceptable salt or solvate thereof, wherein n is 1 and $R^2$ is —CH$_3$. In some embodiments is a compound of Formula (Ib), or a pharmaceutically acceptable salt or solvate thereof, wherein n is 1 and $R^2$ is $C_{1-6}$haloalkyl. In some embodiments is a compound of Formula (Ib), or a pharmaceutically acceptable salt or solvate thereof, wherein n is 1 and $R^2$ is —CF$_3$. In some embodiments is a compound of Formula (Ib), or a pharmaceutically acceptable salt or solvate thereof, wherein n is 1 and $R^2$ is $C_{1-6}$alkoxy. In some embodiments is a compound of Formula (Ib), or a pharmaceutically acceptable salt or solvate thereof, wherein n is 1 and $R^2$ is —OCH$_3$. In some embodiments is a compound of Formula (Ib), or a pharmaceutically acceptable salt or solvate thereof, wherein n is 1 and $R^2$ is $C_{1-6}$haloalkoxy. In some embodiments is a compound of Formula (Ib), or a pharmaceutically acceptable salt or solvate thereof, wherein n is 1 and $R^2$ is —OCF$_3$. In some embodiments is a compound of Formula (Ib), or a pharmaceutically acceptable salt or solvate thereof, wherein n is 1 and $R^2$ is —OH. In some embodiments is a compound of Formula (Ib), or a pharmaceutically acceptable salt or solvate thereof, wherein n is 1 and $R^2$ is —CN.

In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, or —OR$^{17}$. In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, $C_{1-6}$alkoxy, or —OCF$_3$. In some embodiments is a compound of Formula (Ib), or a pharmaceutically acceptable salt or solvate thereof, wherein n is 2 and each $R^2$ is independently halogen, $C_{1-6}$alkyl, $C_{1-6}$haloalkyl, or —OCF$_3$. In some embodiments is a compound of Formula (Ib), or a pharmaceutically acceptable salt or solvate thereof, wherein n is 2 and each $R^2$ is independently halogen, $C_{1-6}$alkyl, or $C_{1-6}$haloalkyl. In some embodiments is a compound of Formula (Ib), or a pharmaceutically acceptable salt or solvate thereof, wherein n is 2 and each $R^2$ is independently halogen or $C_{1-6}$haloalkyl. In some embodiments is a compound of Formula (Ib), or a pharmaceutically acceptable salt or solvate thereof, wherein n is 2 and each $R^2$ is independently halogen or $C_{1-6}$alkyl. In some embodiments is a compound of Formula (Ib), or a pharmaceutically acceptable salt or solvate thereof, wherein n is 2 and each $R^2$ is independently halogen. In some embodiments is a compound of Formula (Ib), or a pharmaceutically acceptable salt or solvate thereof, wherein n is 2 and each $R^2$ is independently $C_{1-6}$alkyl. In some embodiments is a compound of Formula (Ib), or a pharmaceutically acceptable salt or solvate thereof, wherein n is 2 and each $R^2$ is independently $C_{1-6}$haloalkyl.

In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, $C_{1-6}$haloalkoxy, —OH, or —CN. In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, —OCF$_3$, or —CN. In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, $C_{1-6}$alkoxy, or —OCF$_3$. In some embodiments is a compound of Formula (Ib), or a pharmaceutically acceptable salt or solvate thereof, wherein n is 3 and each $R^2$ is independently halogen, $C_{1-6}$alkyl, $C_{1-6}$haloalkyl, or —OCF$_3$. In some embodiments is a compound of Formula (Ib), or a pharmaceutically acceptable salt or solvate thereof, wherein n is 3 and each $R^2$ is independently halogen, $C_{1-6}$alkyl, or $C_{1-6}$haloalkyl. In some embodiments is a compound of Formula (Ib), or a pharmaceutically acceptable salt or solvate thereof, wherein n is 3 and each $R^2$ is independently halogen or $C_{1-6}$haloalkyl. In some embodiments is a compound of Formula (Ib), or a pharmaceutically acceptable salt or solvate thereof, wherein n is 3 and each $R^2$ is independently halogen or $C_{1-6}$alkyl. In some embodiments is a compound of Formula (Ib), or a pharmaceutically acceptable salt or solvate thereof, wherein n is 3 and each $R^2$ is independently halogen. In some embodiments is a compound of Formula (Ib), or a pharmaceutically acceptable salt or solvate thereof, wherein n is 3 and each $R^2$ is independently $C_{1-6}$alkyl. In some embodiments is a compound of Formula (Ib), or a pharmaceutically acceptable salt or solvate thereof, wherein n is 3 and each $R^2$ is independently $C_{1-6}$haloalkyl.

In some embodiments is a compound of Formula (Ib), or a pharmaceutically acceptable salt or solvate thereof, wherein n is 4 and each $R^2$ is independently halogen, $C_{1-6}$alkyl, $C_{1-6}$haloalkyl, and —$OR^{17}$.

Further embodiments provided herein include combinations of one or more of the particular embodiments set forth above.

In some embodiments, the compound disclosed herein has the structure provided in Table 1.

TABLE 1

| Chemical Synthesis Example | Structure | Name |
|---|---|---|
| 1 | 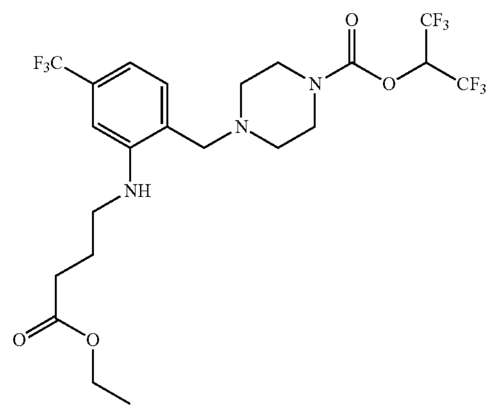 [SMILES: CCOC(=O)CCCNc1cc(C(F)(F)F)ccc1CN1CCN(C(=O)OC(C(F)(F)F)C(F)(F)F)CC1] | 1,1,1,3,3,3-Hexafluoropropan-2-yl 4-(2-((4-ethoxy-4-oxobutyl)amino)-4-(trifluoromethyl)benzyl)piperazine-1-carboxylate |
| 2 | 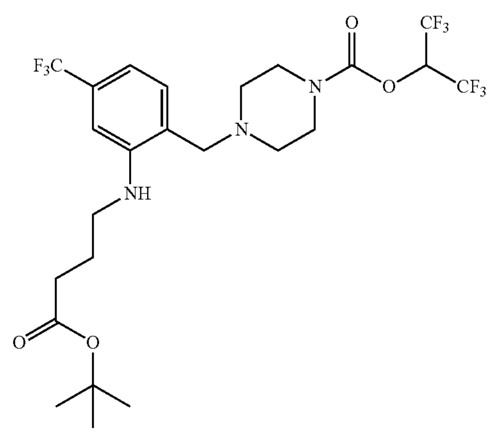 [SMILES: CC(C)(C)OC(=O)CCCNc1cc(C(F)(F)F)ccc1CN1CCN(C(=O)OC(C(F)(F)F)C(F)(F)F)CC1] | 1,1,1,3,3,3-Hexafluoropropan-2-yl 4-(2-((4-(tert-butoxy)-4-oxobutyl)amino)-4-(trifluoromethyl)benzyl)piperazine-1-carboxylate |
| 3 | 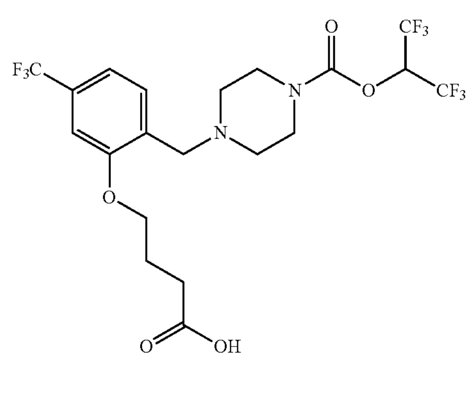 [SMILES: O=C(O)CCCOc1cc(C(F)(F)F)ccc1CN1CCN(C(=O)OC(C(F)(F)F)C(F)(F)F)CC1] | 4-(2-((4-(((1,1,1,3,3,3-Hexafluoropropan-2-yl)oxy)carbonyl)piperazin-1-yl)methyl)-5-(trifluoromethyl)phenoxy)butanoic acid |

TABLE 1-continued

| Chemical Synthesis Example | Structure | Name |
|---|---|---|
| 4 | 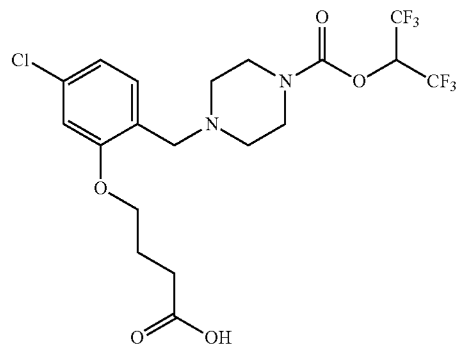 [SMILES: O=C(O)CCCOc1cc(Cl)ccc1CN1CCN(C(=O)OC(C(F)(F)F)C(F)(F)F)CC1] | 4-(5-Chloro-2-((4-(((1,1,1,3,3,3-hexafluoropropan-2-yl)oxy)carbonyl)piperazin-1-yl)methyl)phenoxy)butanoic acid |
| 5 | 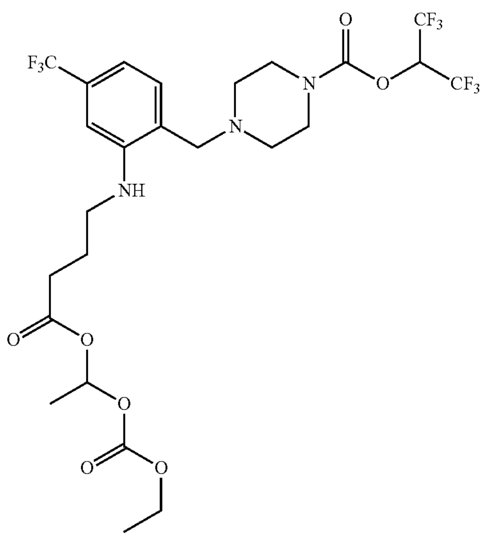 [SMILES: CCOC(=O)OC(C)OC(=O)CCCNc1cc(C(F)(F)F)ccc1CN1CCN(C(=O)OC(C(F)(F)F)C(F)(F)F)CC1] | 1,1,1,3,3,3-Hexafluoropropan-2-yl 4-(2-((4-(1-((ethoxycarbonyl)oxy)ethoxy)-4-oxobutyl)amino)-4-(trifluoromethyl)benzyl)piperazine-1-carboxylate |
| 6 | 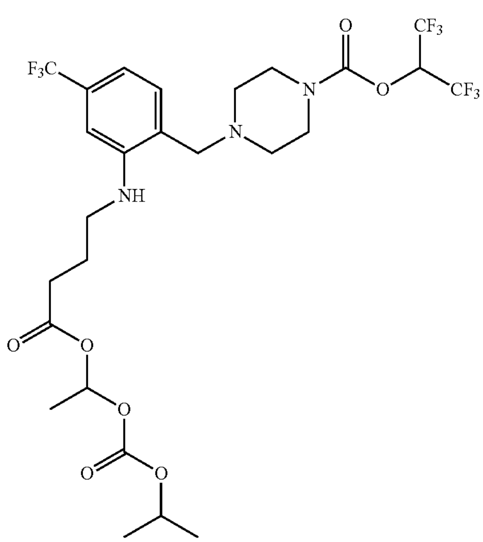 [SMILES: CC(C)OC(=O)OC(C)OC(=O)CCCNc1cc(C(F)(F)F)ccc1CN1CCN(C(=O)OC(C(F)(F)F)C(F)(F)F)CC1] | 1,1,1,3,3,3-Hexafluoropropan-2-yl 4-(2-((4-(1-((isopropoxycarbonyl)oxy)ethoxy)-4-oxobutyl)amino)-4-(trifluoromethyl)benzyl)piperazine-1-carboxylate |

TABLE 1-continued

| Chemical Synthesis Example | Structure | Name |
|---|---|---|
| 7 | 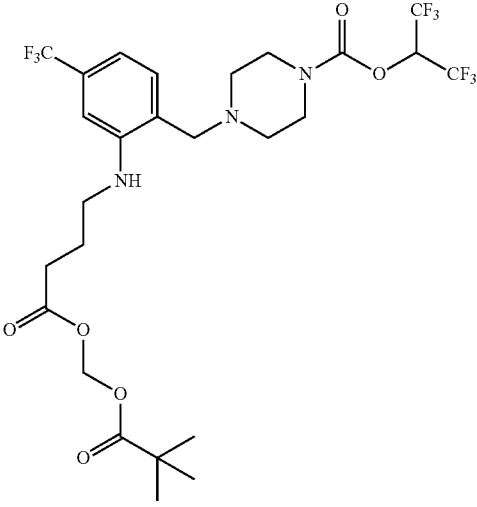 [SMILES: CC(C)(C)C(=O)OCOC(=O)CCCNc1cc(C(F)(F)F)ccc1CN1CCN(C(=O)OC(C(F)(F)F)C(F)(F)F)CC1] | 1,1,1,3,3,3-Hexafluoropropan-2-yl 4-(2-((4-oxo-4-((pivaloyloxy)methoxy)butyl)amino)-4-(trifluoromethyl)benzyl)piperazine-1-carboxylate |
| 8 | 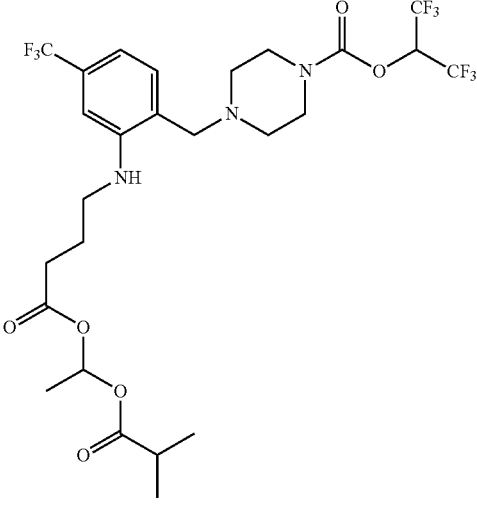 [SMILES: CC(OC(=O)CCCNc1cc(C(F)(F)F)ccc1CN1CCN(C(=O)OC(C(F)(F)F)C(F)(F)F)CC1)OC(=O)C(C)C] | 1,1,1,3,3,3-Hexafluoropropan-2-yl 4-(2-((4-(1-(isobutyryloxy)ethoxy)-4-oxobutyl)amino)-4-(trifluoromethyl)benzyl)piperazine-1-carboxylate |
| 9 | 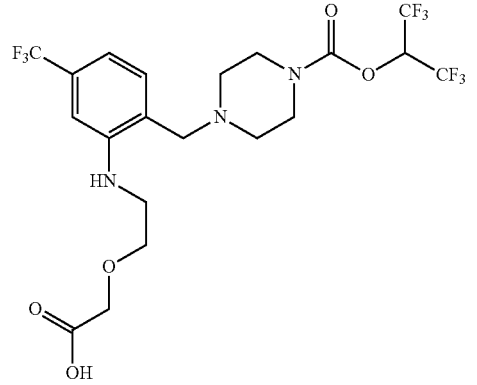 [SMILES: O=C(O)COCCNc1cc(C(F)(F)F)ccc1CN1CCN(C(=O)OC(C(F)(F)F)C(F)(F)F)CC1] | 2-(2-((2-((4-(((1,1,1,3,3,3-Hexafluoropropan-2-yl)oxy)carbonyl)piperazin-1-yl)methyl)-5-(trifluoromethyl)phenyl)amino)ethoxy)acetic acid |

TABLE 1-continued

| Chemical Synthesis Example | Structure | Name |
|---|---|---|
| 10 | 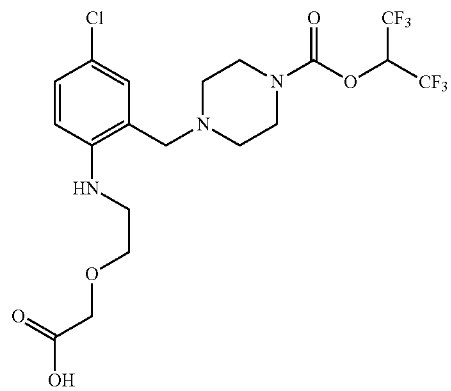 [SMILES: O=C(O)COCCNc1ccc(Cl)cc1CN1CCN(C(=O)OC(C(F)(F)F)C(F)(F)F)CC1] | 2-(2-((4-Chloro-2-((4-((((1,1,1,3,3,3-hexafluoropropan-2-yl)oxy)carbonyl)piperazin-1-yl)methyl)phenyl)amino)ethoxy)acetic acid |
| 11 | 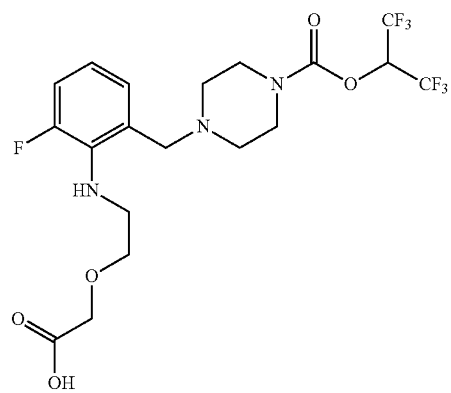 [SMILES: O=C(O)COCCNc1c(F)cccc1CN1CCN(C(=O)OC(C(F)(F)F)C(F)(F)F)CC1] | 2-(2-((2-Fluoro-6-((4-((((1,1,1,3,3,3-hexafluoropropan-2-yl)oxy)carbonyl)piperazin-1-yl)methyl)phenyl)amino)ethoxy)acetic acid |
| 12 | 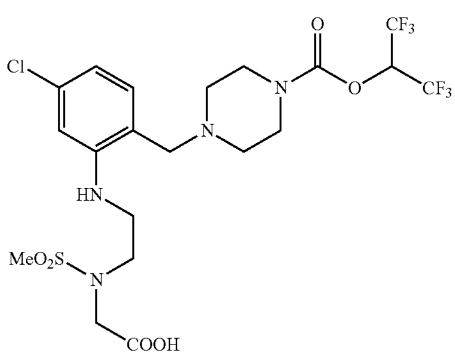 [SMILES: CS(=O)(=O)N(CCNc1cc(Cl)ccc1CN1CCN(C(=O)OC(C(F)(F)F)C(F)(F)F)CC1)CC(=O)O] | N-(2-((5-Chloro-2-((4-((((1,1,1,3,3,3-hexafluoropropan-2-yl)oxy)carbonyl)piperazin-1-yl)methyl)phenyl)amino)ethyl)-N-(methylsulfonyl)glycine |
| 13 | 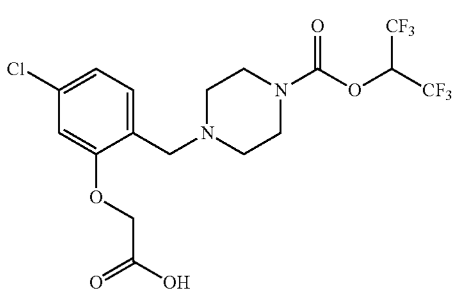 [SMILES: O=C(O)COc1cc(Cl)ccc1CN1CCN(C(=O)OC(C(F)(F)F)C(F)(F)F)CC1] | 2-(5-Chloro-2-((4-((((1,1,1,3,3,3-hexafluoropropan-2-yl)oxy)carbonyl)piperazin-1-yl)methyl)phenoxy)acetic acid |

TABLE 1-continued

| Chemical Synthesis Example | Structure | Name |
|---|---|---|
| 14 | 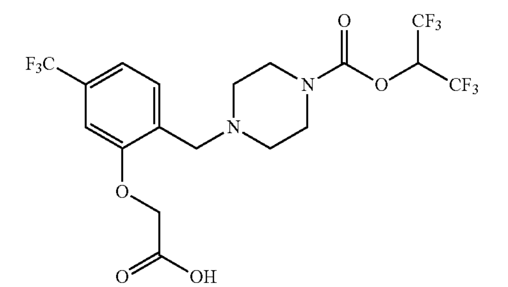 [SMILES: O=C(O)COc1cc(C(F)(F)F)ccc1CN1CCN(C(=O)OC(C(F)(F)F)C(F)(F)F)CC1] | 2-(2-((4-(((1,1,1,3,3,3-Hexafluoropropan-2-yl)oxy)carbonyl)piperazin-1-yl)methyl)-5-(trifluoromethyl)phenoxy)acetic acid |
| 15 | 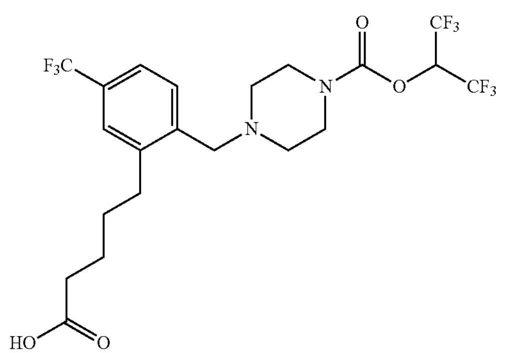 [SMILES: O=C(O)CCCCc1cc(C(F)(F)F)ccc1CN1CCN(C(=O)OC(C(F)(F)F)C(F)(F)F)CC1] | 5-(2-((4-(((1,1,1,3,3,3-Hexafluoropropan-2-yl)oxy)carbonyl)piperazin-1-yl)methyl)-5-(trifluoromethyl)phenyl)pentanoic acid |
| 16 | 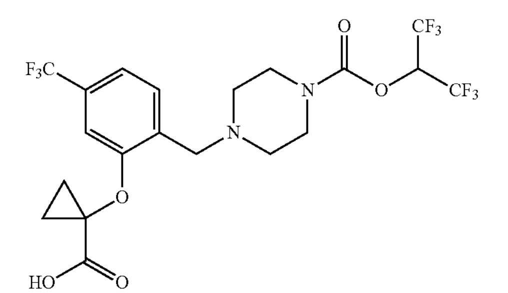 [SMILES: O=C(OC(C(F)(F)F)C(F)(F)F)N1CCN(Cc2ccc(C(F)(F)F)cc2OC2(C(=O)O)CC2)CC1] | 1-(2-((4-(((1,1,1,3,3,3-Hexafluoropropan-2-yl)oxy)carbonyl)piperazin-1-yl)methyl)-5-(trifluoromethyl)phenoxy)cyclopropane-1-carboxylic acid |
| 17 | 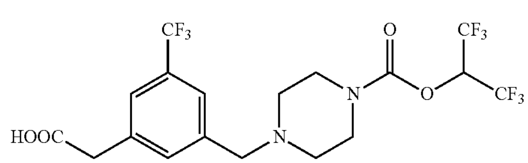 [SMILES: O=C(O)Cc1cc(CN2CCN(C(=O)OC(C(F)(F)F)C(F)(F)F)CC2)cc(C(F)(F)F)c1] | 2-(3-((4-(((1,1,1,3,3,3-hexafluoropropan-2-yl)oxy)carbonyl)piperazin-1-yl)methyl)-5-(trifluoromethyl)phenyl)acetic acid |
| 18 | 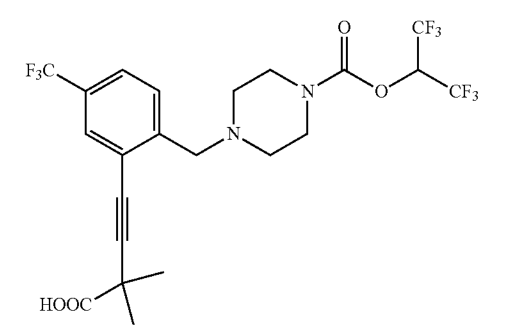 [SMILES: CC(C)(C#Cc1cc(C(F)(F)F)ccc1CN1CCN(C(=O)OC(C(F)(F)F)C(F)(F)F)CC1)C(=O)O] | 4-(2-((4-(((1,1,1,3,3,3-hexafluoropropan-2-yl)oxy)carbonyl)piperazin-1-yl)methyl)-5-(trifluoromethyl)phenyl)-2,2-dimethylbut-3-ynoic acid |

TABLE 1-continued

| Chemical Synthesis Example | Structure | Name |
|---|---|---|
| 19 | 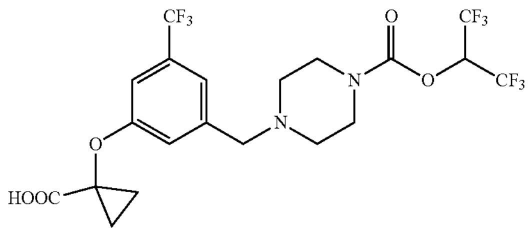 [SMILES: O=C(OC(C(F)(F)F)C(F)(F)F)N1CCN(Cc2cc(OC3(C(=O)O)CC3)cc(C(F)(F)F)c2)CC1] | 1-(3-((4-(((1,1,1,3,3,3-hexafluoropropan-2-yl)oxy)carbonyl)piperazin-1-yl)methyl)-5-(trifluoromethyl)phenoxy)cyclopropane-1-carboxylic acid |
| 20 | 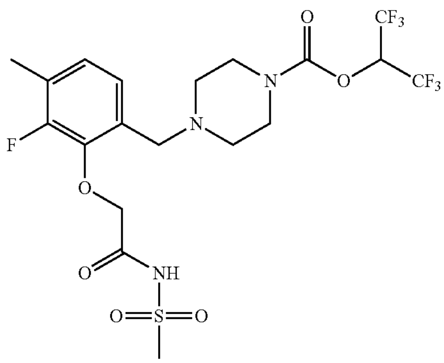 [SMILES: Cc1ccc(CN2CCN(C(=O)OC(C(F)(F)F)C(F)(F)F)CC2)c(OCC(=O)NS(C)(=O)=O)c1F] | 1,1,1,3,3,3-hexafluoropropan-2-yl 4-(3-fluoro-4-methyl-2-(2-(methylsulfonamido)-2-oxoethoxy)benzyl)piperazine-1-carboxylate |
| 21 | 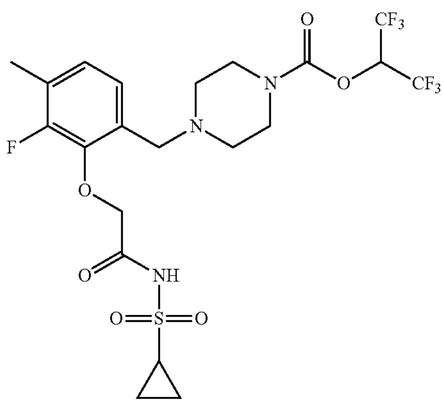 [SMILES: Cc1ccc(CN2CCN(C(=O)OC(C(F)(F)F)C(F)(F)F)CC2)c(OCC(=O)NS(=O)(=O)C2CC2)c1F] | 1,1,1,3,3,3-hexafluoropropan-2-yl 4-(2-(2-(cyclopropanesulfonamido)-2-oxoethoxy)-3-fluoro-4-methylbenzyl)piperazine-1-carboxylate |
| 22 | 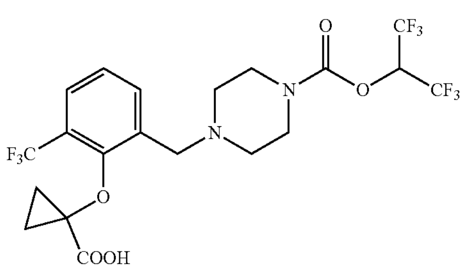 [SMILES: O=C(OC(C(F)(F)F)C(F)(F)F)N1CCN(Cc2cccc(C(F)(F)F)c2OC2(C(=O)O)CC2)CC1] | 1-(2-((4-(((1,1,1,3,3,3-Hexafluoropropan-2-yl)oxy)carbonyl)piperazin-1-yl)methyl)-6-(trifluoromethyl)phenoxy)cyclopropane-1-carboxylic acid |
| 23 | 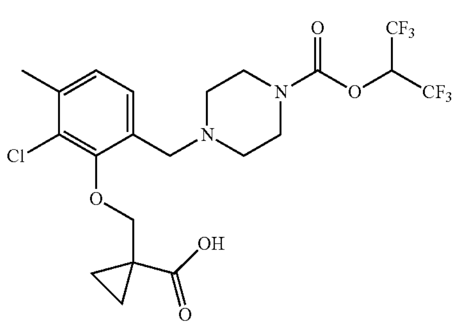 [SMILES: Cc1ccc(CN2CCN(C(=O)OC(C(F)(F)F)C(F)(F)F)CC2)c(OCC2(C(=O)O)CC2)c1Cl] | 1-((2-Chloro-6-((4-(((1,1,1,3,3,3-hexafluoropropan-2-yl)oxy)carbonyl)piperazin-1-yl)methyl)-3-methylphenoxy)methyl)cyclopropane-1-carboxylic acid |

TABLE 1-continued

| Chemical Synthesis Example | Structure | Name |
|---|---|---|
| 24 | 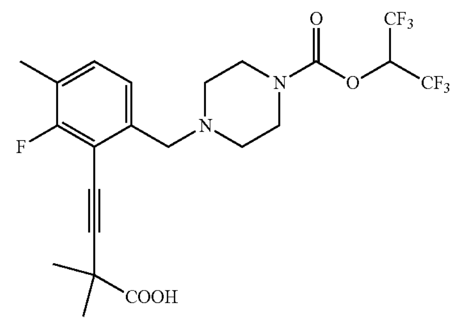 [SMILES: Cc1ccc(CN2CCN(C(=O)OC(C(F)(F)F)C(F)(F)F)CC2)c(C#CC(C)(C)C(=O)O)c1F] | 4-(2-Fluoro-6-((4-(((1,1,1,3,3,3-hexafluoropropan-2-yl)oxy)carbonyl)piperazin-1-yl)methyl)-3-methylphenyl)-2,2-dimethylbut-3-ynoic acid |
| 25 | 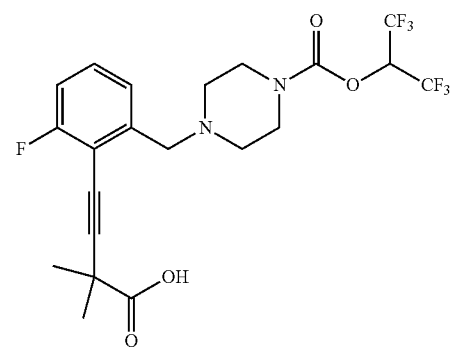 [SMILES: CC(C)(C#Cc1c(F)cccc1CN1CCN(C(=O)OC(C(F)(F)F)C(F)(F)F)CC1)C(=O)O] | 4-(2-Fluoro-6-((4-(((1,1,1,3,3,3-hexafluoropropan-2-yl)oxy)carbonyl)piperazin-1-yl)methyl)phenyl)-2,2-dimethylbut-3-ynoic acid |
| 26 | 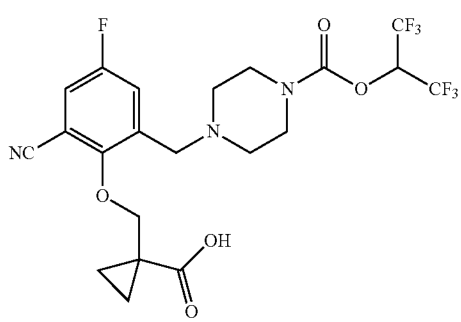 [SMILES: N#Cc1cc(F)cc(CN2CCN(C(=O)OC(C(F)(F)F)C(F)(F)F)CC2)c1OCC1(C(=O)O)CC1] | 1-((2-Cyano-4-fluoro-6-((4-(((1,1,1,3,3,3-hexafluoropropan-2-yl)oxy)carbonyl)piperazin-1-yl)methyl)phenoxy)methyl)cyclopropane-1-carboxylic acid |
| 27 | 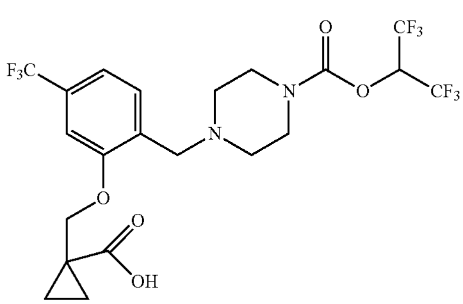 [SMILES: O=C(OC(C(F)(F)F)C(F)(F)F)N1CCN(Cc2ccc(C(F)(F)F)cc2OCC2(C(=O)O)CC2)CC1] | 1-((2-((4-(((1,1,1,3,3,3-hexafluoropropan-2-yl)oxy)carbonyl)piperazin-1-yl)methyl)-5-(trifluoromethyl)phenoxy)methyl)cyclopropane-1-carboxylic acid |

TABLE 1-continued

| Chemical Synthesis Example | Structure | Name |
|---|---|---|
| 28 | 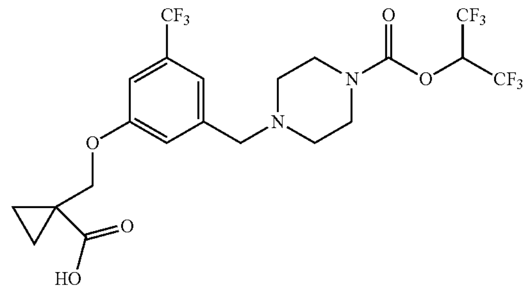 [SMILES: O=C(OC(C(F)(F)F)C(F)(F)F)N1CCN(Cc2cc(OCC3(C(=O)O)CC3)cc(C(F)(F)F)c2)CC1] | 1-((3-((4-(((1,1,1,3,3,3-hexafluoropropan-2-yl)oxy)carbonyl)piperazin-1-yl)methyl)-5-(trifluoromethyl)phenoxy)methyl)cyclopropane-1-carboxylic acid |
| 29 | 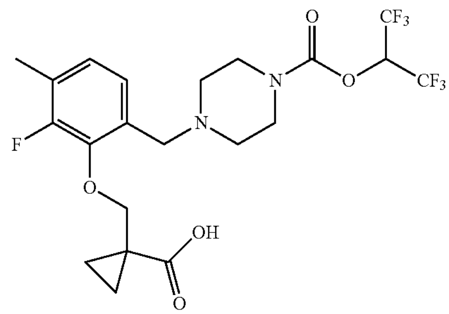 [SMILES: Cc1ccc(CN2CCN(C(=O)OC(C(F)(F)F)C(F)(F)F)CC2)c(OCC2(C(=O)O)CC2)c1F] | 1-((2-fluoro-6-((4-(((1,1,1,3,3,3-hexafluoropropan-2-yl)oxy)carbonyl)piperazin-1-yl)methyl)-3-methylphenoxy)methyl)cyclopropane-1-carboxylic acid |
| 30 | 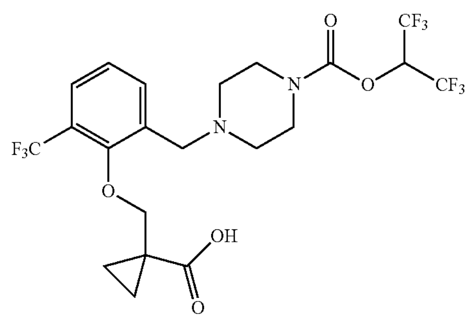 [SMILES: O=C(OC(C(F)(F)F)C(F)(F)F)N1CCN(Cc2cccc(C(F)(F)F)c2OCC2(C(=O)O)CC2)CC1] | 1-((2-((4-(((1,1,1,3,3,3-hexafluoropropan-2-yl)oxy)carbonyl)piperazin-1-yl)methyl)-6-(trifluoromethyl)phenoxy)methyl)cyclopropane-1-carboxylic acid |
| 31 | 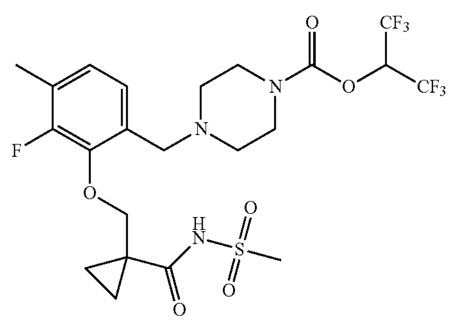 [SMILES: Cc1ccc(CN2CCN(C(=O)OC(C(F)(F)F)C(F)(F)F)CC2)c(OCC2(C(=O)NS(C)(=O)=O)CC2)c1F] | 1,1,1,3,3,3-hexafluoropropan-2-yl 4-(3-fluoro-4-methyl-2-((1-((methylsulfonyl)carbamoyl)cyclopropyl)methoxy)benzyl)piperazine-1-carboxylate |
| 32 | 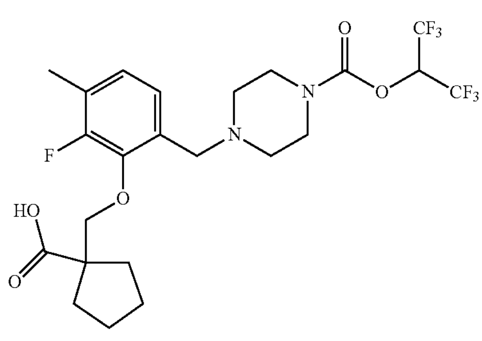 [SMILES: Cc1ccc(CN2CCN(C(=O)OC(C(F)(F)F)C(F)(F)F)CC2)c(OCC2(C(=O)O)CCCC2)c1F] | 1-((2-fluoro-6-((4-(((1,1,1,3,3,3-hexafluoropropan-2-yl)oxy)carbonyl)piperazin-1-yl)methyl)-3-methylphenoxy)methyl)cyclopentane-1-carboxylic acid |

| Chemical Synthesis Example | Structure | Name |
|---|---|---|
| 33 | 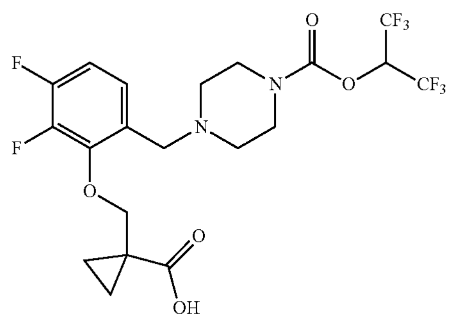 [SMILES: O=C(OC(C(F)(F)F)C(F)(F)F)N1CCN(Cc2ccc(F)c(F)c2OCC2(C(=O)O)CC2)CC1] | 1-((2,3-difluoro-6-((4-((((1,1,1,3,3,3-hexafluoropropan-2-yl)oxy)carbonyl)piperazin-1-yl)methyl)phenoxy)methyl)cyclopropane-1-carboxylic acid |
| 34 | 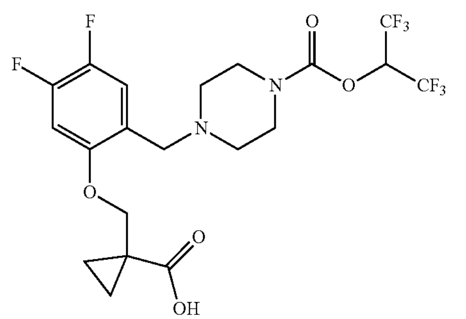 [SMILES: O=C(OC(C(F)(F)F)C(F)(F)F)N1CCN(Cc2cc(F)c(F)cc2OCC2(C(=O)O)CC2)CC1] | 1-((4,5-difluoro-2-((4-((((1,1,1,3,3,3-hexafluoropropan-2-yl)oxy)carbonyl)piperazin-1-yl)methyl)phenoxy)methyl)cyclopropane-1-carboxylic acid |
| 35 | 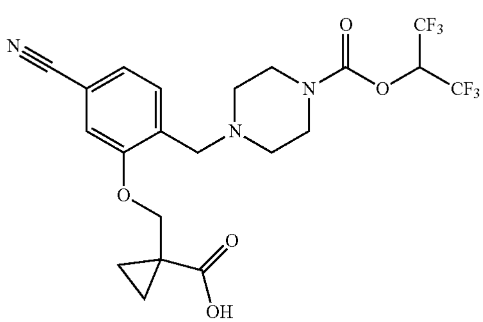 [SMILES: N#Cc1ccc(CN2CCN(C(=O)OC(C(F)(F)F)C(F)(F)F)CC2)c(OCC2(C(=O)O)CC2)c1] | 1-((5-cyano-2-((4-((((1,1,1,3,3,3-hexafluoropropan-2-yl)oxy)carbonyl)piperazin-1-yl)methyl)phenoxy)methyl)cyclopropane-1-carboxylic acid |
| 36 | 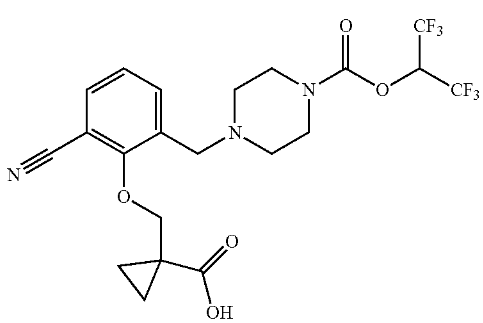 [SMILES: N#Cc1cccc(CN2CCN(C(=O)OC(C(F)(F)F)C(F)(F)F)CC2)c1OCC1(C(=O)O)CC1] | 1-((2-cyano-6-((4-((((1,1,1,3,3,3-hexafluoropropan-2-yl)oxy)carbonyl)piperazin-1-yl)methyl)phenoxy)methyl)cyclopropane-1-carboxylic acid |

TABLE 1-continued

| Chemical Synthesis Example | Structure | Name |
|---|---|---|
| 37 | 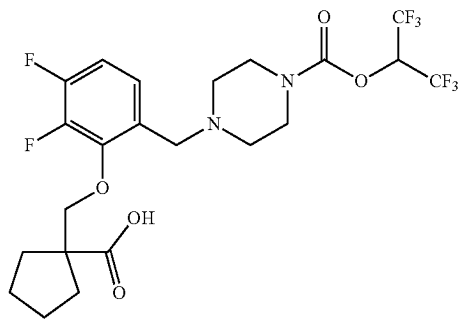 [SMILES: O=C(OC(C(F)(F)F)C(F)(F)F)N1CCN(Cc2ccc(F)c(F)c2OCC2(C(=O)O)CCCC2)CC1] | 1-((2,3-difluoro-6-((4-(((1,1,1,3,3,3-hexafluoropropan-2-yl)oxy)carbonyl)piperazin-1-yl)methyl)phenoxy)methyl)cyclopentane-1-carboxylic acid |
| 38 | 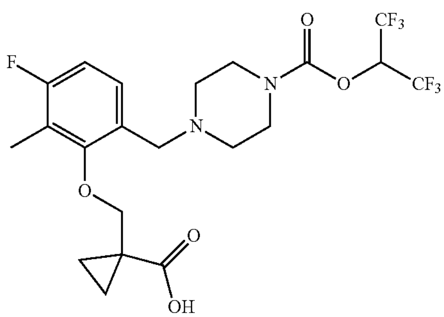 [SMILES: Cc1c(F)ccc(CN2CCN(C(=O)OC(C(F)(F)F)C(F)(F)F)CC2)c1OCC1(C(=O)O)CC1] | 1-((3-fluoro-6-((4-(((1,1,1,3,3,3-hexafluoropropan-2-yl)oxy)carbonyl)piperazin-1-yl)methyl)-2-methylphenoxy)methyl)cyclopropane-1-carboxylic acid |
| 39 | 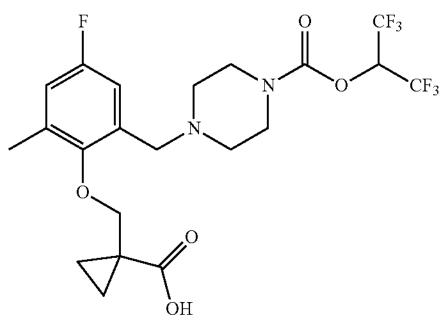 [SMILES: Cc1cc(F)cc(CN2CCN(C(=O)OC(C(F)(F)F)C(F)(F)F)CC2)c1OCC1(C(=O)O)CC1] | 1-((4-fluoro-2-((4-(((1,1,1,3,3,3-hexafluoropropan-2-yl)oxy)carbonyl)piperazin-1-yl)methyl)-6-methylphenoxy)methyl)cyclopropane-1-carboxylic acid |
| 40 | 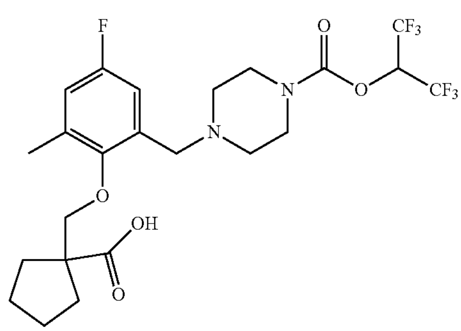 [SMILES: Cc1cc(F)cc(CN2CCN(C(=O)OC(C(F)(F)F)C(F)(F)F)CC2)c1OCC1(C(=O)O)CCCC1] | 1-((4-fluoro-2-((4-(((1,1,1,3,3,3-hexafluoropropan-2-yl)oxy)carbonyl)piperazin-1-yl)methyl)-6-methylphenoxy)methyl)cyclopentane-1-carboxylic acid |

TABLE 1-continued

| Chemical Synthesis Example | Structure | Name |
|---|---|---|
| 41 | 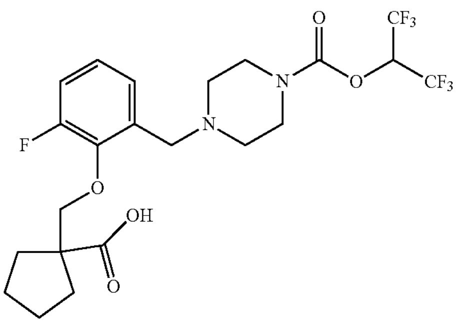 [SMILES: O=C(OC(C(F)(F)F)C(F)(F)F)N1CCN(Cc2cccc(F)c2OCC2(C(=O)O)CCCC2)CC1] | 1-((2-fluoro-6-((4-(((1,1,1,3,3,3-hexafluoropropan-2-yl)oxy)carbonyl)piperazin-1-yl)methyl)phenoxy)methyl)cyclopentane-1-carboxylic acid |
| 42 | 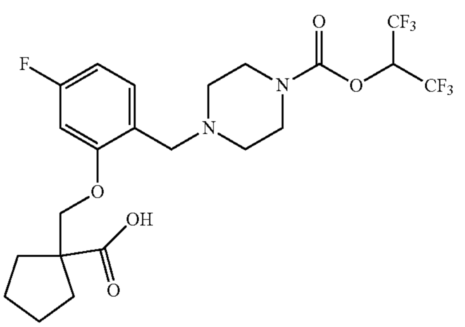 [SMILES: O=C(OC(C(F)(F)F)C(F)(F)F)N1CCN(Cc2ccc(F)cc2OCC2(C(=O)O)CCCC2)CC1] | 1-((5-fluoro-2-((4-(((1,1,1,3,3,3-hexafluoropropan-2-yl)oxy)carbonyl)piperazin-1-yl)methyl)phenoxy)methyl)cyclopentane-1-carboxylic acid |
| 43 | 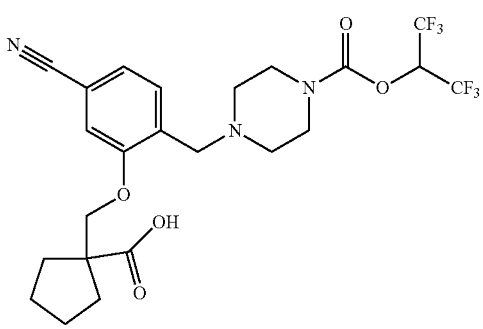 [SMILES: N#Cc1ccc(CN2CCN(C(=O)OC(C(F)(F)F)C(F)(F)F)CC2)c(OCC2(C(=O)O)CCCC2)c1] | 1-((5-cyano-2-((4-(((1,1,1,3,3,3-hexafluoropropan-2-yl)oxy)carbonyl)piperazin-1-yl)methyl)phenoxy)methyl)cyclopentane-1-carboxylic acid |
| 44 | 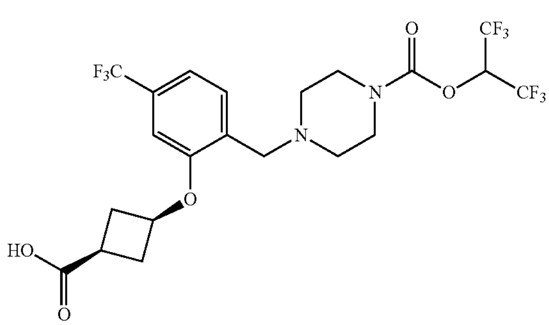 [SMILES: O=C(OC(C(F)(F)F)C(F)(F)F)N1CCN(Cc2ccc(C(F)(F)F)cc2O[C@H]2C[C@@H](C(=O)O)C2)CC1] | (1s,3s)-3-(2-((4-(((1,1,1,3,3,3-hexafluoropropan-2-yl)oxy)carbonyl)piperazin-1-yl)methyl)-5-(trifluoromethyl)phenoxy)cyclobutane-1-carboxylic acid |

TABLE 1-continued

| Chemical Synthesis Example | Structure | Name |
|---|---|---|
| 45 | 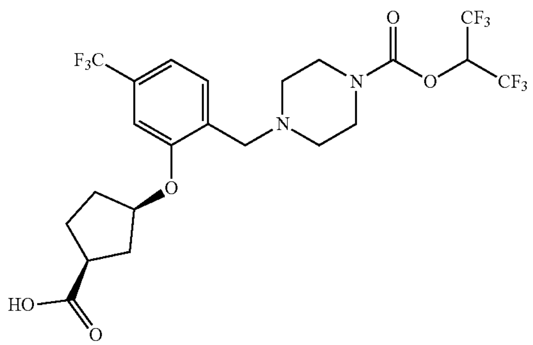 [SMILES: O=C(O)[C@H]1CC[C@@H](Oc2cc(C(F)(F)F)ccc2CN2CCN(C(=O)OC(C(F)(F)F)C(F)(F)F)CC2)C1] | (1S,3R)-3-(2-((4-(((1,1,1,3,3,3-hexafluoropropan-2-yl)oxy)carbonyl)piperazin-1-yl)methyl)-5-(trifluoromethyl)phenoxy)cyclopentane-1-carboxylic acid |
| 46 | 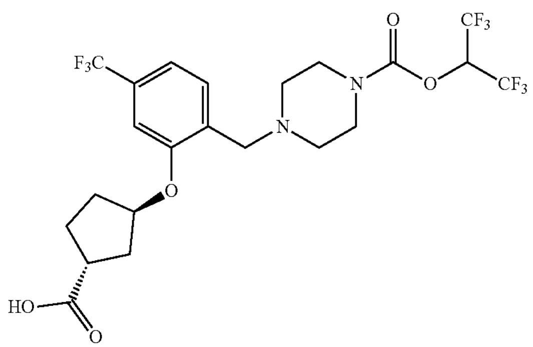 [SMILES: O=C(O)[C@@H]1CC[C@@H](Oc2cc(C(F)(F)F)ccc2CN2CCN(C(=O)OC(C(F)(F)F)C(F)(F)F)CC2)C1] | (1R,3R)-3-(2-((4-(((1,1,1,3,3,3-hexafluoropropan-2-yl)oxy)carbonyl)piperazin-1-yl)methyl)-5-(trifluoromethyl)phenoxy)cyclopentane-1-carboxylic acid |
| 47 | 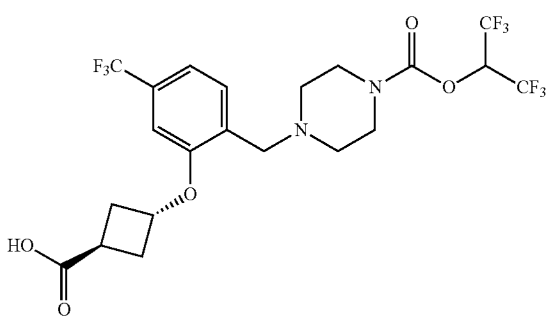 [SMILES: O=C(OC(C(F)(F)F)C(F)(F)F)N1CCN(Cc2ccc(C(F)(F)F)cc2O[C@H]2C[C@H](C(=O)O)C2)CC1] | (1r,3r)-3-(2-((4-(((1,1,1,3,3,3-hexafluoropropan-2-yl)oxy)carbonyl)piperazin-1-yl)methyl)-5-(trifluoromethyl)phenoxy)cyclobutane-1-carboxylic acid |
| 48 | 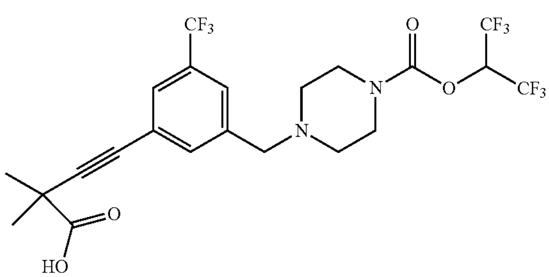 [SMILES: CC(C)(C#Cc1cc(CN2CCN(C(=O)OC(C(F)(F)F)C(F)(F)F)CC2)cc(C(F)(F)F)c1)C(=O)O] | 4-(3-((4-(((1,1,1,3,3,3-hexafluoropropan-2-yl)oxy)carbonyl)piperazin-1-yl)methyl)-5-(trifluoromethyl)phenyl)-2,2-dimethylbut-3-ynoic acid |
| 49 | 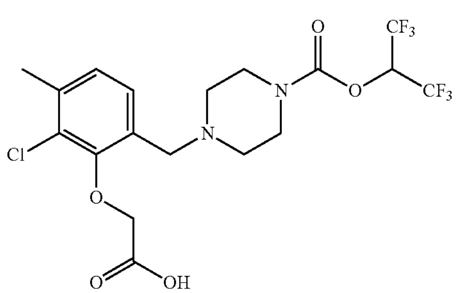 [SMILES: Cc1ccc(CN2CCN(C(=O)OC(C(F)(F)F)C(F)(F)F)CC2)c(OCC(=O)O)c1Cl] | 2-(2-chloro-6-((4-(((1,1,1,3,3,3-hexafluoropropan-2-yl)oxy)carbonyl)piperazin-1-yl)methyl)-3-methylphenoxy)acetic acid |

TABLE 1-continued

| Chemical Synthesis Example | Structure | Name |
|---|---|---|
| 50 | 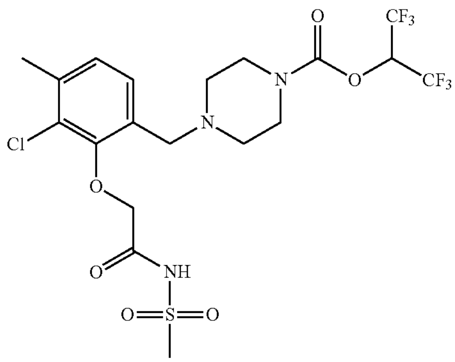 [SMILES: Cc1ccc(CN2CCN(C(=O)OC(C(F)(F)F)C(F)(F)F)CC2)c(OCC(=O)NS(C)(=O)=O)c1Cl] | 1,1,1,3,3,3-hexafluoropropan-2-yl 4-(3-chloro-4-methyl-2-(2-methylsulfonamido)-2-oxoethoxy)benzyl)piperazine-1-carboxylate |
| 51 | 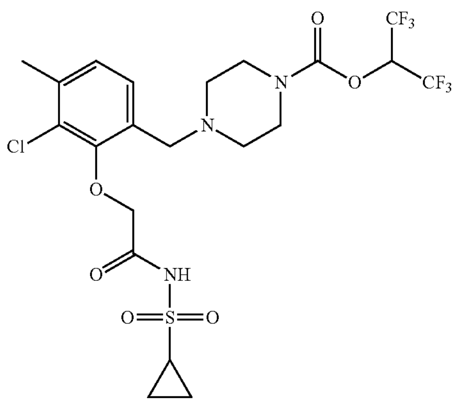 [SMILES: Cc1ccc(CN2CCN(C(=O)OC(C(F)(F)F)C(F)(F)F)CC2)c(OCC(=O)NS(=O)(=O)C2CC2)c1Cl] | 1,1,1,3,3,3-hexafluoropropan-2-yl 4-(3-chloro-2-(2-(cyclopropanesulfonamido)-2-oxoethoxy)-4-methylbenzyl)piperazine-1-carboxylate |
| 52 | 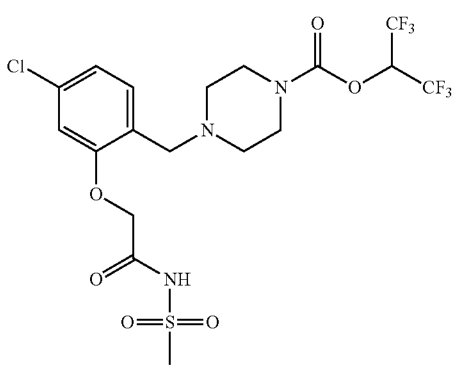 [SMILES: CS(=O)(=O)NC(=O)COc1cc(Cl)ccc1CN1CCN(C(=O)OC(C(F)(F)F)C(F)(F)F)CC1] | 1,1,1,3,3,3-hexafluoropropan-2-yl 4-(4-chloro-2-(2-(methylsulfonamido)-2-oxoethoxy)benzyl)piperazine-1-carboxylate |
| 53 | 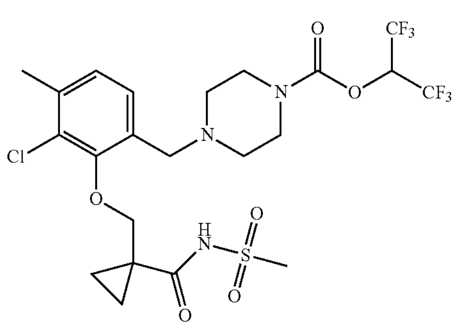 [SMILES: Cc1ccc(CN2CCN(C(=O)OC(C(F)(F)F)C(F)(F)F)CC2)c(OCC2(C(=O)NS(C)(=O)=O)CC2)c1Cl] | 1,1,1,3,3,3-hexafluoropropan-2-yl 4-(3-chloro-4-methyl-2-((1-((methylsulfonyl)carbamoyl)cyclopropyl)methoxy)benzyl)piperazine-1-carboxylate |

TABLE 1-continued

| Chemical Synthesis Example | Structure | Name |
|---|---|---|
| 54 | 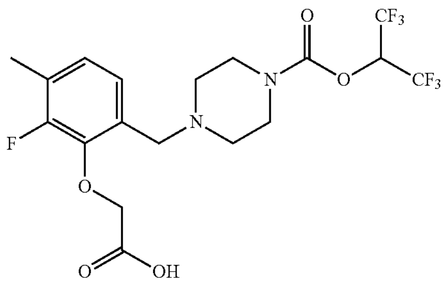 [SMILES: Cc1ccc(CN2CCN(C(=O)OC(C(F)(F)F)C(F)(F)F)CC2)c(OCC(=O)O)c1F] | 2-(2-fluoro-6-((4-(((1,1,1,3,3,3-hexafluoropropan-2-yl)oxy)carbonyl)piperazin-1-yl)methyl)-3-methylphenoxy)acetic acid |
| 55 | 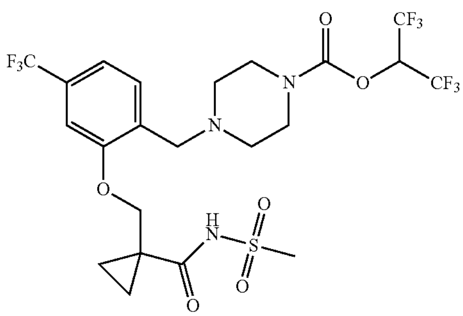 [SMILES: CS(=O)(=O)NC(=O)C1(COc2cc(C(F)(F)F)ccc2CN2CCN(C(=O)OC(C(F)(F)F)C(F)(F)F)CC2)CC1] | 1,1,1,3,3,3-hexafluoropropan-2-yl 4-(2-((1-((methylsulfonyl)carbamoyl)cyclopropyl)methoxy)-4-(trifluoromethyl)benzyl)piperazine-1-carboxylate |
| 56 | 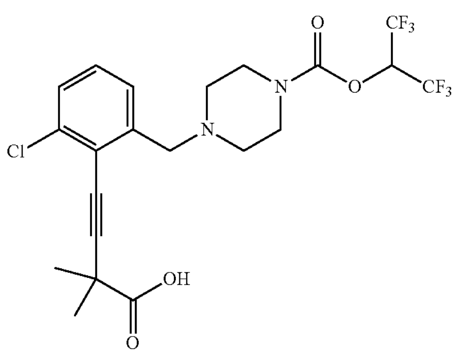 [SMILES: CC(C)(C#Cc1c(Cl)cccc1CN1CCN(C(=O)OC(C(F)(F)F)C(F)(F)F)CC1)C(=O)O] | 4-(2-chloro-6-((4-(((1,1,1,3,3,3-hexafluoropropan-2-yl)oxy)carbonyl)piperazin-1-yl)methyl)phenyl)-2,2-dimethylbut-3-ynoic acid |

In some embodiments the compound disclosed herein is selected from:

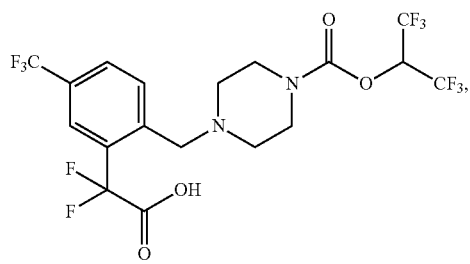

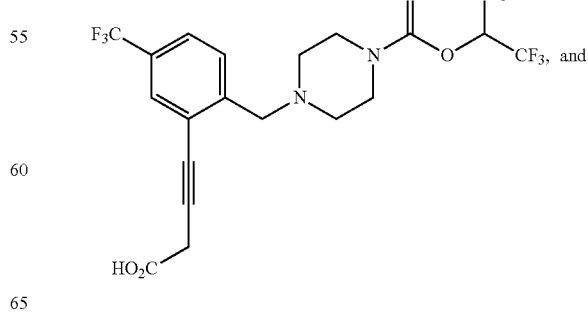

-continued

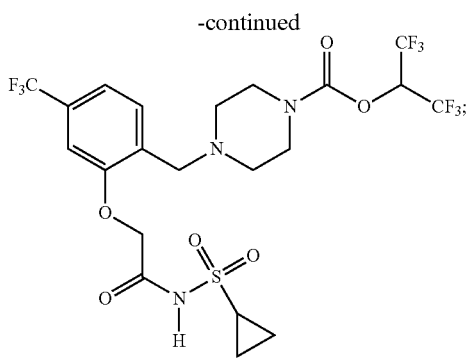

or a pharmaceutically acceptable salt or solvate thereof.

Preparation of the Compounds

The compounds used in the reactions described herein are made according to known organic synthesis techniques, starting from commercially available chemicals and/or from compounds described in the chemical literature. "Commercially available chemicals" are obtained from standard commercial sources including Acros Organics (Geel, Belgium), Aldrich Chemical (Milwaukee, Wis., including Sigma Chemical and Fluka), Apin Chemicals Ltd. (Milton Park, UK), Ark Pharm, Inc. (Libertyville, Ill.), Avocado Research (Lancashire, U.K.), BDH Inc. (Toronto, Canada), Bionet (Cornwall, U.K.), Chemservice Inc. (West Chester, Pa.), Combi-blocks (San Diego, Calif.), Crescent Chemical Co. (Hauppauge, N.Y.), eMolecules (San Diego, Calif.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Matrix Scientific, (Columbia, S.C.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Ryan Scientific, Inc. (Mount Pleasant, S.C.), Spectrum Chemicals (Gardena, Calif.), Sundia Meditech, (Shanghai, China), TCI America (Portland, Oreg.), Trans World Chemicals, Inc. (Rockville, Md.), and WuXi (Shanghai, China).

Suitable reference books and treatises that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd. Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatises that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are also identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the piperazine carbamates described herein is P. H. Stahl & C. G. Wermuth "Handbook of Pharmaceutical Salts", Verlag Helvetica Chimica Acta, Zurich, 2002.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that are incorporated into compounds of the invention include isotopes of hydrogen, carbon, nitrogen, oxygen, phosphorous, sulfur, fluorine and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the pharmaceutically acceptable salts, esters, solvate, hydrates or derivatives thereof which contain the aforementioned isotopes and/or other isotopes of other atoms are within the scope of this invention. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the invention, or by separately reacting a purified compound in its free form with a suitable acid or base, and isolating the salt thus formed.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran or methanol. In addition, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The invention provides for methods of treating diseases by administering such prodrugs. The invention further provides for methods of treating diseases by administering such prodrugs as pharmaceutical compositions.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present invention. The amino acid residues include but are not limited to the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. In other embodiments, prodrugs include compounds wherein a nucleic acid residue, or an oligonucleotide of two or more (e.g., two, three or four) nucleic acid residues is covalently joined to a compound of the present invention.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. In some embodiments, compounds having free amino, amido, hydroxy or carboxylic groups are converted into prodrugs. For instance, free carboxyl groups are derivatized as amides or alkyl esters. In certain instances, all of these prodrug moieties incorporate groups including but not limited to ether, amine and carboxylic acid functionalities.

Hydroxy prodrugs include esters, such as though not limited to, acyloxyalkyl (e.g. acyloxymethyl, acyloxyethyl) esters, alkoxycarbonyloxyalkyl esters, alkyl esters, aryl esters, phosphate esters, sulfonate esters, sulfate esters and disulfide containing esters; ethers, amides, carbamates, hemisuccinates, dimethylaminoacetates and phosphoryloxymethyloxycarbonyls, as outlined in *Advanced Drug Delivery Reviews* 1996, 19, 115.

Amine derived prodrugs include, but are not limited to the following groups and combinations of groups:

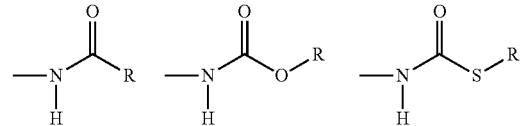

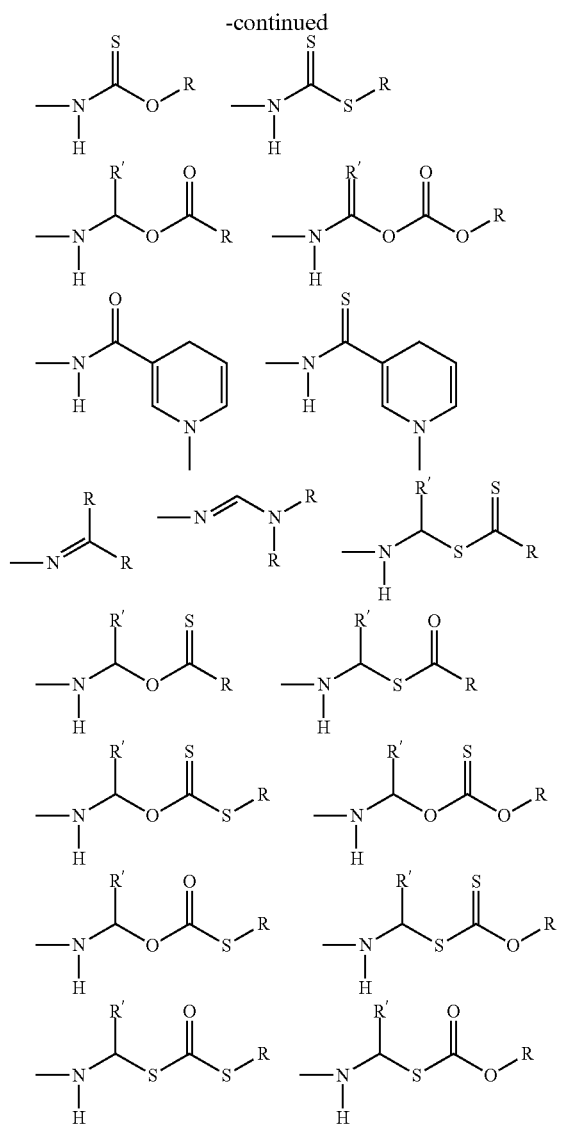

as well as sulfonamides and phosphonamides.

In certain instances, sites on any aromatic ring portions are susceptible to various metabolic reactions, therefore incorporation of appropriate substituents on the aromatic ring structures, reduce, minimize or eliminate this metabolic pathway.

Pharmaceutical Compositions

In certain embodiments, the compound of Formula (I), (Ia), or (Ib) as described herein is administered as a pure chemical. In some embodiments, the compound of Formula (I), (Ia), or (Ib) described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington: The Science and Practice of Pharmacy* (Gennaro, 21$^{st}$ Ed. Mack Pub. Co., Easton, Pa. (2005)).

Accordingly, provided herein is a pharmaceutical composition comprising at least one compound of Formula (I), (Ia), or (Ib) described herein, or a pharmaceutically acceptable salt or solvate thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable excipient and a compound of Formula (I), or a pharmaceutically acceptable salt thereof.

One embodiment provides a pharmaceutical composition comprising a pharmaceutically acceptable excipient and a compound of Formula (Ia), or a pharmaceutically acceptable salt thereof.

One embodiment provides a pharmaceutical composition comprising a pharmaceutically acceptable excipient and a compound of Formula (Ib), or a pharmaceutically acceptable salt thereof.

One embodiment provides a pharmaceutical composition comprising a pharmaceutically acceptable excipient and a compound of Formula (II), or a pharmaceutically acceptable salt thereof.

Another embodiment provides a pharmaceutical composition consisting essentially of a pharmaceutically acceptable excipient and a compound of Formula (I), or a pharmaceutically acceptable salt thereof. Another embodiment provides a pharmaceutical composition consisting essentially of a pharmaceutically acceptable excipient and a compound of Formula (Ia), or a pharmaceutically acceptable salt thereof. Another embodiment provides a pharmaceutical composition consisting essentially of a pharmaceutically acceptable excipient and a compound of Formula (Ib), or a pharmaceutically acceptable salt thereof. Another embodiment provides a pharmaceutical composition consisting essentially of a pharmaceutically acceptable excipient and a compound of Formula (II), or a pharmaceutically acceptable salt thereof.

In certain embodiments, the compound of Formula (I), (Ia), or (Ib) as described herein is substantially pure, in that it contains less than about 5%, or less than about 1%, or less than about 0.1%, of other organic small molecules, such as contaminating intermediates or by-products that are created, for example, in one or more of the steps of a synthesis method.

These pharmaceutical compositions include those suitable for oral, rectal, topical, buccal, parenteral (e.g., subcutaneous, intramuscular, intradermal, or intravenous) vaginal, ophthalmic, or aerosol administration.

Exemplary pharmaceutical compositions are used in the form of a pharmaceutical preparation, for example, in solid, semisolid or liquid form, which includes one or more of a disclosed compound, as an active ingredient, in a mixture with an organic or inorganic carrier or excipient suitable for external, enteral or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

In some embodiments for preparing solid compositions such as tablets, the principal active ingredient is mixed with a pharmaceutical carrier, e.g., conventional tableting ingredients such as corn starch, lactose, sucrose, sorbitol, talc, stearic acid, magnesium stearate, dicalcium phosphate or gums, and other pharmaceutical diluents, e.g., water, to form a solid preformulation composition containing a homogeneous mixture of a disclosed compound or a non-toxic pharmaceutically acceptable salt thereof. When referring to these preformulation compositions as homogeneous, it is meant that the active ingredient is dispersed evenly throughout the composition so that the composition is readily subdivided into equally effective unit dosage forms such as tablets, pills and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, cellulose, microcrystalline cellulose, silicified microcrystalline cellulose, lactose, sucrose, glucose, mannitol, and/or silicic acid; (2) binders, such as, for example, carboxymethylcellulose, hypromellose, alginates, gelatin, polyvinyl pyrrolidone, sucrose and/or acacia; (3) humectants, such as glycerol; (4) disintegrating agents, such as crospovidone, croscarmellose sodium, sodium starch glycolate, agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, docusate sodium, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, in some embodiments, the compositions comprise buffering agents. In some embodiments, solid compositions of a similar type are also employed as fillers in soft and hard-filled gelatin capsules using such excipients as lactose or milk sugars, as well as high molecular weight polyethylene glycols and the like.

In some embodiments, a tablet is made by compression or molding, optionally with one or more accessory ingredients. In some embodiments, compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. In some embodiments, molded tablets are made by molding in a suitable machine a mixture of the subject composition moistened with an inert liquid diluent. In some embodiments, tablets, and other solid dosage forms, such as dragees, capsules, pills and granules, are scored or prepared with coatings and shells, such as enteric coatings and other coatings.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, in some embodiments, the liquid dosage forms contain inert diluents, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

In some embodiments, suspensions, in addition to the subject composition, contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. In some embodiments, the active component is mixed under sterile conditions with a pharmaceutically acceptable carrier, and with any preservatives, buffers, or propellants as required.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. In some embodiments, sprays additionally contain customary propellants, such as chlorofluorohydrocarbons and volatile unsubstituted hydrocarbons, such as butane and propane.

In some embodiments, the compounds described herein are formulated as eye drops for ophthalmic administration.

Compositions and compounds disclosed herein alternatively are administered by aerosol. This is accomplished by preparing an aqueous aerosol, liposomal preparation or solid particles containing the compound. In some embodiments, a non-aqueous (e.g., fluorocarbon propellant) suspension is used. In some embodiments, sonic nebulizers are used because they minimize exposing the agent to shear, which results in degradation of the compounds contained in the subject compositions. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which, in some embodiments, contain antioxidants, buffers, bacteriostats, solutes which render the formulation isotonic with the blood of the intended recipient or suspending or thickening agents.

Examples of suitable aqueous and non-aqueous carriers which are employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methyacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro.

The dose of the composition comprising at least one compound of Formula (I), (Ia), or (Ib) as described herein differs, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

Oral doses typically range from about 1.0 mg to about 1000 mg, one to four times, or more, per day.

Methods

Disclosed herein are methods of modulating the activity of MAGL. Contemplated methods, for example, comprise exposing said enzyme to a compound described herein. In some embodiments, the compound utilized by one or more of the foregoing methods is one of the generic, subgeneric, or specific compounds described herein, such as a compound of Formula (I), (Ia), or (Ib), or a pharmaceutically acceptable salt or solvate thereof. The ability of compounds described herein to modulate or inhibit MAGL is evaluated by procedures known in the art and/or described herein. Another aspect of this disclosure provides methods of treating a disease associated with expression or activity of MAGL in a patient.

Also disclosed herein are methods of treating and/or preventing in a patient in need thereof a disorder such as one or more of acute or chronic pain and neuropathy. Disclosed methods include administering a pharmaceutically effective amount of a compound described herein.

In another embodiment is a method of treating pain in a patient, comprising administering a therapeutically effective amount of a compound of Formula (I), (Ia), or (Ib) described herein, or a pharmaceutically acceptable salt or solvate thereof, to a patient in need thereof to treat said pain. In another embodiment is a method of treating neuropathic pain in a patient, comprising administering a therapeutically effective amount of a compound of Formula (I), (Ia), or (Ib) described herein, or a pharmaceutically acceptable salt or solvate thereof, to a patient in need thereof to treat said neuropathic pain. In another embodiment is a method of treating inflammatory pain in a patient, comprising administering a therapeutically effective amount of a compound of Formula (I), (Ia), or (Ib) described herein, or a pharmaceutically acceptable salt or solvate thereof, to a patient in need thereof to treat said inflammatory pain. In another embodiment is a method of treating complex regional pain syndrome in a patient in need thereof, comprising administering to the patient a therapeutically effective amount of a compound of Formula (I), (Ia), or (Ib) described herein, or a pharmaceutically acceptable salt or solvate thereof.

In another embodiment is a method of treating a disease or disorder in a patient comprising administering to the patient in need thereof a therapeutically effective amount of a compound of Formula (I), (Ia), or (Ib) described herein, or a pharmaceutically acceptable salt or solvate thereof, wherein the disease or disorder is selected from the group consisting of epilepsy/seizure disorder, multiple sclerosis, neuromyelitis optica (NMO), Tourette syndrome, Alzheimer's disease, and abdominal pain associated with irritable bowel syndrome. In another embodiment is a method of treating epilepsy/seizure disorder in a patient comprising administering to the patient in need thereof a therapeutically effective amount of a compound of Formula (I), (Ia), or (Ib) described herein, or a pharmaceutically acceptable salt or solvate thereof. In another embodiment is a method of treating multiple sclerosis in a patient comprising administering to the patient in need thereof a therapeutically effective amount of a compound of Formula (I), (Ia), or (Ib) described herein, or a pharmaceutically acceptable salt or solvate thereof. In another embodiment is a method of treating neuromyelitis optica (NMO) in a patient comprising administering to the patient in need thereof a therapeutically effective amount of a compound of Formula (I), (Ia), or (Ib) described herein, or a pharmaceutically acceptable salt or solvate thereof. In another embodiment is a method of treating Tourette syndrome in a patient comprising administering to the patient in need thereof a therapeutically effective amount of a compound of Formula (I), (Ia), or (Ib)

described herein, or a pharmaceutically acceptable salt or solvate thereof. In another embodiment is a method of treating Alzheimer's disease in a patient comprising administering to the patient in need thereof a therapeutically effective amount of a compound of Formula (I), (Ia), or (Ib) described herein, or a pharmaceutically acceptable salt or solvate thereof. In another embodiment is a method of treating abdominal pain associated with irritable bowel syndrome in a patient comprising administering to the patient in need thereof a therapeutically effective amount of a compound of Formula (I), (Ia), or (Ib) described herein, or a pharmaceutically acceptable salt or solvate thereof.

In another embodiment is a method of treating acute pain, inflammatory pain, cancer pain, pain caused by peripheral neuropathy, central pain, fibromyalgia, migraine, vasoocclussive painful crises in sickle cell disease, spasticity or pain associated with multiple sclerosis, functional chest pain, rheumatoid arthritis, osteoarthritis, or functional dyspepsia in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating acute pain in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating inflammatory pain in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating cancer pain in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating pain caused by peripheral neuropathy in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating central pain in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating fibromyalgia in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating migraine in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating vasoocclussive painful crises in sickle cell disease in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating spasticity or pain associated with multiple sclerosis in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating functional chest pain in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating rheumatoid arthritis in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating osteoarthritis in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating functional dyspepsia in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of treating Persistent Motor Tic Disorder in a patient in need thereof, comprising administering to the patient a therapeutically effective amount of a compound of Formula (I), (Ia), or (Ib) described herein, or a pharmaceutically acceptable salt or solvate thereof. In some embodiments, disclosed herein is a method of treating Persistent Vocal Tic Disorder in a patient in need thereof, comprising administering to the patient a therapeutically effective amount of a compound of Formula (I), (Ia), or (Ib) described herein, or a pharmaceutically acceptable salt or solvate thereof.

In another embodiment is a method of lowering intraocular eye pressure (IOP) in a patient in need thereof, comprising administering to the patient a therapeutically effective amount of a compound of Formula (I), (Ia), or (Ib) described herein, or a pharmaceutically acceptable salt or solvate thereof. In another embodiment is a method of treating glaucoma in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of treating attention deficit and hyperactivity disorder (ADHD) in a patient in need thereof, comprising administering to the patient a therapeutically effective amount of a compound of Formula (I), (Ia), or (Ib) described herein, or a pharmaceutically acceptable salt or solvate thereof. In some embodiments, disclosed herein is a method of treating obsessive-compulsive disorder (OCD) in a patient in need thereof, comprising administering to the patient a therapeutically effective amount of a compound of Formula (I), (Ia), or (Ib) described herein, or a pharmaceutically acceptable salt or solvate thereof.

In another embodiment is a method of treating atopic dermatitis in a patient in need thereof, comprising administering to the patient a therapeutically effective amount of a compound of Formula (I), (Ia), or (Ib) described herein, or a pharmaceutically acceptable salt or solvate thereof.

In another embodiment is a method of treating pruritis in a patient in need thereof, comprising administering to the patient a therapeutically effective amount of a compound of Formula (I), (Ia), or (Ib) described herein, or a pharmaceutically acceptable salt or solvate thereof.

In another embodiment is a method of treating Down's syndrome in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of synergistically potentiating the activity of an opioid analgesic in a patient being treated with an opioid analgesic, comprising administering to the patient a therapeutically effective amount of a compound of Formula (I), (Ia), or (Ib) described herein, or a pharmaceutically acceptable salt or solvate thereof. In some embodiments, disclosed herein is a method of reducing the acute side-effects associated with an opioid analgesic in a patient being treated with an opioid analgesic, comprising administering to the patient a therapeutically effective amount of a compound of Formula (I), (Ia), or (Ib) described herein, or a pharmaceutically acceptable salt or solvate thereof.

In another embodiment is a method of treating dystonia in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of treating Amyotrophic Lateral Sclerosis (ALS) or ALS-related symptoms in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of treating agitation in autism in a patient in need thereof, comprising administering to the patient a therapeutically effective amount of a compound of Formula (I), (Ia), or (Ib) described herein, or a pharmaceutically acceptable salt or solvate thereof.

In another embodiment is a method of treating sleep disturbance or bladder dysfunction associated with multiple sclerosis in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of treating Huntington's Disease in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of Parkinson's Disease in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of improving functional outcome following stroke in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of treating traumatic brain injury in a patient in need thereof, comprising administering to the patient a therapeutically effective amount of a compound of Formula (I), (Ia), or (Ib) described herein, or a pharmaceutically acceptable salt or solvate thereof.

In some embodiments, disclosed herein is a method of treating trigeminal neuralgia in a patient in need thereof, comprising administering to the patient a therapeutically effective amount of a compound of Formula (I), (Ia), or (Ib) described herein, or a pharmaceutically acceptable salt or solvate thereof. In some embodiments, disclosed herein is a method of treating glossopharyngeal neuralgia in a patient in need thereof, comprising administering to the patient a therapeutically effective amount of a compound of Formula (I), (Ia), or (Ib) described herein, or a pharmaceutically acceptable salt or solvate thereof.

In certain embodiments, a disclosed compound utilized by one or more of the foregoing methods is one of the generic, subgeneric, or specific compounds described herein, such as a compound of Formula (I), (Ia), or (Ib).

Disclosed compounds are administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors, with the appropriate dosage ultimately being at the discretion of the attendant physician. For treating clinical conditions and diseases noted above, a contemplated compound disclosed herein is administered orally, subcutaneously, topically, parenterally, by inhalation spray or rectally in dosage unit formulations containing conventional non-toxic pharmaceutically acceptable carriers, adjuvants and vehicles. Parenteral administration include subcutaneous injections, intravenous or intramuscular injections or infusion techniques.

Also contemplated herein are combination therapies, for example, co-administering a disclosed compound and an additional active agent, as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually weeks, months or years depending upon the combination selected). Combination therapy is intended to embrace administration of multiple therapeutic agents in a sequential manner, that is, wherein each therapeutic agent is administered at a different time, as well as administration of these therapeutic agents, or at least two of the therapeutic agents, in a substantially simultaneous manner.

Substantially simultaneous administration is accomplished, for example, by administering to the subject a single formulation or composition, (e.g., a tablet or capsule having a fixed ratio of each therapeutic agent or in multiple, single formulations (e.g., capsules) for each of the therapeutic agents. Sequential or substantially simultaneous administration of each therapeutic agent is effected by any appropriate route including, but not limited to, oral routes, intravenous routes, intramuscular routes, and direct absorption through mucous membrane tissues. The therapeutic agents are administered by the same route or by different routes. For example, a first therapeutic agent of the combination selected is administered by intravenous injection while the other therapeutic agents of the combination are administered orally. Alternatively, for example, all therapeutic agents are administered orally or all therapeutic agents are administered by intravenous injection.

Combination therapy also embraces the administration of the therapeutic agents as described above in further combination with other biologically active ingredients and non-drug therapies. Where the combination therapy further comprises a non-drug treatment, the non-drug treatment is conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The components of the combination are administered to a patient simultaneously or sequentially. It will be appreciated that the components are present in the same pharmaceutically acceptable carrier and, therefore, are administered simultaneously. Alternatively, the active ingredients are present in separate pharmaceutical carriers, such as conventional oral dosage forms, that are administered either simultaneously or sequentially.

For example, e.g., for contemplated treatment of pain, a disclosed compound is co-administered with another therapeutic for pain such as an opioid, a cannabinoid receptor (CB-1 or CB-2) modulator, a COX-2 inhibitor, acetaminophen, and/or a non-steroidal anti-inflammatory agent. Additional therapeutics e.g., for the treatment of pain that are co-administered, include morphine, codeine, hydromorphone, hydrocodone, oxymorphone, fentanyl, tramadol, and levorphanol.

Other contemplated therapeutics for co-administration include aspirin, naproxen, ibuprofen, salsalate, diflunisal, dexibuprofen, fenoprofen, ketoprofen, oxaprozin, loxoprofen, indomethacin, tolmetin, sulindac, etodolac, ketorolac, piroxicam, meloxicam, tenoxicam, droxicam, lornoxicam, celecoxib, parecoxib, rimonabant, and/or etoricoxib.

The following examples are provided merely as illustrative of various embodiments and shall not be construed to limit the invention in any way.

EXAMPLES

List of Abbreviations

As used above, and throughout the description of the invention, the following abbreviations, unless otherwise indicated, shall be understood to have the following meanings:
ACN or MeCN acetonitrile
Bn benzyl
BOC or Boc tert-butyl carbamate
CDI 1,1'-carbonyldiimidazole
Cy cyclohexyl
DCE dichloroethane (ClCH$_2$CH$_2$C$_1$)
DCM dichloromethane (CH$_2$Cl$_2$)
DIPEA or DIEA diisopropylethylamine
DMAP 4-(N,N-dimethylamino)pyridine
DMF dimethylformamide
DMA N,N-dimethylacetamide
DMSO dimethylsulfoxide
equiv equivalent(s)
Et ethyl
EtOH ethanol
EtOAc ethyl acetate
HATU 1-[bis(dimethylamino)methylene]-1H-1,2,3-triazolo[4,5-b]pyridinium 3-oxid hexafluorophosphate
HFIP 1,1,1,3,3,3-hexafluoropropan-2-ol
HPLC high performance liquid chromatography
LAH lithium aluminum hydride
LCMS liquid chromatography-mass spectrometry
Me methyl
MeOH methanol
MS mass spectroscopy
NMM N-methylmorpholine
NMR nuclear magnetic resonance
PMB para-methoxybenzyl
rt room temperature
TEA triethylamine
TFA trifluoroacetic acid
THF tetrahydrofuran
TLC thin layer chromatography I. Chemical Synthesis Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For proton spectra the solvent peak was used as the reference peak.

Example 1: 1,1,1,3,3,3-Hexafluoropropan-2-yl 4-(2-((4-ethoxy-4-oxobutyl)amino)-4-(trifluoromethyl)benzyl)piperazine-1-carboxylate

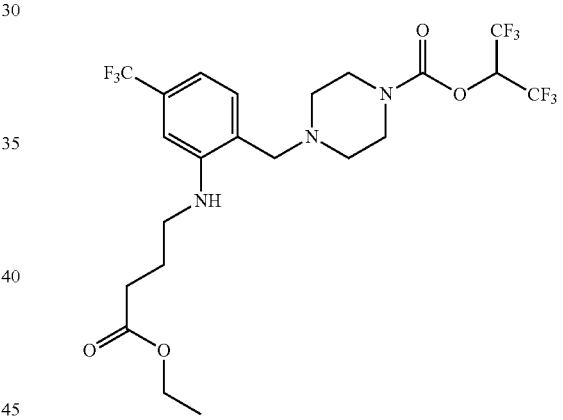

Step 1: Preparation of ethyl 4-((4-methoxybenzyl)amino)butanoate

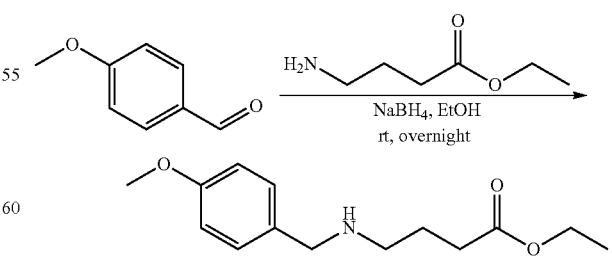

A flask was charged with ethyl 4-aminobutanoate (1.00 g, 7.62 mmol, 1.00 equiv), EtOH (15 mL), and 4-methoxybenzaldehyde (1.04 mg, 7.62 mmol, 1.00 equiv). The resulting solution was stirred for 5 h at 70° C. Sodium borohydride (176 mg, 4.65 mmol, 0.60 equiv) was added and the resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with EtOAc/petroleum ether (3/17) to provide 800 mg (42% yield) of ethyl 4-((4-methoxybenzyl)amino)butanoate as a white oil. LCMS (ESI, m/z): 252 [M+H]$^+$.

Step 2: Preparation of ethyl 4-((2-formyl-5-(trifluoromethyl)phenyl)(4-methoxybenzyl)amino)butanoate

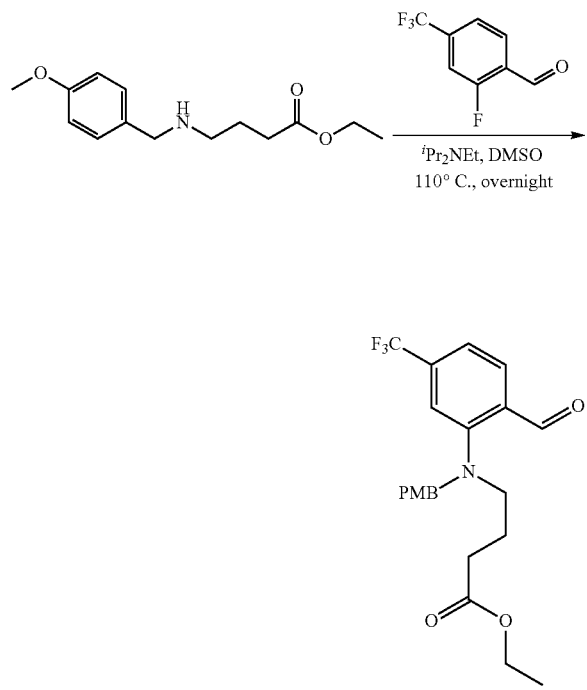

A flask was charged with ethyl 4-((4-methoxybenzyl)amino)butanoate (400 mg, 1.59 mmol, 1.00 equiv), 2-fluoro-4-(trifluoromethyl)benzaldehyde (304 mg, 1.59 mmol, 1.00 equiv), DMSO (15 mL), and DIPEA (620 mg, 4.77 mmol, 3.00 equiv). The resulting solution was stirred overnight at 110° C. and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with EtOAc/petroleum ether (1/4) to provide 110 mg (16% yield) of ethyl 4-((2-formyl-5-(trifluoromethyl)phenyl)(4-methoxybenzyl)amino)butanoate as a light yellow oil. LCMS (ESI, m/z): 424 [M+H]$^+$.

Step 3: Preparation of 1-(tert-butyl) 4-(1,1,1,3,3,3-hexafluoropropan-2-yl) piperazine-1,4-dicarboxylate

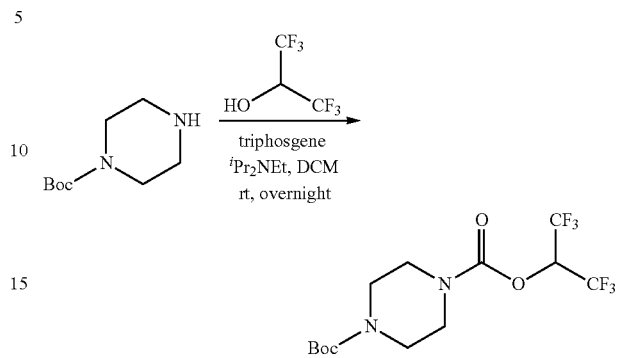

A flask was charged with triphosgene (7.98 g, 26.9 mmol, 0.50 equiv), DCM (150 mL), and HFIP (18.1 g, 108 mmol, 2.00 equiv) under nitrogen. DIPEA (20.8 g, 161 mmol, 3.00 equiv) was added at 0° C. and the resulting solution was stirred for 2 h at 0° C. tert-Butyl piperazine-1-carboxylate (10.0 g, 53.7 mmol, 1.00 equiv) was added and the resulting solution was stirred overnight at rt and quenched with water (150 mL). The resulting solution was extracted with DCM (2×200 mL) and the organic layers were combined, washed with brine (2×150 mL), dried over anhydrous sodium sulfate, filtered and concentrated. The residue was chromatographed on a silica gel column with EtOAc/petroleum ether (1/4) to provide 15.5 g (76% yield) of 1-(tert-butyl) 4-(1,1,1,3,3,3-hexafluoropropan-2-yl) piperazine-1,4-dicarboxylate as a white solid. LCMS (ESI, m/z): 381 [M+H]$^+$.

Step 4: Preparation of 1,1,1,3,3,3-hexafluoropropan-2-yl piperazine-1-carboxylate, 2,2,2-trifluoroacetate salt

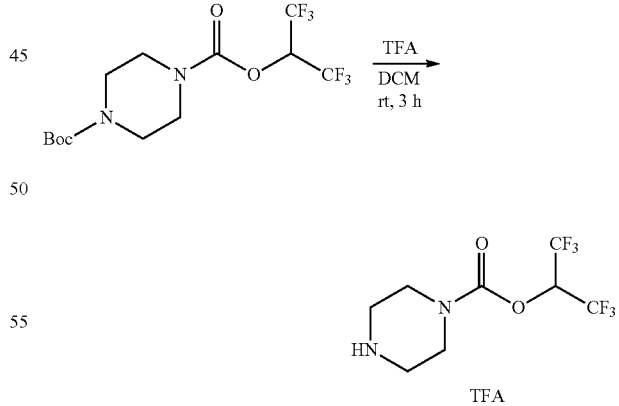

A flask was charged with 1-(tert-butyl) 4-(1,1,1,3,3,3-hexafluoropropan-2-yl) piperazine-1,4-dicarboxylate (200 mg, 0.530 mmol, 1.00 equiv), DCM (10 mL), and TFA (2 mL). The resulting solution was stirred for 3 h at rt and concentrated to provide 250 mg of 1,1,1,3,3,3-hexafluoropropan-2-yl piperazine-1-carboxylate, 2,2,2-trifluoroacetate salt as a light yellow oil. LCMS (ESI, m/z): 281 [M+H]$^+$.

Step 5: Preparation of 1,1,1,3,3,3-hexafluoropropan-2-yl 4-(2-((4-ethoxy-4-oxobutyl)(4-methoxybenzyl)amino)-4-(trifluoromethyl)benzyl)piperazine-1-carboxylate

Step 6: Preparation of 1,1,1,3,3,3-hexafluoropropan-2-yl 4-(2-((4-ethoxy-4-oxobutyl)amino)-4-(trifluoromethyl)benzyl)piperazine-1-carboxylate

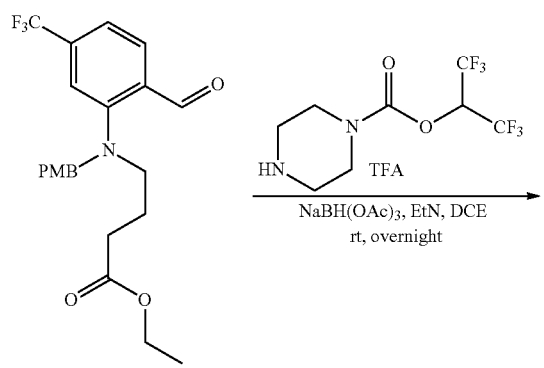

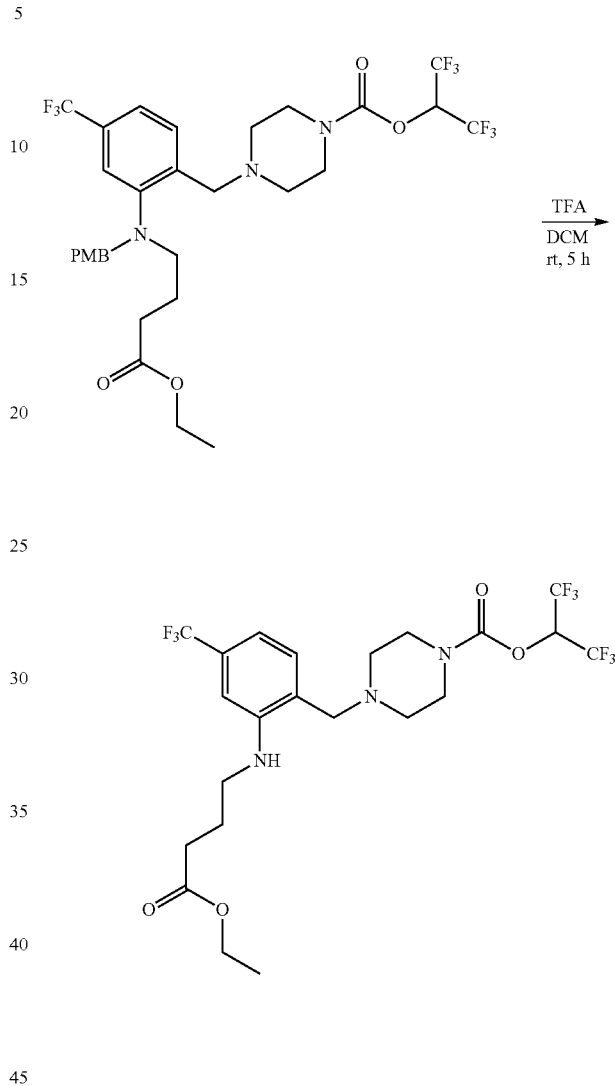

A flask was charged with ethyl 4-((2-formyl-5-(trifluoromethyl)phenyl)(4-methoxybenzyl)amino)butanoate (110 mg, 0.260 mmol, 1.00 equiv), DCE (10 mL), TEA (79.0 mg, 0.780 mmol, 3.00 equiv), and 1,1,1,3,3,3-hexafluoropropan-2-yl piperazine-1-carboxylate, 2,2,2-trifluoroacetate salt (73.0 mg, 0.260 mmol, 1.00 equiv). The mixture was stirred for 1 h at rt and sodium triacetoxyborohydride (129 mg, 0.780 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (96/4) to provide 170 mg (95% yield) of 1,1,1,3,3,3-hexafluoropropan-2-yl 4-(2-((4-ethoxy-4-oxobutyl)(4-methoxybenzyl)amino)-4-(trifluoromethyl)benzyl)piperazine-1-carboxylate as a light yellow oil. LCMS (ESI, m/z): 688 [M+H]+.

A flask was charged with 1,1,1,3,3,3-hexafluoropropan-2-yl 4-(2-((4-ethoxy-4-oxobutyl)(4-methoxybenzyl)amino)-4-(trifluoromethyl)benzyl)piperazine-1-carboxylate (170 mg, 0.250 mmol, 1.00 equiv), DCM (10 mL), and TFA (2 mL). The resulting solution was stirred for 3 h at rt and concentrated. The crude product (180 mg) was purified by preparative HPLC to provide 28.9 mg (21% yield) of 1,1,1,3,3,3-hexafluoropropan-2-yl 4-(2-((4-ethoxy-4-oxobutyl)amino)-4-(trifluoromethyl)benzyl)piperazine-1-carboxylate as a light yellow oil. $^1$H NMR (300 MHz, Methanol-$d_4$) δ 7.15-7.18 (m, 1H), 6.84-6.87 (m, 2H), 6.13-6.21 (m, 1H), 4.11-4.18 (m, 2H), 3.57-3.60 (m, 6H), 3.24 (t, J=6 Hz, 2H), 2.46-2.53 (m, 6H), 1.95-2.04 (m, 2H) 1.26 (t, J=3 Hz, 3H). LCMS (ESI, m/z): 568 [M+H]+.

Example 2: 1,1,1,3,3,3-Hexafluoropropan-2-yl 4-(2-((4-(tert-butoxy)-4-oxobutyl)amino)-4-(trifluoromethyl)benzyl)piperazine-1-carboxylate

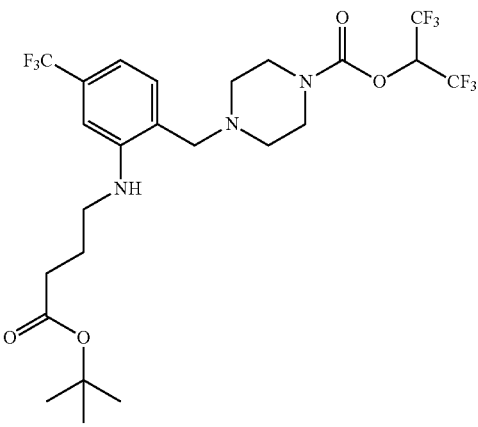 [SMILES: CC(C)(C)OC(=O)CCCNc1cc(C(F)(F)F)ccc1CN1CCN(C(=O)OC(C(F)(F)F)C(F)(F)F)CC1]

Step 1: Preparation of 1,1,1,3,3,3-Hexafluoropropan-2-yl 4-(2-((4-(tert-butoxy)-4-oxobutyl)amino)-4-(trifluoromethyl)benzyl)piperazine-1-carboxylate

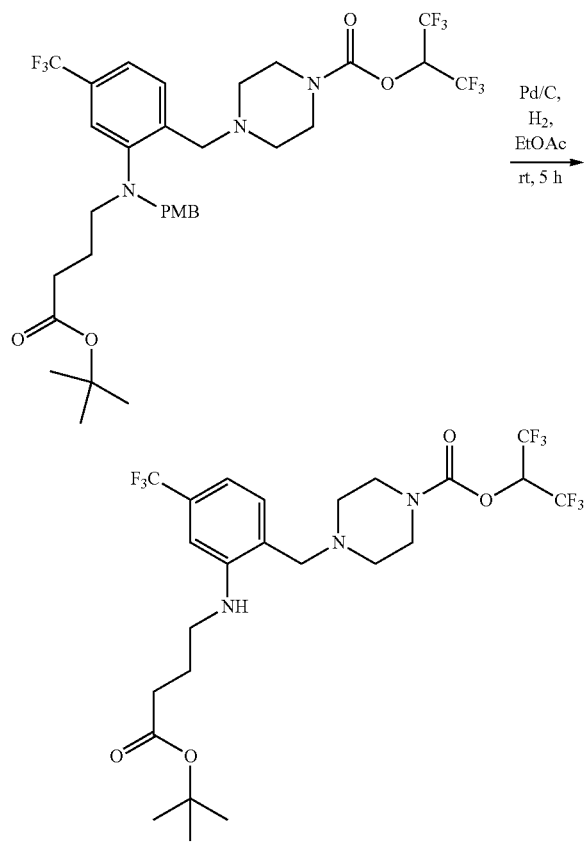

A flask was charged with EtOAc (10 mL) and 1,1,1,3,3,3-hexafluoropropan-2-yl 4-(2-((4-(tert-butoxy)-4-oxobutyl)(4-methoxybenzyl)amino)-4-(trifluoromethyl)benzyl)piperazine-1-carboxylate (200 mg, 0.280 mmol, 1.00 equiv, prepared as described in Example 1, Steps 1-5 using tert-butyl 4-aminobutanoate in Step 1). Hydrogen was introduced and the resulting solution was stirred for 5 h at rt before the solids were filtered and the filtrate concentrated. The crude product was purified by preparative HPLC to provide 64.6 mg (39% yield) of 1,1,1,3,3,3-hexafluoropropan-2-yl 4-(2-((4-(tert-butoxy)-4-oxobutyl)amino)-4-(trifluoromethyl)benzyl)piperazine-1-carboxylate as a light yellow oil. $^1$H NMR (400 MHz, Chloroform-d) δ 7.05 (d, J=7.2 Hz, 1H), 6.86 (d, J=7.6 Hz, 1H), 6.78 (s, 1H), 6.13 (br s, 1H), 5.73-5.76 (m, 1H), 3.56 (br s, 6H), 3.19 (t, J=6.6 Hz, 2H), 2.45 (s, 4H), 2.37 (t, J=7.2 Hz, 2H), 1.93-1.97 (m, 2H), 1.45 (s, 9H). LCMS (ESI, m/z): 596 [M+H]$^+$.

Example 3: 4-(2-((4-(((1,1,1,3,3,3-Hexafluoropropan-2-yl)oxy)carbonyl)piperazin-1-yl)methyl)-5-(trifluoromethyl)phenoxy)butanoic acid

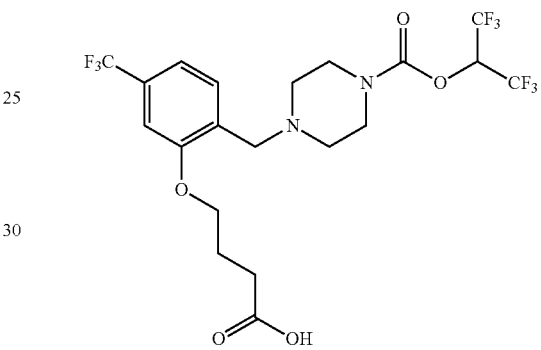

Step 1: Preparation of 2-hydroxy-4-(trifluoromethyl)benzaldehyde

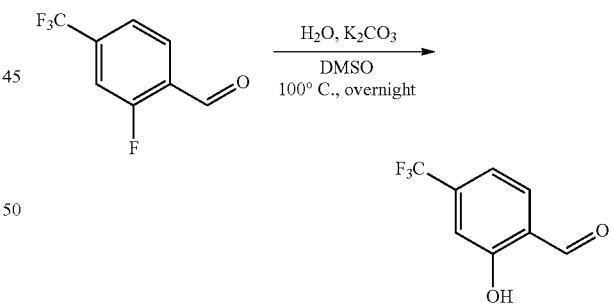

A flask was charged with 2-fluoro-4-(trifluoromethyl)benzaldehyde (1.00 g, 5.21 mmol, 1.00 equiv), water (2 mL), DMSO (10 mL), and potassium carbonate (2.16 g, 15.6 mmol, 3.00 equiv) under nitrogen. The resulting solution was stirred overnight at 110° C. and quenched with water (50 mL). The resulting solution was extracted with EtOAc (2×80 mL) and the organic layers were combined, washed with brine (2×50 mL), dried over anhydrous sodium sulfate, filtered and concentrated. The residue was chromatographed on a silica gel column with EtOAc/petroleum ether (1/19) to provide 500 mg (51% yield) of 2-hydroxy-4-(trifluoromethyl)benzaldehyde as a light yellow oil.

Step 2: Preparation of tert-butyl 4-(2-formyl-5-(trifluoromethyl)phenoxy)butanoate

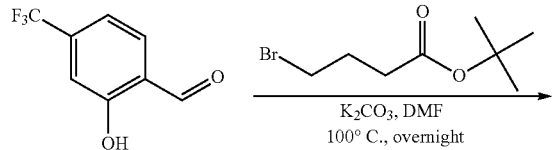

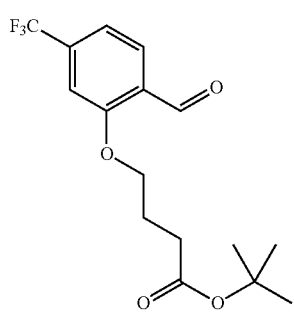

A flask was charged with 2-hydroxy-4-(trifluoromethyl)benzaldehyde (300 mg, 1.58 mmol, 1.00 equiv), DMF (10 mL), potassium carbonate (654 mg, 4.73 mmol, 3.00 equiv), and tert-butyl 4-bromobutanoate (702 mg, 3.15 mmol, 2.00 equiv). The resulting solution was stirred overnight at 100° C. and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with EtOAc/petroleum ether (1/10) to provide 450 mg (86% yield) of tert-butyl 4-(2-formyl-5-(trifluoromethyl)phenoxy)butanoate as a light yellow solid. $^1$H NMR (300 MHz, Chloroform-d) δ 10.5 (s, 1H), 7.96 (d, J=7.5 Hz, 1H), 7.29-7.33 (m, 2H), 4.22 (t, J=6.0 Hz, 2H), 2.50 (t, J=6.0 Hz, 2H), 2.18-2.25 (m, 2H), 1.49 (s, 9H).

Step 3: Preparation of 1,1,1,3,3,3-hexafluoropropan-2-yl 4-(2-(4-(tert-butoxy)-4-oxobutoxy)-4-(trifluoromethyl)benzyl)piperazine-1-carboxylate

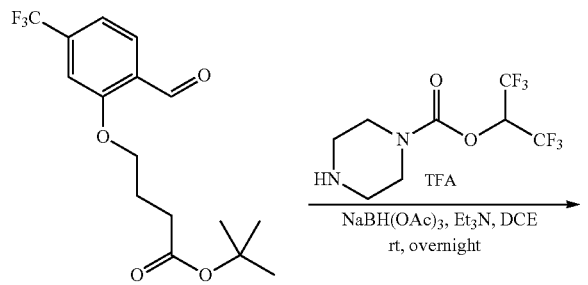

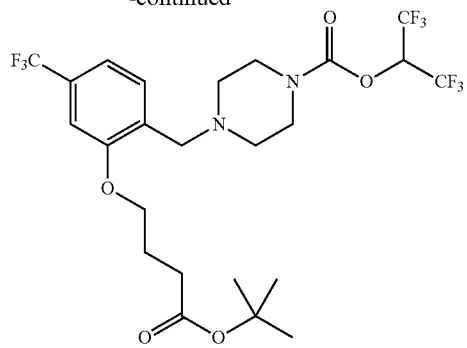

A flask was charged with 1,1,1,3,3,3-hexafluoropropan-2-yl piperazine-1-carboxylate, 2,2,2-trifluoroacetate salt (202 mg, 0.720 mmol, 1.20 equiv, prepared as described in Example 1, Steps 3-4), DCE (10 mL), TEA (183 mg, 1.80 mmol, 3.00 equiv), and tert-butyl 4-(2-formyl-5-(trifluoromethyl)phenoxy)butanoate (200 mg, 0.600 mmol, 1.00 equiv). The mixture was stirred for 1 h at rt. Sodium triacetoxyborohydride (382 mg, 1.80 mmol, 3.00 equiv) was added and the reaction mixture was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 230 mg (64% yield) of 1,1,1,3,3,3-hexafluoropropan-2-yl 4-(2-(4-(tert-butoxy)-4-oxobutoxy)-4-(trifluoromethyl)benzyl)piperazine-1-carboxylate as a light yellow oil. LCMS (ESI, m/z): 597 [M+H]$^+$.

Step 4: Preparation of 4-(2-((4-(((1,1,1,3,3,3-hexafluoropropan-2-yl)oxy)carbonyl)piperazin-1-yl)methyl)-5-(trifluoromethyl)phenoxy)butanoic acid

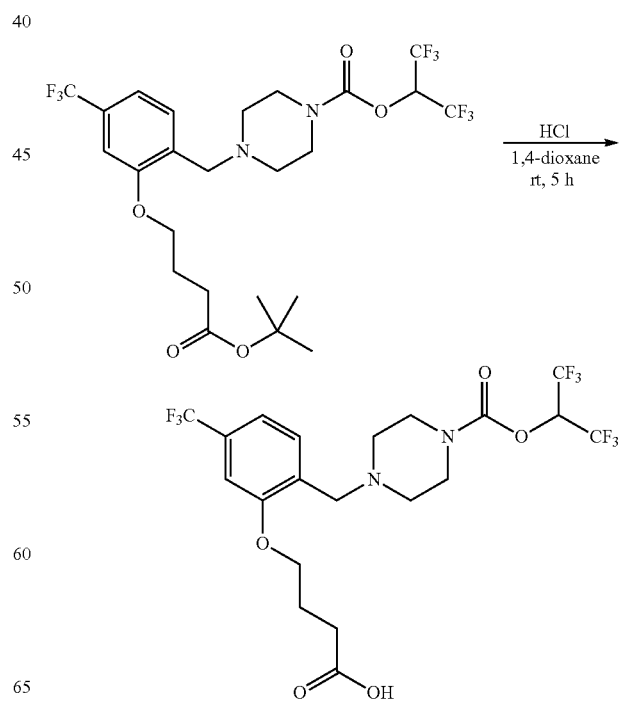

A flask was charged with 1,1,1,3,3,3-hexafluoropropan-2-yl 4-(2-(4-(tert-butoxy)-4-oxobutoxy)-4-(trifluoromethyl)benzyl)piperazine-1-carboxylate (200 mg, 0.340 mmol, 1.00 equiv), 1,4-dioxane (10 mL), and hydrochloric acid (3 mL). The resulting solution was stirred for 3 h at rt and concentrated. The crude product (400 mg) was purified by preparative HPLC to provide 46.4 mg (26% yield) of 4-(2-((4-(((1,1,1,3,3,3-hexafluoropropan-2-yl)oxy)carbonyl)piperazin-1-yl)methyl)-5-(trifluoromethyl)phenoxy)butanoic acid as a white solid. $^1$H NMR (300 MHz, Methanol-$d_4$) δ 7.53 (d, J=7.8 Hz, 1H), 7.19-7.24 (m, 2H), 6.10-6.18 (m, 1H), 4.11 (t, J=6.2 Hz, 2H), 3.68 (s, 2H), 3.56-3.62 (m, 4H), 2.58-2.61 (m, 4H), 2.49 (t, J=7.2 Hz, 2H), 2.08-2.17 (m, 2H). LCMS (ESI, m/z): 541 [M+H]$^+$.

Example 4: 4-(5-Chloro-2-((4-(((1,1,1,3,3,3-hexafluoropropan-2-yl)oxy)carbonyl)piperazin-1-yl)methyl)phenoxy)butanoic acid

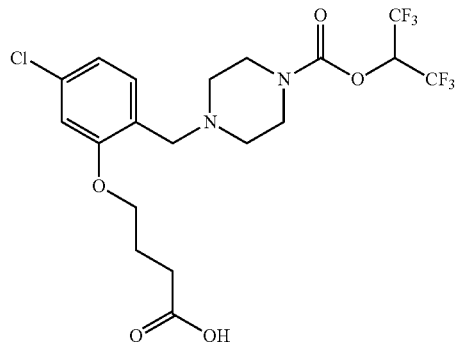

The title compound was prepared according to the representative procedure of Example 3 using commercially available 4-chloro-2-hydroxybenzaldehyde in Step 2 to provide 4-(5-chloro-2-((4-(((1,1,1,3,3,3-hexafluoropropan-2-yl)oxy)carbonyl)piperazin-1-yl)methyl)phenoxy)butanoic acid as an off-white solid. $^1$H NMR (300 MHz, Methanol-$d_4$) δ 7.29 (d, J=8.1 Hz, 1H), 7.01 (s, 1H), 6.92-6.96 (m, 1H), 6.10-6.19 (m, 1H), 4.07 (t, J=6.0 Hz, 2H), 3.70 (s, 2H), 3.63 (br s, 4H), 2.67-2.68 (m, 4H), 2.48 (t, J=7.0 Hz, 2H), 2.07-2.16 (m, 2H). LCMS (ESI, m/z): 507 [M+H]$^+$.

Example 5: 1,1,1,3,3,3-Hexafluoropropan-2-yl 4-(2-((4-(1-((ethoxycarbonyl)oxy)ethoxy)-4-oxobutyl)amino)-4-(trifluoromethyl)benzyl)piperazine-1-carboxylate

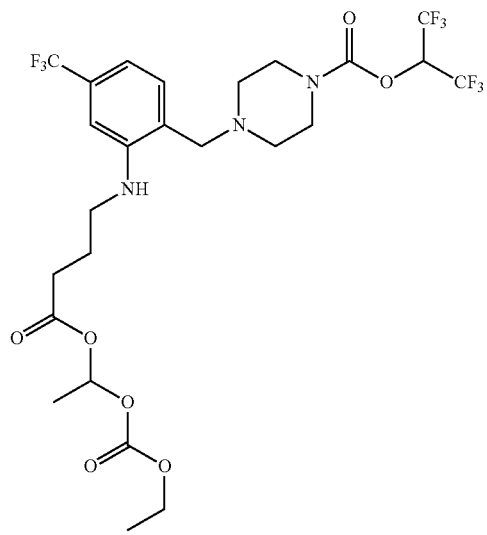 [SMILES: CCOC(=O)OC(C)OC(=O)CCCNc1cc(C(F)(F)F)ccc1CN1CCN(C(=O)OC(C(F)(F)F)C(F)(F)F)CC1]

Step 1: Preparation of tert-butyl 4-(benzyl(2-formyl-5-(trifluoromethyl)phenyl)amino)butanoate

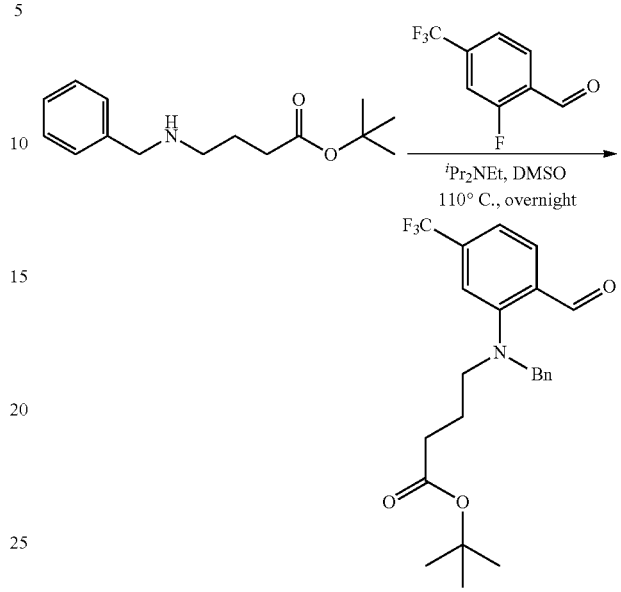

A flask was charged with tert-butyl 4-(benzylamino)butanoate (230 mg, 0.920 mmol, 1.00 equiv, prepared as described in Example 1, Step 1 using benzaldehyde and tert-butyl 4-aminobutanoate), 2-fluoro-4-(trifluoromethyl)benzaldehyde (177 mg, 0.920 mmol, 1.00 equiv), DMSO (10 mL), and DIPEA (356 mg, 2.75 mmol, 3.00 equiv). The reaction mixture was stirred overnight at 110° C. and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with EtOAc/petroleum ether (1/9) to provide 135 mg (35% yield) of tert-butyl 4-(benzyl(2-formyl-5-(trifluoromethyl)phenyl)amino)butanoate as a yellow oil. LCMS (ESI, m/z): 422 [M+H]$^+$.

Step 2: Preparation of 4-(benzyl(2-formyl-5-(trifluoromethyl)phenyl)amino)butanoic acid, 2,2,2-trifluoroacetate salt

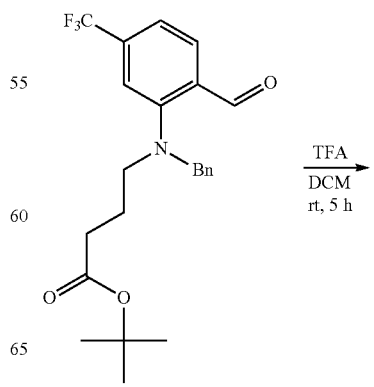

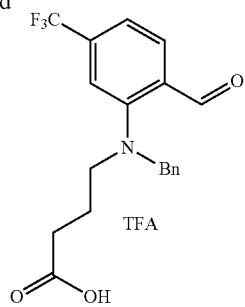

A flask was charged with tert-butyl 4-(benzyl(2-formyl-5-(trifluoromethyl)phenyl)amino)butanoate (800 mg, 1.90 mmol, 1.00 equiv), DCM (2 mL), and TFA (10 mL). The resulting solution was stirred for 5 h at rt and concentrated to provide 830 mg (crude) of 4-(benzyl(2-formyl-5-(trifluoromethyl)phenyl)amino)butanoic acid, 2,2,2-trifluoroacetate salt as a yellow oil. LCMS (ESI, m/z): 366 [M+H]+.

Step 3: Preparation of 1-((ethoxycarbonyl)oxy)ethyl 4-(benzyl(2-formyl-5-(trifluorometh)phenyl)amino) butanoate

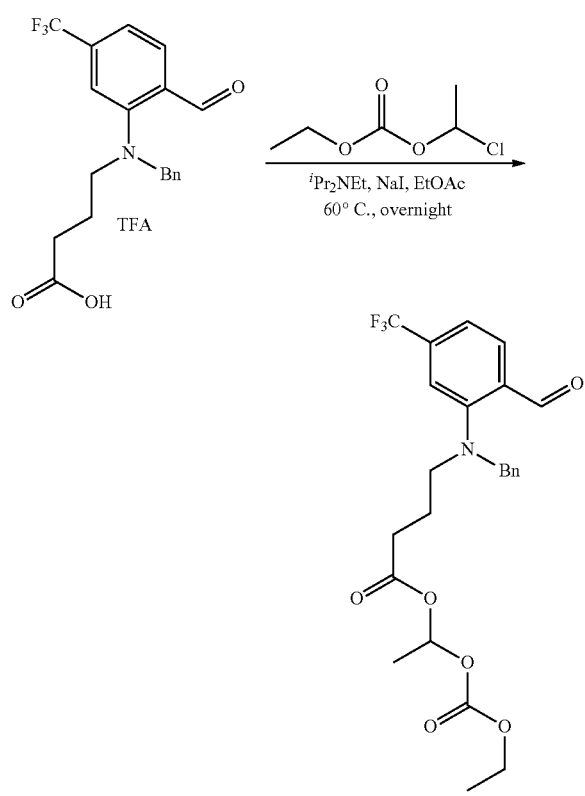

A flask was charged with 4-(benzyl(2-formyl-5-(trifluoromethyl)phenyl)amino)butanoic acid, 2,2,2-trifluoroacetate salt (300 mg, 0.820 mmol, 1.00 equiv), EtOAc (10 mL), 1-chloroethyl ethyl carbonate (138 mg, 0.900 mmol, 1.10 equiv), DIPEA (99.0 mg, 0.770 mmol, 1.20 equiv), and sodium iodide (49.0 mg, 0.328 mmol, 0.400 equiv) under nitrogen. The reaction mixture was stirred overnight at 60° C. and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with EtOAc/petroleum ether (1/4) to provide 330 mg (83% yield) of 1-((ethoxycarbonyl)oxy)ethyl 4-(benzyl(2-formyl-5-(trifluoromethyl)phenyl)amino)butanoate as a yellow oil. LCMS (ESI, m/z): 482 [M+H]+.

Step 4: Preparation of 1,1,1,3,3,3-hexafluoropropan-2-yl 4-(2-(benzyl(4-(1-((ethoxycarbonyl)oxy)ethoxy)-4-oxobutyl)amino)-4-(trifluoromethyl)benzyl)piperazine-1-carboxylate

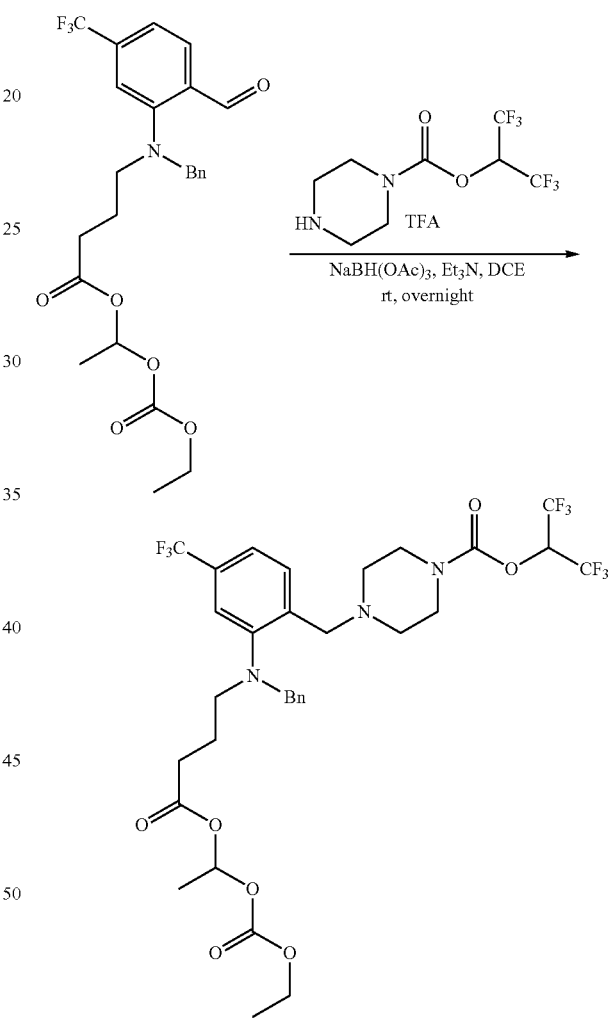

A flask was charged with 1-((ethoxycarbonyl)oxy)ethyl 4-(benzyl(2-formyl-5-(trifluoromethyl)phenyl)amino)butanoate (250 mg, 0.520 mmol, 1.00 equiv), DCE (10 mL), and 1,1,1,3,3,3-hexafluoropropan-2-yl piperazine-1-carboxylate, 2,2,2-trifluoroacetate salt (145 g, 0.520 mmol, 1.00 equiv, prepared as described in Example 1, Steps 3-4). The mixture was stirred for 1 h at rt and then sodium triacetoxyborohydride (330 mg, 1.56 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 320 mg (83% yield) of 1,1,1,3,3,3-hexafluoropropan-2-yl 4-(2-(benzyl(4-(1-((ethoxycarbonyl)oxy)ethoxy)-4-oxobutyl)amino)-4-(trifluoromethyl)benzyl)piperazine-1-carboxylate as a yellow oil. LCMS (ESI, m/z): 746 [M+H]+.

Step 5: Preparation of 1,1,1,3,3,3-hexafluoropropan-2-yl 4-(2-((4-(1-((ethoxycarbonyl)oxy)ethoxy)-4-oxobutyl)amino)-4-(trifluoromethyl)benzyl)piperazine-1-carboxylate

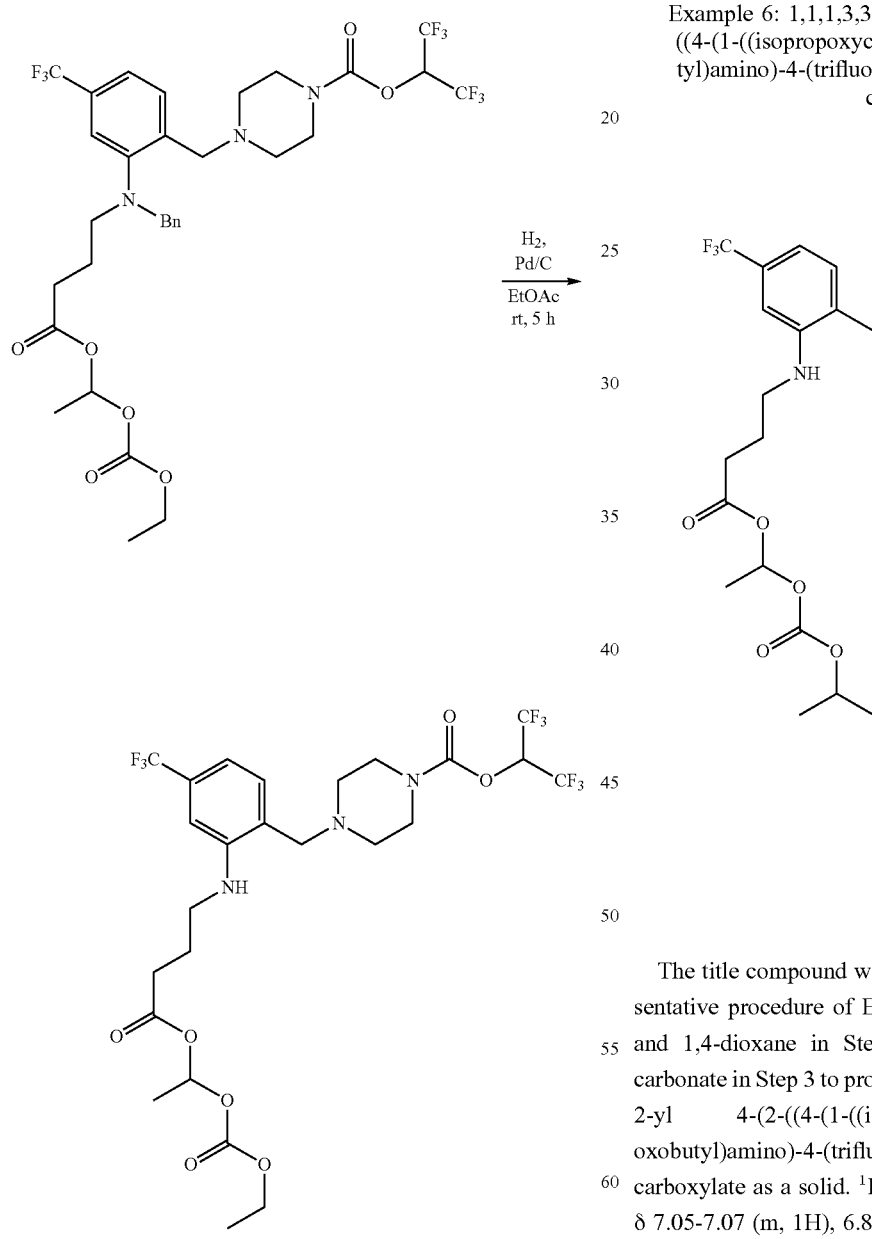

A flask was charged with 1,1,1,3,3,3-hexafluoropropan-2-yl 4-(2-(benzyl(4-(1-((ethoxycarbonyl)oxy)ethoxy)-4-oxobutyl)amino)-4-(trifluoromethyl)benzyl)piperazine-1-carboxylate (320 mg, 0.430 mmol, 1.00 equiv), EtOAc (10 mL) and palladium on carbon (107 mg). Hydrogen was introduced into the reaction mixture. After 5 h at rt, the solids were removed by filtration. The filtrate was then concentrated and purified by preparative HPLC to provide 133.6 mg (47% yield) of 1,1,1,3,3,3-hexafluoropropan-2-yl 4-(2-((4-(1-((ethoxycarbonyl)oxy)ethoxy)-4-oxobutyl)amino)-4-(trifluoromethyl)benzyl)piperazine-1-carboxylate as a colorless oil. $^1$H NMR (300 MHz, Chloroform-d) δ 7.05-7.07 (m, 1H), 6.86-6.91 (m, 1H), 6.75-6.80 (m, 2H), 6.13 (br s, 1H), 5.70-5.79 (m, 1H), 4.15-4.25 (m, 2H), 3.55 (br s, 6H), 3.19-3.23 (m, 2H), 2.47-2.52 (m, 6H), 1.99-2.03 (m, 2H), 1.51 (d, J=5.4 Hz, 3H), 1.30 (t, J=7.2 Hz, 3H). LCMS (ESI, m/z): 656 [M+H]+.

Example 6: 1,1,1,3,3,3-Hexafluoropropan-2-yl 4-(2-((4-(1-((isopropoxycarbonyl)oxy)ethoxy)-4-oxobutyl)amino)-4-(trifluoromethyl)benzyl)piperazine-1-carboxylate

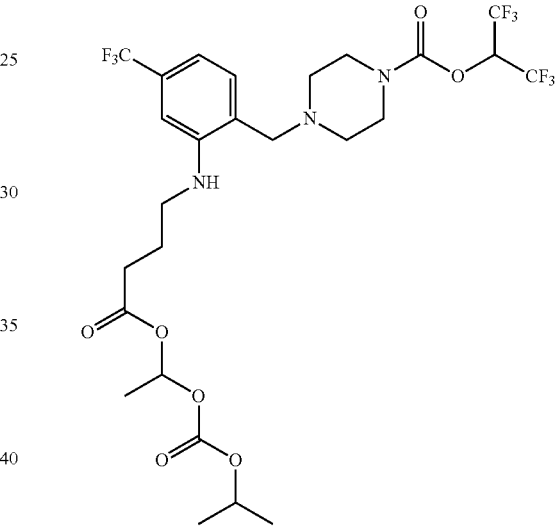

The title compound was prepared according to the representative procedure of Example 5 using hydrochloric acid and 1,4-dioxane in Step 2 and 1-chloroethyl isopropyl carbonate in Step 3 to provide 1,1,1,3,3,3-hexafluoropropan-2-yl 4-(2-((4-(1-((isopropoxycarbonyl)oxy)ethoxy)-4-oxobutyl)amino)-4-(trifluoromethyl)benzyl)piperazine-1-carboxylate as a solid. $^1$H NMR (300 MHz, Chloroform-d) δ 7.05-7.07 (m, 1H), 6.87 (d, J=6.0 Hz, 1H), 6.77-6.80 (m, 2H), 6.12 (br s, 1H), 5.70-5.79 (m, 1H), 4.82-4.91 (m, 1H), 3.56 (br s, 6H), 3.19-3.23 (m, 2H), 2.47-2.52 (m, 6H), 1.99-2.03 (m, 2H), 1.51 (d, J=5.7 Hz, 3H), 1.27-1.31 (m, 6H). LCMS (ESI, m/z): 670 [M+H]+.

Example 7: 1,1,1,3,3,3-Hexafluoropropan-2-yl 4-(2-((4-oxo-4-((pivaloyloxy)methoxy)butyl)amino)-4-(trifluoromethyl)benzyl)piperazine-1-carboxylate

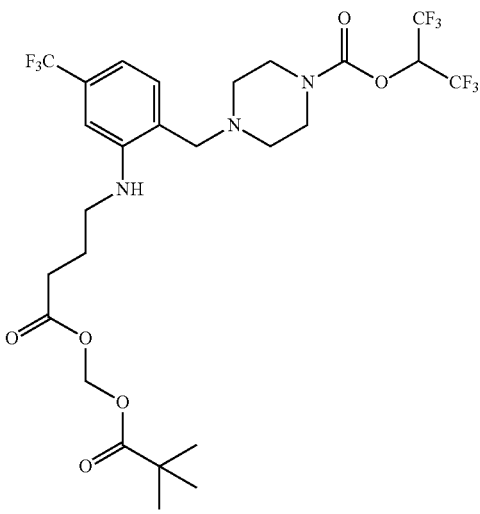 [SMILES: CC(C)(C)C(=O)OCOC(=O)CCCNc1cc(C(F)(F)F)ccc1CN1CCN(C(=O)OC(C(F)(F)F)C(F)(F)F)CC1]

Step 1: Preparation of 4-(benzyl(2-formyl-5-(trifluoromethyl)phenyl)amino)butanoic acid hydrochloride

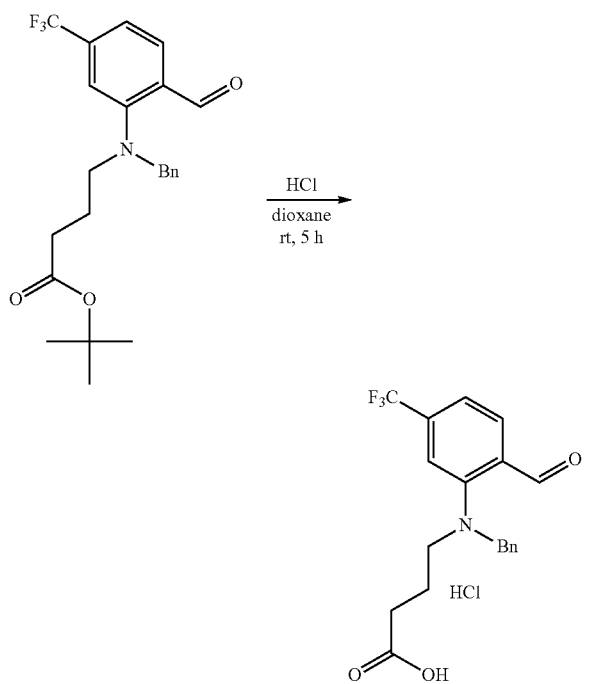

A flask was charged with tert-butyl 4-(benzyl(2-formyl-5-(trifluoromethyl)phenyl)amino)butanoate hydrochloride (350 mg, 0.830 mmol, 1.00 equiv, prepared as described in Example 5, Step 1), 1,4-dioxane (10 mL), and hydrochloric acid (2 mL). The resulting solution was stirred overnight at rt and concentrated to provide 360 mg (crude) of 4-(benzyl (2-formyl-5-(trifluoromethyl)phenyl)amino)butanoic acid hydrochloride as a light yellow oil. LCMS (ESI, m/z): 366 [M+H]$^+$.

Step 2: Preparation of 1-(pivaloyloxy)methyl 4-(benzyl(2-formyl-5-(trifluoromethyl)phenyl) amino)butanoate

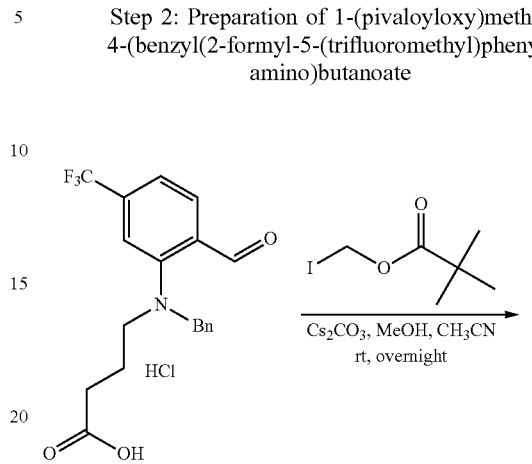

A flask was charged with 4-(benzyl(2-formyl-5-(trifluoromethyl)phenyl)amino)butanoic acid hydrochloride (303 mg, 0.830 mmol, 1.00 equiv), MeOH (10 mL), and cesium carbonate (270 mg, 0.830 mmol, 1.00 equiv). The resulting solution was stirred for 3 h at rt and concentrated. MeCN (10 mL) and iodomethyl pivalate (602 mg, 2.49 mmol, 3.00 equiv) were added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered, and concentrated. The residue was chromatographed on a silica gel column with EtOAc/petroleum ether (1/4) to provide 300 mg (75% yield) of 1-(pivaloyloxy)methyl 4-(benzyl(2-formyl-5-(trifluoromethyl)phenyl)amino)butanoate as a yellow oil. LCMS (ESI, m/z): 480 [M+H]$^+$.

Step 3: Preparation of 1,1,1,3,3,3-hexafluoropropan-2-yl 4-(2-(benzyl(4-oxo-4-((pivaloyloxy)methoxy)butyl)amino)-4-(trifluoromethyl)benzyl)piperazine-1-carboxylate

Step 4: Preparation of 1,1,1,3,3,3-hexafluoropropan-2-yl 4-(2-((4-oxo-4-((pivaloyloxy)methoxy)butyl)amino)-4-(trifluoromethyl)benzyl)piperazine-1-carboxylate

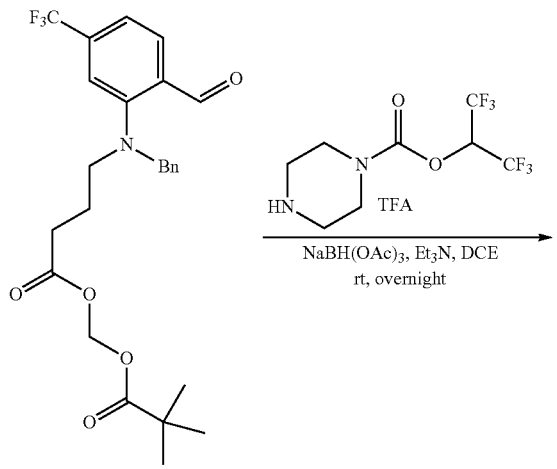

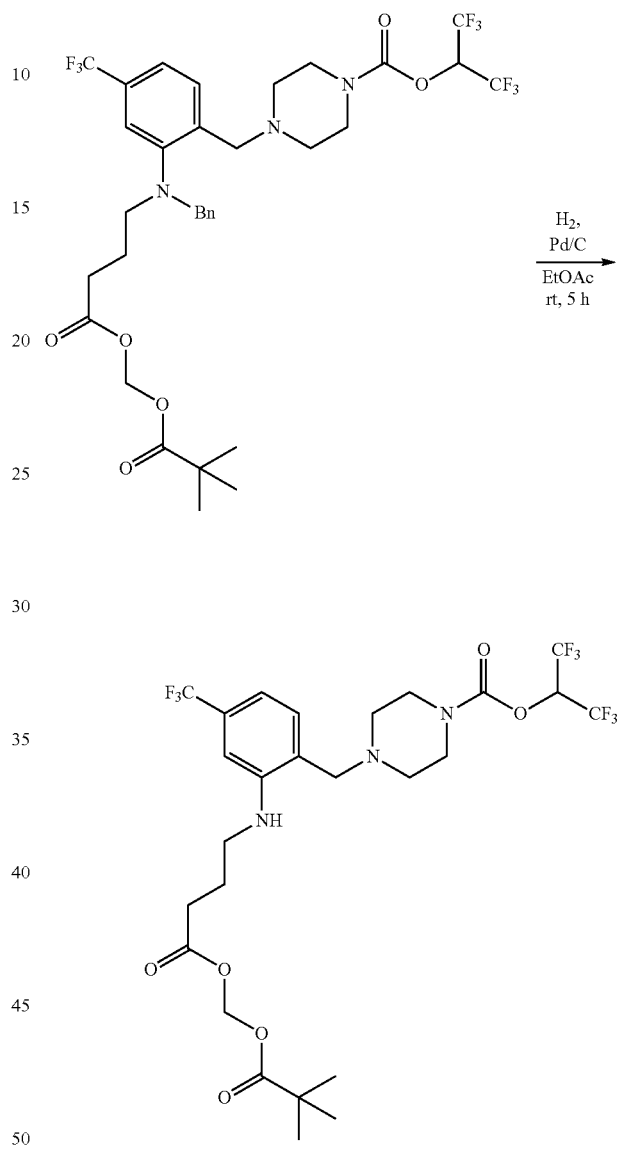

A flask was charged with 1-(pivaloyloxy)methyl 4-(benzyl(2-formyl-5-(trifluoromethyl)phenyl)amino)butanoate (300 mg, 0.630 mmol, 1.00 equiv), DCE (10 mL), TEA (199 mg, 1.97 mmol, 3.00 equiv), and 1,1,1,3,3,3-hexafluoropropan-2-yl piperazine-1-carboxylate, 2,2,2-trifluoroacetate salt (175 mg, 0.620 mmol, 1.00 equiv, prepared as described in Example 1, Steps 3-4). The mixture was stirred for 1 h at rt and sodium triacetoxyborohydride (398 mg, 1.97 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered, and concentrated. The residue was chromatographed on a silica gel column with DCM/MeOH (96/4) to provide 200 mg (43% yield) of 1,1,1,3,3,3-hexafluoropropan-2-yl 4-(2-(benzyl(4-oxo-4-((pivaloyloxy)methoxy)butyl)amino)-4-(trifluoromethyl)benzyl)piperazine-1-carboxylate as a yellow oil. LCMS (ESI, m/z): 744 [M+H]$^+$.

A flask was charged with 1,1,1,3,3,3-hexafluoropropan-2-yl 4-(2-(benzyl(4-oxo-4-((pivaloyloxy)methoxy)butyl)amino)-4-(trifluoromethyl)benzyl)piperazine-1-carboxylate (200 mg, 0.270 mmol, 1.00 equiv), EtOAc (10 mL), and 10% palladium on carbon (67.0 mg). Hydrogen was introduced into the reaction mixture. After 5 h at rt, the reaction was filtered and the filtrate was concentrated and purified by preparative HPLC to provide 22.4 mg (13% yield) of 1,1,1,3,3,3-hexafluoropropan-2-yl 4-(2-((4-oxo-4-((pivaloyloxy)methoxy)butyl)amino)-4-(trifluoromethyl)benzyl)piperazine-1-carboxylate as a colorless oil. $^1$H NMR (300 MHz, Chloroform-d) δ 7.06 (d, J=7.5 Hz, 1H), 6.87 (d, J=7.8 Hz, 1H), 6.77 (s, 1H), 6.15 (br s, 1H), 5.73-5.77 (m, 3H), 3.55 (s, 6H), 3.20 (t, J=6.8 Hz, 2H), 2.45-2.54 (m, 6H), 1.99-2.03 (m, 2H), 1.19 (s, 9H). LCMS (ESI, m/z): 654 [M+H]$^+$.

Example 8: 1,1,1,3,3,3-Hexafluoropropan-2-yl 4-(2-((4-(1-(isobutyryloxy)ethoxy)-4-oxobutyl)amino)-4-(trifluoromethyl)benzyl)piperazine-1-carboxylate

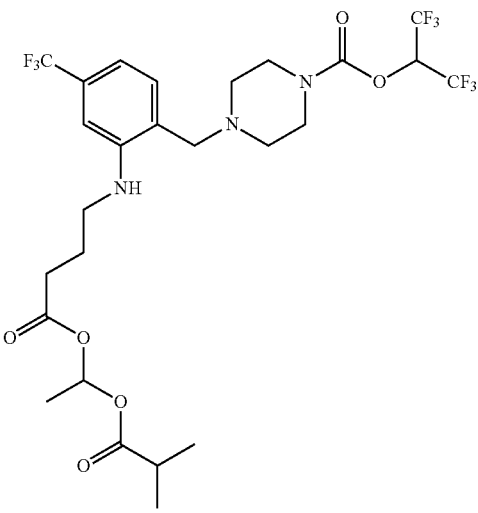 [SMILES: CC(OC(=O)CCCNc1cc(C(F)(F)F)ccc1CN1CCN(C(=O)OC(C(F)(F)F)C(F)(F)F)CC1)OC(=O)C(C)C]

Step 1: Preparation of 1-(isobutyryloxy)ethyl 4-(benzyl(2-formyl-5-(trifluoromethyl)phenyl)amino)butanoate

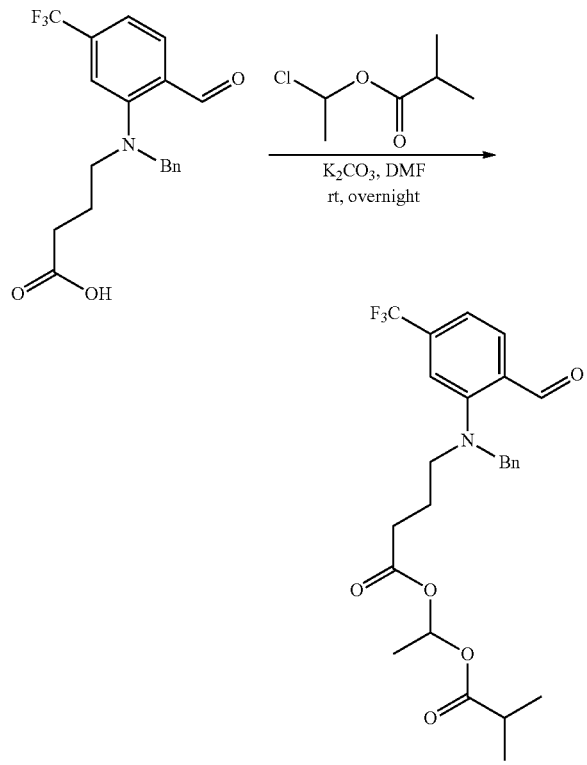

A flask was charged with 4-(benzyl(2-formyl-5-(trifluoromethyl)phenyl)amino)butanoic acid (260 mg, 0.710 mmol, 1.00 equiv, prepared as described in Example 7, Step 1), DMF (10 mL), 1-chloroethyl isobutyrate (215 mg, 1.43 mmol, 2.00 equiv), and potassium carbonate (295 mg, 2.13 mmol, 3.00 equiv). The resulting solution was stirred overnight at rt and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with EtOAc/petroleum ether (1/9) to provide 170 mg (50% yield) of 1-(isobutyryloxy)ethyl 4-(benzyl(2-formyl-5-(trifluoromethyl)phenyl)amino)butanoate as a yellow oil. LCMS (ESI, m/z): 480 [M+H]$^+$.

Step 2: Preparation of 1,1,1,3,3,3-hexafluoropropan-2-yl 4-(2-(benzyl(4-(1-(isobutyryloxy)ethoxy)-4-oxobutyl)amino)-4-(trifluoromethyl)benzyl)piperazine-1-carboxylate

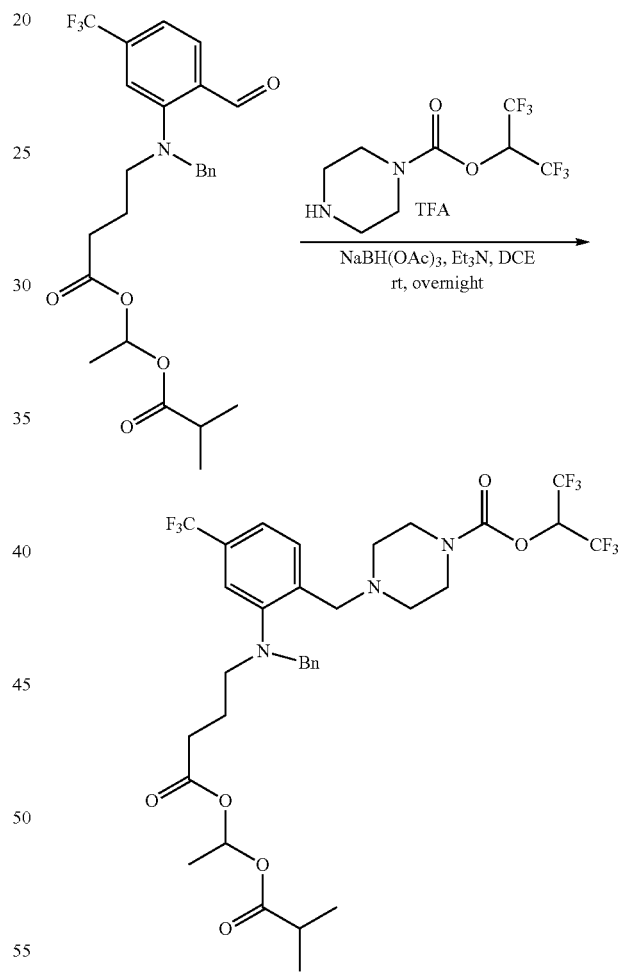

A flask was charged with 1-(isobutyryloxy)ethyl 4-(benzyl(2-formyl-5-(trifluoromethyl)phenyl)amino)butanoate (170 mg, 0.350 mmol, 1.00 equiv), 1,1,1,3,3,3-hexafluoropropan-2-yl piperazine-1-carboxylate, 2,2,2-trifluoroacetate salt (99.0 mg, 0.350 mmol, 1.00 equiv, prepared as described in Example 1, Steps 3-4), DCE (10 mL), and TEA (108 mg, 1.07 mmol, 3.00 equiv). The mixture was stirred for 1 h at rt and then sodium triacetoxyborohydride (226 mg, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 200 mg (76% yield) of 1,1,1,3,3,3-hexafluoropropan-2-yl 4-(2-(benzyl(4-(1-(isobutyryloxy)ethoxy)-4-oxobutyl)amino)-4-(trifluoromethyl)benzyl)piperazine-1-carboxylate as yellow oil. LCMS (ESI, m/z): 744 [M+H]$^+$.

Step 3: Preparation of 1,1,1,3,3,3-hexafluoropropan-2-yl 4-(2-((4-(1-(isobutyryloxy)ethoxy)-4-oxobutyl)amino)-4-(trifluoromethyl)benzyl)piperazine-1-carboxylate

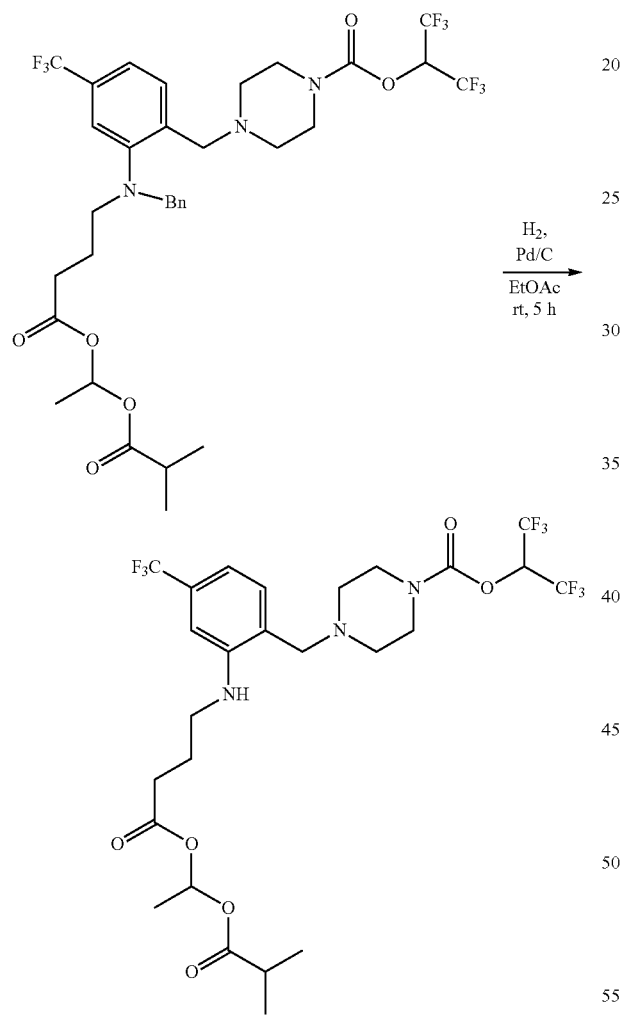

A flask was charged with 1,1,1,3,3,3-hexafluoropropan-2-yl 4-(2-(benzyl(4-(1-(isobutyryloxy)ethoxy)-4-oxobutyl)amino)-4-(trifluoromethyl)benzyl)piperazine-1-carboxylate (200 mg, 0.270 mmol, 1.00 equiv), EtOAc (10 mL), and palladium on carbon (100 mg). Hydrogen was introduced into the reaction and the resulting mixture was stirred for 5 h at rt. The solids were filtered out and the filtrate was concentrated. The crude product (180 mg) was purified by preparative HPLC to provide 59.9 mg (34% yield) of 1,1,1,3,3,3-hexafluoropropan-2-yl 4-(2-((4-(1-(isobutyryloxy)ethoxy)-4-oxobutyl)amino)-4-(trifluoromethyl)benzyl) piperazine-1-carboxylate as a light yellow oil. $^1$H NMR (300 MHz, Methanol-d$_4$) δ 7.05 (d, J=7.5 Hz, 1H), 6.84-6.89 (m, 2H), 6.77 (s, 1H), 6.13 (br s, 1H), 5.71-5.79 (m, 1H), 3.54 (br s, 6H), 3.20 (t, J=6.6 Hz, 2H), 2.44-2.60 (m, 7H), 1.94-2.04 (m, 2H), 1.46 (d, J=5.4 Hz, 3H), 1.13-1.16 (m, 6H). LCMS (ESI, m/z): 654 [M+H]$^+$.

Example 9: 2-(2-((2-((4-(((1,1,1,3,3,3-Hexafluoropropan-2-yl)oxy)carbonyl)piperazin-1-yl)methyl)-5-(trifluoromethyl)phenyl)amino)ethoxy)acetic acid

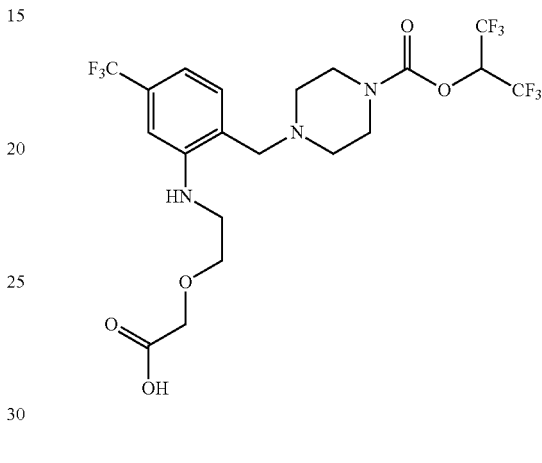

Step 1: Preparation of tert-butyl 2-(2-(((benzyloxy)carbonyl)amino)ethoxy)acetate

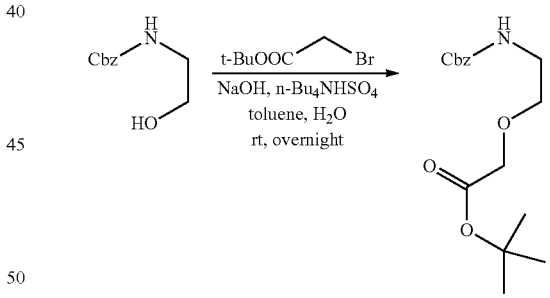

A flask was charged with tert-butyl 2-bromoacetate (6.00 g, 30.8 mmol, 1.00 equiv), toluene (180 mL), benzyl (2-hydroxyethyl)carbamate (12.0 g, 61.5 mmol, 2.00 equiv), tetrabutylammonium hydrogen sulfate (5.22 g, 15.40 mmol, 0.50 equiv), and 30% sodium hydroxide aqueous solution (90 mL), The resulting solution was stirred overnight at rt and quenched with water (80 mL). The resulting solution was extracted with EtOAc (2×100 mL) and the organic layers were combined, washed with brine (2×80 mL), dried over anhydrous sodium sulfate, filtered and concentrated. The residue was chromatographed on a silica gel column with EtOAc/petroleum ether (1/3) to provide 3.70 g (39% yield) of tert-butyl 2-(2-(((benzyloxy)carbonyl)amino) ethoxy)acetate as a light yellow oil. LCMS (ESI, m/z): 332 [M+Na]$^+$.

Step 2: Preparation of tert-butyl 2-(2-aminoethoxy)acetate

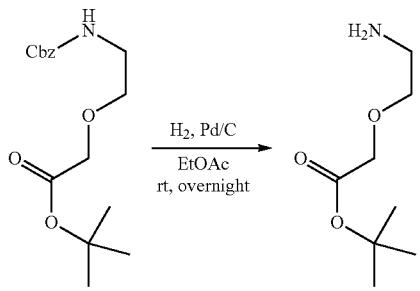 [SMILES: CC(C)(C)OC(=O)COCCNC(=O)OCc1ccccc1 ; CC(C)(C)OC(=O)COCCN]

A flask was charged with tert-butyl 2-(2-(((benzyloxy)carbonyl)amino)ethoxy)acetate (3.80 g, 12.3 mmol, 1.00 equiv), EtOAc (40 mL), and palladium on carbon (2.00 g). Hydrogen was introduced and the resulting solution was stirred overnight at rt. The reaction mixture was filtered and the filtrate concentrated under vacuum to provide 1.80 g (84% yield) of tert-butyl 2-(2-aminoethoxy)acetate as a colorless oil. LCMS (ESI, m/z): 176 [M+H]+.

Step 3: Preparation of tert-butyl 2-(2-((2-formyl-5-(trifluoromethyl)phenyl)(4-methoxybenzyl)amino)ethoxy)acetate

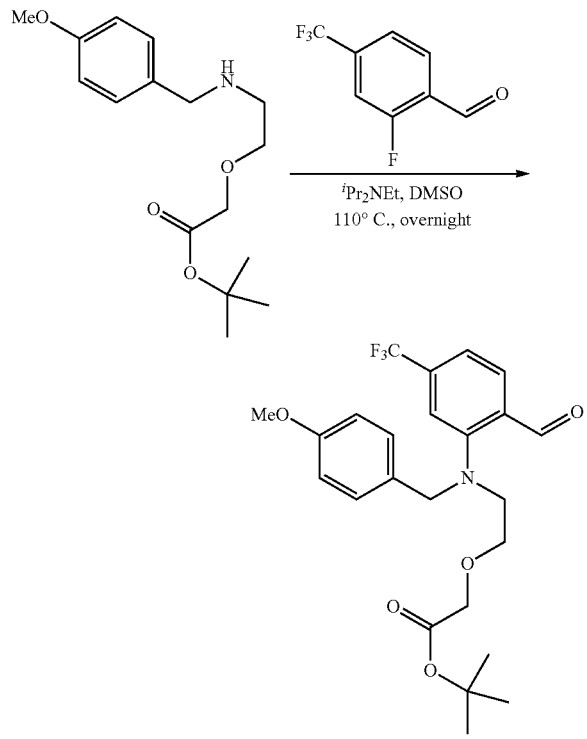

A flask was charged with tert-butyl 2-(2-((4-methoxybenzyl)amino)ethoxy)acetate (300 mg, 1.02 mmol, 1.00 equiv, prepared as described in Example 1, Step 1 using tert-butyl 2-(2-aminoethoxy)acetate), DMSO (10 mL), 2-fluoro-4-(trifluoromethyl)benzaldehyde (235 mg, 1.22 mmol, 1.20 equiv), and DIPEA (395 mg, 3.06 mmol, 3.00 equiv). The resulting solution was stirred overnight at 110° C. and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with ethyl acetate/petroleum ether (1/10) to provide 160 mg (34% yield) of tert-butyl 2-(2-((2-formyl-5-(trifluoromethyl)phenyl)(4-methoxybenzyl)amino)ethoxy)acetate as a yellow oil. LCMS (ESI, m/z): 468 [M+H]+.

Step 4: Preparation of 1,1,1,3,3,3-hexafluoropropan-2-yl 4-(2-((2-(2-(tert-butoxy)-2-oxoethoxy)ethyl)(4-methoxybenzyl)amino)-4-(trifluoromethyl)benzyl)piperazine-1-carboxylate

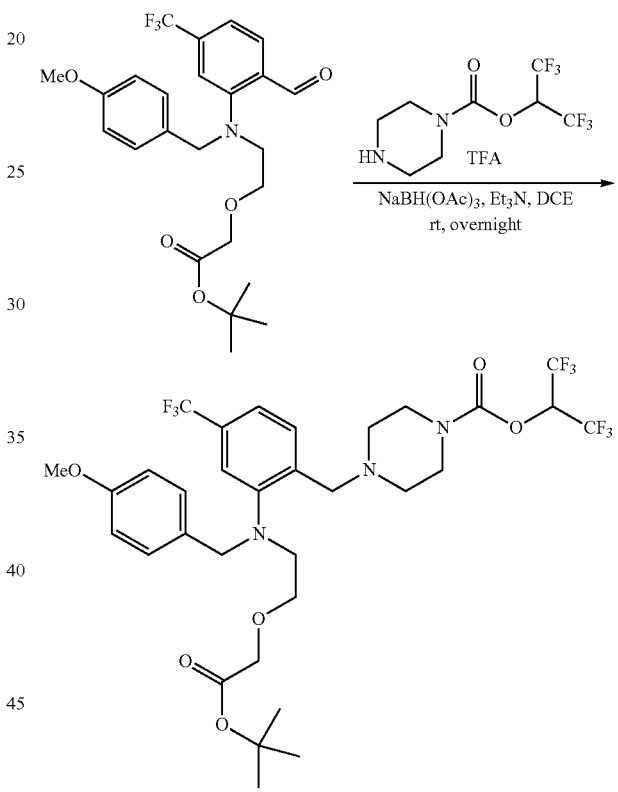

A flask was charged with 1,1,1,3,3,3-hexafluoropropan-2-yl piperazine-1-carboxylate, 2,2,2-trifluoroacetate salt (115 mg, 0.410 mmol, 1.20 equiv, prepared as described in Example 1, Steps 3-4), DCE (10 mL), TEA (104 mg, 1.03 mmol, 3.00 equiv), and tert-butyl 2-(2-((2-formyl-5-(trifluoromethyl)phenyl)(4-methoxybenzyl)amino)ethoxy)acetate (160 mg, 0.340 mmol, 1.00 equiv). The mixture was stirred for 1 h at rt and then sodium triacetoxyborohydride (218 mg, 1.03 mmol, 3.00 equiv) was added. The reaction mixture was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 160 mg (64% yield) of 1,1,1,3,3,3-hexafluoropropan-2-yl 4-(2-((2-(2-(tert-butoxy)-2-oxoethoxy)ethyl)(4-methoxybenzyl)

amino)-4-(trifluoromethyl)benzyl)piperazine-1-carboxylate as a yellow oil. LCMS (ESI, m/z): 732 [M+H]+.

Step 5: Preparation of 2-(2-((2-((4-(((1,1,1,3,3,3-hexafluoropropan-2-yl)oxy)carbonyl)piperazin-1-yl)methyl)-5-(trifluoromethyl)phenyl)amino)ethoxy)acetic acid

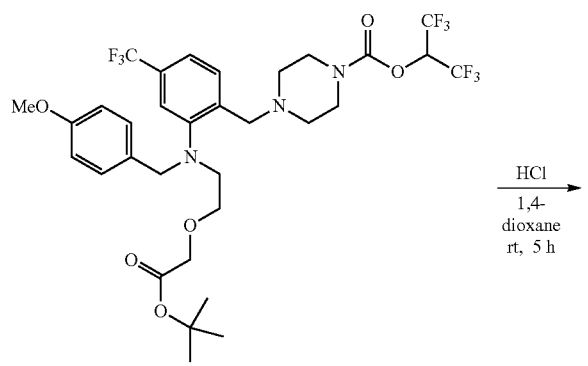

A flask was charged with 1,1,1,3,3,3-hexafluoropropan-2-yl 4-(2-((2-(2-(tert-butoxy)-2-oxoethoxy)ethyl)(4-methoxybenzyl)amino)-4-(trifluoromethyl)benzyl)piperazine-1-carboxylate (160 mg, 0.220 mmol, 1.00 equiv), 1,4-dioxane (10 mL), and hydrochloric acid (3 mL). The resulting solution was stirred for 5 h at rt and concentrated. The crude product (300 mg) was purified by preparative HPLC to provide 17.0 mg (14%) of 2-(2-((2-((4-(((1,1,1,3,3,3-hexafluoropropan-2-yl)oxy)carbonyl)piperazin-1-yl)methyl)-5-(trifluoromethyl)phenyl)amino)ethoxy)acetic acid as an off-white solid. ¹H NMR (400 MHz, Methanol-d₄) δ 7.16 (d, J=7.6 Hz, 1H), 6.84-6.88 (m, 2H), 6.09-6.18 (m, 1H), 3.94 (s, 2H), 3.82 (t, J=5.2 Hz, 2H), 3.60 (br s, 6H), 3.35-3.36 (m, 2H), 2.45-2.51 (m, 4H). LCMS (ESI, m/z): 556 [M+H]+.

Example 10: 2-(2-((4-Chloro-2-((4-(((1,1,1,3,3,3-hexafluoropropan-2-yl)oxy)carbonyl)piperazin-1-yl)methyl)phenyl)amino)ethoxy)acetic acid

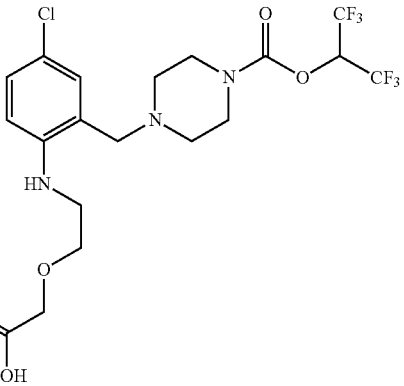

The title compound was prepared according to the representative procedure of Example 9 using 5-chloro-2-fluorobenzaldehyde in Step 3 to provide 2-(2-((4-chloro-2-((4-(((1,1,1,3,3,3-hexafluoropropan-2-yl)oxy)carbonyl)piperazin-1-yl)methyl)phenyl)amino)ethoxy)acetic acid as a yellow solid. ¹H NMR (400 MHz, Methanol-d₄) δ 7.12-7.14 (m, 1H), 7.02 (s, 1H), 6.64 (d, J=8.4 Hz, 1H), 6.11-6.17 (m, 1H), 4.05 (s, 2H), 3.82 (t, J=6.8 Hz, 2H), 3.54-3.66 (m, 6H), 3.29-3.32 (m, 2H), 2.46-2.48 (m, 4H). LCMS (ESI, m/z): 522 [M+H]+.

Example 11: 2-(2-((2-Fluoro-6-((4-(((1,1,1,3,3,3-hexafluoropropan-2-yl)oxy)carbonyl)piperazin-1-yl)methyl)phenyl)amino)ethoxy)acetic acid

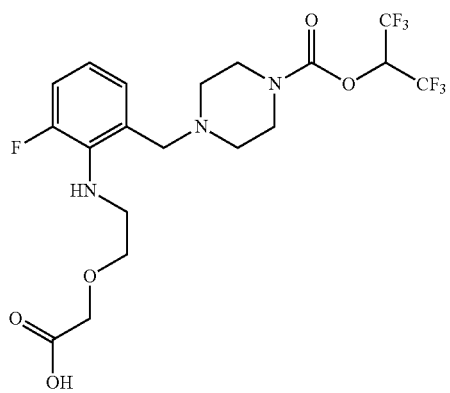 [SMILES: O=C(O)COCCNc1c(F)cccc1CN1CCN(C(=O)OC(C(F)(F)F)C(F)(F)F)CC1]

The title compound was prepared according to the representative procedure of Example 9 using 2,3-difluorobenzaldehyde in Step 3 to provide 2-(2-((2-fluoro-6-((4-(((1,1,1,3,3,3-hexafluoropropan-2-yl)oxy)carbonyl)piperazin-1-yl)methyl)phenyl)amino)ethoxy)acetic acid as a light yellow oil. ¹H NMR (300 MHz, Methanol-d₄) δ 6.86-6.99 (m, 2H), 6.69-6.78 (m, 1H), 6.08-6.18 (m, 1H), 3.98 (s, 2H), 3.62-3.65 (m, 4H), 3.56 (br s, 4H), 3.45-3.46 (m, 2H), 2.46 (br s, 4H). LCMS (ESI, m/z): 506 [M+H]+.

Example 12: N-(2-((5-Chloro-2-((4-(((1,1,1,3,3,3-hexafluoropropan-2-yl)oxy)carbonyl)piperazin-1-yl)methyl)phenyl)amino)ethyl)-N-(methylsulfonyl)glycine

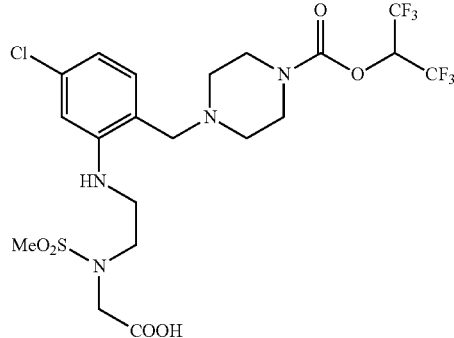

Step 1: Preparation of N-(2-(1,3-dioxoisoindolin-2-yl)ethyl)methanesulfonamide

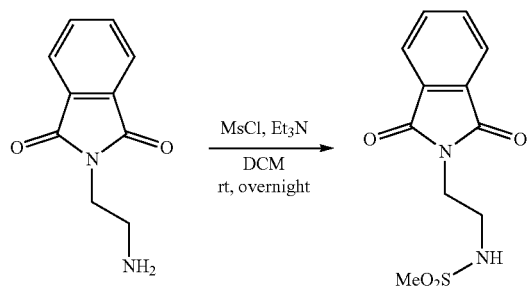

A flask was charged with 2-(2-aminoethyl)isoindoline-1,3-dione (2.00 g, 10.5 mmol, 1.00 equiv), DCM (20 mL), TEA (2.12 g, 21.0 mmol, 2.00 equiv), and methanesulfonyl chloride (1.44 g, 12.6 mmol, 1.20 equiv). The resulting solution was stirred overnight at rt and quenched with water (80 mL). The resulting solution was extracted with EtOAc (2×100 mL) and the organic layers were combined, washed with brine (2×80 mL), dried over anhydrous sodium sulfate, filtered and concentrated to provide 800 mg (crude) of N-(2-(1,3-dioxoisoindolin-2-yl)ethyl)methanesulfonamide as a light yellow solid. LCMS (ESI, m/z): 269 [M+H]⁺.

Step 2: Preparation of tert-butyl N-(2-(1,3-dioxoisoindolin-2-yl)ethyl)-N-(methylsulfonyl)glycinate

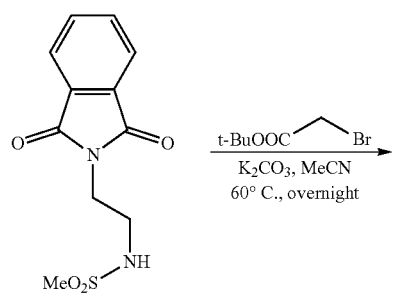

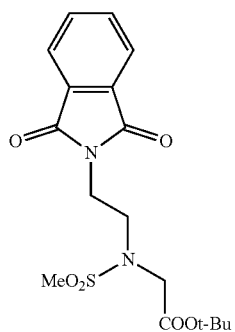

A flask was charged with N-(2-(1,3-dioxoisoindolin-2-yl)ethyl)methanesulfonamide (750 mg, 2.80 mmol, 1.00 equiv), MeCN (10 mL), potassium carbonate (1.16 g, 8.40 mmol, 3.00 equiv), and tert-butyl 2-bromoacetate (652 mg, 3.36 mmol, 1.20 equiv). The resulting solution was stirred overnight at 60° C. The solids were filtered out and concentrated. The residue was chromatographed on a silica gel column with DCM/MeOH (3/97) to provide 700 mg (65% yield) of tert-butyl N-(2-(1,3-dioxoisoindolin-2-yl)ethyl)-N-(methylsulfonyl)glycinate as an off-white solid. LCMS (ESI, m/z): 383 [M+H]⁺.

Step 3: Preparation of tert-butyl N-(2-aminoethyl)-N-(methylsulfonyl)glycinate

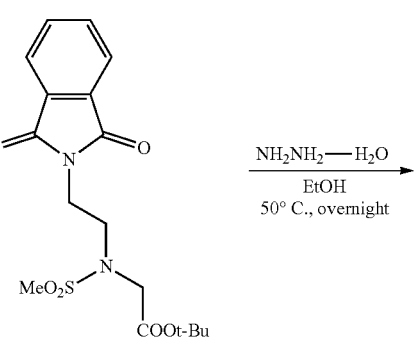

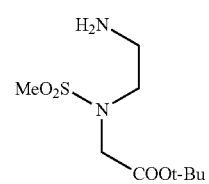

A flask was charged with tert-butyl N-(2-(1,3-dioxoisoindolin-2-yl)ethyl)-N-(methylsulfonyl)glycinate (500 mg, 1.31 mmol, 1.00 equiv), EtOH (10 mL), and hydrazine hydrate (328 mg, 6.55 mmol, 5.00 equiv). The resulting solution was stirred overnight at 50° C. and concentrated to provide 300 mg (crude) of tert-butyl N-(2-aminoethyl)-N-(methylsulfonyl)glycinate as a light yellow solid. LCMS (ESI, m/z): 253 [M+H]⁺.

Step 4: Preparation of tert-butyl N-(2-((4-methoxybenzyl)amino)ethyl)-N-(methylsulfonyl)glycinate

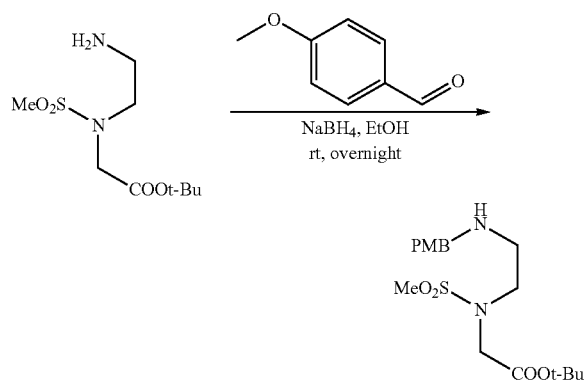

A flask was charged with tert-butyl N-(2-aminoethyl)-N-(methylsulfonyl)glycinate (300 mg, 1.19 mmol, 1.00 equiv), EtOH (10 mL), and 4-methoxybenzaldehyde (162 mg, 1.19 mmol, 1.00 equiv) The resulting solution was stirred for 5 h at 60° C. Sodium borohydride (27.0 mg, 0.714 mmol, 0.60 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (96/4) to provide 240 mg (54% yield) of tert-butyl N-(2-((4-methoxybenzyl)amino)ethyl)-N-(methylsulfonyl)glycinate as a yellow oil. LCMS (ESI, m/z): 373 [M+H]⁺.

Step 5: Preparation of tert-butyl N-(2-((5-chloro-2-formylphenyl)(4-methoxybenzyl)amino)ethyl)-N-(methylsulfonyl)glycinate

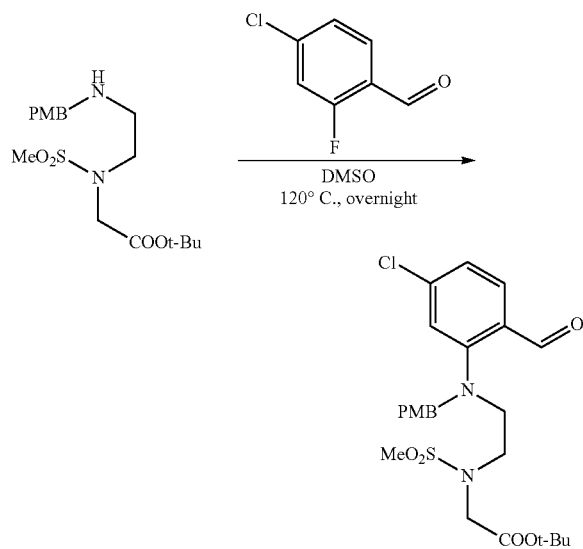

A flask was charged with tert-butyl N-(2-((4-methoxybenzyl)amino)ethyl)-N-(methylsulfonyl)glycinate (200 mg, 0.540 mmol, 1.00 equiv), DMSO (10 mL), and 4-chloro-2-fluorobenzaldehyde (128 mg, 0.810 mmol, 1.50 equiv) under nitrogen. The resulting solution was stirred overnight at 120° C. and quenched with water (30 mL). The resulting solution was extracted with EtOAc (2×50 mL) and the organic layers were combined, washed with brine (2×30 mL), dried over anhydrous sodium sulfate, filtered and concentrated. The residue was chromatographed on a silica gel column with EtOAc/petroleum ether (1/4) to provide 80.0 mg (29% yield) of tert-butyl N-(2-((5-chloro-2-formylphenyl)(4-methoxybenzyl)amino)ethyl)-N-(methylsulfonyl)glycinate as a yellow oil. LCMS (ESI, m/z): 511 [M+H]⁺.

Step 6: Preparation of 1,1,1,3,3,3-hexafluoropropan-2-yl 4-(2-((2-(N-(2-(tert-butoxy)-2-oxoethyl)methylsulfonamido)ethyl)(4-methoxybenzyl)amino)-4-chlorobenzyl)piperazine-1-carboxylate

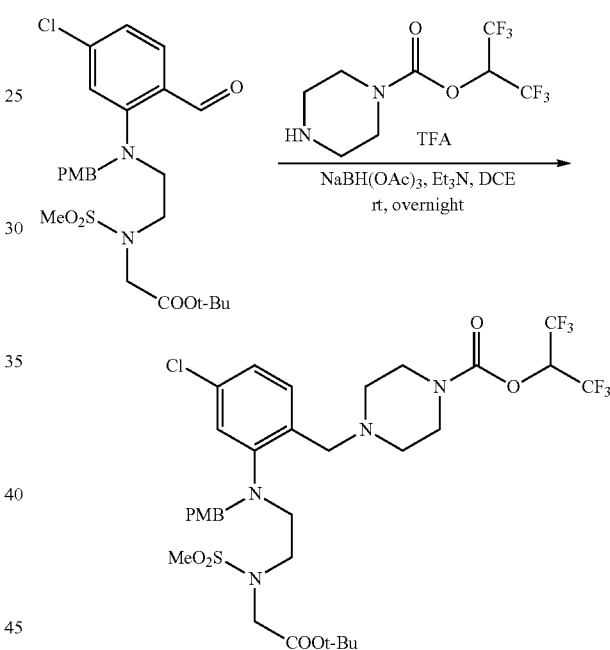

A flask was charged with 1,1,1,3,3,3-hexafluoropropan-2-yl piperazine-1-carboxylate, 2,2,2-trifluoroacetate salt (53.0 mg, 0.190 mmol, 1.20 equiv, prepared as described in Example 1, Steps 3-4), DCE (10 mL), TEA (48.0 mg, 0.470 mmol, 3.00 equiv), and tert-butyl N-(2-((5-chloro-2-formylphenyl)(4-methoxybenzyl)amino)ethyl)-N-(methylsulfonyl)glycinate (80.0 mg, 0.160 mmol, 1.00 equiv). The mixture was stirred for 1 h at rt and then sodium triacetoxyborohydride (100 mg, 0.470 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (96/4) to provide 100 mg (82% yield) of 1,1,1,3,3,3-hexafluoropropan-2-yl 4-(2-((2-(N-(2-(tert-butoxy)-2-oxoethyl)methylsulfonamido)ethyl)(4-methoxybenzyl)amino)-4-chlorobenzyl)piperazine-1-carboxylate as a yellow oil. LCMS (ESI, m/z): 775 [M+H]⁺.

127

Step 7: Preparation of N-(2-((5-chloro-2-((4-(((1,1,1,3,3,3-hexafluoropropan-2-yl)oxy)carbonyl)piperazin-1-yl)methyl)phenyl)amino)ethyl)-N-(methylsulfonyl)glycine

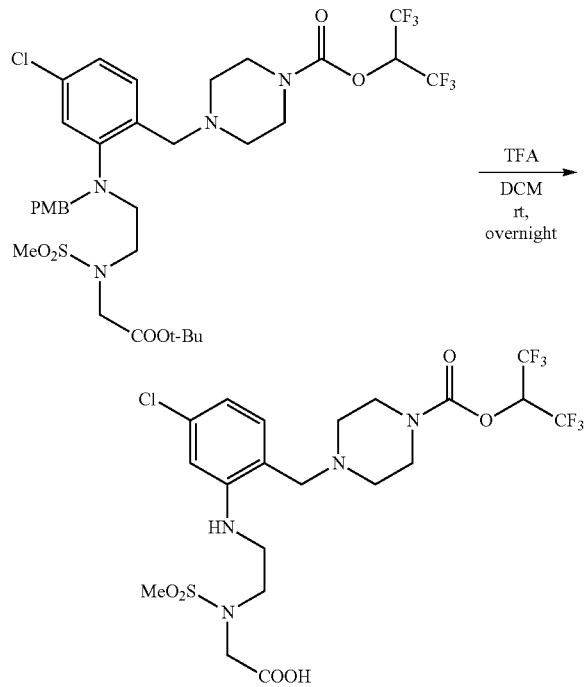

A flask was charged with 1,1,1,3,3,3-hexafluoropropan-2-yl 4-(2-((2-(N-(2-(tert-butoxy)-2-oxoethyl)methylsulfonamido)ethyl)(4-methoxybenzyl)amino)-4-chlorobenzyl)piperazine-1-carboxylate (100 mg, 0.130 mmol, 1.00 equiv), DCM (10 mL), and TFA (5 mL). The resulting solution was stirred overnight at rt and concentrated. The crude product was purified by preparative HPLC to provide 6.4 mg (8% yield) of N-(2-((5-chloro-2-((4-(((1,1,1,3,3,3-hexafluoropropan-2-yl)oxy)carbonyl)piperazin-1-yl)methyl)phenyl)amino)ethyl)-N-(methylsulfonyl)glycine as a white solid. $^1$H NMR (300 MHz, Methanol-$d_4$) δ 6.95 (d, J=7.8 Hz, 1H), 6.63 (s, 1H), 6.57-6.58 (m, 1H), 6.17-6.15 (m, 1H), 3.98 (s, 2H), 3.60-3.64 (m, 4H), 3.52 (s, 2H), 3.25-3.30 (m, 4H), 3.06 (s, 3H), 2.46-2.48 (m, 4H). LCMS (ESI, m/z): 599 [M+H]$^+$.

Example 13: 2-(5-Chloro-2-((4-(((1,1,1,3,3,3-hexafluoropropan-2-yl)oxy)carbonyl)piperazin-1-yl)methyl)phenoxy)acetic acid

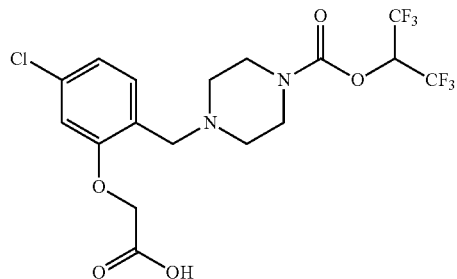 [SMILES: O=C(O)COc1cc(Cl)ccc1CN1CCN(C(=O)OC(C(F)(F)F)C(F)(F)F)CC1]

128

Step 1: Preparation of tert-butyl 4-(4-chloro-2-hydroxybenzyl)piperazine-1-carboxylate

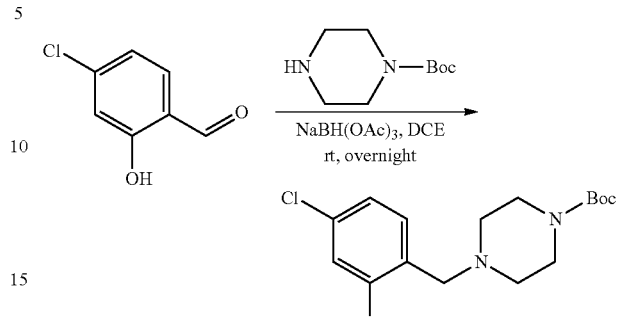

A flask was charged with 4-chloro-2-hydroxybenzaldehyde (1.00 g, 6.39 mmol, 1.00 equiv), DCE (15 mL), and tert-butyl piperazine-1-carboxylate (1.43 g, 7.67 mmol, 1.20 equiv). The mixture was stirred for 1 h at rt and then sodium triacetoxyborohydride (4.08 g, 19.2 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (95/5) to provide 1.20 g (57% yield) of tert-butyl 4-(4-chloro-2-hydroxybenzyl)piperazine-1-carboxylate as a yellow oil. LCMS (ESI, m/z): 327 [M+H]$^+$.

Step 2: Preparation of tert-butyl 4-(2-(2-(tert-butoxy)-2-oxoethoxy)-4-chlorobenzyl)piperazine-1-carboxylate

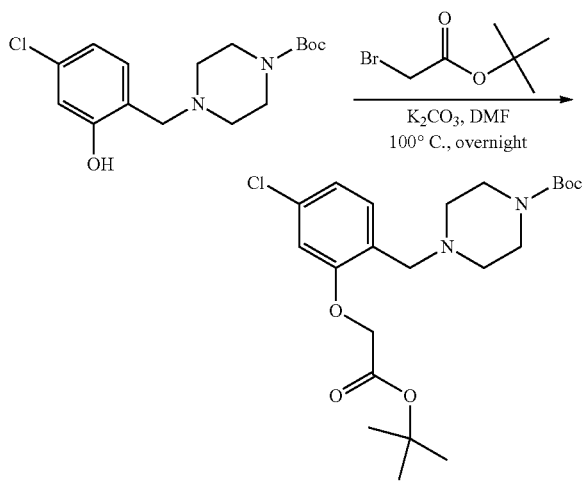

A flask was charged with tert-butyl 4-(4-chloro-2-hydroxybenzyl)piperazine-1-carboxylate (300 mg, 0.920 mmol, 1.00 equiv), DMF (10 mL), tert-butyl 2-bromoacetate (215 mg, 1.10 mmol, 1.20 equiv), and potassium carbonate (381 mg, 2.76 mmol, 3.00 equiv). The resulting solution was stirred overnight at 100° C. and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 200 mg (49% yield) of tert-butyl 4-(2-(2-(tert-butoxy)-2-oxoethoxy)-4-chlorobenzyl)piperazine-1-carboxylate as a yellow oil. LCMS (ESI, m/z): 441 [M+H]⁺.

Step 3: Preparation of 2-(5-chloro-2-(piperazin-1-ylmethyl)phenoxy)acetic acid hydrochloride

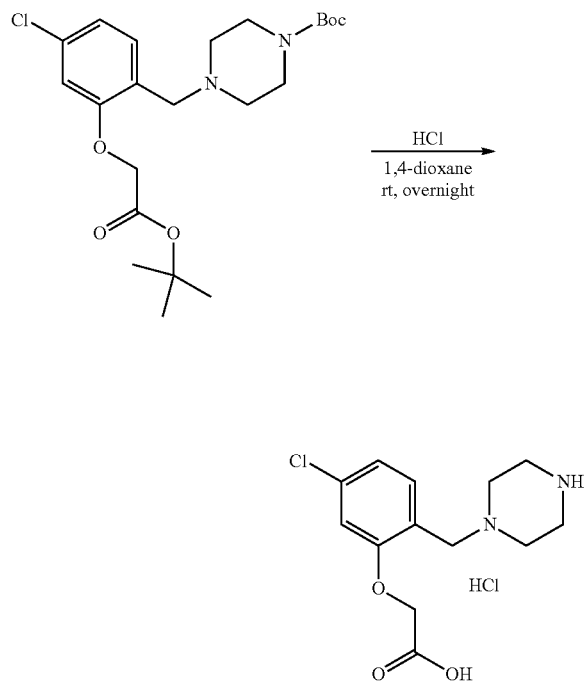

A flask was charged with tert-butyl 4-(2-(2-(tert-butoxy)-2-oxoethoxy)-4-chlorobenzyl)piperazine-1-carboxylate (200 mg, 0.450 mmol, 1.00 equiv), 1,4-dioxane (10 mL), and hydrochloric acid (3 mL). The resulting solution was stirred overnight at rt and concentrated to provide 300 mg (crude) of 2-(5-chloro-2-(piperazin-1-ylmethyl)phenoxy)acetic acid hydrochloride as a yellow semi-solid. LCMS (ESI, m/z): 285 [M+H]⁺.

Step 4: Preparation of 2-(5-chloro-2-((4-(((1,1,1,3,3,3-hexafluoropropan-2-yl)oxy)carbonyl)piperazin-1-yl)methyl)phenoxy)acetic acid

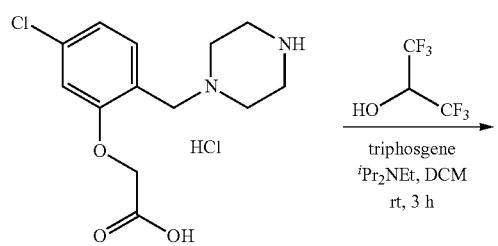

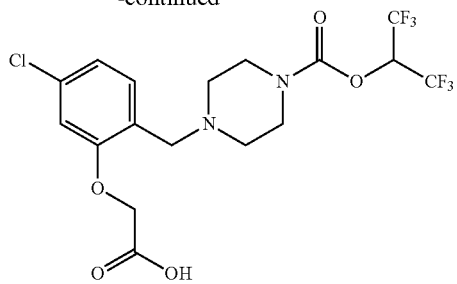

A flask was charged with triphosgene (94.0 mg, 0.315 mmol, 0.70 equiv), DCM (10 mL), and HFIP (152 mg, 0.900 mmol, 2.00 equiv) under nitrogen. DIPEA (175 mg, 1.35 mmol, 3.00 equiv) was added at 0° C. The mixture was stirred for 1 h at rt. 2-(5-Chloro-2-(piperazin-1-ylmethyl)phenoxy)acetic acid hydrochloride (128 mg, 0.450 mmol, 1.00 equiv) was added. The resulting solution was stirred for 3 h at rt and quenched with water (30 mL). The resulting solution was extracted with DCM (2×50 mL) and the organic layers were combined, washed with brine (2×30 mL), dried over anhydrous sodium sulfate, filtered and concentrated. The crude product (300 mg) was purified by preparative HPLC to provide 145.3 mg (68% yield) of 2-(5-chloro-2-((4-(((1,1,1,3,3,3-hexafluoropropan-2-yl)oxy)carbonyl)piperazin-1-yl)methyl)phenoxy)acetic acid as a white solid. ¹H NMR (300 MHz, Methanol-d₄) δ 7.36 (d, J=7.8 Hz, 1H), 7.25 (s, 1H), 7.07-7.10 (m, 1H), 6.17-6.30 (m, 1H), 4.68 (s, 2H), 4.21 (s, 2H), 3.86 (br s, 4H), 3.19 (br s, 4H). LCMS (ESI, m/z): 479 [M+H]⁺.

Example 14: 2-(2-((4-(((1,1,1,3,3,3-Hexafluoropropan-2-yl)oxy)carbonyl)piperazin-1-yl)methyl)-5-(trifluoromethyl)phenoxy)acetic acid

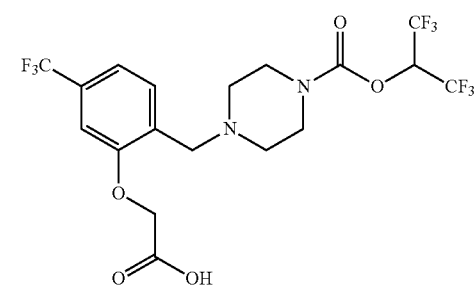

The title compound was prepared according to the representative procedure of Example 13 using 2-hydroxy-4-(trifluoromethyl)benzaldehyde, prepared as described in Step 1 of Example 3, in Step 1 to provide 2-(2-((4-(((1,1,1,3,3,3-hexafluoropropan-2-yl)oxy)carbonyl)piperazin-1-yl)methyl)-5-(trifluoromethyl)phenoxy)acetic acid as a white solid. ¹H NMR (300 MHz, Methanol-d₄) δ 7.57 (d, J=7.8 Hz, 1H), 7.45 (s, 1H), 7.35 (d, J=7.8 Hz, 1H), 6.15-6.28 (m, 1H), 4.88 (s, 2H), 4.26 (br s, 2H), 3.83 (br s, 4H), 3.83 (br s, 4H). LCMS (ESI, m/z): 513 [M+H]⁺.

Example 15: 5-(2-((4-(((1,1,1,3,3,3-Hexafluoropropan-2-yl)oxy)carbonyl)piperazin-1-yl)methyl)-5-(trifluoromethyl)phenyl)pentanoic acid

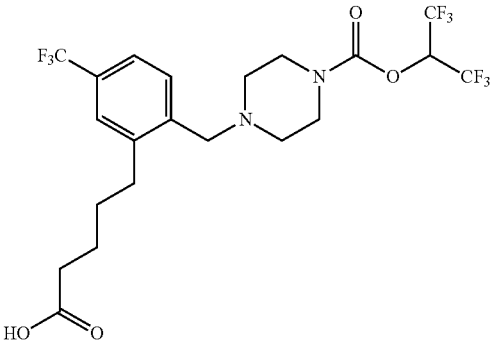 [SMILES: O=C(O)CCCCc1cc(C(F)(F)F)ccc1CN1CCN(C(=O)OC(C(F)(F)F)C(F)(F)F)CC1]

Step 1: Preparation of tert-butyl 4-(2-bromo-4-(trifluoromethyl)benzyl)piperazine-1-carboxylate

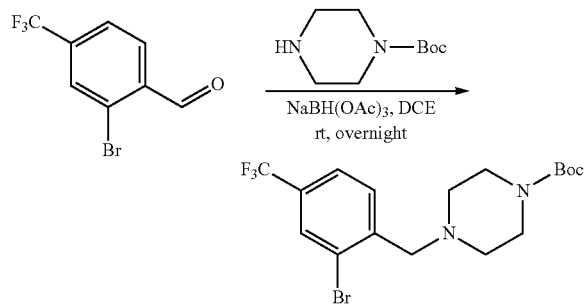

A flask was charged with 2-bromo-4-(trifluoromethyl)benzaldehyde (1.00 g, 3.95 mmol, 1.00 equiv), DCE (15 mL), and tert-butyl piperazine-1-carboxylate (813 mg, 4.35 mmol, 1.10 equiv). The mixture was stirred for 1 h at rt and then sodium triacetoxyborohydride (2.52 g, 11.9 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (98/2) to provide 1.50 g (90% yield) of tert-butyl 4-(2-bromo-4-(trifluoromethyl)benzyl)piperazine-1-carboxylate as a light yellow oil. LCMS (ESI, m/z): 423 [M+H]+.

Step 2: Preparation of tert-butyl 4-(2-formyl-4-(trifluoromethyl)benzyl)piperazine-1-carboxylate

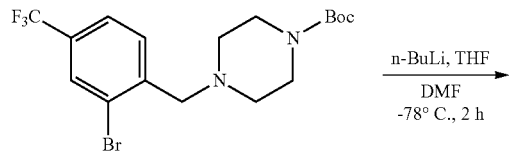

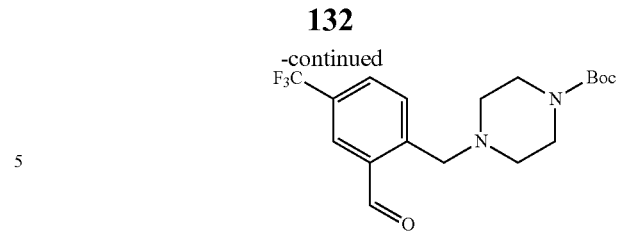

A flask was charged with tert-butyl 4-(2-bromo-4-(trifluoromethyl)benzyl)piperazine-1-carboxylate (2.00 g, 4.73 mmol, 1.00 equiv) and THF (15 mL) under nitrogen. The mixture was cooled to −78° C., and n-butyllithium (2.5M in hexane, 2.30 mL, 5.68 mmol, 1.20 equiv) was added dropwise over 20 min. After 1 h at −78° C., DMF (1.73 g, 23.7 mmol, 5.00 equiv) was added. The mixture was stirred for 1 h at −78° C. and concentrated to provide 1.20 g (68% yield) of tert-butyl 4-(2-formyl-4-(trifluoromethyl)benzyl)piperazine-1-carboxylate as a red oil. LCMS (ESI, m/z): 373 [M+H]+.

Step 3: Preparation of (4-(tert-butoxy)-4-oxobutyl)triphenylphosphonium bromide

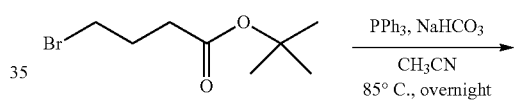

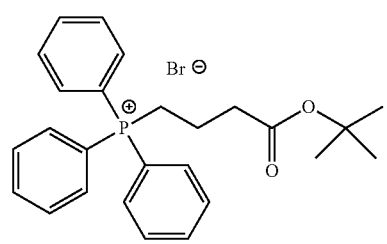

A flask was charged with tert-butyl 4-bromobutanoate (500 mg, 2.24 mmol, 1.00 equiv), MeCN (15 mL), triphenylphosphine (590 mg, 2.25 mmol, 1.00 equiv), and sodium bicarbonate (378 mg, 4.50 mmol, 2.00 equiv). The resulting solution was stirred overnight at 85° C. and cooled to rt. The mixture was filtered and the filtrate was concentrated. The residue was triturated with diethyl ether to provide 650 mg (60% yield) of (4-(tert-butoxy)-4-oxobutyl)triphenylphosphonium bromide as a white solid. LCMS (ESI, m/z): 405 [M−Br]+.

Step 4: Preparation of tert-butyl (E)-4-(2-(5-(tert-butoxy)-5-oxopent-1-en-1-yl)-4-(trifluoromethyl)benzyl)piperazine-1-carboxylate

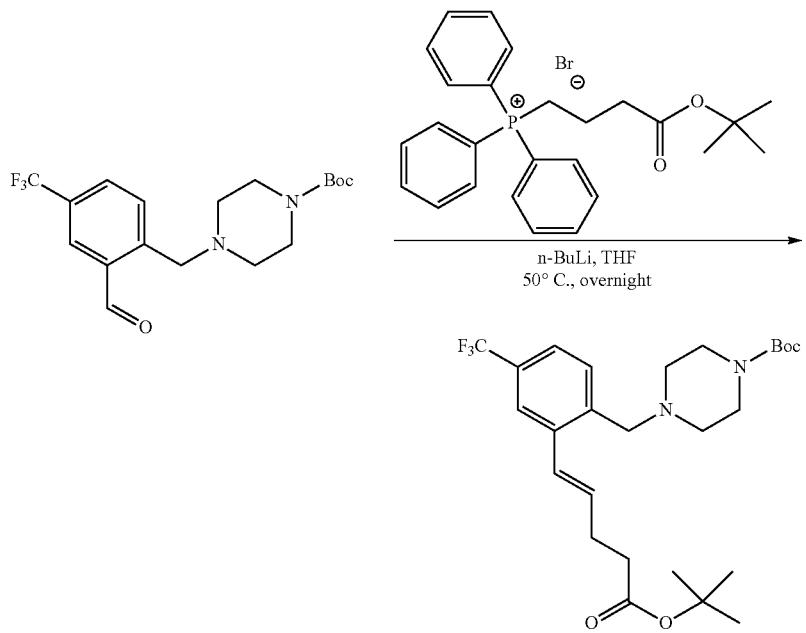

A flask was charged with (4-(tert-butoxy)-4-oxobutyl)triphenylphosphonium bromide (650 mg, 1.34 mmol, 1.00 equiv) and THF (15 mL) under nitrogen. The mixture was cooled to −78° C. and n-butyllithium (2.5M in hexane, 0.540 mL, 1.34 mmol, 1.00 equiv) was added dropwise over 10 min. The mixture was stirred for 30 min at −78° C. and tert-butyl 4-(2-formyl-4-(trifluoromethyl)benzyl)piperazine-1-carboxylate (500 mg, 1.34 mmol, 1.00 equiv) was added. The reaction mixture was stirred overnight at 50° C. and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (95/5) to provide 210 mg (31% yield) of tert-butyl (E)-4-(2-(5-(tert-butoxy)-5-oxopent-1-en-1-yl)-4-(trifluoromethyl)benzyl)piperazine-1-carboxylate as a yellow oil. LCMS (ESI, m/z): 499 [M+H]$^+$.

Step 5: Preparation of tert-butyl 4-(2-(5-(tert-butoxy)-5-oxopentyl)-4-(trifluoromethyl)benzyl)piperazine-1-carboxylate

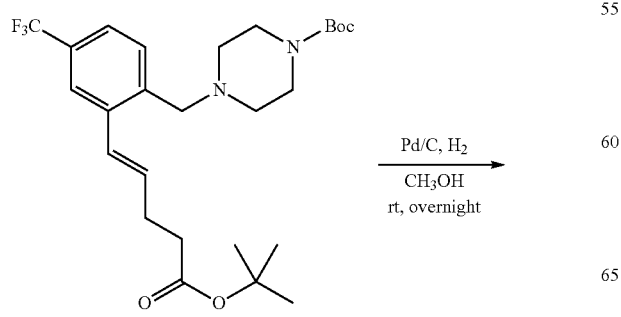

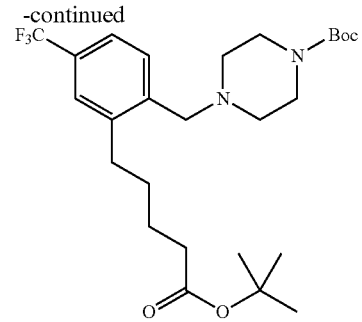

A flask was charged with tert-butyl (E)-4-(2-(5-(tert-butoxy)-5-oxopent-1-en-1-yl)-4-(trifluoromethyl)benzyl)piperazine-1-carboxylate (150 mg, 0.300 mmol, 1.00 equiv), MeOH (10 mL), and palladium on carbon (100 mg). Hydrogen was introduced into the reaction and the mixture was stirred overnight at rt and the solids were removed by filtration. The filtrate was concentrated to provide 100 mg (crude) of tert-butyl 4-(2-(5-(tert-butoxy)-5-oxopentyl)-4-(trifluoromethyl)benzyl)piperazine-1-carboxylate as a light yellow oil. LCMS (ESI, m/z): 501 [M+H]$^+$.

Step 6: Preparation of 5-(2-(piperazin-1-ylmethyl)-5-(trifluoromethyl)phenyl)pentanoic acid hydrochloride

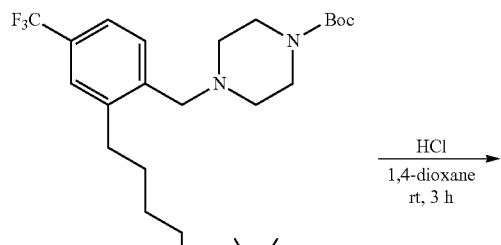

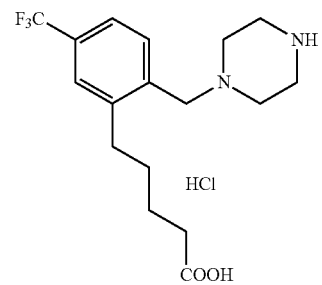

A flask was charged with tert-butyl 4-(2-(5-(tert-butoxy)-5-oxopentyl)-4-(trifluoromethyl)benzyl)piperazine-1-carboxylate (100 mg, 0.220 mmol, 1.00 equiv), 1,4-dioxane (10 mL), and hydrochloric acid (2 mL). The resulting solution was stirred for 3 h at rt and concentrated to provide 150 mg (crude) of 5-(2-(piperazin-1-ylmethyl)-5-(trifluoromethyl)phenyl)pentanoic acid hydrochloride as a light yellow oil. LCMS (ESI, m/z): 345 [M+H]$^+$.

Step 7: Preparation of 5-(2-((4-(((1,1,1,3,3,3-hexafluoropropan-2-yl)oxy)carbonyl)piperazin-1-yl)methyl)-5-(trifluoromethyl)phenyl)pentanoic acid

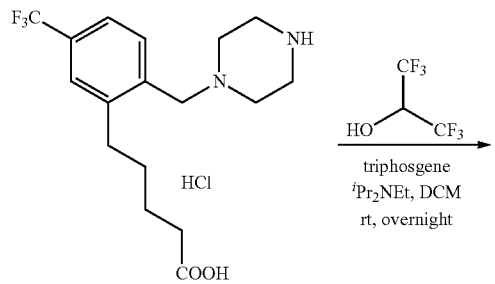

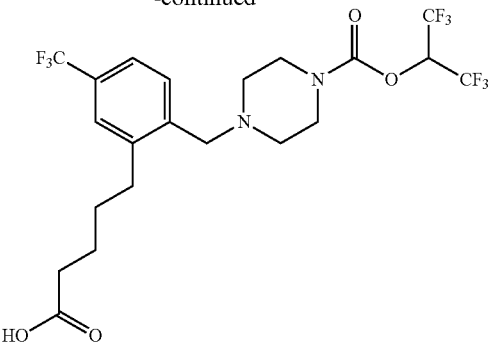

A flask was charged with triphosgene (39.0 mg, 0.130 mmol, 0.70 equiv), DCM (10 mL), and HFIP (64.0 mg, 0.380 mmol, 2.00 equiv) under nitrogen. DIPEA (73.0 mg, 0.560 mmol, 3.00 equiv) was added at 0° C. and the mixture was stirred for 1 h at rt. 5-(2-(Piperazin-1-ylmethyl)-5-(trifluoromethyl)phenyl)pentanoic acid hydrochloride (65.0 mg, 0.190 mmol, 1.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The crude product (300 mg) was purified by preparative HPLC to provide 21.5 mg (21% yield) of 5-(2-((4-(((1,1,1,3,3,3-hexafluoropropan-2-yl)oxy)carbonyl)piperazin-1-yl)methyl)-5-(trifluoromethyl)phenyl)pentanoic acid as a colorless oil. $^1$H NMR (300 MHz, Methanol-d$_4$) δ 7.41-7.50 (m, 3H), 6.07-6.19 (m, 1H), 3.60 (s, 2H), 3.47-3.58 (m, 4H), 2.79-2.84 (m, 2H), 2.47-2.49 (m, 4H), 2.30 (t, J=6.9 Hz, 2H), 1.64-1.75 (m, 4H). LCMS (ESI, m/z): 539 [M+H]$^+$.

Example 16: 1-(2-((4-(((1,1,1,3,3,3-Hexafluoropropan-2-yl)oxy)carbonyl)piperazin-1-yl)methyl)-5-(trifluoromethyl)phenoxy)cyclopropane-1-carboxylic acid

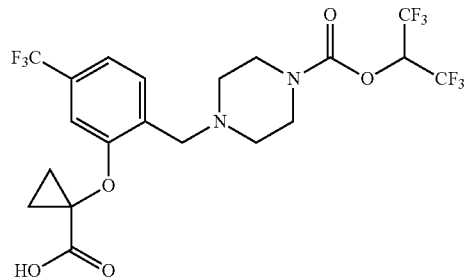 [SMILES: O=C(OC(C(F)(F)F)C(F)(F)F)N1CCN(Cc2ccc(C(F)(F)F)cc2OC2(C(=O)O)CC2)CC1]

Step 1: Preparation of methyl 1-(2-formyl-5-(trifluoromethyl)phenoxy)cyclopropane-1-carboxylate

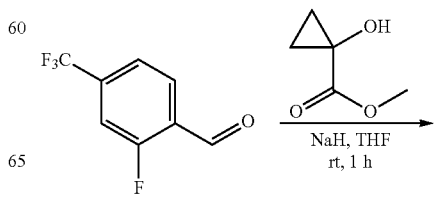

-continued

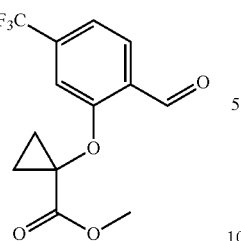

A flask was charged with methyl 1-hydroxycyclopropane-1-carboxylate (362 mg, 3.12 mmol, 1.50 equiv) and THF (10 mL). Sodium hydride (125 mg, 3.12 mmol, 1.50 equiv, 60% in mineral oil) was added at 0° C. The mixture was stirred for 20 min at rt before 2-fluoro-4-(trifluoromethyl)benzaldehyde (400 mg, 2.08 mmol, 1.00 equiv) was added. The resulting solution was stirred for 1 h at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with EtOAc/petroleum ether (1/10) to provide 180 mg (29% yield) of methyl 1-(2-formyl-5-(trifluoromethyl)phenoxy)cyclopropane-1-carboxylate as a light yellow oil.

Step 2: Preparation of tert-butyl 4-(2-(1-(methoxycarbonyl)cyclopropoxy)-4-(trifluoromethyl)benzyl)piperazine-1-carboxylate

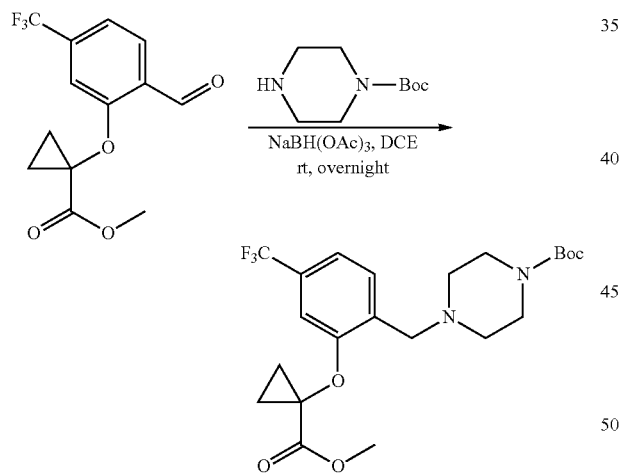

A flask was charged with methyl 1-(2-formyl-5-(trifluoromethyl)phenoxy)cyclopropane-1-carboxylate (200 mg, 0.690 mmol, 1.00 equiv), DCE (10 mL), and tert-butyl piperazine-1-carboxylate (155 mg, 0.828 mmol, 1.20 equiv). The mixture was stirred for 1 h at rt and sodium triacetoxyborohydride (441 mg, 2.07 mmol, 3.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The residue was chromatographed on a silica gel column with DCM/MeOH (97/3) to provide 250 mg (79% yield) of tert-butyl 4-(2-(1-(methoxycarbonyl)cyclopropoxy)-4-(trifluoromethyl)benzyl)piperazine-1-carboxylate as a colorless oil. LCMS (ESI, m/z): 459 [M+H]⁺.

Step 3: Preparation of 1-(2-((4-(tert-butoxycarbonyl)piperazin-1-yl)methyl)-5-(trifluoromethyl)phenoxy)cyclopropane-1-carboxylic acid

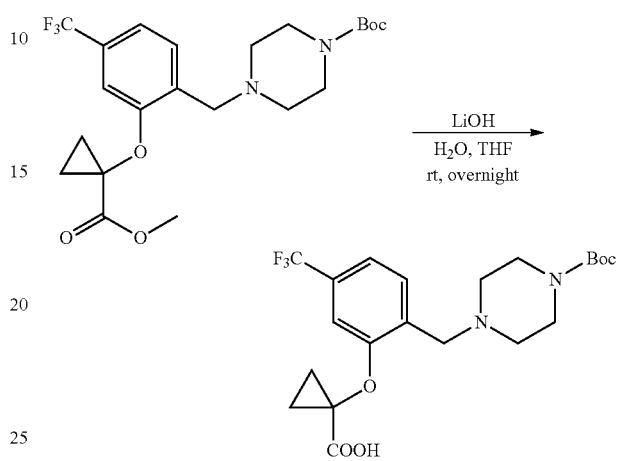

A flask was charged with tert-butyl 4-(2-(1-(methoxycarbonyl)cyclopropoxy)-4-(trifluoromethyl)benzyl)piperazine-1-carboxylate (200 mg, 0.440 mmol, 1.00 equiv), THF (5 mL), water (5 mL), and lithium hydroxide (157 mg, 6.56 mmol, 15.0 equiv). The resulting solution was stirred overnight at rt, and then pH value of the solution was adjusted to 5 with hydrochloric acid (1 mol/L). The resulting solution was extracted with DCM (2×50 mL) and the organic layers were combined, washed with brine (2×30 mL), dried over anhydrous sodium sulfate, filtered and concentrated to provide 190 mg (crude) of 1-(2-((4-(tert-butoxycarbonyl)piperazin-1-yl)methyl)-5-(trifluoromethyl)phenoxy)cyclopropane-1-carboxylic acid as a light yellow solid. LCMS (ESI, m/z): 445 [M+H]⁺.

Step 4: Preparation of 1-(2-(piperazin-1-ylmethyl)-5-(trifluoromethyl)phenoxy)cyclopropane-1-carboxylic acid hydrochloride

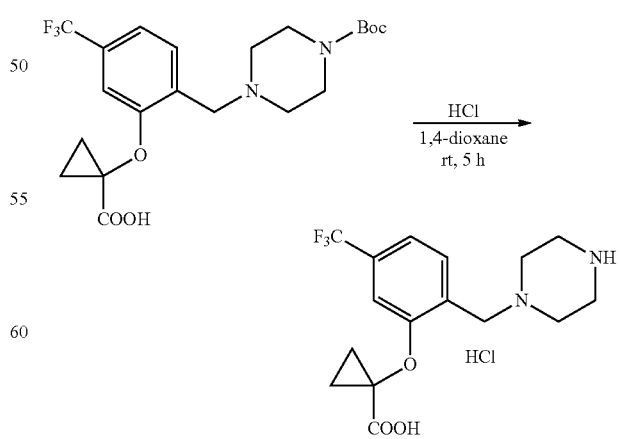

A flask was charged with 1-(2-((4-(tert-butoxycarbonyl)piperazin-1-yl)methyl)-5-(trifluoromethyl)phenoxy)cyclopropane-1-carboxylic acid (190 mg, 0.430 mmol, 1.00 equiv), 1,4-dioxane (10 mL), and hydrochloric acid (3 mL). The resulting solution was stirred for 5 h at rt and concentrated to provide 140 mg (crude) of 1-(2-(piperazin-1-ylmethyl)-5-(trifluoromethyl)phenoxy)cyclopropane-1-carboxylic acid hydrochloride as a light yellow solid. LCMS (ESI, m/z): 345 [M+H]+.

Step 5: Preparation of 1-(2-((4-(((1,1,1,3,3,3-hexafluoropropan-2-yl)oxy)carbonyl)piperazin-1-yl)methyl)-5-(trifluoromethyl)phenoxy)cyclopropane-1-carboxylic acid

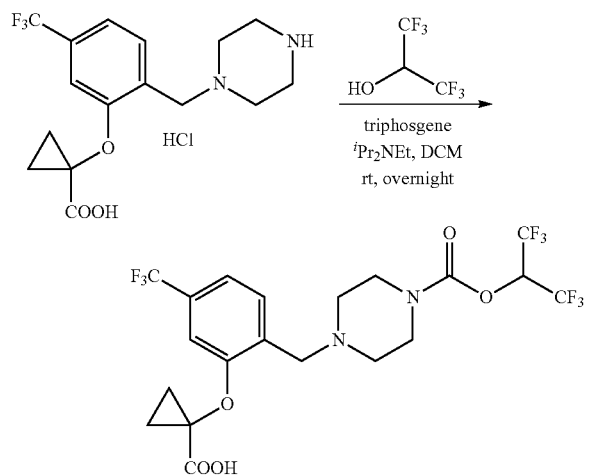

A flask was charged with triphosgene (85.0 mg, 0.290 mmol, 0.70 equiv), DCM (10 mL), 1,1,1,3,3,3-hexafluoropropan-2-ol (137 mg, 0.820 mmol, 2.00 equiv) under nitrogen. DIPEA (158 mg, 1.22 mmol, 3.00 equiv) was added at 0° C. The mixture was stirred for 1 h at rt and 1-(2-(piperazin-1-ylmethyl)-5-(trifluoromethyl)phenoxy)cyclopropane-1-carboxylic acid hydrochloride (140 mg, 0.410 mmol, 1.00 equiv) was added. The resulting solution was stirred overnight at rt and quenched with water (30 mL). The resulting solution was extracted with DCM (2×50 mL) and the organic layers were combined, washed with brine (2×30 mL), dried over anhydrous sodium sulfate, filtered and concentrated. The crude product (300 mg) was purified by preparative HPLC to provide 84.9 mg (39% yield) of 1-(2-((4-(((1,1,1,3,3,3-hexafluoropropan-2-yl)oxy)carbonyl)piperazin-1-yl)methyl)-5-(trifluoromethyl)phenoxy)cyclopropane-1-carboxylic acid as a white solid. $^1$H NMR (300 MHz, Methanol-$d_4$) δ 7.55 (d, J=7.8 Hz, 1H), 7.41 (s, 1H), 7.30 (d, J=7.8 Hz, 1H), 6.10-6.19 (m, 1H), 3.86 (s, 2H), 3.65-3.66 (m, 4H), 2.78 (br s, 4H), 1.50-1.54 (m, 2H), 1.16-1.20 (m, 2H). LCMS (ESI, m/z): 539 [M+H]+.

Example 17: 2-(3-((4-(((1,1,1,3,3,3-hexafluoropropan-2-yl)oxy)carbonyl)piperazin-1-yl)methyl)-5-(trifluoromethyl)phenyl)acetic acid

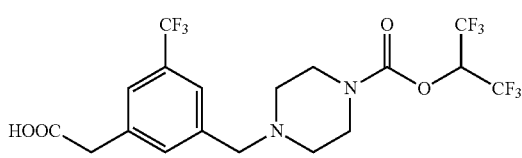 [SMILES: O=C(O)Cc1cc(CN2CCN(C(=O)OC(C(F)(F)F)C(F)(F)F)CC2)cc(C(F)(F)F)c1]

Step 1: Synthesis of tert-butyl 4-(3-bromo-5-(trifluoromethyl)benzyl)piperazine-1-carboxylate

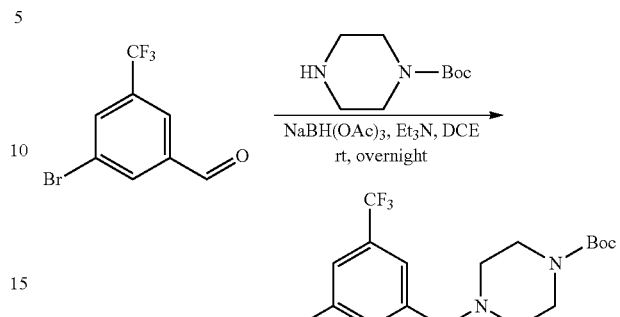

A flask was charged with 3-bromo-5-(trifluoromethyl)benzaldehyde (2.53 g, 10.0 mmol, 1.00 equiv), tert-butyl piperazine-1-carboxylate (2.23 g, 12.0 mmol, 1.20 equiv), DCE (25 mL), and triethylamine (3.03 g, 29.9 mmol, 3.00 equiv). The mixture was stirred for 30 min at rt prior to addition of sodium triacetoxyborohydride (6.36 g, 30.0 mmol, 3.00 equiv). The resulting solution was stirred overnight at rt and quenched with water (25 mL), as described in Example 1, Step 5. The residue was chromatographed on a silica gel column to provide 1.90 g (45% yield) of tert-butyl 4-(3-bromo-5-(trifluoromethyl)benzyl)piperazine-1-carboxylate. LCMS (ESI, m/z): 423 [M+H]+.

Step 2: Synthesis of tert-butyl 4-(3-(2-(tert-butoxy)-2-oxoethyl)-5-(trifluoromethyl)benzyl)piperazine-1-carboxylate

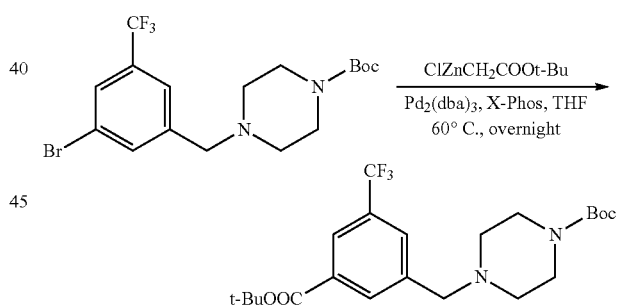

A flask was charged with tert-butyl 4-(3-bromo-5-(trifluoromethyl)benzyl)piperazine-1-carboxylate (2.00 g, 4.73 mmol, 1.00 equiv), (2-tert-butoxy-2-oxoethyl)zinc(II) chloride (28.4 mL, 14.2 mmol, 3.00 equiv, 0.5M in ethylether), tris(dibenzylideneacetone)dipalladium (433 mg, 0.473 mmol, 0.10 equiv), 2-(dicyclohexylphosphino)-2',4',6'-triisopropylbiphenyl (451 mg, 0.946 mmol, 0.20 equiv), and THF (30 mL) under nitrogen. The resulting solution was stirred overnight at 60° C. and quenched with water (30 mL). The resulting solution was extracted with DCM (3×30 mL), and the organic layers were combined, washed with brine (2×10 mL), dried over anhydrous sodium sulfate, filtered and concentrated under reduced pressure. The residue was chromatographed on a silica gel column to provide 1.00 g (46% yield) of tert-butyl 4-(3-(2-(tert-butoxy)-2-oxoethyl)-5-(trifluoromethyl)benzyl)piperazine-1-carboxylate. LCMS (ESI, m/z): 459 [M+H]+.

Step 3: Synthesis of 2-(3-(piperazin-1-ylmethyl)-5-(trifluoromethyl)phenyl)acetic acid

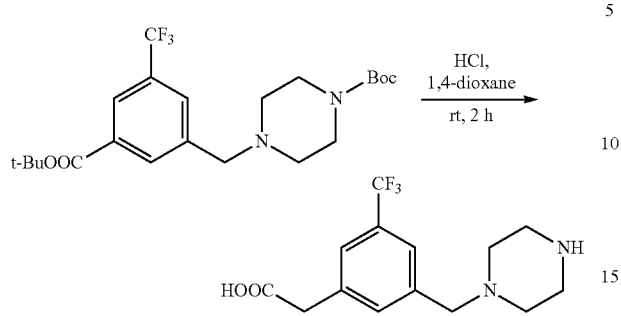

A flask was charged with tert-butyl 4-(3-(2-(tert-butoxy)-2-oxoethyl)-5-(trifluoromethyl)benzyl)piperazine-1-carboxylate (200 mg, 0.436 mmol, 1.00 equiv), 1,4-dioxane (4 mL), and concentrated hydrogen chloride (1 mL). The resulting solution was stirred for 2 h at rt and concentrated under reduced pressure, as described in Example 3, Step 4 to provide 180 mg (crude) of 2-(3-(piperazin-1-ylmethyl)-5-(trifluoromethyl)phenyl)acetic acid. LCMS (ESI, m/z): 303 [M+H]$^+$.

Step 4: Synthesis of 2-(3-((4-(((1,1,1,3,3,3-hexafluoropropan-2-yl)oxy)carbonyl)piperazin-1-yl)methyl)-5-(trifluoromethyl)phenyl)acetic acid

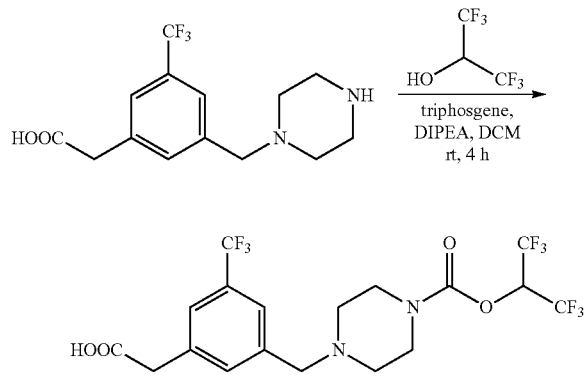

A flask was charged with triphosgene (63.9 mg, 0.215 mmol, 0.50 equiv), DCM (5 mL), and 1,1,1,3,3,3-hexafluoropropan-2-ol (145 mg, 0.861 mmol, 2.00 equiv). DIPEA (222 mg, 1.72 mmol, 4.00 equiv) was added dropwise at 0° C., and the mixture was stirred for 2 h at room temperature. 2-(3-(Piperazin-1-ylmethyl)-5-(trifluoromethyl)phenyl)acetic acid (130 mg, 0.430 mmol, 1.00 equiv) was added and the resulting solution was stirred for 2 h at rt before quenching with saturated sodium bicarbonate solution (20 mL), as described in Example 1, Step 1. The crude product (200 mg) was purified by preparative HPLC to provide 54.9 mg (26% yield) of 2-(3-((4-(((1,1,1,3,3,3-hexafluoropropan-2-yl)oxy)carbonyl)piperazin-1-yl)methyl)-5-(trifluoromethyl)phenyl)acetic acid. $^1$H NMR (300 MHz, Methanol-d$_4$) δ 7.58-7.53 (m, 3H), 6.18-6.08 (m, 1H), 3.72 (br s, 2H), 3.64-3.56 (m, 6H), 2.52-2.51 (m, 4H). LCMS (ESI, m/z): 497 [M+H]$^+$.

Example 18: 4-(2-((4-(((1,1,1,3,3,3-hexafluoropropan-2-yl)oxy)carbonyl)piperazin-1-yl)methyl)-5-(trifluoromethyl)phenyl)-2,2-dimethylbut-3-ynoic acid

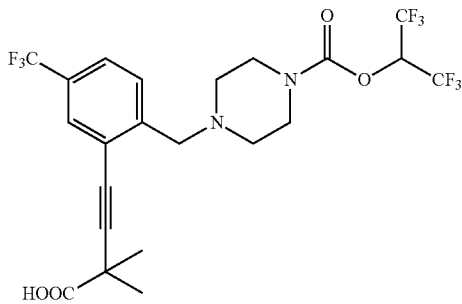 [SMILES: CC(C)(C#Cc1cc(C(F)(F)F)ccc1CN1CCN(C(=O)OC(C(F)(F)F)C(F)(F)F)CC1)C(=O)O]

Step 1: Synthesis of tert-butyl 4-(2-iodo-4-(trifluoromethyl)benzyl)piperazine-1-carboxylate

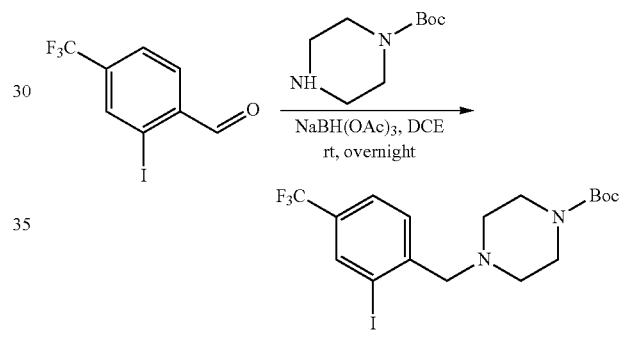

A flask was charged with 2-iodo-4-(trifluoromethyl)benzaldehyde (1.00 g, 3.33 mmol, 1.00 equiv), tert-butyl piperazine-1-carboxylate (0.744 g, 3.99 mmol, 1.20 equiv), and DCE (15 mL). The mixture was stirred for 1 h at rt prior to addition of sodium triacetoxyborohydride (2.12 g, 10.0 mmol, 3.00 equiv). The resulting solution was stirred overnight at rt and quenched with water (20 mL), as described in Example 15, Step 1. The residue was chromatographed on a silica gel column to provide 1.39 g (89% yield) of tert-butyl 4-(2-iodo-4-(trifluoromethyl)benzyl)piperazine-1-carboxylate. LCMS (ESI, m/z): 471 [M+H]$^+$.

Step 2: Synthesis of tert-butyl 4-(2-(4-ethoxy-3,3-dimethyl-4-oxobut-1-yn-1-yl)-4-(trifluoromethyl)benzyl)piperazine-1-carboxylate

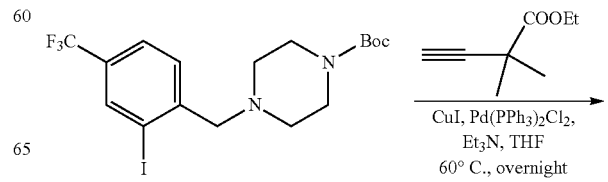

-continued

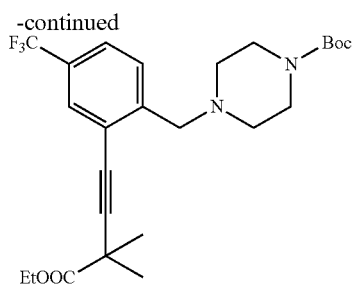

A flask was charged with tert-butyl 4-(2-iodo-4-(trifluoromethyl)benzyl)piperazine-1-carboxylate (400 mg, 0.851 mmol, 1.00 equiv), ethyl 2,2-dimethylbut-3-ynoate (238 mg, 1.70 mmol, 2.00 equiv), bis(triphenylphosphine)palladium (II) chloride (59.6 mg, 0.0851 mmol, 0.10 equiv), copper(I) iodide (32.3 mg, 0.170 mmol, 0.20 equiv), triethylamine (258 mg, 2.55 mmol, 3.00 equiv), and THF (10 mL) under nitrogen. The reaction mixture was stirred overnight at 60° C. and quenched with water (15 mL). The resulting solution was extracted with DCM (3×20 mL), and the organic layers were combined, washed with brine (1×50 mL), dried over anhydrous Na$_2$SO$_4$, filtered and concentrated under reduced pressure. The residue was chromatographed on a silica gel column to provide 320 mg (78% yield) of tert-butyl 4-(2-(4-ethoxy-3,3-dimethyl-4-oxobut-1-yn-1-yl)-4-(trifluoromethyl)benzyl)piperazine-1-carboxylate. LCMS (ESI, m/z): 483 [M+H]$^+$.

Step 3: Synthesis of 4-(2-((4-(tert-butoxycarbonyl)piperazin-1-yl)methyl)-5-(trifluoromethyl)phenyl)-2,2-dimethylbut-3-ynoic acid

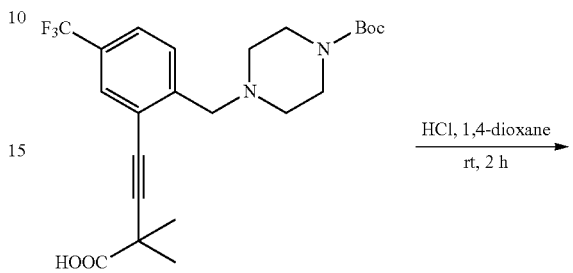

A flask was charged with tert-butyl 4-(2-(4-ethoxy-3,3-dimethyl-4-oxobut-1-yn-1-yl)-4-(trifluoromethyl)benzyl)piperazine-1-carboxylate (320 mg, 0.660 mmol, 1.00 equiv), THF (10 mL), lithium hydroxide (313 mg, 13.1 mmol, 20.00 equiv), and water (2 mL). The resulting solution was stirred overnight at 35° C. and quenched with water (10 mL). The pH value of the solution was adjusted to 6 with hydrochloric acid (1M), as described in Example 16, Step 3 to provide 280 mg (93% yield) of 4-(2-((4-(tert-butoxycarbonyl)piperazin-1-yl)methyl)-5-(trifluoromethyl)phenyl)-2,2-dimethylbut-3-ynoic acid. LCMS (ESI, m/z): 455 [M+H]$^+$.

Step 4: Synthesis of 2,2-dimethyl-4-(2-(piperazin-1-ylmethyl)-5-(trifluoromethyl)phenyl)but-3-ynoic acid

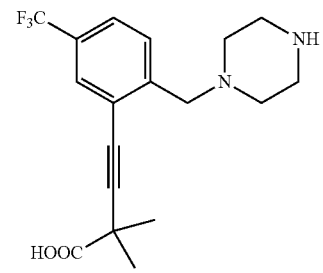

A flask was charged with 4-(2-((4-(tert-butoxycarbonyl)piperazin-1-yl)methyl)-5-(trifluoromethyl)phenyl)-2,2-dimethylbut-3-ynoic acid (280 mg, 0.620 mmol, 1.00 equiv), 1,4-dioxane (10 mL), and concentrated hydrochloric acid (2 mL). The resulting solution was stirred for 2 h at rt and concentrated under reduced pressure to provide 300 mg (crude) of 2,2-dimethyl-4-(2-(piperazin-1-ylmethyl)-5-(trifluoromethyl)phenyl)but-3-ynoic acid as a yellow solid. LCMS (ESI, m/z): 355 [M+H]$^+$.

Step 5: Synthesis of 4-(2-((4-(((1,1,1,3,3,3-hexafluoropropan-2-yl)oxy)carbonyl)piperazin-1-yl)methyl)-5-(trifluoromethyl)phenyl)-2,2-dimethylbut-3-ynoic acid

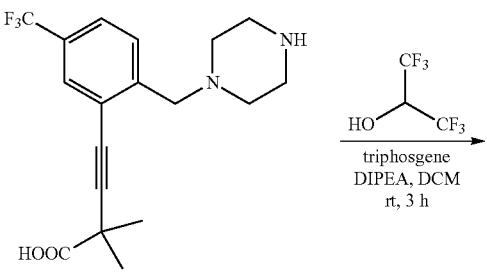

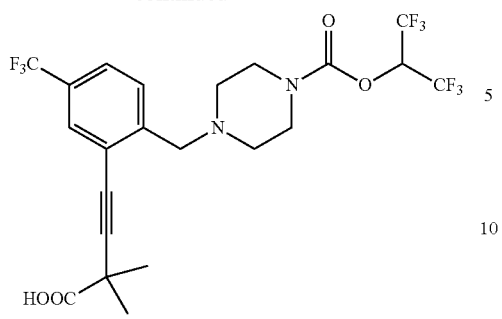

A flask was charged with triphosgene (117 mg, 0.390 mmol, 0.70 equiv), DCM (10 mL). 1,1,1,3,3,3-hexafluoropropan-2-ol (190 mg, 1.13 mmol, 2.00 equiv) was added at 0° C. N,N-DIPEA (292 mg, 2.26 mmol, 4.00 equiv) was added at 0° C. The mixture was stirred for 2 h at 0° C. 2,2-Dimethyl-4-(2-(piperazin-1-ylmethyl)-5-(trifluoromethyl)phenyl)but-3-ynoic acid (200 mg, 0.560 mmol, 1.00 equiv) was added. The resulting solution was stirred for 1 h at rt and quenched with water (10 mL), as described in Example 1, Step 1. The crude product (400 mg) was purified by preparative HPLC to provide 21.1 mg (7% yield) of 4-(2-((4-(((1,1,1,3,3,3-hexafluoropropan-2-yl)oxy)carbonyl)piperazin-1-yl)methyl)-5-(trifluoromethyl)phenyl)-2,2-dimethylbut-3-ynoic acid. $^1$H NMR (400 MHz, Methanol-$d_4$) δ 7.69-7.68 (m, 2H), 7.63-7.61 (m, 1H), 6.19-6.13 (m, 1H), 3.84 (s, 2H), 3.63-3.60 (m, 4H), 2.63-2.59 (m, 4H), 1.60 (s, 6H). LCMS (ESI, m/z): 549 [M+H]$^+$.

Example 19: 1-(3-((4-(((1,1,1,3,3,3-hexafluoropropan-2-yl)oxy)carbonyl)piperazin-1-yl)methyl)-5-(trifluoromethyl)phenoxy)cyclopropane-1-carboxylic acid

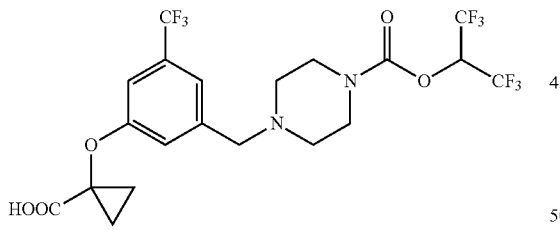

Step 1: Synthesis of tert-butyl 4-(3-hydroxy-5-(trifluoromethyl)benzyl)piperazine-1-carboxylate

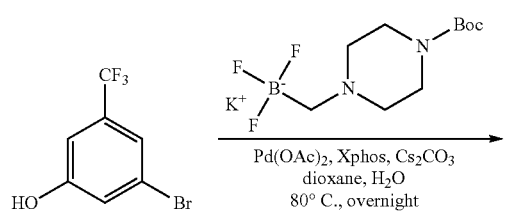

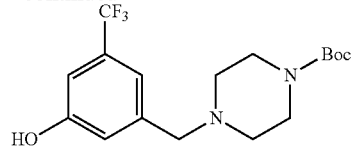

A flask was charged with 3-bromo-5-(trifluoromethyl)phenol (400 mg, 1.66 mmol, 1.00 equiv), palladium acetate (18.6 mg, 0.0830 mmol, 0.05 equiv), 2-(dicyclohexylphosphino)-2',4',6'-triisopropylbiphenyl (79.2 mg, 0.166 mmol, 0.10 equiv), cesium carbonate (1.62 g, 4.98 mmol, 3.00 equiv), potassium (4-[(tert-butoxy)carbonyl]piperazin-1-yl-methyl)trifluoroboranuide (765 mg, 2.50 mmol, 1.50 equiv), dioxane (10 mL), and water (2 mL) under nitrogen. The reaction mixture was stirred overnight at 80° C. and quenched with water (10 mL). The resulting solution was extracted with DCM (3×20 mL), and the organic layers were combined, washed with brine (1×20 mL), dried over anhydrous Na$_2$SO$_4$, filtered and concentrated under reduced pressure. The residue was chromatographed on a silica gel column to provide 580 mg (97% yield) of tert-butyl 4-(3-hydroxy-5-(trifluoromethyl)benzyl)piperazine-1-carboxylate. LCMS (ESI, m/z): 361 [M+H]$^+$.

Step 2: Synthesis of tert-butyl 4-(3-((4-bromo-1-methoxy-1-oxobutan-2-yl)oxy)-5-(trifluoromethyl)benzyl)piperazine-1-carboxylate

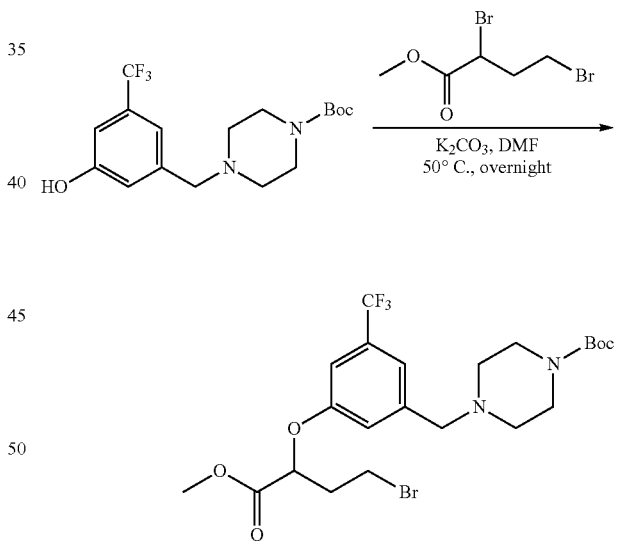

A flask was charged with tert-butyl 4-(3-hydroxy-5-(trifluoromethyl)benzyl)piperazine-1-carboxylate (500 mg, 1.39 mmol, 1.00 equiv), methyl 4-bromo-2-oxobutanoate (723 mg, 2.78 mmol, 2.00 equiv), potassium carbonate (384 mg, 2.78 mmol, 2.00 equiv), and DMF (10 mL) under nitrogen. The resulting solution was stirred overnight at 50° C. and quenched with water (10 mL), as described in Example 3, Step 4. The residue was chromatographed on a silica gel column to provide 500 mg (67% yield) of tert-butyl 4-(3-((4-bromo-1-methoxy-1-oxobutan-2-yl)oxy)-5-(trifluoromethyl)benzyl)piperazine-1-carboxylate. LCMS (ESI, m/z): 539 [M+H]$^+$.

147

Step 3: Synthesis of 1-(3-((4-(tert-butoxycarbonyl) piperazin-1-yl)methyl)-5-(trifluoromethyl)phenoxy) cyclopropane-1-carboxylic acid

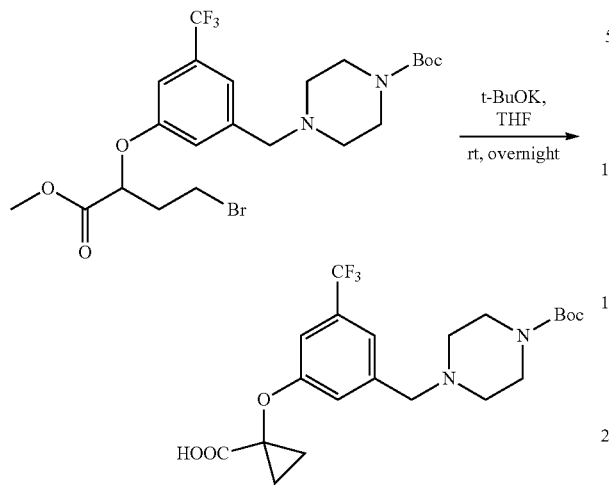

A flask was charged with tert-butyl 4-(3-((4-bromo-1-methoxy-1-oxobutan-2-yl)oxy)-5-(trifluoromethyl)benzyl)piperazine-1-carboxylate (500 mg, 0.930 mmol, 1.00 equiv), potassium tert-butoxide (208 mg, 1.86 mmol, 2.00 equiv), and THF (5 mL). The reaction mixture was stirred overnight at rt and quenched with water (10 mL). The resulting solution was extracted with DCM (3×30 mL), and the organic layers were combined, washed with brine (1×20 mL), dried over anhydrous $Na_2SO_4$, filtered and concentrated under reduced pressure. The residue was chromatographed on a silica gel column to provide 150 mg (36% yield) of 1-(3-((4-(tert-butoxycarbonyl)piperazin-1-yl)methyl)-5-(trifluoromethyl)phenoxy)cyclopropane-1-carboxylic acid. LCMS (ESI, m/z): 445 [M+H]+.

Step 4: Synthesis of 1-(3-(piperazin-1-ylmethyl)-5-(trifluoromethyl)phenoxy)cyclopropane-1-carboxylic acid

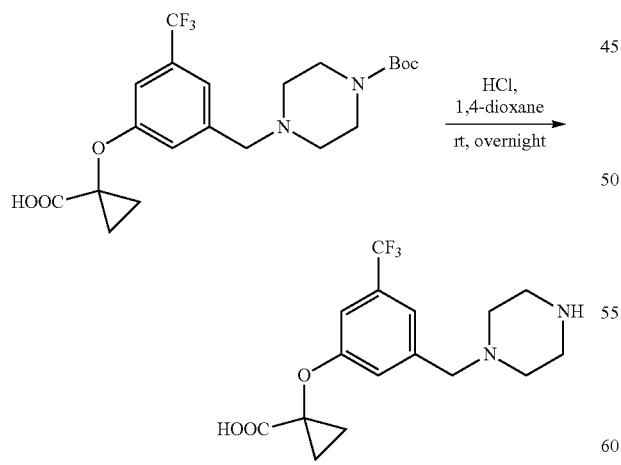

A flask was charged with 1-(3-((4-(tert-butoxycarbonyl)piperazin-1-yl)methyl)-5-(trifluoromethyl)phenoxy)cyclopropane-1-carboxylic acid (100 mg, 0.220 mmol, 1.00 equiv), concentrated hydrochloric acid (1 mL), and 1,4-dioxane (4 mL). The resulting solution was stirred overnight at rt and concentrated under reduced pressure to provide 110 mg (crude) of 1-(3-(piperazin-1-ylmethyl)-5-(trifluoromethyl)phenoxy)cyclopropane-1-carboxylic acid. LCMS (ESI, m/z): 345 [M+H]+.

Step 5: Synthesis of 1-(3-((4-(((1,1,1,3,3,3-hexafluoropropan-2-yl)oxy)carbonyl)piperazin-1-yl) methyl)-5-(trifluoromethyl)phenoxy)cyclopropane-1-carboxylic acid

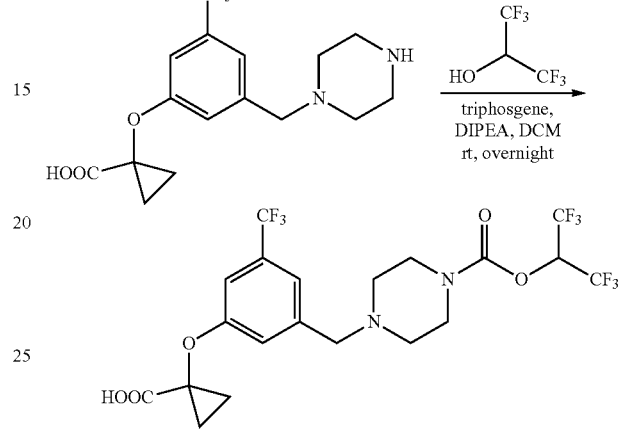

A flask was charged with triphosgene (42.2 mg, 0.142 mmol, 0.70 equiv), and DCM (5 mL). 1,1,1,3,3,3-Hexafluoropropan-2-ol (68.2 mg, 0.406 mmol, 2.00 equiv) was added at 0° C. followed by DIPEA (105 mg, 0.812 mmol, 4.00 equiv). The mixture was stirred for 2 h at room temperature prior to addition of 1-(3-(piperazin-1-ylmethyl)-5-(trifluoromethyl)phenoxy)cyclopropane-1-carboxylic acid (70.0 mg, 0.203 mmol, 1.00 equiv). The resulting solution was stirred overnight at rt and quenched with water (10 mL), as described in Example 1, Step 1. The crude product (400 mg) was purified by preparative HPLC to provide 7.40 mg (7% yield) of 1-(3-((4-(((1,1,1,3,3,3-hexafluoropropan-2-yl)oxy)carbonyl)piperazin-1-yl)methyl)-5-(trifluoromethyl)phenoxy)cyclopropane-1-carboxylic acid. $^1$H NMR (300 MHz, Methanol-$d_4$) δ 7.26 (s, 2H), 7.08 (s, 1H), 6.19-6.10 (m, 1H), 3.67-3.59 (m, 6H), 2.55 (br s, 4H), 1.65-1.61 (m, 2H), 1.33-1.28 (m, 2H). LCMS (ESI, m/z): 539 [M+H]+.

Example 20: 1,1,1,3,3,3-hexafluoropropan-2-yl 4-(3-fluoro-4-methyl-2-(2-(methylsulfonamido)-2-oxoethoxy)benzyl)piperazine-1-carboxylate

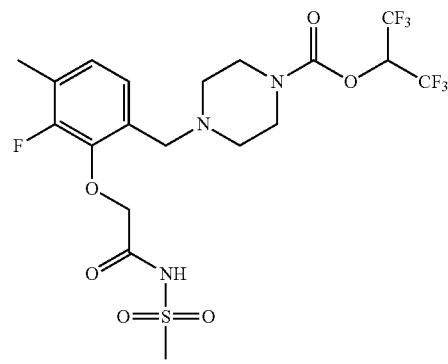 [SMILES: Cc1ccc(CN2CCN(C(=O)OC(C(F)(F)F)C(F)(F)F)CC2)c(OCC(=O)NS(C)(=O)=O)c1F]

Step 1: Synthesis of tert-butyl 2-(6-bromo-2-fluoro-3-methylphenoxy)acetate

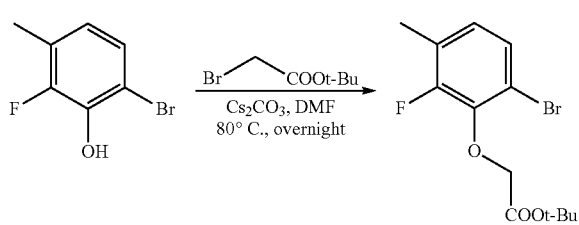

A flask was charged with 6-bromo-2-fluoro-3-methylphenol (1.00 g, 4.90 mmol, 1.00 equiv), DMF (10 mL), cesium carbonate (4.79 g, 14.7 mmol, 3.00 equiv), and tert-butyl 2-bromoacetate (1.43 g, 7.35 mmol, 1.50 equiv). The reaction mixture was stirred overnight at 80° C. and quenched with water (30 mL). The resulting solution was extracted with EtOAc (2×50 mL), and the organic layers were combined, washed with brine (2×30 mL), dried over anhydrous $Na_2SO_4$, filtered and concentrated under reduced pressure. The residue was chromatographed on a silica gel column to provide 0.950 g (61% yield) of tert-butyl 2-(6-bromo-2-fluoro-3-methylphenoxy)acetate. LCMS (ESI, m/z): 319 $[M+H]^+$.

Step 2. Synthesis of tert-butyl 4-(2-(2-(tert-butoxy)-2-oxoethoxy)-3-fluoro-4-methylbenzyl)piperazine-1-carboxylate

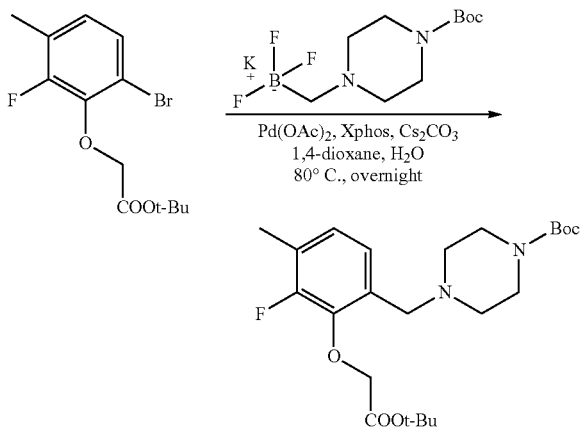

A flask was charged with tert-butyl 2-(6-bromo-2-fluoro-3-methylphenoxy)acetate (900 mg, 2.82 mmol, 1.00 equiv), 1,4-dioxane (10 mL), water (2 mL), potassium ((4-(tert-butoxycarbonyl)piperazin-1-yl)methyl)trifluoroborate (1004 mg, 3.38 mmol, 1.20 equiv), palladium acetate (21.0 mg, 0.0850 mmol, 0.03 equiv), 2-(dicyclohexylphosphino)-2',4',6'-triisopropylbiphenyl (81.0 mg, 0.170 mmol, 0.06 equiv), and cesium carbonate (2770 mg, 8.50 mmol, 3.00 equiv) under nitrogen. The resulting solution was stirred overnight at 80° C. and quenched with water (30 mL), as described in Example 19, Step 1. The residue was chromatographed on a silica gel column to provide 1.00 g (81% yield) of tert-butyl 4-(2-(2-(tert-butoxy)-2-oxoethoxy)-3-fluoro-4-methylbenzyl)piperazine-1-carboxylate. LCMS (ESI, m/z): 439 $[M+H]^+$.

Step 3: Synthesis of 2-(2-fluoro-3-methyl-6-(piperazin-1-ylmethyl)phenoxy)acetic acid

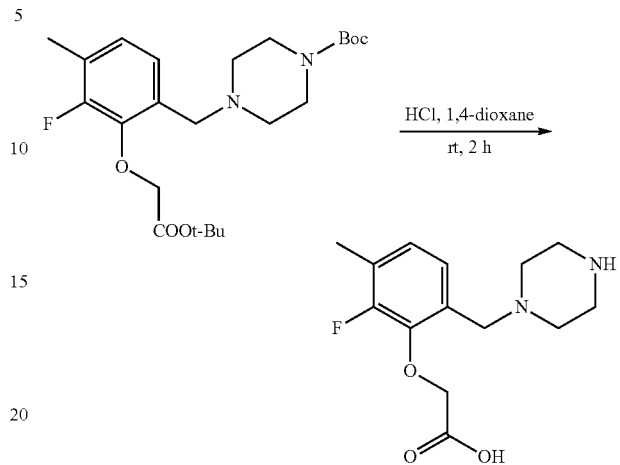

A flask was charged with tert-butyl 4-(2-(2-(tert-butoxy)-2-oxoethoxy)-3-fluoro-4-methylbenzyl)piperazine-1-carboxylate (650 mg, 1.48 mmol, 1.00 equiv), 1,4-dioxane (10 mL), and concentrated hydrochloric acid (2 mL) as described in Example 3, Step 4. The resulting solution was stirred for 2 h at rt and concentrated under reduced pressure to provide 417 mg (quantitative) of 2-(2-fluoro-3-methyl-6-(piperazin-1-ylmethyl)phenoxy) acetic acid. LCMS (ESI, m/z): 283 $[M+H]^+$.

Step 4: Synthesis of 2-(2-fluoro-6-((4-(((1,1,1,3,3,3-hexafluoropropan-2-yl)oxy)carbonyl)piperazin-1-yl)methyl)-3-methylphenoxy)acetic acid

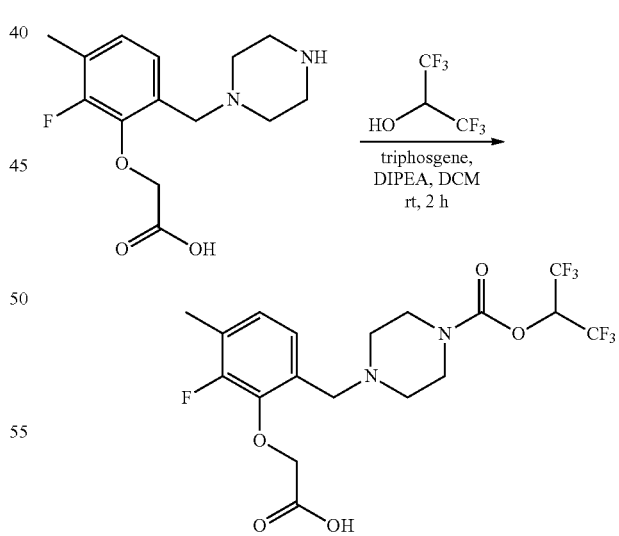

A flask was charged with triphosgene (220 mg, 0.740 mmol, 0.50 equiv), DCM (10 mL), and 1,1,1,3,3,3-hexafluoropropan-2-ol (497 mg, 2.96 mmol, 2.00 equiv), DIPEA (573 mg, 4.43 mmol, 3.00 equiv) was added at 0° C. The mixture was stirred for 1 h at rt prior to addition of 2-(2-fluoro-3-methyl-6-(piperazin-1-ylmethyl)phenoxy) acetic acid (417 mg, 1.48 mmol, 1.00 equiv). The resulting solution was stirred for 2 h at rt and quenched with saturated NaHCO₃ solution (30 mL) under nitrogen, as described in Example 1, Step 1. The crude product (300 mg) was purified by preparative HPLC to provide 400 mg (57% yield) of 2-(2-fluoro-6-((4-(((1,1,1,3,3,3-hexafluoropropan-2-yl)oxy)carbonyl)piperazin-1-yl)methyl)-3-methylphenoxy)acetic acid. ¹H NMR (400 MHz, Chloroform-d) δ 6.89 (d, J=7.2 Hz, 1H), 6.83 (d, J=7.6 Hz, 1H), 5.79-5.73 (m, 1H), 4.92 (s, 2H), 3.82 (br s, 4H), 3.73 (s, 2H), 2.78 (br s, 4H), 2.31 (s, 3H). LCMS (ESI, m/z): 477 [M+H]⁺.

Step 5: Synthesis of 1,1,1,3,3,3-hexafluoropropan-2-yl 4-(3-fluoro-4-methyl-2-(2-(methylsulfonamido)-2-oxoethoxy)benzyl)piperazine-1-carboxylate

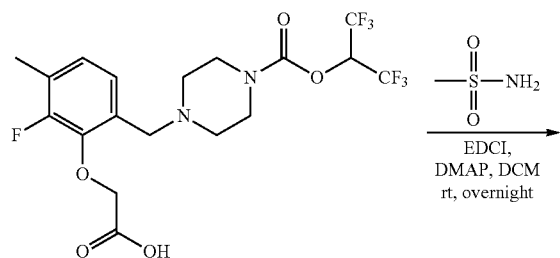

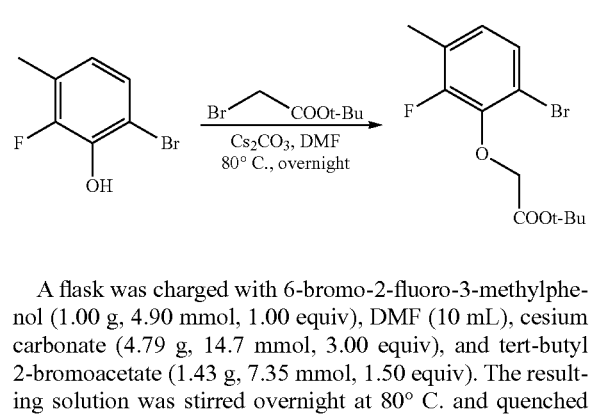

A flask was charged with 2-(2-fluoro-6-((4-(((1,1,1,3,3,3-hexafluoropropan-2-yl)oxy)carbonyl)piperazin-1-yl)methyl)-3-methylphenoxy)acetic acid (300 mg, 0.630 mmol, 1.00 equiv), DCM (10 mL), DMAP (230 mg, 1.89 mmol, 3.00 equiv), methanesulfonamide (180 mg, 1.89 mmol, 3.00 equiv), and N-(3-dimethylaminopropyl)-N'-ethylcarbodiimide hydrochloride (242 mg, 1.26 mmol, 2.00 equiv). The reaction mixture was stirred overnight at rt and quenched with water (30 mL). The resulting solution was extracted with DCM (2×50 mL), and the organic layers were combined, washed with brine (2×30 mL), dried over anhydrous Na₂SO₄, filtered and concentrated under reduced pressure. The crude product (400 mg) was purified by preparative HPLC to provide 17.3 mg (5% yield) of 1,1,1,3,3,3-hexafluoropropan-2-yl 4-(3-fluoro-4-methyl-2-(2-(methylsulfonamido)-2-oxoethoxy)benzyl)piperazine-1-carboxylate. ¹H NMR (300 MHz, Chloroform-d) δ 6.95-6.85 (m, 2H), 5.75-5.71 (m, 1H), 4.76 (s, 2H), 3.76-3.72 (m, 6H), 3.31 (s, 3H), 2.75 (br s, 4H), 2.29 (s, 3H). LCMS (ESI, m/z): 554 [M+H]⁺.

Example 21: 1,1,1,3,3,3-hexafluoropropan-2-yl 4-(2-(2-(cyclopropanesulfonamido)-2-oxoethoxy)-3-fluoro-4-methylbenzyl)piperazine-1-carboxylate

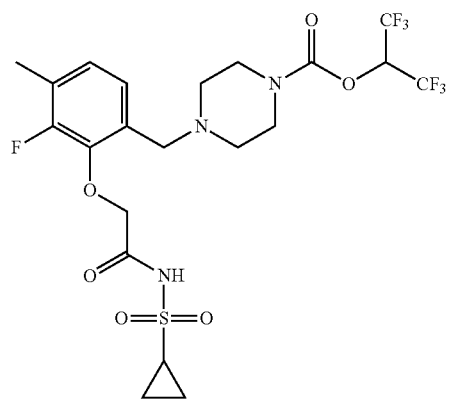 [SMILES: Cc1ccc(CN2CCN(C(=O)OC(C(F)(F)F)C(F)(F)F)CC2)c(OCC(=O)NS(=O)(=O)C2CC2)c1F]

Step 1: Synthesis of tert-butyl 2-(6-bromo-2-fluoro-3-methylphenoxy)acetate

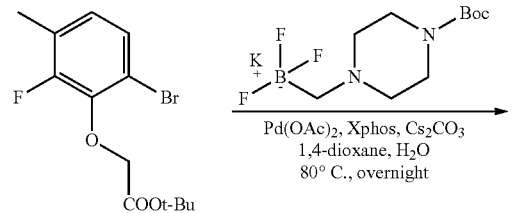

A flask was charged with 6-bromo-2-fluoro-3-methylphenol (1.00 g, 4.90 mmol, 1.00 equiv), DMF (10 mL), cesium carbonate (4.79 g, 14.7 mmol, 3.00 equiv), and tert-butyl 2-bromoacetate (1.43 g, 7.35 mmol, 1.50 equiv). The resulting solution was stirred overnight at 80° C. and quenched with water (30 mL), as described in Example 3, Step 4. The residue was chromatographed on a silica gel column to provide 0.950 g (61% yield) of tert-butyl 2-(6-bromo-2-fluoro-3-methylphenoxy)acetate. LCMS (ESI, m/z): 319 [M+H]⁺.

Step 2: Synthesis of tert-butyl 4-(2-(2-(tert-butoxy)-2-oxoethoxy)-3-fluoro-4-methylbenzyl)piperazine-1-carboxylate -continued

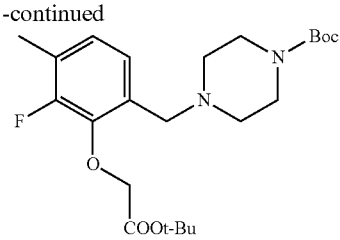

A flask was charged with tert-butyl 2-(6-bromo-2-fluoro-3-methylphenoxy)acetate (900 mg, 2.82 mmol, 1.00 equiv), 1,4-dioxane (10 mL), water (2 mL), potassium ((4-(tert-butoxycarbonyl)piperazin-1-yl)methyl)trifluoroborate (1004 mg, 3.38 mmol, 1.20 equiv), palladium acetate (21.0 mg, 0.0850 mmol, 0.03 equiv), 2-(dicyclohexylphosphino)-2',4',6'-triisopropylbiphenyl (81.0 mg, 0.170 mmol, 0.06 equiv), and cesium carbonate (2770 mg, 8.50 mmol, 3.00 equiv) under nitrogen. The resulting solution was stirred overnight at 80° C. and quenched with water (30 mL), as described in Example 19, Step 1. The residue was chromatographed on a silica gel column to provide 1.00 g (81% yield) of tert-butyl 4-(2-(2-(tert-butoxy)-2-oxoethoxy)-3-fluoro-4-methylbenzyl)piperazine-1-carboxylate. LCMS (ESI, m/z): 439 [M+H]+.

Step 3: Synthesis of 2-(2-fluoro-3-methyl-6-(piperazin-1-ylmethyl)phenoxy)acetic acid

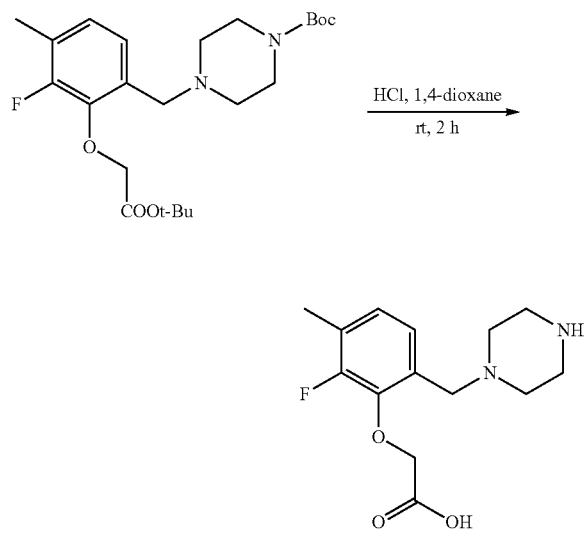

A flask was charged with tert-butyl 4-(2-(2-(tert-butoxy)-2-oxoethoxy)-3-fluoro-4-methylbenzyl)piperazine-1-carboxylate (650 mg, 1.48 mmol, 1.00 equiv), 1,4-dioxane (10 mL), and concentrated hydrochloric acid (2 mL). The resulting solution was stirred for 2 h at rt and concentrated under reduced pressure as described in Example 3, Step 4 to provide 417 mg (quantitative) of 2-(2-fluoro-3-methyl-6-(piperazin-1-ylmethyl)phenoxy) acetic acid. LCMS (ESI, m/z): 283 [M+H]+.

Step 4: Synthesis of 2-(2-fluoro-6-((4-(((1,1,1,3,3,3-hexafluoropropan-2-yl)oxy)carbonyl)piperazin-1-yl)methyl)-3-methylphenoxy)acetic acid

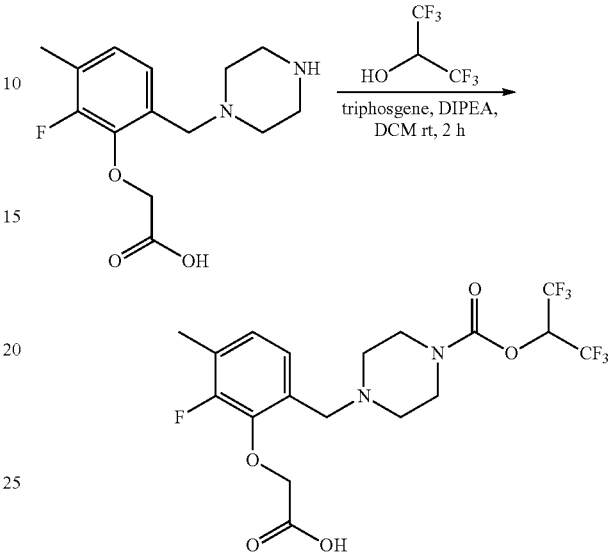

A flask was charged with triphosgene (220 mg, 0.740 mmol, 0.50 equiv), DCM (10 mL), and 1,1,1,3,3,3-hexafluoropropan-2-ol (497 mg, 2.96 mmol, 2.00 equiv). DIPEA (573 mg, 4.43 mmol, 3.00 equiv) was added at 0° C. The mixture was stirred for 1 h at rt prior to addition of 2-(2-fluoro-3-methyl-6-(piperazin-1-ylmethyl)phenoxy) acetic acid (417 mg, 1.48 mmol, 1.00 equiv). The resulting solution was stirred for 2 h at rt and quenched with saturated NaHCO$_3$ solution (30 mL) under nitrogen, as described in Example 1, Step 1. The crude product (300 mg) was purified by preparative HPLC to provide 400 mg (57% yield) of 2-(2-fluoro-6-((4-(((1,1,1,3,3,3-hexafluoropropan-2-yl)oxy)carbonyl)piperazin-1-yl)methyl)-3-methylphenoxy)acetic acid. $^1$H NMR (400 MHz, Chloroform-d) δ 6.89 (d, J=7.2 Hz, 1H), 6.83 (d, J=7.6 Hz, 1H), 5.79-5.73 (m, 1H), 4.92 (s, 2H), 3.82 (br s, 4H), 3.73 (s, 2H), 2.78 (br s, 4H), 2.31 (s, 3H). LCMS (ESI, m/z): 477 [M+H]+.

Step 5: Synthesis of 1,1,1,3,3,3-hexafluoropropan-2-yl 4-(2-(2-chloro-2-oxoethoxy)-3-fluoro-4-methylbenzyl)piperazine-1-carboxylate

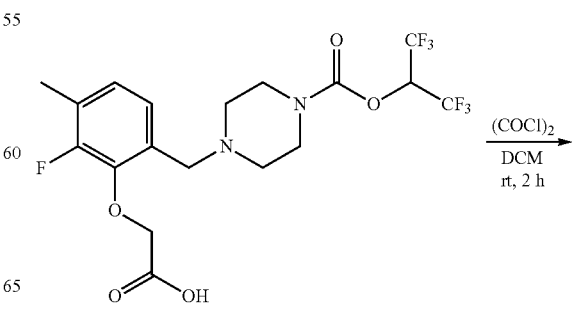

-continued

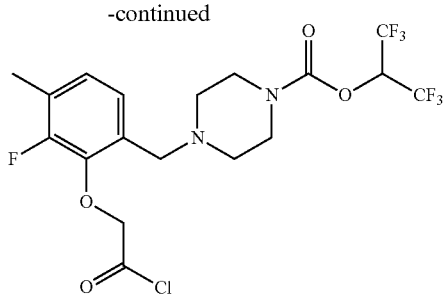

A flask was charged with 2-(2-fluoro-6-((4-(((1,1,1,3,3,3-hexafluoropropan-2-yl)oxy)carbonyl)piperazin-1-yl) methyl)-3-methylphenoxy)acetic acid (300 mg, 0.630 mmol, 1.00 equiv), and DCM (10 mL). Oxalyl dichloride (234 mg, 1.86 mmol, 3.00 equiv) was added at 0° C. The resulting solution was stirred for 2 h at rt and concentrated under reduced pressure to provide 311 mg (crude) of 1,1,1,3,3,3-hexafluoropropan-2-yl 4-(2-(2-chloro-2-oxoethoxy)-3-fluoro-4-methylbenzyl)piperazine-1-carboxylate.

Step 6: Synthesis of 1,1,1,3,3,3-hexafluoropropan-2-yl 4-(2-(2-(cyclopropanesulfonamido)-2-oxoethoxy)-3-fluoro-4-methylbenzyl)piperazine-1-carboxylate

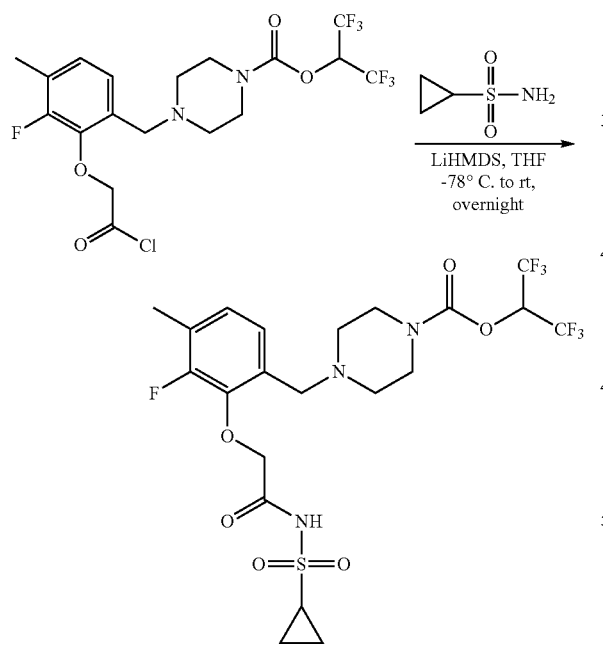

A flask was charged with cyclopropanesulfonamide (229 mg, 1.89 mmol, 3.00 equiv), and THF (10 mL) under nitrogen. The mixture was cooled to −78° C. and lithium bis(trimethylsilyl)amide (2.52 mL, 2.52 mmol, 4.00 equiv, 1M in tetrahydrofuran) was added dropwise at −78° C. The mixture was stirred for 30 min at −78° C. prior to drop-wise addition of 1,1,1,3,3,3-hexafluoropropan-2-yl 4-(2-(2-chloro-2-oxoethoxy)-3-fluoro-4-methylbenzyl)piperazine-1-carboxylate (311 mg, 0.630 mmol, 1.00 equiv) over 10 min at −78° C. The reaction mixture was stirred overnight at rt and quenched with saturated NH$_4$Cl solution (30 mL). The resulting solution was extracted with DCM (2×50 mL), and the organic layers were combined, washed with brine (2×30 mL), dried over anhydrous Na$_2$SO$_4$, filtered and concentrated under reduced pressure. The crude product (200 mg) was purified by preparative HPLC to provide 77.6 mg (21% yield) of 1,1,1,3,3,3-hexafluoropropan-2-yl 4-(2-(2-(cyclopropanesulfonamido)-2-oxoethoxy)-3-fluoro-4-methylbenzyl)piperazine-1-carboxylate. $^1$H NMR (300 MHz, Chloroform-d) δ 6.94-6.84 (m, 2H), 5.78-5.69 (m, 1H), 4.72 (s, 2H), 3.61 (br s, 6H), 3.02-2.96 (m, 1H), 2.56-2.55 (m, 4H), 2.28 (s, 3H), 1.39-1.38 (m, 2H), 1.17-1.10 (m, 2H). LCMS (ESI, m/z): 580 [M+H]$^+$.

Example 22: 1-(2-((4-(((1,1,1,3,3,3-Hexafluoropropan-2-yl)oxy)carbonyl)piperazin-1-yl)methyl)-6-(trifluoromethyl)phenoxy)cyclopropane-1-carboxylic acid

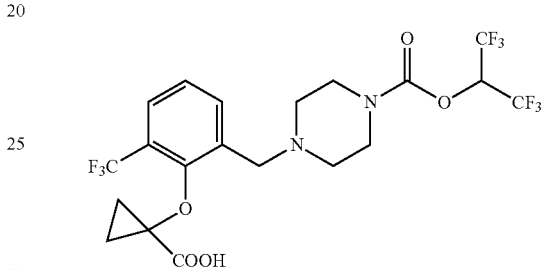

Step 1: Synthesis of tert-butyl 4-bromo-2-(2-bromo-6-(trifluoromethyl)phenoxy)butanoate

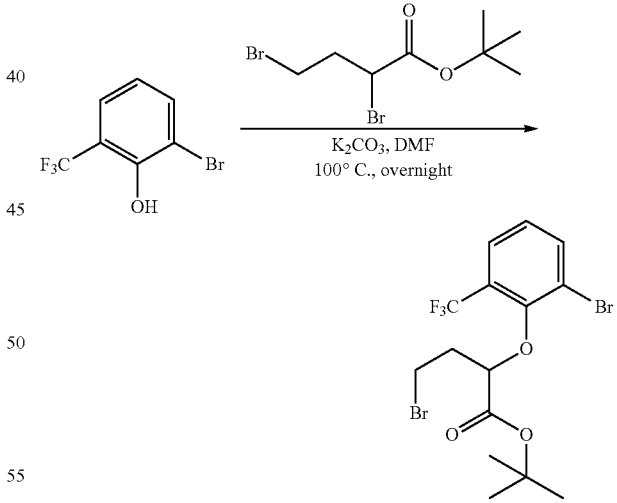

A round-bottom flask was charged with 2-bromo-6-(trifluoromethyl)phenol (0.500 g, 2.07 mmol, 1.00 equiv), tert-butyl 2,4-dibromobutanoate (1.25 g, 4.14 mmol, 2.00 equiv), potassium carbonate (0.857 g, 6.21 mmol, 3.00 equiv) and DMF (15 mL) under nitrogen. The reaction mixture was stirred overnight at 100° C. and quenched with water (10 mL). The resulting solution was extracted with EtOAc (3×20 mL), and the organic layers were combined, washed with brine (20 mL), dried over anhydrous Na$_2$SO$_4$, filtered and concentrated under reduced pressure. The residue was chromatographed on a silica gel column to provide 0.200 g (21% yield) of tert-butyl 4-bromo-2-(2-bromo-6-(trifluoromethyl)phenoxy)butanoate. LCMS (ESI, m/z): 461 [M+H]+.

Step 2: Synthesis of tert-butyl 1-(2-bromo-6-(trifluoromethyl)phenoxy)cyclopropane-1-carboxylate

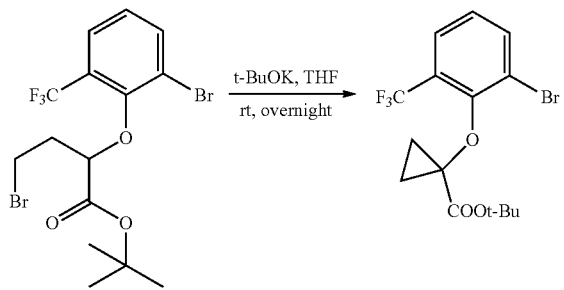

A round-bottom flask was charged with tert-butyl 4-bromo-2-(2-bromo-6-(trifluoromethyl)phenoxy)butanoate (1.50 g, 3.26 mmol, 1.00 equiv), potassium tert-butoxide (0.730 g, 6.52 mmol, 2.00 equiv) and THF (20 mL) under nitrogen. The reaction mixture was stirred overnight at rt and quenched with water (30 mL). The resulting solution was extracted with EtOAc (3×40 mL), and the organic layers were combined, washed with brine (40 mL), dried over anhydrous Na$_2$SO$_4$, filtered and concentrated under reduced pressure. The residue was chromatographed on a silica gel column to provide 0.600 g (49% yield) of tert-butyl 1-(2-bromo-6-(trifluoromethyl)phenoxy)cyclopropane-1-carboxylate. LCMS (ESI, m/z): 381 [M+H]+.

Step 3: Synthesis of Potassium trifluoro((4-(((1,1,1,3,3,3-hexafluoropropan-2-yl)oxy)carbonyl)piperazin-1-yl)methyl)borate

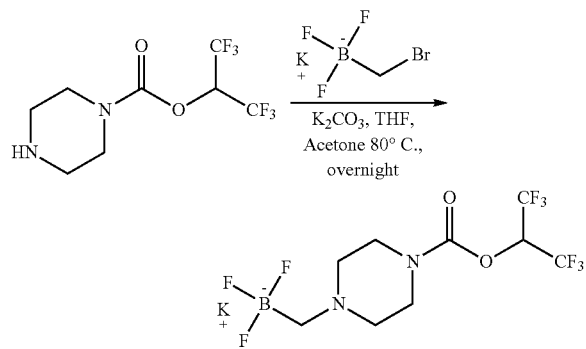

A round-bottom flask was charged with 1,1,1,3,3,3-hexafluoropropan-2-yl piperazine-1-carboxylate (7.30 g, 26.1 mmol, 1.00 equiv, Example 1, Step 2), potassium (bromomethyl)trifluoroboranuide (5.30 g, 26.1 mmol, 1.00 equiv) and THF (120 mL) under nitrogen. The mixture was stirred overnight at 80° C. and concentrated under reduced pressure. Potassium carbonate (3.56 g, 26.1 mmol, 1.00 equiv) and acetone (150 mL) were added, and the resulting solution was stirred for 2 h at rt prior to dilution with acetone (400 mL). The mixture was filtered and the filtrate was concentrated under reduced pressure to provide 10.1 g (97% yield) of potassium trifluoro((4-(((1,1,1,3,3,3-hexafluoropropan-2-yl)oxy)carbonyl)piperazin-1-yl)methyl)borate. $^1$H NMR (300 MHz, Chloroform-d) δ 6.56-6.45 (m, 1H), 3.38-3.33 (m, 4H), 2.28-2.22 (m, 4H), 1.28-1.22 (m, 2H). LCMS (ESI, m/z): 361 [M–K]−.

Step 4: Synthesis of 1,1,1,3,3,3-hexafluoropropan-2-yl 4-(2-(1-(tert-butoxycarbonyl)cyclopropoxy)-3-(trifluoromethyl)benzyl)piperazine-1-carboxylate

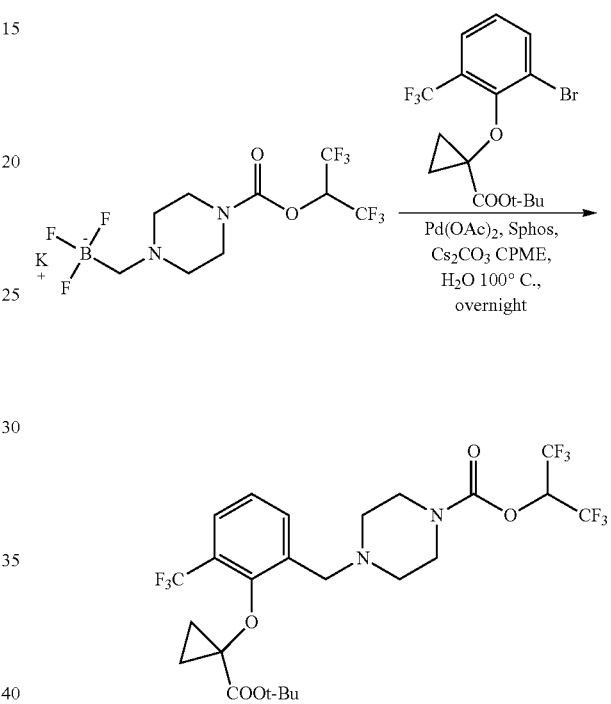

A round-bottom flask was charged with tert-butyl 1-(2-bromo-6-(trifluoromethyl)phenoxy)cyclopropane-1-carboxylate (500 mg, 1.31 mmol, 1.00 equiv), potassium trifluoro((4-(((1,1,1,3,3,3-hexafluoropropan-2-yl)oxy)carbonyl)piperazin-1-yl)methyl)borate (632 mg, 1.58 mmol, 1.20 equiv), palladium acetate (20.2 mg, 0.0660 mmol, 0.05 equiv), 2-dicyclohexylphosphino-2',6'-dimethoxybiphenyl (54.3 mg, 0.132 mmol, 0.10 equiv), cesium carbonate (1.28 g, 3.93 mmol, 3.00 equiv), cyclopentyl methyl ether (10 mL), and water (2 mL) under nitrogen. The reaction mixture was stirred overnight at 100° C. and quenched with water (10 mL). The resulting solution was extracted with dichloromethane (3×20 mL), and the organic layers were combined, washed with brine (20 mL), dried over anhydrous Na$_2$SO$_4$, filtered and concentrated under reduced pressure. The residue was chromatographed on a silica gel column to provide 90.0 mg (12% yield) of 1,1,1,3,3,3-hexafluoropropan-2-yl 4-(2-(1-(tert-butoxycarbonyl)cyclopropoxy)-3-(trifluoromethyl)benzyl)piperazine-1-carboxylate. LCMS (ESI, m/z): 595 [M+H]+.

Step 5: Synthesis of 1-(2-((4-(((1,1,1,3,3,3-hexafluoropropan-2-yl)oxy)carbonyl)piperazin-1-yl)methyl)-6-(trifluoromethyl)phenoxy)cyclopropane-1-carboxylic acid

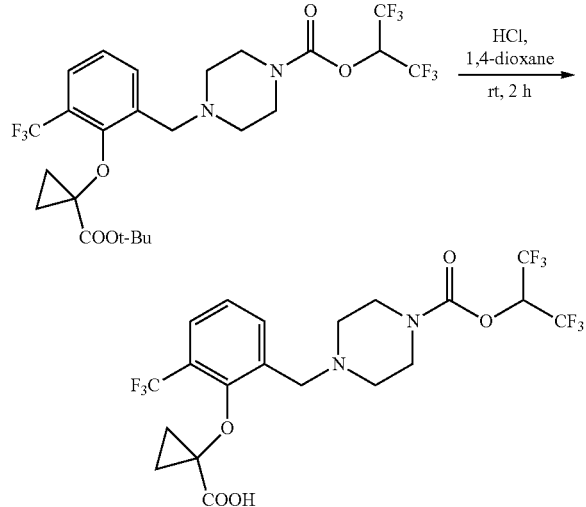

A round-bottom flask was charged with 1,1,1,3,3,3-hexafluoropropan-2-yl 4-(2-(1-(tert-butoxycarbonyl)cyclopropoxy)-3-(trifluoromethyl)benzyl)piperazine-1-carboxylate (90.0 mg, 0.150 mmol, 1.00 equiv), 1,4-dioxane (5 mL), and concentrated hydrochloric acid (2 mL). The resulting solution was stirred for 2 h at rt and concentrated under reduced pressure. The crude product was dissolved in saturated NaHCO$_3$ solution (10 mL) and extracted with DCM (3×20 mL). The organic layers were combined, washed with brine (30 mL), dried over anhydrous Na$_2$SO$_4$, filtered and concentrated under reduced pressure. The crude product (78 mg) was purified by preparative HPLC to afford 4.7 mg (6% yield) of 1-(2-((4-(((1,1,1,3,3,3-hexafluoropropan-2-yl)oxy)carbonyl)piperazin-1-yl)methyl)-6-(trifluoromethyl)phenoxy)cyclopropane-1-carboxylic acid. $^1$H NMR (400 MHz, Methanol-d$_4$) δ 7.88 (d, J=7.6 Hz, 1H), 7.50 (d, J=7.6 Hz, 1H), 7.21 (t, J=7.6 Hz, 1H), 6.31-6.11 (m, 1H), 3.82 (s, 2H), 3.61-3.50 (m, 4H), 2.62-2.45 (m, 4H), 1.38 (br s, 2H), 0.98-0.94 (m, 2H). LCMS (ESI, m/z): 539 [M+H]$^+$.

Example 23: 1-((2-Chloro-6-((4-(((1,1,1,3,3,3-hexafluoropropan-2-yl)oxy)carbonyl)piperazin-1-yl)methyl)-3-methylphenoxy)methyl)cyclopropane-1-carboxylic acid

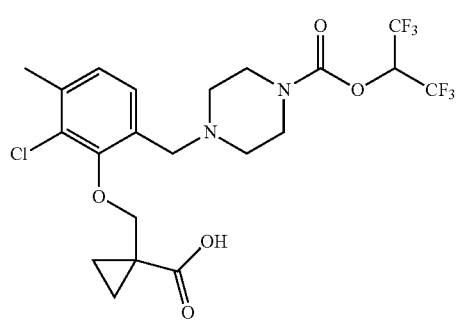 [SMILES: Cc1ccc(CN2CCN(C(=O)OC(C(F)(F)F)C(F)(F)F)CC2)c(OCC2(C(=O)O)CC2)c1Cl]

Step 1: Synthesis of ethyl 1-(((methylsulfonyl)oxy)methyl)cyclopropane-1-carboxylate

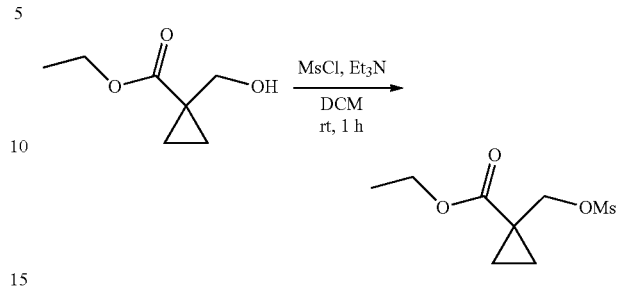

A 100-mL round-bottom flask was charged with ethyl 1-(hydroxymethyl)cyclopropane-1-carboxylate (1.91 g, 13.3 mmol, 1.00 equiv), TEA (4.03 g, 39.9 mmol, 3.00 equiv), and DCM (40 mL). Methanesulfonyl chloride (2.27 g, 20.0 mmol, 1.50 equiv) was added at 0° C., and the reaction mixture was stirred for 1 h at rt prior to quenching with saturated NH$_4$Cl (30 mL). The resulting solution was extracted with dichloromethane (2×50 mL), and the organic layers were combined, washed with saturated NaHCO$_3$ (30 mL) and brine (30 mL), dried over anhydrous Na$_2$SO$_4$, filtered and concentrated under reduced pressure to provide 2.83 g (crude) of ethyl 1-(((methylsulfonyl)oxy)methyl)cyclopropane-1-carboxylate.

Step 2: Synthesis of ethyl 1-((6-bromo-2-chloro-3-methylphenoxy)methyl)cyclopropane-1-carboxylate

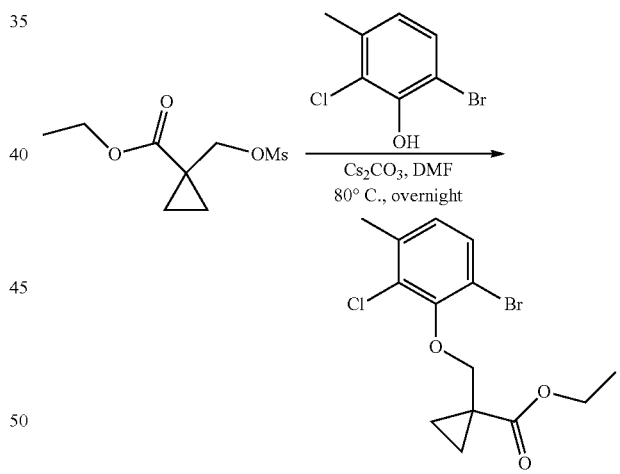

A round-bottom flask was charged with 6-bromo-2-chloro-3-methylphenol (0.900 g, 4.09 mmol, 1.00 equiv), ethyl 1-(((methylsulfonyl)oxy)methyl)cyclopropane-1-carboxylate (1.36 g, 6.14 mmol, 1.50 equiv), cesium carbonate (4.00 g, 12.3 mmol, 3.00 equiv), and DMF (20 mL). The reaction mixture was stirred overnight at 80° C. and quenched with water (30 mL). The resulting solution was extracted with EtOAc (2×50 mL), and the organic layers were combined, washed with brine (2×30 mL), dried over anhydrous Na$_2$SO$_4$, filtered and concentrated under reduced pressure. The residue was chromatographed on a silica gel column to provide 1.18 g (84% yield) of ethyl 1-((6-bromo-2-chloro-3-methylphenoxy)methyl)cyclopropane-1-carboxylate. LCMS (ESI, m/z): 347 [M+H]$^+$.

Step 3: Synthesis of tert-butyl 4-(3-chloro-2-((1-(ethoxycarbonyl)cyclopropyl)methoxy)-4-methylbenzyl) piperazine-1-carboxylate

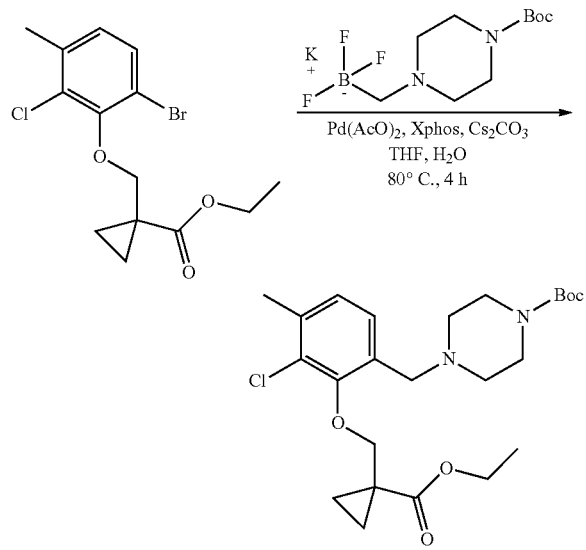

A round-bottom flask was charged with ethyl 1-((6-bromo-2-chloro-3-methylphenoxy)methyl)cyclopropane-1-carboxylate (700 mg, 2.02 mmol, 1.00 equiv), palladium acetate (90.0 mg, 0.202 mmol, 0.10 equiv), 2-(dicyclohexylphosphino)-2',4',6'-triisopropylbiphenyl (181 mg, 0.404 mmol, 0.20 equiv, Xphos), cesium carbonate (1980 mg, 6.06 mmol, 3.00 equiv), potassium ((4-(tert-butoxycarbonyl)piperazin-1-yl)methyl)trifluoroborate (927 mg, 3.03 mmol, 1.50 equiv), THF (8 mL), and water (2 mL) under nitrogen. The reaction mixture was stirred for 4 h at 80° C. and quenched with water (30 mL). The resulting solution was extracted with DCM (2×50 mL), and the organic layers were combined, washed with brine (2×30 mL), dried over anhydrous $Na_2SO_4$, filtered and concentrated under reduced pressure. The residue was chromatographed on a silica gel column to provide 700 mg (74% yield) of tert-butyl 4-(3-chloro-2-((1-(ethoxycarbonyl)cyclopropyl)methoxy)-4-methylbenzyl)piperazine-1-carboxylate. LCMS (ESI, m/z): 467 [M+H]+.

Step 4: Synthesis of 1-((6-((4-(tert-butoxycarbonyl)piperazin-1-yl)methyl)-2-chloro-3-methylphenoxy)methyl)cyclopropane-1-carboxylic acid

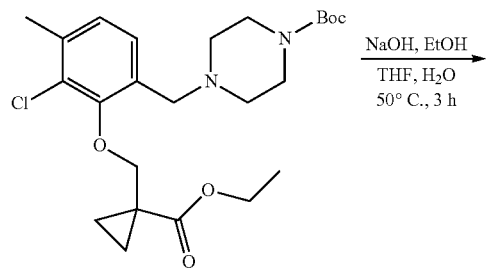

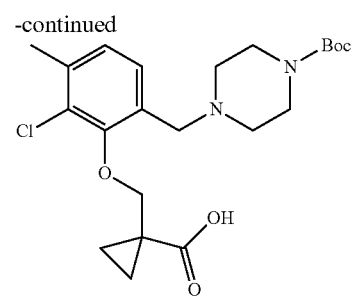

A round-bottom flask was charged with tert-butyl 4-(3-chloro-2-((1-(ethoxycarbonyl)cyclopropyl)methoxy)-4-methylbenzyl)piperazine-1-carboxylate (700 mg, 1.50 mmol, 1.00 equiv), tetrahydrofuran (3 mL), ethanol (3 mL), water (5 mL), and sodium hydroxide (600 mg, 15.0 mmol, 10.0 equiv). The reaction mixture was stirred for 3 h at 50° C. The pH value of the solution was adjusted to 5 with hydrochloric acid (1 mol/L). The resulting solution was extracted with dichloromethane (2×50 mL), and the organic layers were combined, washed with brine (2×30 mL), dried over anhydrous $Na_2SO_4$, filtered and concentrated under reduced pressure to provide 610 mg (93% yield) of 1-((6-((4-(tert-butoxycarbonyl)piperazin-1-yl)methyl)-2-chloro-3-methylphenoxy)methyl)cyclopropane-1-carboxylic acid. LCMS (ESI, m/z): 439 [M+H]+.

Step 5: Synthesis of 1-((2-chloro-3-methyl-6-(piperazin-1-ylmethyl)phenoxy)methyl)cyclopropane-1-carboxylic acid

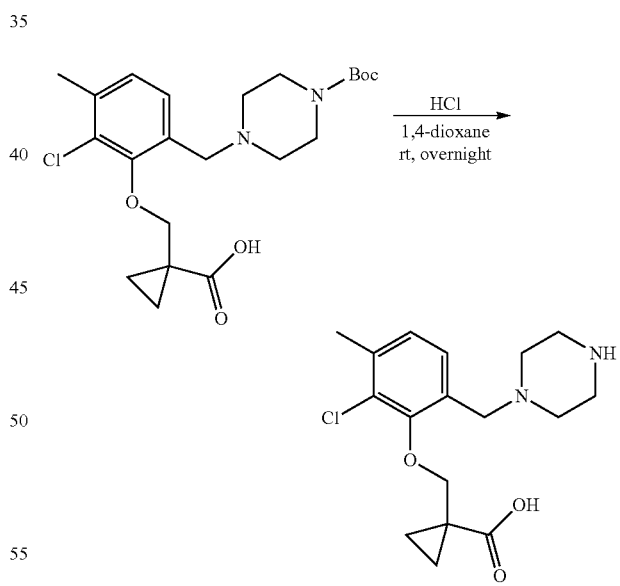

A round-bottom flask was charged with 1-((6-((4-(tert-butoxycarbonyl)piperazin-1-yl)methyl)-2-chloro-3-methylphenoxy)methyl)cyclopropane-1-carboxylic acid (630 mg, 1.44 mmol, 1.00 equiv), 1,4-dioxane (10 mL), and concentrated hydrochloric acid (3 mL). The resulting solution was stirred overnight at rt and concentrated under reduced pressure to provide 600 mg (crude) of 1-((2-chloro-3-methyl-6-(piperazin-1-ylmethyl)phenoxy)methyl)cyclopropane-1-carboxylic acid. LCMS (ESI, m/z): 339 [M+H]+.

Step 6: Synthesis of 1-((2-chloro-6-((4-(((1,1,1,3,3,3-hexafluoropropan-2-yl)oxy)carbonyl)piperazin-1-yl)methyl)-3-methylphenoxy)methyl)cyclopropane-1-carboxylic acid

Example 24: 4-(2-Fluoro-6-((4-(((1,1,1,3,3,3-hexafluoropropan-2-yl)oxy)carbonyl)piperazin-1-yl)methyl)-3-methylphenyl)-2,2-dimethylbut-3-ynoic acid

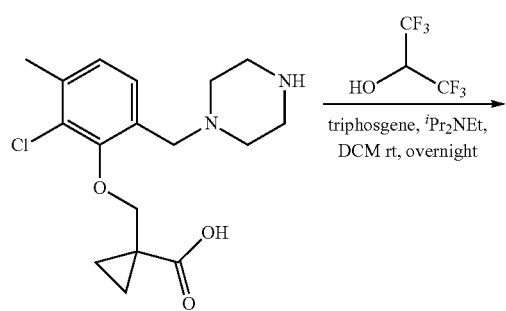

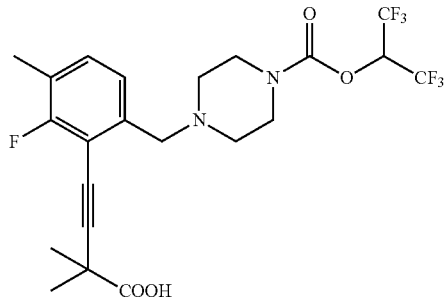 [SMILES: Cc1ccc(CN2CCN(C(=O)OC(C(F)(F)F)C(F)(F)F)CC2)c(C#CC(C)(C)C(=O)O)c1F]

Step 1: Synthesis of tert-butyl 4-(3-fluoro-2-hydroxy-4-methylbenzyl)piperazine-1-carboxylate

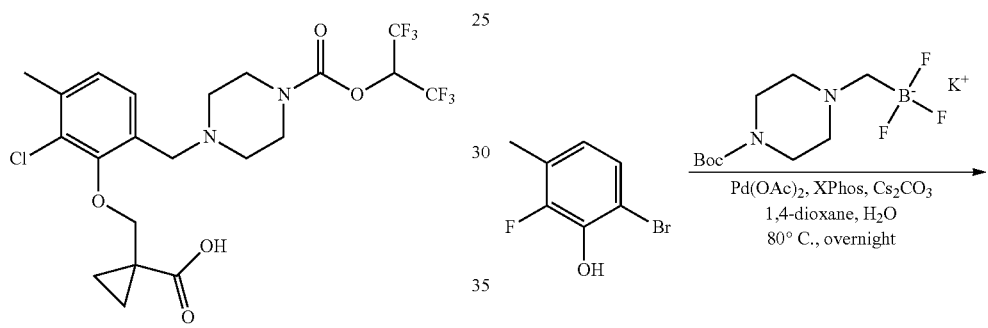

A round-bottom flask was charged with triphosgene (270 mg, 0.910 mmol, 0.70 equiv), dichloromethane (10 mL), and 1,1,1,3,3,3-hexafluoropropan-2-ol (437 mg, 2.60 mmol, 2.00 equiv). N,N-Diisopropylethylamine (503 mg, 3.90 mmol, 3.00 equiv) was added at 0° C., and the mixture was stirred for 1 h at rt prior to addition of 1-((2-chloro-3-methyl-6-(piperazin-1-ylmethyl)phenoxy)methyl)cyclopropane-1-carboxylic acid (440 mg, 1.30 mmol, 1.00 equiv). The reaction mixture was stirred overnight at rt and quenched with saturated NaHCO$_3$ (30 mL). The resulting solution was extracted with DCM (2×50 mL), and the organic layers were combined, washed with brine (2×30 mL), dried over anhydrous Na$_2$SO$_4$, filtered and concentrated under reduced pressure. The crude product (200 mg) was purified by preparative HPLC to provide 155 mg (22% yield) of 1-((2-chloro-3-methyl-6-(piperazin-1-ylmethyl)phenoxy)methyl)cyclopropane-1-carboxylic acid. $^1$H NMR (300 MHz, Methanol-d$_4$) δ 7.21 (d, J=7.8 Hz, 1H), 7.07 (d, J=8.1 Hz, 1H), 6.18-6.09 (m, 1H), 4.11 (s, 2H), 3.89 (s, 2H), 3.63-3.54 (m, 4H), 2.69-2.68 (m, 4H), 2.35 (s, 3H), 1.32-1.28 (m, 2H), 1.11-1.08 (m, 2H). LCMS (ESI, m/z): 533 [M+H]$^+$.

A round-bottom flask was charged with 6-bromo-2-fluoro-3-methylphenol (2.00 g, 9.75 mmol, 1.00 equiv), potassium (4-[(tert-butoxy)carbonyl]piperazin-1-ylmethyl)trifluoroboranuide (3.90 g, 12.7 mmol, 1.30 equiv), palladium acetate (0.439 g, 1.96 mmol, 0.20 equiv), 2-(dicyclohexylphosphino)-2',4',6'-triisopropylbiphenyl (1.87 g, 3.93 mmol, 0.40 equiv, Xphos), cesium carbonate (9.59 g, 29.4 mmol, 3.00 equiv), 1,4-dioxane (20 mL), and water (4 mL) under nitrogen. The reaction mixture was stirred overnight at 80° C. and quenched with water (20 mL). The resulting solution was extracted with EtOAc (3×30 mL), and the organic layers were combined, washed with brine (1×50 mL), dried over anhydrous Na$_2$SO$_4$, filtered and concentrated under reduced pressure. The residue was chromatographed on a silica gel column to provide 2.20 g (70% yield) of tert-butyl 4-(3-fluoro-2-hydroxy-4-methylbenzyl)piperazine-1-carboxylate. LCMS (ESI, m/z): 325 [M+H]$^+$.

Step 2: Synthesis of tert-butyl 4-(3-fluoro-4-methyl-2-(((trifluoromethyl)sulfonyl)oxy)benzyl)piperazine-1-carboxylate

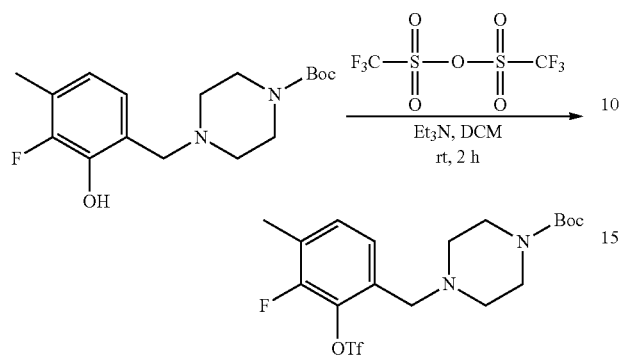

A round-bottom flask was charged with tert-butyl 4-(3-fluoro-2-hydroxy-4-methylbenzyl)piperazine-1-carboxylate (2.00 g, 6.17 mmol, 1.00 equiv), TEA (1.87 g, 18.5 mmol, 3.00 equiv), and DCM (40 mL). Trifluoromethanesulfonic anhydride (2.61 g, 9.25 mmol, 1.50 equiv) was added at 0° C., and the reaction mixture was stirred for 2 h at rt before quenching with water (30 mL). The resulting solution was extracted with DCM (3×50 mL), and the organic layers were combined, washed with brine (1×50 mL), dried over anhydrous $Na_2SO_4$, filtered and concentrated under reduced pressure. The residue was chromatographed on a silica gel column to provide 1.80 g (64% yield) of tert-butyl 4-(3-fluoro-4-methyl-2-(((trifluoromethyl)sulfonyl)oxy)benzyl)piperazine-1-carboxylate. LCMS (ESI, m/z): 457 [M+H]+.

Step 3: Synthesis of tert-butyl 4-(2-(4-ethoxy-3,3-dimethyl-4-oxobut-1-yn-1-yl)-3-fluoro-4-methylbenzyl)piperazine-1-carboxylate

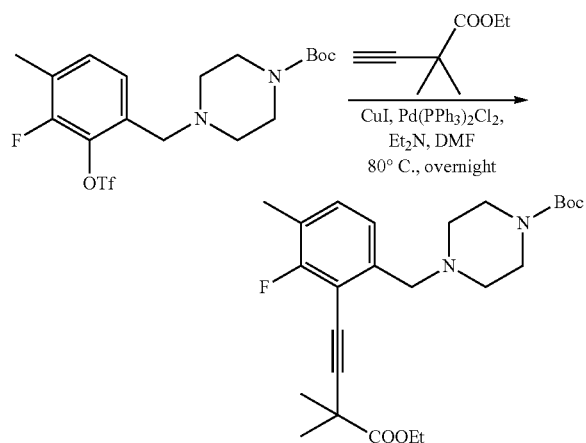

A round-bottom flask was charged with tert-butyl 4-(3-fluoro-4-methyl-2-(((trifluoromethyl)sulfonyl)oxy)benzyl)piperazine-1-carboxylate (850 mg, 1.86 mmol, 1.00 equiv), ethyl 2,2-dimethylbut-3-ynoate (522 mg, 3.72 mmol, 2.00 equiv), copper(I) iodide (70.8 mg, 0.370 mmol, 0.20 equiv), bis(triphenylphosphine)palladium(II) chloride (130 mg, 0.190 mmol, 0.10 equiv), TEA (565 mg, 5.58 mmol, 3.00 equiv), and DMF (10 mL) under nitrogen. The reaction mixture was stirred overnight at 80° C. and quenched with water (20 mL). The resulting solution was extracted with EtOAc (3×30 mL), and the organic layers were combined, washed with brine (1×50 mL), dried over anhydrous $Na_2SO_4$, filtered and concentrated under reduced pressure. The residue was chromatographed on a silica gel column to provide 100 mg (12% yield) of tert-butyl 4-(2-(4-ethoxy-3,3-dimethyl-4-oxobut-1-yn-1-yl)-3-fluoro-4-methylbenzyl)piperazine-1-carboxylate. LCMS (ESI, m/z): 447 [M+H]+.

Step 4: Synthesis of 4-(6-((4-(tert-butoxycarbonyl)piperazin-1-yl)methyl)-2-fluoro-3-methylphenyl)-2,2-dimethylbut-3-ynoic acid

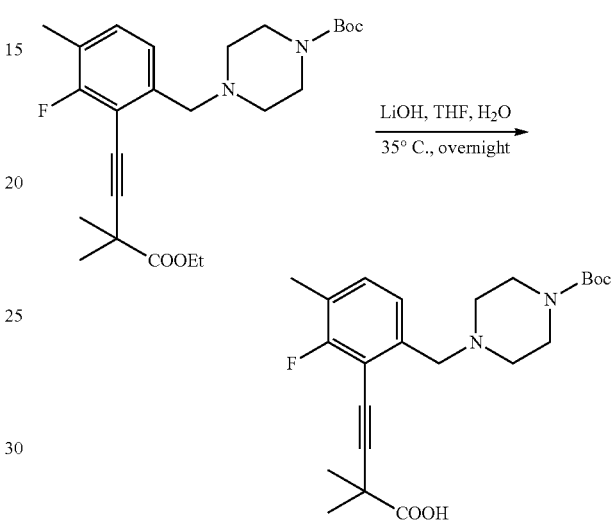

A round-bottom flask was charged with tert-butyl 4-(2-(4-ethoxy-3,3-dimethyl-4-oxobut-1-yn-1-yl)-3-fluoro-4-methylbenzyl)piperazine-1-carboxylate (100 mg, 0.224 mmol, 1.00 equiv), lithium hydroxide (322 mg, 13.4 mmol, 60.00 equiv), tetrahydrofuran (5 mL), and water (1 mL). The reaction mixture was stirred overnight at 35° C. and quenched with water (10 mL), prior to adjustment of the pH value to pH 6 with hydrochloric acid (IM). The resulting solution was extracted with DCM (3×15 mL), and the organic layers were combined, washed with brine (1×20 mL), dried over anhydrous $Na_2SO_4$, filtered and concentrated under reduced pressure to provide 90.0 mg (96% yield) of 4-(6-((4-(tert-butoxycarbonyl)piperazin-1-yl)methyl)-2-fluoro-3-methylphenyl)-2,2-dimethylbut-3-ynoic acid. LCMS (ESI, m/z): 419 [M+H]+.

Step 5: Synthesis of 4-(2-fluoro-3-methyl-6-(piperazin-1-ylmethyl)phenyl)-2,2-dimethylbut-3-ynoic acid

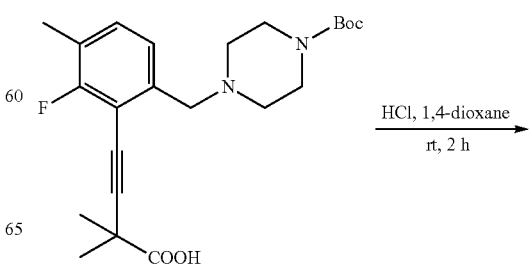

-continued

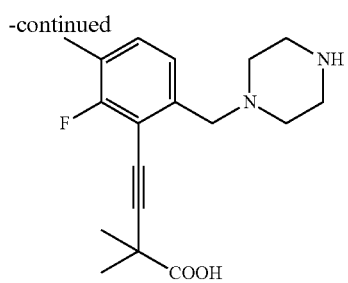

A round-bottom flask was charged with 4-(6-((4-(tert-butoxycarbonyl)piperazin-1-yl)methyl)-2-fluoro-3-methylphenyl)-2,2-dimethylbut-3-ynoic acid (90.0 mg, 0.220 mmol, 1.00 equiv), 1,4-dioxane (8 mL), and concentrated hydrochloric acid (1 mL). The resulting solution was stirred for 2 h at rt and concentrated under reduced pressure to provide 100 mg (crude) of 4-(2-fluoro-3-methyl-6-(piperazin-1-ylmethyl)phenyl)-2,2-dimethylbut-3-ynoic acid. LCMS (ESI, m/z): 319 [M+H]$^+$.

Step 6: Synthesis of 4-(2-fluoro-6-((4-(((1,1,1,3,3,3-hexafluoropropan-2-yl)oxy)carbonyl)piperazin-1-yl)methyl)-3-methylphenyl)-2,2-dimethylbut-3-ynoic acid

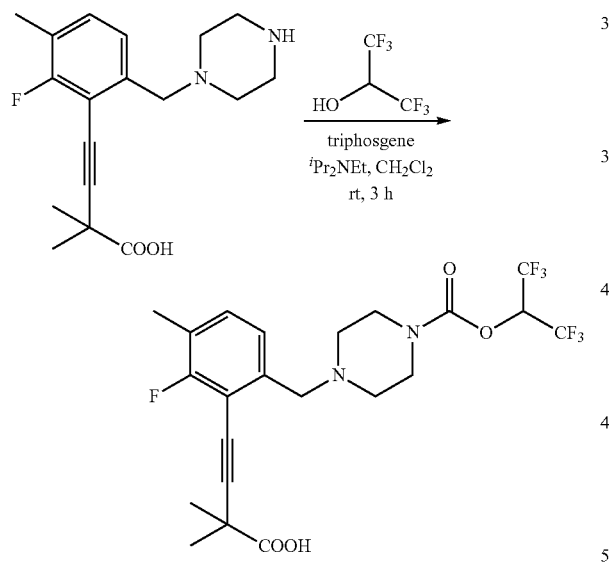

A round-bottom flask was charged with triphosgene (42.5 mg, 0.143 mmol, 0.70 equiv) and DCM (10 mL). 1,1,1,3,3,3-Hexafluoropropan-2-ol (85.8 mg, 0.510 mmol, 2.50 equiv) and DIPEA (105 mg, 0.816 mmol, 4.00 equiv) were added sequentially at 0° C. The mixture was stirred for 1 h at rt prior to addition of 4-(2-fluoro-3-methyl-6-(piperazin-1-ylmethyl)phenyl)-2,2-dimethylbut-3-ynoic acid (65.0 mg, 0.204 mmol, 1.00 equiv). The reaction mixture was stirred for 2 h at rt and quenched with water (10 mL). The resulting solution was extracted with DCM (3×15 mL), and the organic layers were combined, washed with brine (1×40 mL), dried over anhydrous Na$_2$SO$_4$, filtered and concentrated under reduced pressure. The crude product (200 mg) was purified by preparative HPLC to afford 34.2 mg (33% yield) of 4-(2-fluoro-6-((4-(((1,1,1,3,3,3-hexafluoropropan-2-yl)oxy)carbonyl)piperazin-1-yl)methyl)-3-methylphenyl)-2,2-dimethylbut-3-ynoic acid. $^1$H NMR (300 MHz, Methanol-d$_4$) δ 7.23-7.13 (m, 2H), 6.20-6.11 (m, 1H), 3.83 (s, 2H), 3.63-3.60 (m, 4H), 2.68-2.67 (m, 4H), 2.27 (s, 3H), 1.58 (s, 6H). LCMS (ESI, m/z): 513 [M+H]$^+$.

Example 25: 4-(2-Fluoro-6-((4-(((1,1,1,3,3,3-hexafluoropropan-2-yl)oxy)carbonyl)piperazin-1-yl)methyl)phenyl)-2,2-dimethylbut-3-ynoic acid

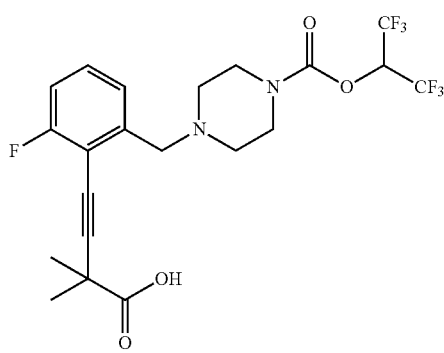 [SMILES: CC(C)(C#Cc1c(F)cccc1CN1CCN(C(=O)OC(C(F)(F)F)C(F)(F)F)CC1)C(=O)O]

Step 1: Synthesis of 2-(trimethylsilyl)ethyl 2,2-dimethylbut-3-ynoate

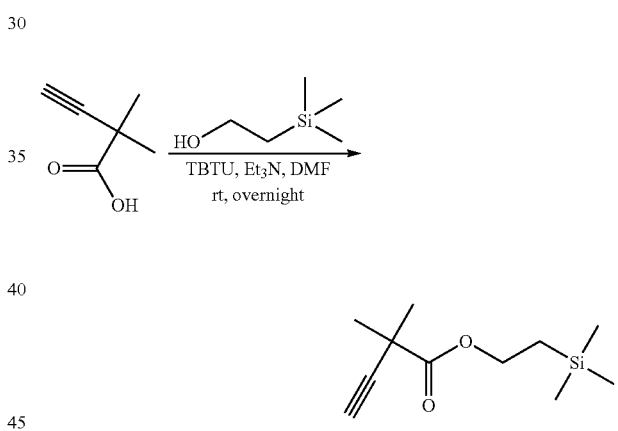

A round-bottom flask was charged with 2,2-dimethylbut-3-ynoic acid (1.00 g, 8.93 mmol, 1.00 equiv), 2-(trimethylsilyl)ethan-1-ol (1.05 g, 8.93 mmol, 1.00 equiv), 2-(1H-benzotriazole-1-yl)-1,1,3,3-tetramethyluronium tetrafluoroborate (3.72 g, 11.6 mmol, 1.30 equiv), TEA (1.81 g, 17.9 mmol, 2.00 equiv), and DMF (10 mL). The resulting solution was stirred overnight at room temperature. The reaction mixture was diluted with ethyl ether (30 mL), and the resulting solution was washed with water (1×30 mL) and brine (1×20 mL), dried over anhydrous Na$_2$SO$_4$, filtered and concentrated under reduced pressure. The residue was chromatographed on a silica gel column to provide 1.30 g (69% yield) of 2-(trimethylsilyl)ethyl 2,2-dimethylbut-3-ynoate as yellow oil. $^1$H NMR (300 MHz, Chloroform-d) δ 4.28-4.22 (m, 2H), 2.27 (s, 1H), 1.50 (s, 6H), 1.08-1.02 (m, 2H), 0.07 (s, 9H).

Step 2: Synthesis of 2-(trimethylsilyl)ethyl 4-(2-fluoro-6-formylphenyl)-2,2-dimethylbut-3-ynoate

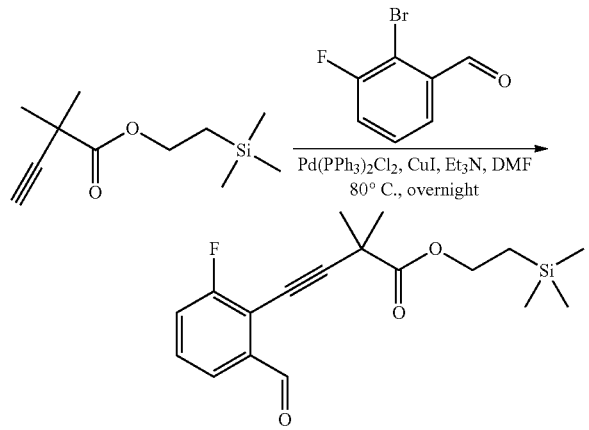

A round-bottom flask was charged with 2-bromo-3-fluorobenzaldehyde (300 mg, 1.49 mmol, 1.00 equiv), 2-(trimethylsilyl)ethyl 2,2-dimethylbut-3-ynoate (475 mg, 2.24 mmol, 1.50 equiv), bis(triphenylphosphine)palladium(II) chloride (52.3 mg, 0.0745 mmol, 0.05 equiv), copper(I) iodide (28.3 mg, 0.149 mmol, 0.10 equiv), TEA (451 mg, 4.46 mmol, 3.00 equiv), and DMF (10 mL) under nitrogen. The reaction mixture was stirred overnight at 80° C. and then quenched with water (10 mL). The resulting solution was extracted with DCM (3×15 mL), and the organic layers were combined, washed with brine (1×20 mL), dried over anhydrous Na$_2$SO$_4$, filtered and concentrated under reduced pressure. The residue was chromatographed on a silica gel column to provide 340 mg (72% yield) of 2-(trimethylsilyl) ethyl 4-(2-fluoro-6-formylphenyl)-2,2-dimethylbut-3-ynoate. LCMS (ESI, m/z): 357 [M+Na]$^+$.

Step 3: Synthesis of 1,1,1,3,3,3-hexafluoropropan-2-yl 4-(2-(3,3-dimethyl-4-oxo-4-(2-(trimethylsilyl)ethoxy)but-1-yn-1-yl)-3-fluorobenzyl)piperazine-1-carboxylate

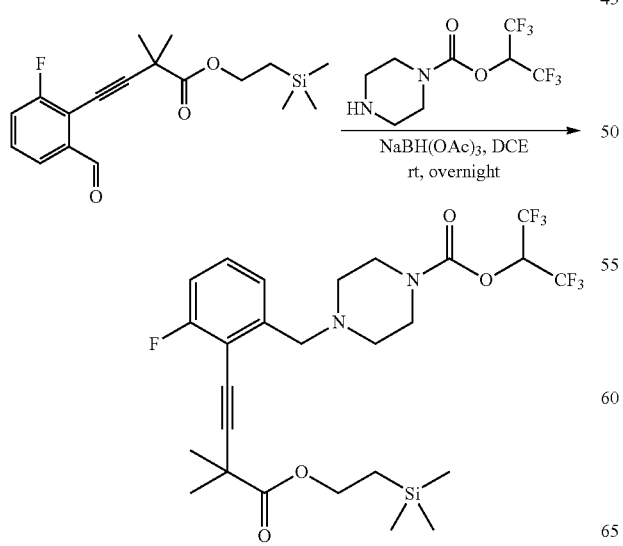

A round-bottom flask was charged with 2-(trimethylsilyl) ethyl 4-(2-fluoro-6-formylphenyl)-2,2-dimethylbut-3-ynoate (334 mg, 1.00 mmol, 1.00 equiv), 1,1,1,3,3,3-hexafluoropropan-2-yl piperazine-1-carboxylate (364 mg, 1.30 mmol, 1.30 equiv), and DCE (15 mL). The mixture was stirred for 1 h at rt prior to addition of sodium triacetoxyborohydride (848 mg, 4.00 mmol, 4.00 equiv). The resulting solution was stirred overnight at rt and then quenched with water (10 mL). The mixture was extracted with DCM (3×15 mL), and the organic layers were combined, washed with brine (1×20 mL), dried over anhydrous Na$_2$SO$_4$, filtered and concentrated under reduced pressure. The residue was chromatographed on a silica gel column to provide 350 mg (59% yield) of 1,1,1,3,3,3-hexafluoropropan-2-yl 4-(2-(3,3-dimethyl-4-oxo-4-(2-(trimethylsilyl)ethoxy)but-1-yn-1-yl)-3-fluorobenzyl)piperazine-1-carboxylate. LCMS (ESI, m/z): 599 [M+H]$^+$.

Step 4: Synthesis of 4-(2-fluoro-6-((4-(((1,1,1,3,3,3-hexafluoropropan-2-yl)oxy)carbonyl)piperazin-1-yl)methyl)phenyl)-2,2-dimethylbut-3-ynoic acid

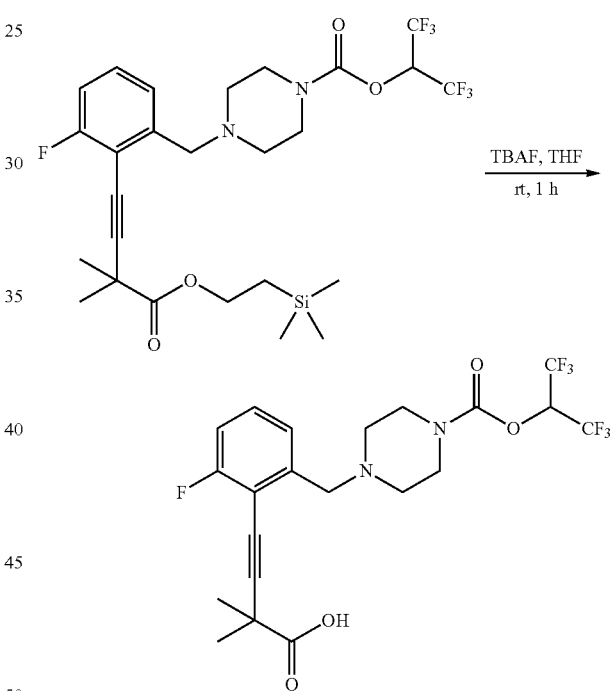

A round-bottom flask was charged with 1,1,1,3,3,3-hexafluoropropan-2-yl 4-(2-(3,3-dimethyl-4-oxo-4-(2-(trimethylsilyl)ethoxy)but-1-yn-1-yl)-3-fluorobenzyl)piperazine-1-carboxylate (350 mg, 0.584 mmol, 1.00 equiv), tetrabutylammonium fluoride (0.9 mL, 1M in tetrahydrofuran, 0.900 mmol, 1.50 equiv), and THF (10 mL). The reaction mixture was stirred for 1 h at rt and quenched with water (10 mL). The resulting solution was extracted with DCM (3×15 mL), and the organic layers were combined, washed with brine (1×20 mL), dried over anhydrous Na$_2$SO$_4$, filtered and concentrated under reduced pressure. The crude product (280 mg) was purified by preparative HPLC to afford 107.6 mg (37% yield) of 4-(2-fluoro-6-((4-(((1,1,1,3,3,3-hexafluoropropan-2-yl)oxy)carbonyl)piperazin-1-yl)methyl)phenyl)-2,2-dimethylbut-3-ynoic acid. $^1$H NMR (400 MHz, Methanol-d$_4$) δ 7.34-7.25 (m, 2H), 7.08-

7.04 (m, 1H), 6.17-6.10 (m, 1H), 3.81 (s, 2H), 3.62-3.57 (m, 4H), 2.62 (br s, 4H), 1.56 (s, 6H). LCMS (ESI, m/z): 499 [M+H]⁺.

Example 26: 1-((2-Cyano-4-fluoro-6-((4-(((1,1,1,3,3,3-hexafluoropropan-2-yl)oxy)carbonyl)piperazin-1-yl)methyl)phenoxy)methyl)cyclopropane-1-carboxylic acid

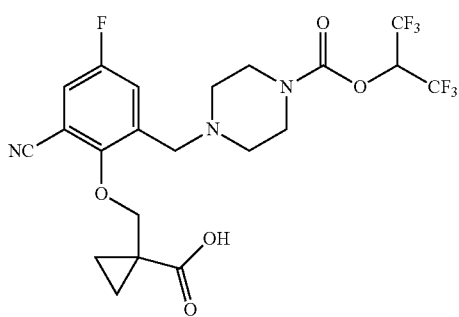 [SMILES: N#Cc1cc(F)cc(CN2CCN(C(=O)OC(C(F)(F)F)C(F)(F)F)CC2)c1OCC1(C(=O)O)CC1]

Step 1: Synthesis of ethyl 1-((2-bromo-4-fluoro-6-formylphenoxy)methyl)cyclopropane-1-carboxylate

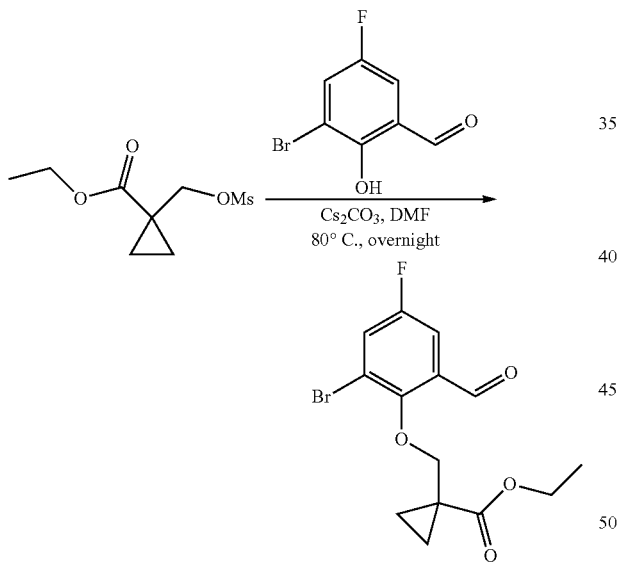

A round-bottom flask was charged with 3-bromo-5-fluoro-2-hydroxybenzaldehyde (1.00 g, 4.59 mmol, 1.00 equiv), ethyl 1-[(methanesulfonyloxy)methyl]cyclopropane-1-carboxylate (1.53 g, 6.88 mmol, 1.50 equiv), cesium carbonate (4.49 g, 13.8 mmol, 3.00 equiv), and DMF (10 mL). The reaction mixture was stirred overnight at 80° C. and quenched with water (30 mL). The resulting solution was extracted with EtOAc (2×50 mL), and the organic layers were combined, washed with brine (2×30 mL), dried over anhydrous Na₂SO₄, filtered and concentrated under reduced pressure. The residue was chromatographed on a silica gel column to provide 0.600 g (38% yield) of ethyl 1-(2-bromo-4-fluoro-6-formylphenoxymethyl)cyclopropane-1-carboxylate. LCMS (ESI, m/z): 345 [M+H]⁺.

Step 2: Synthesis of tert-butyl 4-(3-bromo-2-((1-(ethoxycarbonyl)cyclopropyl)methoxy)-5-fluorobenzyl)piperazine-1-carboxylate

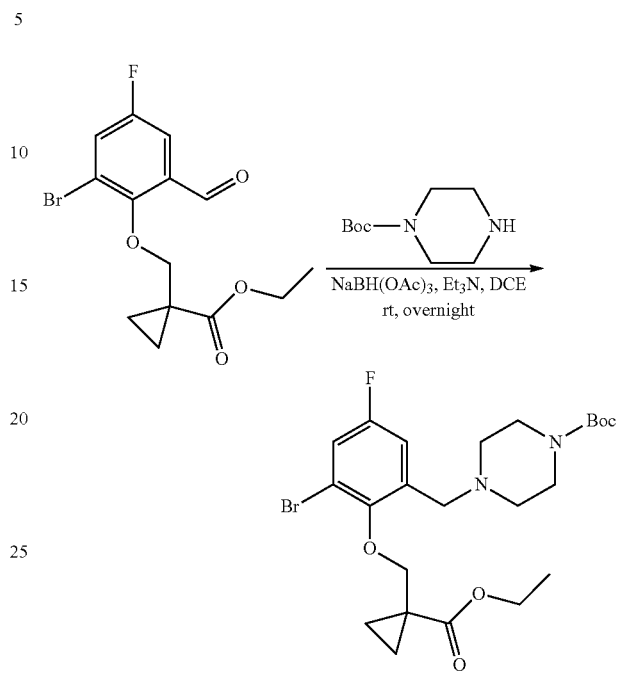

A round-bottom flask was charged with ethyl 1-(2-bromo-4-fluoro-6-formylphenoxymethyl)cyclopropane-1-carboxylate (600 mg, 1.74 mmol, 1.00 equiv), TEA (527 mg, 5.22 mmol, 3.00 equiv), tert-butyl piperazine-1-carboxylate (390 mg, 2.09 mmol, 1.20 equiv), and DCE (10 mL). The solution was stirred for 1 h at rt prior to addition of sodium triacetoxyborohydride (1110 mg, 5.22 mmol, 3.00 equiv). The reaction mixture was stirred overnight at rt and quenched with water (30 mL). The resulting solution was extracted with DCM (2×50 mL), and the organic layers were combined, washed with brine (2×30 mL), dried over anhydrous Na₂SO₄, filtered and concentrated under reduced pressure. The residue was chromatographed on a silica gel column to provide 540 mg (60% yield) of tert-butyl 4-(3-bromo-2-((1-(ethoxycarbonyl)cyclopropyl)methoxy)-5-fluorobenzyl)piperazine-1-carboxylate. LCMS (ESI, m/z): 515 [M+H]⁺.

Step 3: Synthesis of tert-butyl 4-(3-cyano-2-((1-(ethoxycarbonyl)cyclopropyl)methoxy)-5-fluorobenzyl) piperazine-1-carboxylate

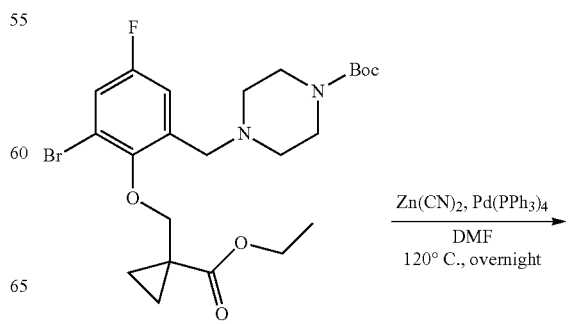

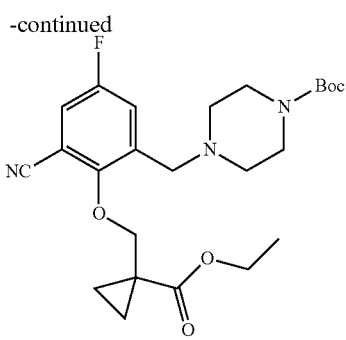

A round-bottom flask was charged with tert-butyl 4-(3-bromo-2-((1-(ethoxycarbonyl)cyclopropyl)methoxy)-5-fluorobenzyl)piperazine-1-carboxylate (240 mg, 0.470 mmol, 1.00 equiv), zinc cyanide (108 mg, 0.940 mmol, 2.00 equiv), tetrakis(triphenylphosphine)palladium (58.0 mg, 0.0500 mmol, 0.10 equiv), and DMF (10 mL) under nitrogen. The reaction mixture was stirred overnight at 120° C. and quenched with water (30 mL). The resulting solution was extracted with EtOAc (2×50 mL), and the organic layers were combined, washed with brine (2×30 mL), dried over anhydrous $Na_2SO_4$, filtered and concentrated under reduced pressure. The residue was chromatographed on a silica gel column to provide 125 mg (58% yield) of tert-butyl 4-(3-cyano-2-((1-(ethoxycarbonyl)cyclopropyl)methoxy)-5-fluorobenzyl)piperazine-1-carboxylate. LCMS (ESI, m/z): 462 [M+H]+.

Step 4: Synthesis of 1-((2-((4-(tert-butoxycarbonyl)piperazin-1-yl)methyl)-6-cyano-4-fluorophenoxy)methyl)cyclopropane-1-carboxylic acid

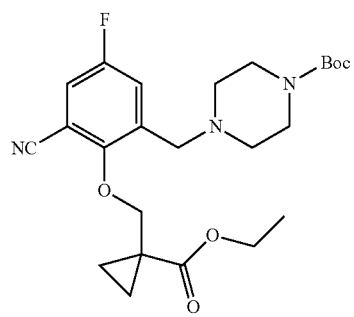

A round-bottom flask was charged with tert-butyl 4-(3-cyano-2-((1-(ethoxycarbonyl)cyclopropyl)methoxy)-5-fluorobenzyl)piperazine-1-carboxylate (125 mg, 0.270 mmol, 1.00 equiv), lithium hydroxide (130 mg, 5.43 mmol, 20.0 equiv), THF (5 mL), and water (5 mL). The reaction mixture was stirred overnight at room temperature. The pH value of the solution was adjusted to 5 with hydrochloric acid (1 mol/L). The resulting solution was extracted with DCM (2×50 mL), and the organic layers were combined, washed with brine (2×30 mL), dried over anhydrous $Na_2SO_4$, filtered and concentrated under reduced pressure to provide 110 mg (94% yield) of 1-((2-((4-(tert-butoxycarbonyl)piperazin-1-yl)methyl)-6-cyano-4-fluorophenoxy)methyl)cyclopropane-1-carboxylic acid. LCMS (ESI, m/z): 434 [M+H]+.

Step 5: Synthesis of 1-((2-cyano-4-fluoro-6-(piperazin-1-ylmethyl)phenoxy)methyl)cyclopropane-1-carboxylic acid

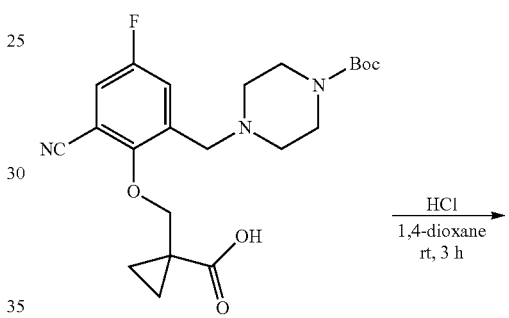

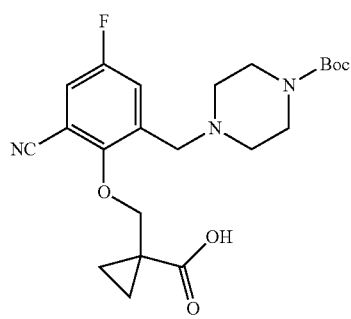

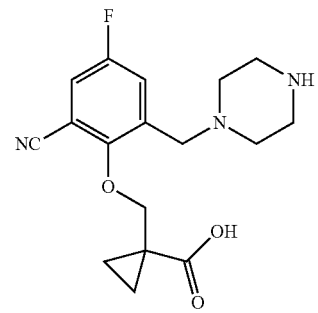

A round-bottom flask was charged with 1-((2-((4-(tert-butoxycarbonyl)piperazin-1-yl)methyl)-6-cyano-4-fluorophenoxy)methyl)cyclopropane-1-carboxylic acid (160 mg, 0.370 mmol, 1.00 equiv), concentrated hydrochloric acid (2 mL), and 1,4-dioxane (8 mL). The resulting solution was stirred for 3 h at rt and concentrated under reduced pressure to provide 123 mg (quantitative) of 1-((2-cyano-4-fluoro-6-(piperazin-1-ylmethyl)phenoxy)methyl)cyclopropane-1-carboxylic acid. LCMS (ESI, m/z): 334 [M+H]+.

Step 6: Synthesis of 1-((2-cyano-4-fluoro-6-((4-(((1,1,1,3,3,3-hexafluoropropan-2-yl)oxy)carbonyl)piperazin-1-yl)methyl)phenoxy)methyl)cyclopropane-1-carboxylic acid

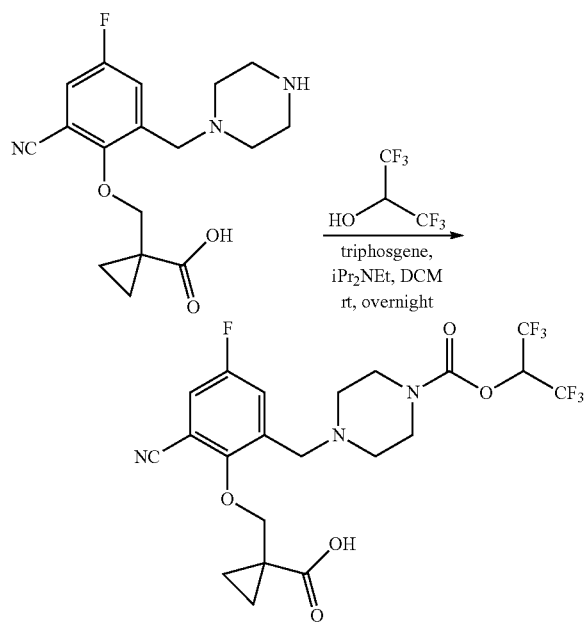

A round-bottom flask was charged with triphosgene (77.0 mg, 0.260 mmol, 0.700 equiv), 1,1,1,3,3,3-hexafluoropropan-2-ol (124 mg, 0.740 mmol, 2.00 equiv), and DCM (5 mL). N,N-Diisopropylethylamine (143 mg, 1.11 mmol, 3.00 equiv) was added at 0° C. and the mixture was stirred for 1 h at rt prior to addition of 1-((2-cyano-4-fluoro-6-(piperazin-1-ylmethyl)phenoxy)methyl)cyclopropane-1-carboxylic acid (123 mg, 0.370 mmol, 1.00 equiv) was added. The reaction mixture was stirred overnight at rt and quenched with water (30 mL). The resulting solution was extracted with DCM (2×50 mL), and the organic layers were combined, washed with brine (2×30 mL), dried over anhydrous $Na_2SO_4$, filtered and concentrated under reduced pressure. The crude product (250 mg) was purified by preparative HPLC to afford 39.9 mg (21% yield) of 1-((2-cyano-4-fluoro-6-((4-(((1,1,1,3,3,3-hexafluoropropan-2-yl)oxy)carbonyl)piperazin-1-yl)methyl)phenoxy)methyl)cyclopropane-1-carboxylic acid. $^1$H NMR (400 MHz, Chloroform-d) δ 7.46-7.43 (m, 1H), 7.24-7.22 (m, 1H), 5.81-5.73 (m, 1H), 4.22 (s, 2H), 3.73 (s, 2H), 3.61-3.60 (m, 4H), 2.56-2.53 (m, 4H), 1.57-1.54 (m, 2H), 1.32-1.29 (m, 2H). LCMS (ESI, m/z): 528 [M+H]$^+$.

Examples 27-56

Examples 27-56 were prepared by similar procedures as described in Examples 1-26.

| Ex | Name | Structure | NMR ($^1$H NMR, 300 MHz or 400 MHz, Chloroform-d) | MS [M + H]$^+$ |
|---|---|---|---|---|
| 27 | 1-((2-((4-(((1,1,1,3,3,3-hexafluoropropan-2-yl)oxy)carbonyl)piperazin-1-yl)methyl)-5-(trifluoromethyl)phenoxy)methyl)cyclopropane-1-carboxylic acid | 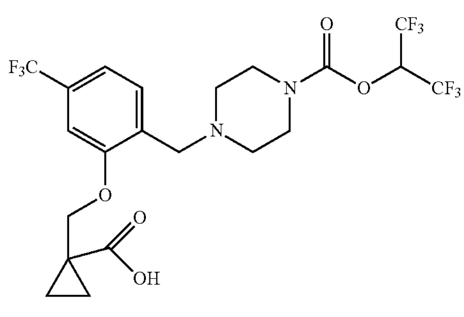 [SMILES: O=C(OC(C(F)(F)F)C(F)(F)F)N1CCN(Cc2ccc(C(F)(F)F)cc2OCC2(C(=O)O)CC2)CC1] | (Methanol-d$_4$) δ 7.53 (d, J = 7.5 Hz, 1H), 7.26-7.23 (m, 2H), 6.16-6.10 (m, 1H), 4.19 (s, 2H), 3.80 (s, 2H), 3.65-3.62 (m, 4H), 2.70-2.67 (m, 4H), 1.33-1.30 (m, 2H), 1.05-1.02 (m, 2H) | 553.4 |
| 28 | 1-((3-((4-(((1,1,1,3,3,3-hexafluoropropan-2-yl)oxy)carbonyl)piperazin-1-yl)methyl)-5-(trifluoromethyl)phenoxy)methyl)cyclopropane-1-carboxylic acid | 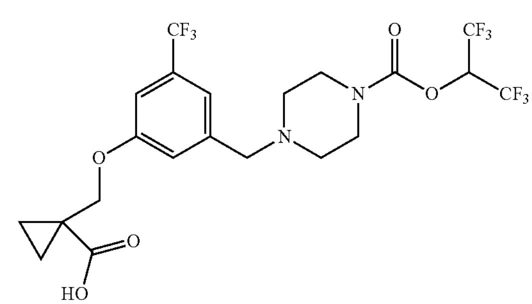 [SMILES: O=C(OC(C(F)(F)F)C(F)(F)F)N1CCN(Cc2cc(OCC3(C(=O)O)CC3)cc(C(F)(F)F)c2)CC1] | (Methanol-d$_4$) δ 7.22-7.13 (m, 2H), 7.08 (s, 1H), 6.17-6.09 (m, 1H), 4.17 (s, 2H), 3.58-3.55 (m, 6H), 2.49-2.48 (m, 4H), 1.34-1.25 (m, 2H), 1.07-1.03 (m, 2H) | 553.5 |

| Ex | Name | Structure | NMR (¹H NMR, 300 MHz or 400 MHz, Chloroform-d) | MS [M + H]⁺ |
|---|---|---|---|---|
| 29 | 1-((2-fluoro-6-((4-(((1,1,1,3,3,3-hexafluoropropan-2-yl)oxy)carbonyl)piperazin-1-yl)methyl)-3-methylphenoxy)methyl)cyclopropane-1-carboxylic acid | 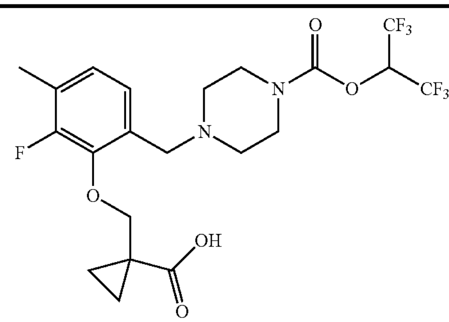 | (Methanol-d₄) δ 7.02 (d, J = 8.7 Hz, 1H), 6.91 (t, J = 7.4 Hz, 1H), 6.21-6.10 (m, 1H), 4.21 (s, 2H), 3.85 (s, 2H), 3.68 (br s, 4H), 2.75-2.67 (m, 4H), 2.25 (s, 3H), 1.25-1.22 (m, 2H), 0.94-0.92 (m, 2H) | 517.1 |
| 30 | 1-((2-((4-(((1,1,1,3,3,3-hexafluoropropan-2-yl)oxy)carbonyl)piperazin-1-yl)methyl)-6-(trifluoromethyl)phenoxy)methyl)cyclopropane-1-carboxylic acid | 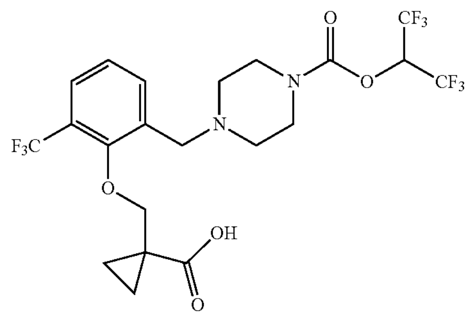 [SMILES: O=C(OC(C(F)(F)F)C(F)(F)F)N1CCN(Cc2cccc(C(F)(F)F)c2OCC2(C(=O)O)CC2)CC1] | (Methanol-d₄) δ 7.74 (d, J = 7.8 Hz, 1H), 7.61 (d, J = 7.8 Hz, 1H), 7.29 (t, J = 7.6 Hz, 1H), 6.19-6.11 (m, 1H), 4.18 (s, 2H), 3.93 (s, 2H), 3.61 (br s, 4H), 2.63 (br s, 4H), 1.35-1.32 (m, 2H), 1.14-1.04 (m, 2H) | 553.2 |
| 31 | 1,1,1,3,3,3-hexafluoropropan-2-yl 4-(3-fluoro-4-methyl-2-((1-((methylsulfonyl)carbamoyl)cyclopropyl)methoxy)benzyl)piperazine-1-carboxylate | 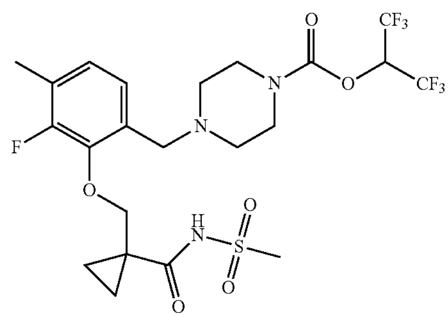 [SMILES: Cc1ccc(CN2CCN(C(=O)OC(C(F)(F)F)C(F)(F)F)CC2)c(OCC2(C(=O)NS(C)(=O)=O)CC2)c1F] | δ 6.97-6.91 (μ, 2H), 5.80-5.70 (μ, 1H), 4.11 (σ, 2H), 3.49 (βρ σ, 6H), 3.34 (σ, 3H), 2.48 (δ, ϑ = 5.0 Ηζ, 4H), 2.28 (σ, 3H), 1.54-1.50 (μ, 2H), 1.01-0.97 (μ, 2H) | 594.2 |
| 32 | 1-((2-fluoro-6-((4-(((1,1,1,3,3,3-hexafluoropropan-2-yl)oxy)carbonyl)piperazin-1-yl)methyl)-3-methylphenoxy)methyl)cyclopentane-1-carboxylic acid | 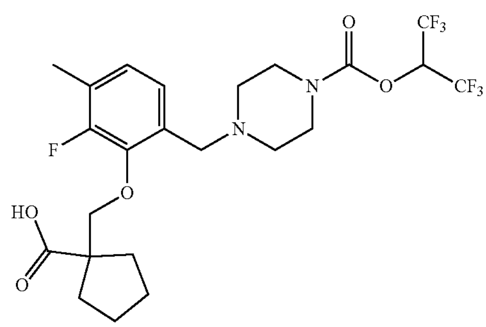 [SMILES: Cc1ccc(CN2CCN(C(=O)OC(C(F)(F)F)C(F)(F)F)CC2)c(OCC2(C(=O)O)CCCC2)c1F] | (Methanol-d₄) δ 7.02 (d, J = 8.4 Hz, 1H), 6.92 (t, J = 7.4 Hz, 1H), 6.20-6.10 (m, 1H), 4.16 (s 2H), 3.68 (s, 2H), 3.60 (br s, 4H), 2.61-2.59 (m, 4H), 2.26 (s, 3H), 2.20-2.16 (m, 2H), 1.82-1.75 (br s, 6H) | 544.9 |
| 33 | 1-((2,3-difluoro-6-((4-(((1,1,1,3,3,3-hexafluoropropan-2-yl)oxy)carbonyl)piperazin-1-yl)methyl)phenoxy)methyl)cyclopropane-1-carboxylic acid | 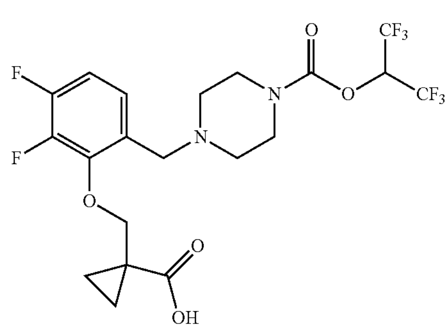 [SMILES: O=C(OC(C(F)(F)F)C(F)(F)F)N1CCN(Cc2ccc(F)c(F)c2OCC2(C(=O)O)CC2)CC1] | δ 7.02-6.96 (m, 1H), 6.93-6.84 (m, 1H), 5.76-5.66 (m, 1H), 4.21 (s, 2H), 3.87 (s, 2H), 3.59 (br s, 4H), 2.59 (br s, 4H), 1.46-1.42 (m, 2H), 1.09-1.01 (m, 2H) | 520.8 |

| Ex | Name | Structure | NMR (¹H NMR, 300 MHz or 400 MHz, Chloroform-d) | MS [M + H]⁺ |
|---|---|---|---|---|
| 34 | 1-((4,5-difluoro-2-((4-(((1,1,1,3,3,3-hexafluoropropan-2-yl)oxy)carbonyl)piperazin-1-yl)methyl)phenoxy)methyl)cyclopropane-1-carboxylic acid | 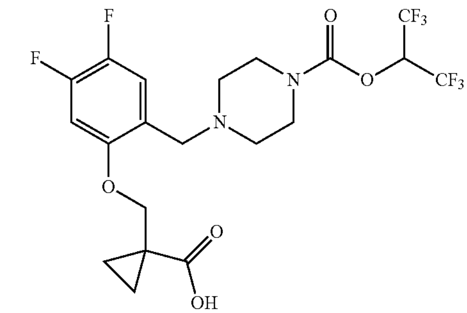 [SMILES: O=C(OC(C(F)(F)F)C(F)(F)F)N1CCN(Cc2cc(F)c(F)cc2OCC2(C(=O)O)CC2)CC1] | (Methanol-d₄) δ 7.34-7.27 (m, 1H), 7.03-6.97 (m, 1H), 6.21-6.12 (m, 1H), 4.12 (s, 2H), 3.76 (s, 2H), 3.69 (br s, 4H), 2.72-2.68 (m, 4H), 1.36-1.32 (m, 2H), 1.06-1.02 (m, 2H) | 521.1 |
| 35 | 1-((5-cyano-2-((4-(((1,1,1,3,3,3-hexafluoropropan-2-yl)oxy)carbonyl)piperazin-1-yl)methyl)phenoxy)methyl)cyclopropane-1-carboxylic acid | 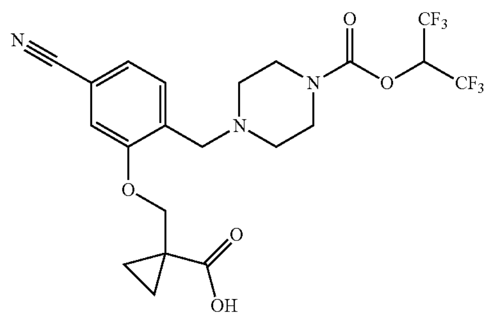 [SMILES: N#Cc1ccc(CN2CCN(C(=O)OC(C(F)(F)F)C(F)(F)F)CC2)c(OCC2(C(=O)O)CC2)c1] | δ 7.45 (d, J = 7.8 Hz, 1H), 7.28-7.25 (m, 1H), 7.09 (s, 1H), 5.80-5.70 (m, 1H), 4.14 (s, 2H), 3.61-3.56 (m, 6H), 2.51 (br s, 4H), 1.47 (br s, 2H), 1.12 (br s, 2H) | 510.1 |
| 36 | 1-((2-cyano-6-((4-(((1,1,1,3,3,3-hexafluoropropan-2-yl)oxy)carbonyl)piperazin-1-yl)methyl)phenoxy)methyl)cyclopropane-1-carboxylic acid | 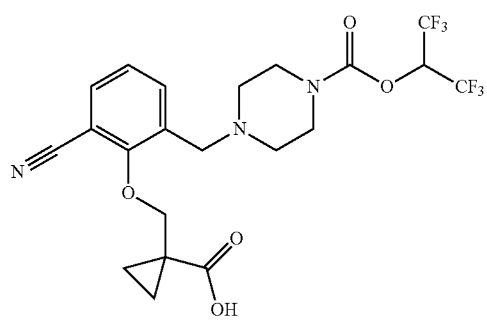 [SMILES: N#Cc1cccc(CN2CCN(C(=O)OC(C(F)(F)F)C(F)(F)F)CC2)c1OCC1(C(=O)O)CC1] | (Methanol-d₄) δ 7.77-7.74 (m, 1H), 7.65-7.62 (m, 1H), 7.28 (t, J = 7.6 Hz, 1H), 6.20-6.11 (m, 1H), 4.33 (s, 2H), 3.83 (s, 2H), 3.62 (br s, 4H), 2.63-2.62 (m, 4H), 1.40-1.36 (m, 2H), 1.21-1.17 (m, 2H) | 510.2 |
| 37 | 1-((2,3-difluoro-6-((4-(((1,1,1,3,3,3-hexafluoropropan-2-yl)oxy)carbonyl)piperazin-1-yl)methyl)phenoxy)methyl)cyclopentane-1-carboxylic acid | 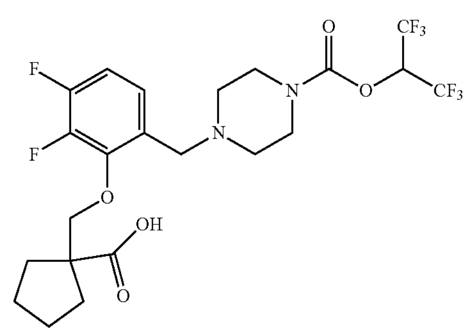 [SMILES: O=C(OC(C(F)(F)F)C(F)(F)F)N1CCN(Cc2ccc(F)c(F)c2OCC2(C(=O)O)CCCC2)CC1] | δ 6.97-6.93 (m, 1H), 6.92-6.80 (m, 1H), 5.76-5.65 (m, 1H), 4.24 (s, 2H), 3.64 (s, 2H), 3.55 (br s, 4H), 2.52 (br s, 4H), 2.20-2.18 (m, 2H), 1.78-1.71 (m, 6H) | 549.1 |

| Ex | Name | Structure | NMR (¹H NMR, 300 MHz or 400 MHz, Chloroform-d) | MS [M + H]⁺ |
|---|---|---|---|---|
| 38 | 1-((3-fluoro-6-((4-(((1,1,1,3,3,3-hexafluoropropan-2-yl)oxy)carbonyl)piperazin-1-yl)methyl)-2-methylphenoxy)methyl)cyclopropane-1-carboxylic acid | 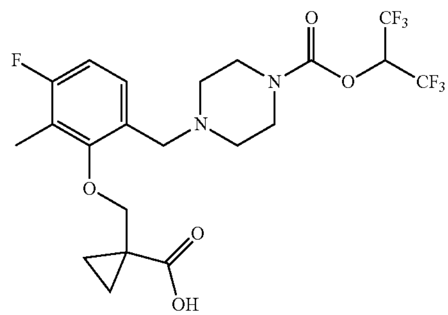 [SMILES: Cc1c(F)ccc(CN2CCN(C(=O)OC(C(F)(F)F)C(F)(F)F)CC2)c1OCC1(C(=O)O)CC1] | δ 7.10 (t, J = 7.4 Hz, 1H), 6.85 (t, J = 8.6 Hz, 1H), 5.76-5.68 (m, 1H), 3.96 (s, 2H), 3.92 (s, 2H), 3.77 (br s, 4H), 2.64-2.62 (m, 4H), 2.23 (s, 3H), 1.50-1.44 (m, 2H), 1.09-1.06 (m, 2H) | 517 |
| 39 | 1-((4-fluoro-2-((4-(((1,1,1,3,3,3-hexafluoropropan-2-yl)oxy)carbonyl)piperazin-1-yl)methyl)-6-methylphenoxy)methyl)cyclopropane-1-carboxylic acid | 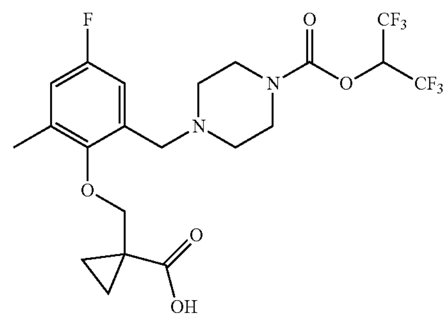 [SMILES: Cc1cc(F)cc(CN2CCN(C(=O)OC(C(F)(F)F)C(F)(F)F)CC2)c1OCC1(C(=O)O)CC1] | δ 6.92-6.84 (m, 2H), 5.77-5.71 (m, 1H), 3.96 (s, 2H), 3.91 (br s, 2H), 3.61 (br s, 4H), 2.60 (br s, 4H), 2.31 (s, 3H), 1.46 (br s, 2H), 1.07 (br s, 2H) | 517.1 |
| 40 | 1-((4-fluoro-2-((4-(((1,1,1,3,3,3-hexafluoropropan-2-yl)oxy)carbonyl)piperazin-1-yl)methyl)-6-methylphenoxy)methyl)cylcopentane-1-carboxylic acid | 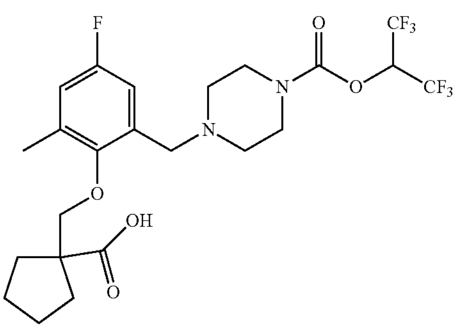 [SMILES: Cc1cc(F)cc(CN2CCN(C(=O)OC(C(F)(F)F)C(F)(F)F)CC2)c1OCC1(C(=O)O)CCCC1] | δ 6.93-6.90 (m, 1H), 6.84-6.82 (m, 1H), 5.79-5.72 (m, 1H), 3.88 (s, 2H), 3.64 (s, 2H), 3.59-3.58 (m, 4H), 2.54-2.47 (m, 4H), 2.31 (s, 3H), 2.26-2.23 (m, 2H), 1.82-1.72 (m, 6H) | 545.2 |
| 41 | 1-((2-fluoro-6-((4-(((1,1,1,3,3,3-hexafluoropropan-2-yl)oxy)carbonyl)piperazin-1-yl)methyl)phenoxy)methyl)cyclopentane-1-carboxylic acid | 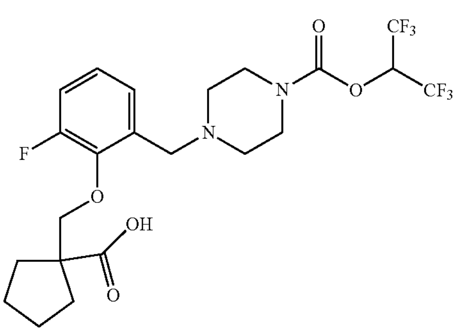 [SMILES: O=C(OC(C(F)(F)F)C(F)(F)F)N1CCN(Cc2cccc(F)c2OCC2(C(=O)O)CCCC2)CC1] | δ 7.10-6.97 (m, 3H), 5.78-5.63 (m, 1H), 4.22 (s, 2H), 3.74 (s, 2H), 3.60-3.58 (m, 4H), 2.59-2.56 (m, 4H), 2.23-2.21 (m, 2H), 1.80-1.73 (m, 6H) | 531.2 |

| Ex | Name | Structure | NMR (¹H NMR, 300 MHz or 400 MHz, Chloroform-d) | MS [M + H]⁺ |
|---|---|---|---|---|
| 42 | 1-((5-fluoro-2-((4-(((1,1,1,3,3,3-hexafluoropropan-2-yl)oxy)carbonyl)piperazin-1-yl)methyl)phenoxy)methyl)cyclopentane-1-carboxylic acid | 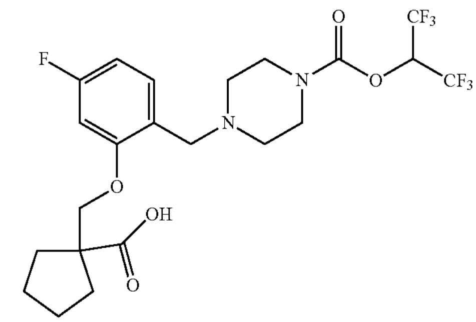 [SMILES: O=C(OC(C(F)(F)F)C(F)(F)F)N1CCN(Cc2ccc(F)cc2OCC2(C(=O)O)CCCC2)CC1] | δ 7.16 (t, J = 7.4 Hz, 1H), 6.68-6.64 (m, 2H), 5.78-5.71 (m, 1H), 4.05 (s, 2H), 3.66-3.61 (m, 6H), 2.61 (br s, 4H), 2.29-2.23 (m, 2H), 1.81-1.72 (m, 6H) | 531.2 |
| 43 | 1-((5-cyano-2-((4-(((1,1,1,3,3,3-hexafluoropropan-2-yl)oxy)carbonyl)piperazin-1-yl)methyl)phenoxy)methyl)cyclopentane-1-carboxylic acid | 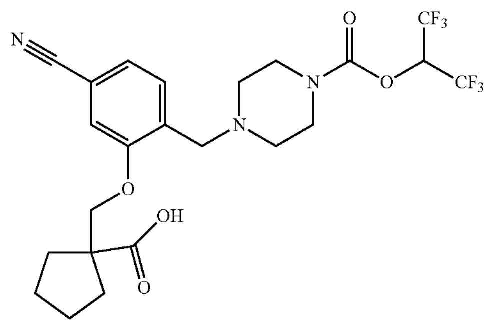 [SMILES: N#Cc1ccc(CN2CCN(C(=O)OC(C(F)(F)F)C(F)(F)F)CC2)c(OCC2(C(=O)O)CCCC2)c1] | δ 7.40 (d, J = 7.6 Hz, 1H), 7.26-7.24 (m, 1H), 7.11 (s, 1H), 5.76-5.69 (m, 1H), 4.07 (s, 2H), 3.56-3.49 (m, 6H), 2.48-2.47 (m, 4H), 2.24-2.22 (m, 2H), 1.81-1.73 (m, 6H) | 538.2 |
| 44 | (1s,3s)-3-(2-((4-(((1,1,1,3,3,3-hexafluoropropan-2-yl)oxy)carbonyl)piperazin-1-yl)methyl)-5-(trifluoromethyl)phenoxy)cyclobutane-1-carboxylic acid | 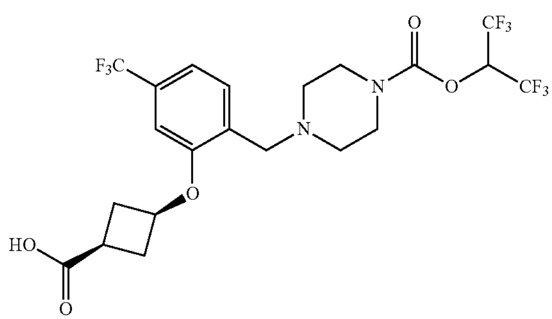 [SMILES: O=C(OC(C(F)(F)F)C(F)(F)F)N1CCN(Cc2ccc(C(F)(F)F)cc2O[C@H]2C[C@@H](C(=O)O)C2)CC1] | (Methanol-d₄) δ 7.55 (d, J = 7.8 Hz, 1H), 7.24 (d, J = 7.8 Hz, 1H), 7.03 (s, 1H), 6.19-6.09 (m, 1H), 4.78-4.74 (m, 1H), 3.66-3.55 (m, 6H), 2.90-2.73 (m, 3H), 2.56-2.52 (m, 4H, 2.39-2.30 (m, 2H) | 553.4 |
| 45 | (1S,3R)-3-(2-((4-(((1,1,1,3,3,3-hexafluoropropan-2-yl)oxy)carbonyl)piperazin-1-yl)methyl)-5-(trifluoromethyl)phenoxy)cyclopentane-1-carboxylic acid | 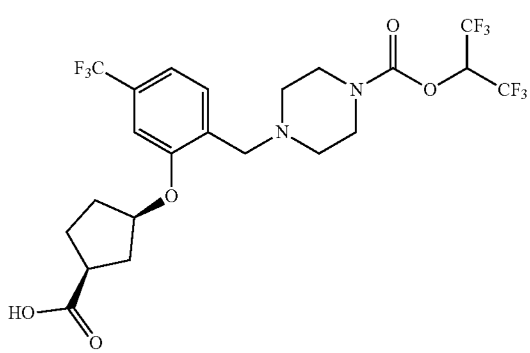 [SMILES: O=C(O)[C@H]1CC[C@@H](Oc2cc(C(F)(F)F)ccc2CN2CCN(C(=O)OC(C(F)(F)F)C(F)(F)F)CC2)C1] | (Methanol-d₄) δ 7.58 (d, J = 7.8 Hz, 1H), 7.29-7.27 (m, 2H), 6.21-6.17 (m, 1H), 5.08-5.06 (m, 1H), 4.08-3.95 (m, 2H), 3.73 (br s, 4H), 3.98 (br s, 5H), 2.33-2.26 (m, 2H), 2.13-1.99 (m, 4H) | 567.2 |

| Ex | Name | Structure | NMR (¹H NMR, 300 MHz or 400 MHz, Chloroform-d) | MS [M + H]⁺ |
|---|---|---|---|---|
| 46 | (1R,3R)-3-(2-((4-(((1,1,1,3,3,3-hexafluoropropan-2-yl)oxy)carbonyl)piperazin-1-yl)methyl)-5-(trifluoromethyl)phenoxy)cyclopentane-1-carboxylic acid | 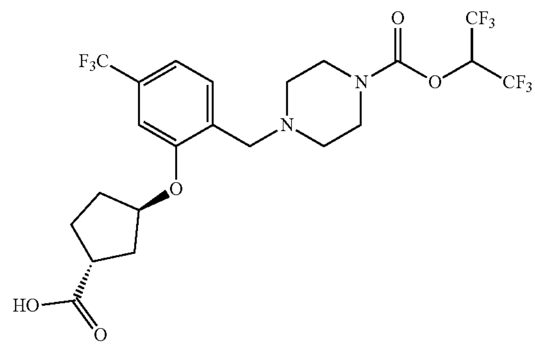 [SMILES: O=C(O)[C@@H]1CC[C@@H](Oc2cc(C(F)(F)F)ccc2CN2CCN(C(=O)OC(C(F)(F)F)C(F)(F)F)CC2)C1] | (Methanol-d₄) δ 7.66 (d, J = 7.8 Hz, 1H), 7.34-7.31 (m, 2H), 6.26-6.18 (m, 1H), 5.12-5.11 (m, 1H), 4.20 (s, 2H), 3.78 (br s, 4H), 3.17-3.07 (m, 5H), 2.29-2.13 (m, 4H), 1.99-1.92 (m, 2H) | 567.2 |
| 47 | (1r,3r)-3-(2-((4-(((1,1,1,3,3,3-hexafluoropropan-2-yl)oxy)carbonyl)piperazin-1-yl)methyl)-5-(trifluoromethyl)phenoxy)cyclobutane-1-carboxylic acid | 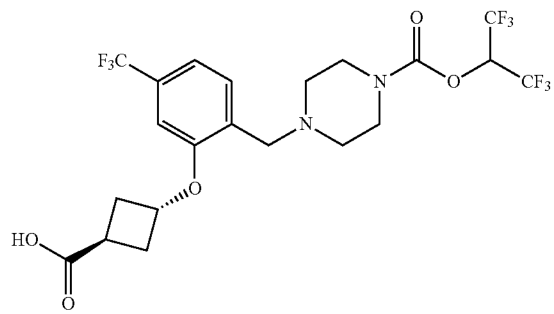 [SMILES: O=C(OC(C(F)(F)F)C(F)(F)F)N1CCN(Cc2ccc(C(F)(F)F)cc2O[C@H]2C[C@H](C(=O)O)C2)CC1] | (Methanol-d₄) δ 7.59 (d, J = 7.2 Hz, 1H), 7.26 (d, J = 7.2 Hz, 1H), 6.98 (s, 1H), 6.19-6.11 (m, 1H), 5.03-4.95 (m, 1H), 3.70 (s, 2H), 3.61-3.55 (m, 4H), 3.25-3.16 (m, 1H), 2.81-2.73 (m, 2H), 2.60-2.44 (m, 6H) | 553.2 |
| 48 | 4-(3-((4-(((1,1,1,3,3,3-hexafluoropropan-2-yl)oxy)carbonyl)piperazin-1-yl)methyl)-5-(trifluoromethyl)phenyl)-2,2-dimethylbut-3-ynoic acid | 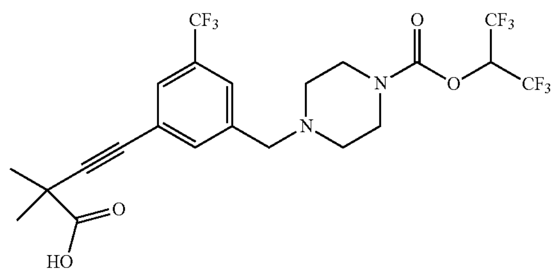 [SMILES: CC(C)(C#Cc1cc(CN2CCN(C(=O)OC(C(F)(F)F)C(F)(F)F)CC2)cc(C(F)(F)F)c1)C(=O)O] | (Methanol-d₄) δ 7.64-7.57 (m, 3H), 6.17-6.08 (m, 1H), 3.62-3.52 (m, 6H), 2.49 (br s, 4H), 1.55 (s, 6H) | 549.4 |
| 49 | 2-(2-chloro-6-((4-(((1,1,1,3,3,3-hexafluoropropan-2-yl)oxy)carbonyl)piperazin-1-yl)methyl)-3-methylphenoxy)acetic acid | 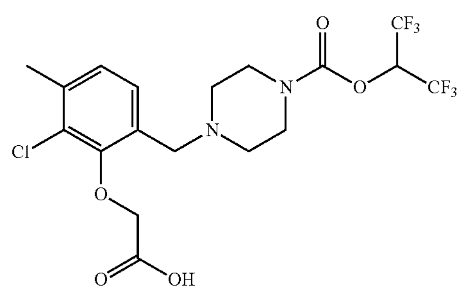 [SMILES: Cc1ccc(CN2CCN(C(=O)OC(C(F)(F)F)C(F)(F)F)CC2)c(OCC(=O)O)c1Cl] | (Methanol-d₄) δ 7.21-7.12 (m, 2H), 6.28-6.20 (m, 1H), 4.78 (s, 2H), 4.25 (s, 2H), 3.90 (br s, 4H), 3.22 (br s, 4H), 2.43 (s, 3H) | 493.1 |
| 50 | 1,1,1,3,3,3-hexafluoropropan-2-yl 4-(3-chloro-4-methyl-2-(2-(methylsulfonamido)-2-oxoethoxy)benzyl)piperazine-1-carboxylate | 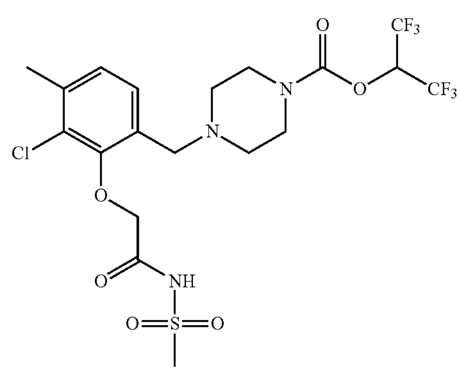 [SMILES: Cc1ccc(CN2CCN(C(=O)OC(C(F)(F)F)C(F)(F)F)CC2)c(OCC(=O)NS(C)(=O)=O)c1Cl] | δ 7.07-7.01 (m, 2H), 5.77-5.69 (m, 1H), 4.69 (s, 2H), 3.56-3.49 (m, 6H), 3.37 (s, 3H), 2.49 (t, J = 5.0 Hz, 4H), 2.39 (s, 3H) | 570.1 |

| Ex | Name | Structure | NMR (¹H NMR, 300 MHz or 400 MHz, Chloroform-d) | MS [M + H]⁺ |
|---|---|---|---|---|
| 51 | 1,1,1,3,3,3-hexafluoropropan-2-yl 4-(3-chloro-2-(2-(cyclopropanesulfonamido)-2-oxoethoxy)-4-methylbenzyl)piperazine-1-carboxylate | 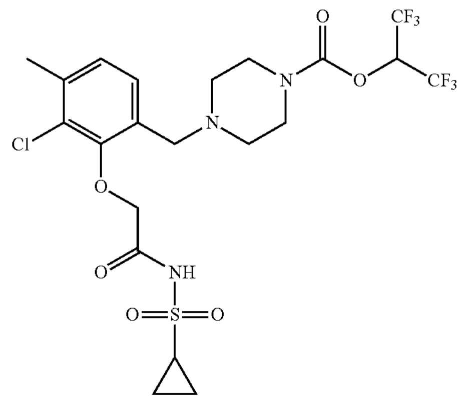 [SMILES: Cc1ccc(CN2CCN(C(=O)OC(C(F)(F)F)C(F)(F)F)CC2)c(OCC(=O)NS(=O)(=O)C2CC2)c1Cl] | δ 7.07-7.02 (m, 2H), 5.77-5.69 (m, 1H), 4.70 (s, 2H), 3.53-3.49 (m, 6H), 3.07-2.99 (m, 1H), 2.46-2.39 (m, 7H), 1.48-1.45 (m, 2H), 1.21-1.14 (m, 2H) | 595.9 |
| 52 | 1,1,1,3,3,3-hexafluoropropan-2-yl 4-(4-chloro-2-(2-(methylsulfonamido)-2-oxoethoxy)benzyl)piperazine-1-carboxylate | 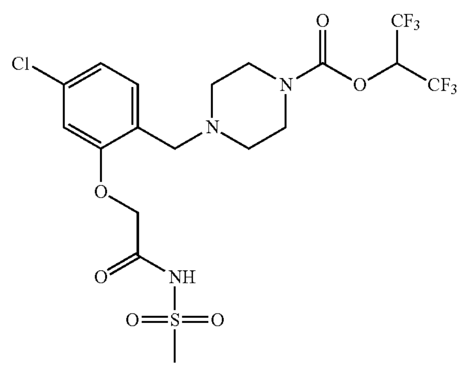 [SMILES: CS(=O)(=O)NC(=O)COc1cc(Cl)ccc1CN1CCN(C(=O)OC(C(F)(F)F)C(F)(F)F)CC1] | δ 7.12 (d, J = 8.1 Hz, 1H), 7.04-7.00 (m, 1H), 6.90 (s, 1H), 5.76-5.72 (m, 1H), 4.68 (s, 2H), 3.69-3.67 (m, 6H), 3.24 (s, 3H), 2.68-2.66 (m, 5H) | 556.4 |
| 53 | 1,1,1,3,3,3-hexafluoropropan-2-yl 4-(3-chloro-4-methyl-2-((1-((methylsulfonyl)carbamoyl)cyclopropyl)methoxy)benzyl)piperazine-1-carboxylate | 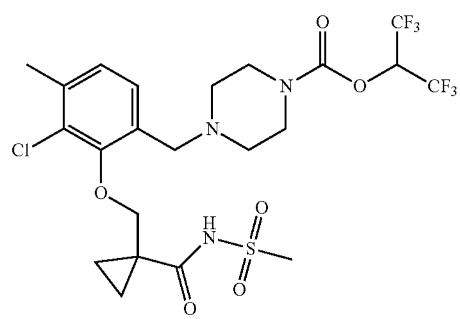 [SMILES: Cc1ccc(CN2CCN(C(=O)OC(C(F)(F)F)C(F)(F)F)CC2)c(OCC2(C(=O)NS(C)(=O)=O)CC2)c1Cl] | δ 7.12-7.05 (m, 2H), 5.78-5.70 (m, 1H), 4.13 (s, 2H), 3.56-3.53 (m, 6H), 3.34 (s, 3H), 2.50-2.47 (m, 4H), 2.39 (s, 3H), 1.56-1.52 (m, 2H), 1.07-1.03 (m, 2H) | 609.9 |
| 54 | 2-(2-fluoro-6-((4-(((1,1,1,3,3,3-hexafluoropropan-2-yl)oxy)carbonyl)piperazin-1-yl)methyl)-3-methylphenoxy)acetic acid | 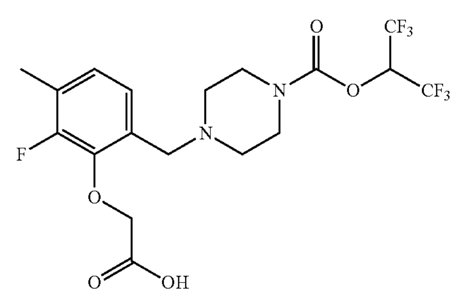 [SMILES: Cc1ccc(CN2CCN(C(=O)OC(C(F)(F)F)C(F)(F)F)CC2)c(OCC(=O)O)c1F] | δ 6.91-6.82 (m, 2H), 5.79-5.73 (m, 1H), 4.92 (s, 2H), 3.82-3.73 (m, 6H), 2.78 (br s, 4H), 2.31 (s, 3H) | 477.4 |

-continued

| Ex | Name | Structure | NMR (¹H NMR, 300 MHz or 400 MHz, Chloroform-d) | MS [M + H]⁺ |
|---|---|---|---|---|
| 55 | 1,1,1,3,3,3-hexafluoropropan-2-yl 4-(2-((1-((methylsulfonyl)carbamoyl)cyclopropyl)methoxy)-4-(trifluoromethyl)benzyl)piperazine-1-carboxylate | 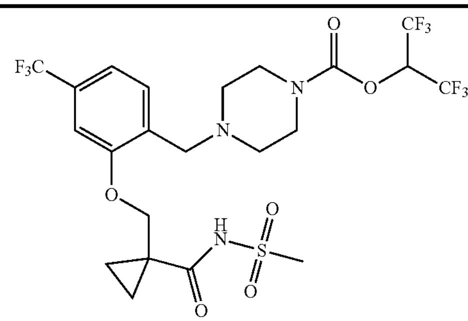 | δ 7.51 (d, J = 8.1 Hz, 1H), 7.32 (d, J = 8.1 Hz, 1H), 7.05 (s, 1H), 5.79-5.71 (m, 1H), 4.11 (s, 2H), 3.64-3.55 (m, 6H), 3.31 (s, 3H), 2.45-2.45 (m, 4H), 1.58-1.54 (m, 2H), 1.05-1.01 (m, 2H) | 630.1 |
| 56 | 4-(2-chloro-6-((4-(((1,1,1,3,3,3-hexafluoropropan-2-yl)oxy)carbonyl)piperazin-1-yl)methyl)phenyl)-2,2-dimethylbut-3-ynoic acid | 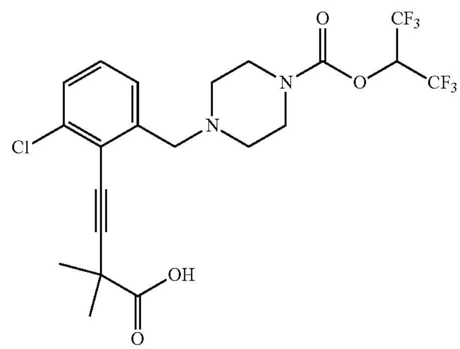 [SMILES: CC(C)(C#Cc1c(Cl)cccc1CN1CCN(C(=O)OC(C(F)(F)F)C(F)(F)F)CC1)C(=O)O] | (Methanol-d₄) δ 7.40-7.37 (m, 2H), 7.30-7.26 (m, 1H), 6.17-6.11 (m, 1H), 3.83 (s, 2H), 3.63-3.58 (m, 4H), 2.65-2.61 (m, 4H), 1.57 (s, 6H) | 515.2 |

II. Biological Evaluation

Compounds were tested to assess their MAGL and serine hydrolase activity using the following in vitro and in vivo assays.

In Vitro Competitive Activity-Based Protein Profiling (Human)

Proteomes (human prefrontal cortex or cell membrane fractions) (50 μL, 1.0-2.0 mg/mL total protein concentration) were preincubated with varying concentrations of inhibitors at 37° C. After 30 min, FP-Rh or JW912 (1.0 μL, 50 μM in DMSO) was added and the mixture was incubated for another 30 min at room temperature. Reactions were quenched with SDS loading buffer (15 μL—4×) and run on SDS-PAGE. Following gel imaging, serine hydrolase activity was determined by measuring fluorescent intensity of gel bands corresponding to MAGL using ImageJ 1.49k software. $IC_{50}$ data from this assay are shown in Table 2.

TABLE 2

| Example | MAGL Human ($IC_{50}$) |
|---|---|
| 1 | *** |
| 2 | *** |
| 3 | *** |
| 4 | *** |
| 5 | *** |
| 6 | *** |
| 7 | *** |
| 8 | *** |
| 9 | *** |
| 10 | *** |
| 11 | *** |
| 12 | *** |
| 13 | *** |

TABLE 2-continued

| Example | MAGL Human ($IC_{50}$) |
|---|---|
| 14 | *** |
| 15 | *** |
| 16 | *** |
| 17 | *** |
| 18 | *** |
| 19 | *** |
| 20 | *** |
| 21 | *** |
| 22 | *** |
| 23 | *** |
| 24 | *** |
| 25 | *** |
| 26 | *** |
| 27 | *** |
| 28 | *** |
| 29 | *** |
| 30 | *** |
| 31 | *** |
| 32 | *** |
| 33 | *** |
| 34 | *** |
| 35 | *** |
| 36 | *** |
| 37 | *** |
| 38 | *** |
| 39 | *** |
| 40 | *** |
| 41 | *** |
| 42 | *** |
| 43 | *** |
| 44 | *** |
| 45 | *** |
| 46 | *** |
| 47 | *** |
| 48 | *** |
| 49 | *** |
| 50 | *** |

TABLE 2-continued

| Example | MAGL Human (IC$_{50}$) |
|---|---|
| 51 | *** |
| 52 | *** |
| 53 | *** |
| 54 | ** |
| 55 | *** |
| 56 | *** |

*** IC$_{50}$ is less than or equal to 100 nM;
** IC$_{50}$ is greater than 100 nM and less than 1 µM;
* IC$_{50}$ is greater than or equal to 1 µM and less than or equal to 10 µM.

In Vitro Competitive Activity-Based Protein Profiling (Mouse)

Proteomes (mouse brain membrane fraction or cell lysates) (50 µL, 1.0 mg/mL total protein concentration) were preincubated with varying concentrations of inhibitors at 37° C. After 30 min, FP-Rh (1.0 µL, 50 µM in DMSO) was added and the mixture was incubated for another 30 min at 37° C. Reactions were quenched with SDS loading buffer (50 µL—4×) and run on SDS-PAGE. Following gel imaging, serine hydrolase activity was determined by measuring fluorescent intensity of gel bands corresponding to MAGL using ImageJ 1.49k software.

Preparation of Mouse Brain Proteomes from Inhibitor Treated Mice

Inhibitors were administered to wild-type C$_{57}$Bl/6J by oral gavage in a vehicle of polyethylene glycol. Each animal was sacrificed 4 h following administration and brain proteomes were prepared and analyzed according to previously established methods (See Niphakis, M. J., et al. (2011) ACS Chem. Neurosci. and Long, J. Z., et al. Nat. Chem. Biol. 5:37-44). Percent inhibition data are shown in Table 3.

TABLE 3

| Example | MGLL % Inhibition at 5 mg/kg (Mouse) |
|---|---|
| 1 | NT |
| 2 | NT |
| 3 | ### |
| 4 | NT |
| 5 | NT |
| 6 | NT |
| 7 | NT |
| 8 | NT |
| 9 | NT |
| 10 | NT |
| 11 | NT |
| 12 | ## |
| 13 | # |
| 14 | # |
| 15 | NT |
| 16 | # |
| 17 | NT |
| 18 | NT |
| 19 | NT |
| 20 | NT |
| 21 | # |
| 22 | # |
| 23 | ### |
| 24 | NT |
| 25 | NT |
| 26 | # |
| 27 | ### |
| 28 | NT |
| 29 | ### |
| 30 | # |
| 31 | # |
| 32 | ### |
| 33 | NT |
| 34 | NT |
| 35 | NT |
| 36 | # |
| 37 | NT |
| 38 | ### |
| 39 | ### |
| 40 | ### |
| 41 | NT |
| 42 | ### |
| 43 | NT |
| 44 | NT |
| 45 | NT |
| 46 | NT |
| 47 | NT |
| 48 | NT |
| 49 | # |
| 50 | # |
| 51 | # |
| 52 | # |
| 53 | # |
| 54 | NT |
| 55 | NT |
| 56 | NT |

% Inhibition:
### is ≥75%;
## is between 25 and 75%;
# is ≤25%;
NT is not tested

We claim:

1. A compound having the structure of Formula (I):

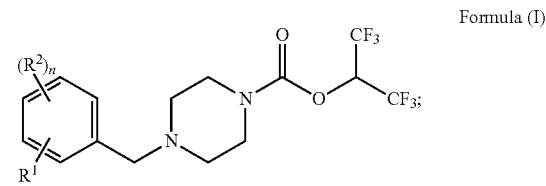

Formula (I)

wherein:
R$^1$ is —R$^{14}$, —OR$^3$, —SR$^4$, —S(O)$_2$R$^4$, or —C≡C—(CR$^6$R$^7$)—R$^8$;
each R$^2$ is independently selected from C$_{1-6}$alkyl, halogen, —CN, C$_{1-6}$haloalkyl, —C$_{1-6}$alkyl(heterocycloalkyl), —OR$^{17}$, and —C(O)NR$^{18}$R$^{19}$;
R$^3$ is —(CR$^6$R$^7$)$_m$—R$^8$, —(CR$^6$R$^7$)$_p$—Y—(CR$^6$R$^7$)$_q$—R$^8$, or —(CR$^6$R$^7$)$_t$—C$_{3-6}$cycloalkyl-R$^8$;
R$^4$ is —(CR$^6$R$^7$)$_m$—R$^{8'}$, —(CR$^6$R$^7$)$_v$—C(O)OH, or —(CR$^6$R$^7$)$_p$—Y—(CR$^6$R$^7$)$_q$—R$^8$;
Y is —O— or —N(R$^{22}$)—;
each R$^6$ and R$^7$ is each independently selected from H, F, and C$_{1-6}$alkyl; or R$^6$ and R$^7$, together with the carbon to which they are attached, form a C$_{3-6}$cycloalkyl ring;
R$^8$ is —C(O)OR$^9$, —C(O)R$^{10}$, or —C(O)O—(CR$^{12}$R$^{13}$)—OC(O)R$^{11}$;
R$^{8'}$ is —C(O)OR$^{9'}$, —C(O)R$^{10'}$, or —C(O)O—(CR$^{12}$R$^{13}$)—OC(O)R$^{11}$;
R$^9$ is H or C$_{1-6}$alkyl;
R$^{9'}$ is C$_{1-6}$alkyl;
R$^{10}$ is C$_{1-6}$alkyl or —NHSO$_2$R$^{21}$;
R$^{10'}$ is C$_{2-6}$alkyl or —NHSO$_2$R$^{21}$;
R$^{11}$ is C$_{1-6}$alkyl or C$_{1-6}$alkoxy;
R$^{12}$ and R$^{13}$ is each independently H or C$_{1-6}$alkyl;

$R^{14}$ is $-(CR^{15}R^{16})_m-R^8$ or $-(CR^6R^7)_p-Y-(CR^6R^7)_q-R^8$;

each $R^{15}$ and $R^{16}$ is each independently selected from H, F, and $C_{1-6}$alkyl;

each $R^{17}$ is independently selected from H, $C_{1-6}$alkyl, $C_{1-6}$haloalkyl, and $C_{3-6}$cycloalkyl;

each $R^{18}$ and $R^{19}$ is each independently selected from H, $C_{1-6}$alkyl, $C_{3-6}$cycloalkyl, aryl, and heteroaryl; or $R^{18}$ and $R^{19}$, together with the nitrogen to which they are attached, form a heterocycloalkyl ring optionally substituted with one, two, or three $R^{20}$;

each $R^{20}$ is independently selected from halogen, $C_{1-6}$alkyl, $C_{1-6}$haloalkyl, oxo, —CN, and $C_{3-6}$cycloalkyl;

$R^{21}$ is $C_{1-6}$alkyl or $C_{3-6}$cycloalkyl;

$R^{22}$ is H, $C_{1-6}$alkyl, or —$SO_2R^{23}$;

$R^{23}$ is $C_{1-6}$alkyl;

m is 1, 2, 3 or 4;

n is 0, 1, 2, 3, or 4;

p is 2, 3, or 4;

q is 1, 2, or 3;

t is 0, 1, or 2; and v is 3 or 4;

or a pharmaceutically acceptable salt or solvate thereof.

2. The compound of claim 1, or a pharmaceutically acceptable salt or solvate thereof, wherein $R^1$ is —$OR^3$.

3. The compound of claim 2, or a pharmaceutically acceptable salt or solvate thereof, wherein $R^3$ is —$(CR^6R^7)_m-R^8$.

4. The compound of claim 3, or a pharmaceutically acceptable salt or solvate thereof, wherein m is 1, 2, or 3.

5. The compound of claim 4, or a pharmaceutically acceptable salt or solvate thereof, wherein each $R^6$ and $R^7$ is each independently selected from H and $C_{1-6}$alkyl, or $R^6$ and $R^7$, together with the carbon to which they are attached, form a $C_{3-6}$cycloalkyl ring.

6. The compound of claim 5, or a pharmaceutically acceptable salt or solvate thereof, wherein $R^8$ is —$C(O)OR^9$.

7. The compound of claim 6, or a pharmaceutically acceptable salt or solvate thereof, wherein $R^9$ is H.

8. The compound of claim 6, or a pharmaceutically acceptable salt or solvate thereof, wherein $R^9$ is $C_{1-6}$alkyl.

9. The compound of claim 5, or a pharmaceutically acceptable salt or solvate thereof, wherein $R^8$ is —$C(O)R^{10}$.

10. The compound of claim 9, or a pharmaceutically acceptable salt or solvate thereof, wherein $R^{10}$ is —$NHSO_2R^{21}$.

11. The compound of claim 10, or a pharmaceutically acceptable salt or solvate thereof, wherein $R^{21}$ is $C_{1-6}$alkyl.

12. The compound of claim 10, or a pharmaceutically acceptable salt or solvate thereof, wherein $R^{21}$ is $C_{3-6}$cycloalkyl.

13. The compound of claim 7, or a pharmaceutically acceptable salt or solvate thereof, wherein each $R^2$ is independently selected from $C_{1-6}$alkyl, halogen, and $C_{1-6}$haloalkyl.

14. The compound of claim 13, or a pharmaceutically acceptable salt or solvate thereof, wherein n is 2.

15. The compound of claim 13, or a pharmaceutically acceptable salt or solvate thereof, wherein n is 1.

16. The compound of claim 1 having the structure selected from:

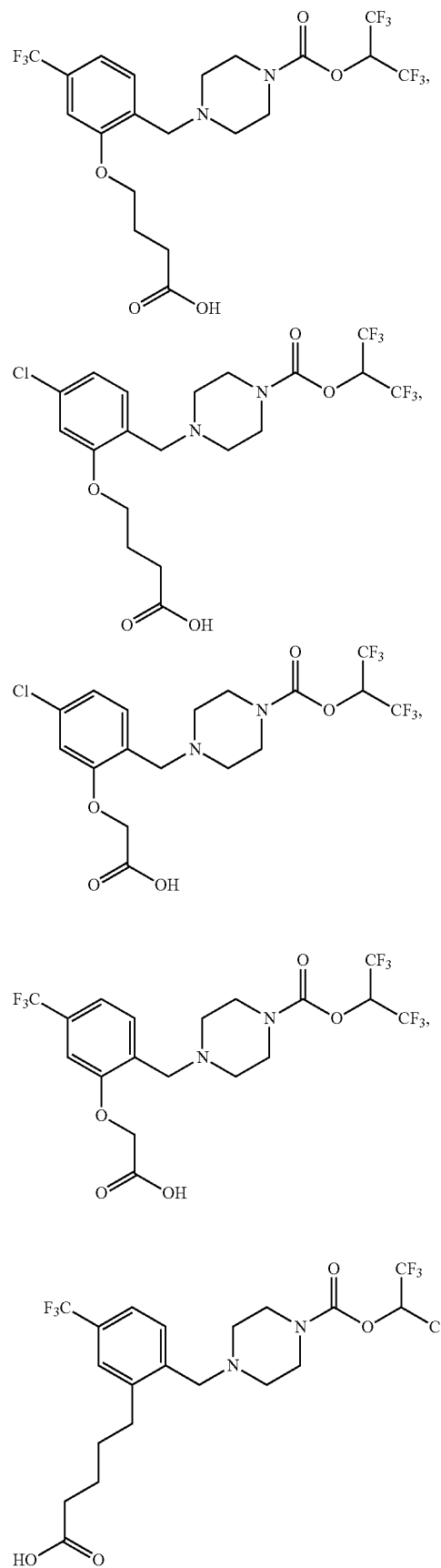

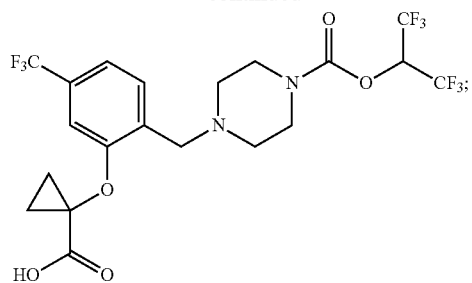
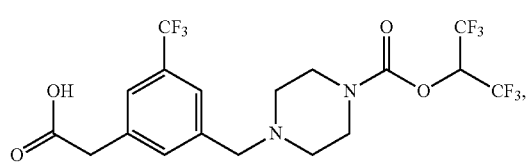
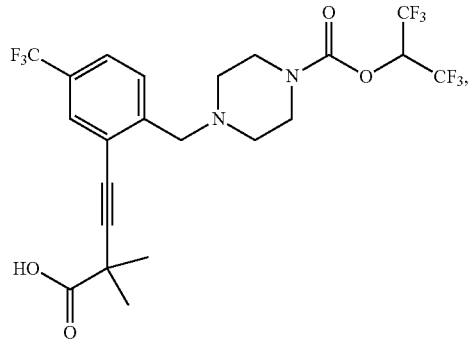
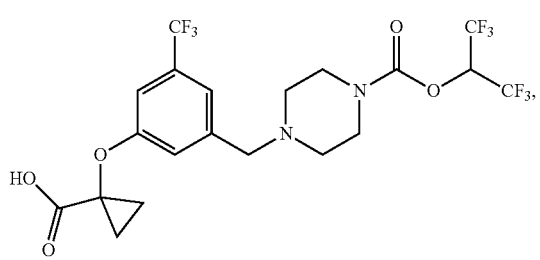
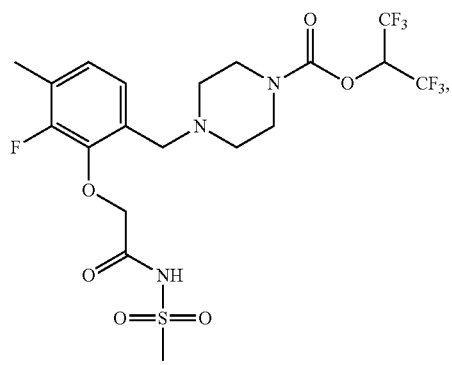
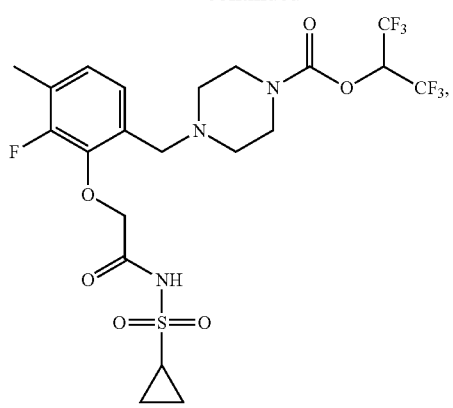
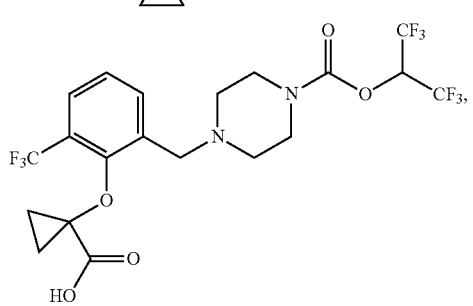
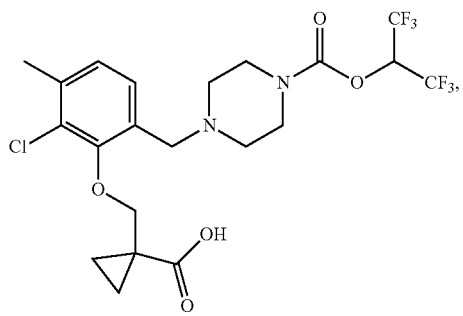
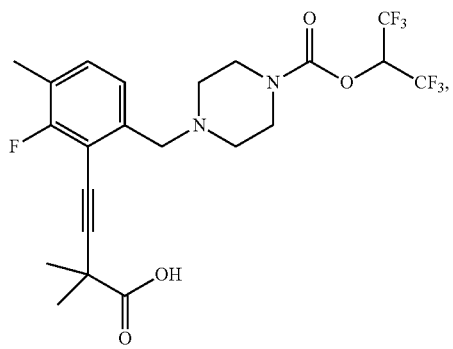
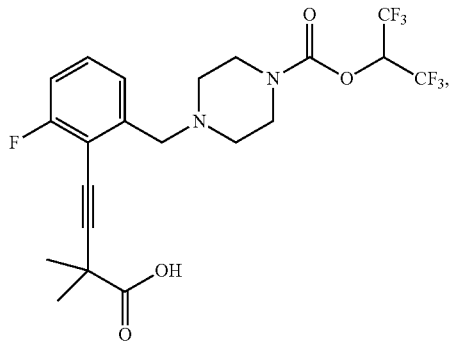

197
-continued
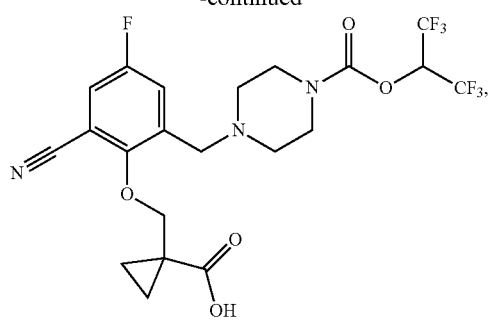
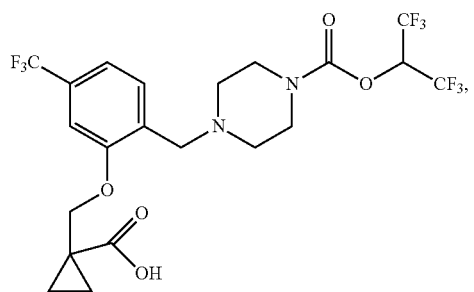
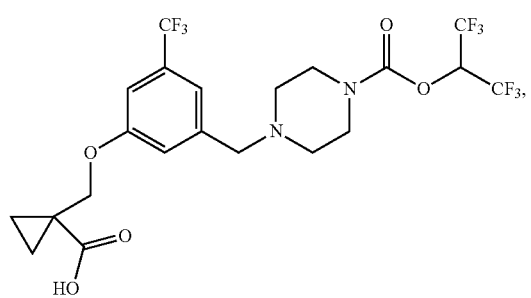
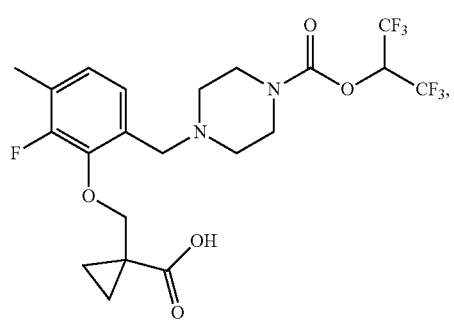
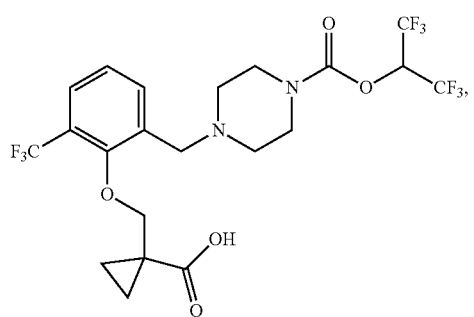
198
-continued
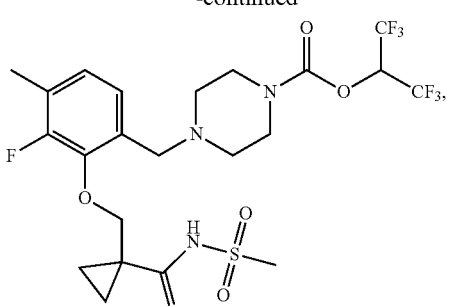
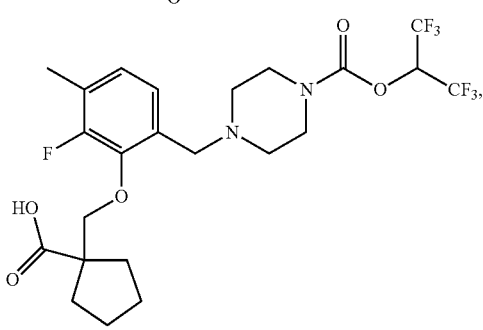
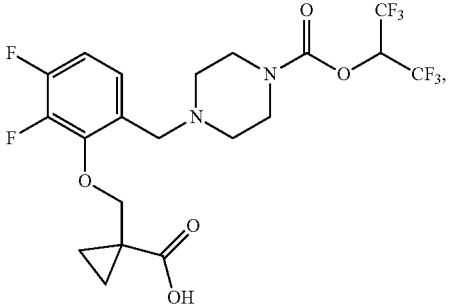
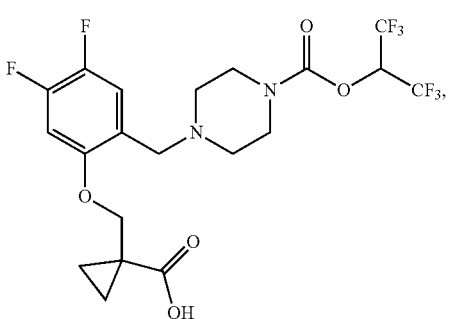
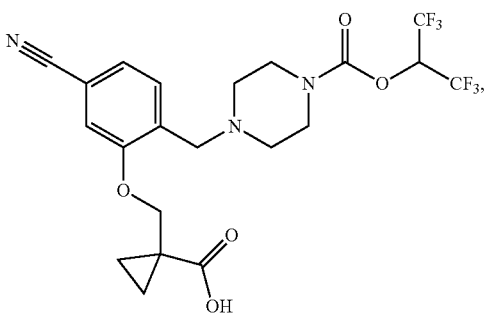

199 -continued
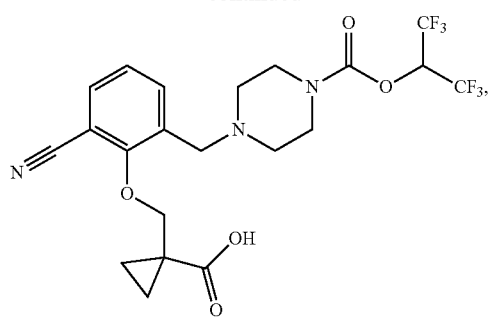
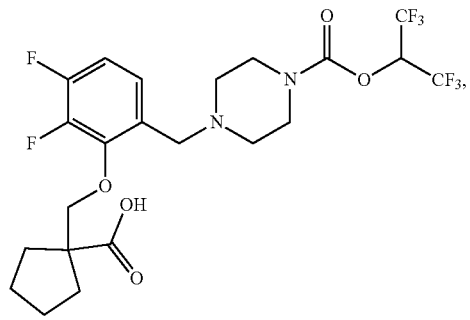
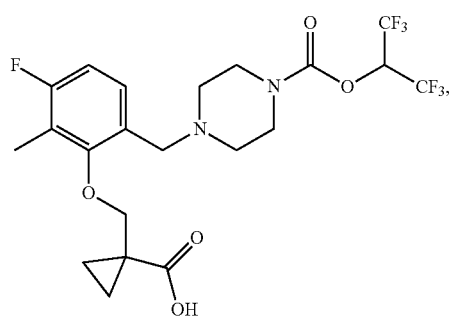
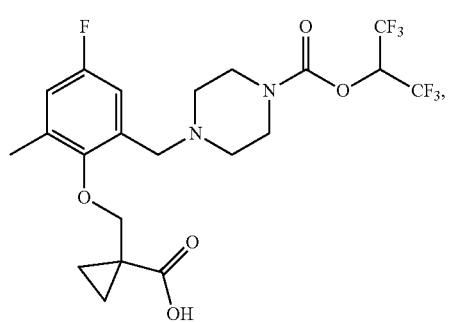
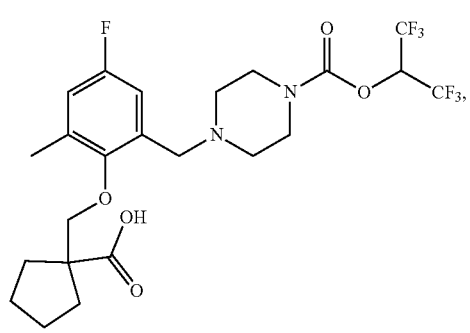
200 -continued
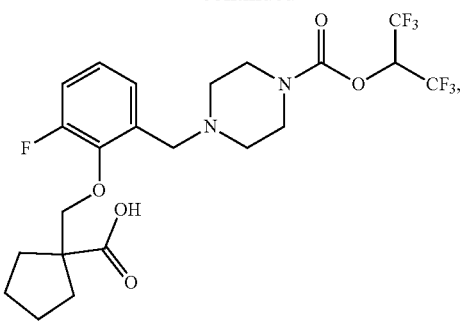
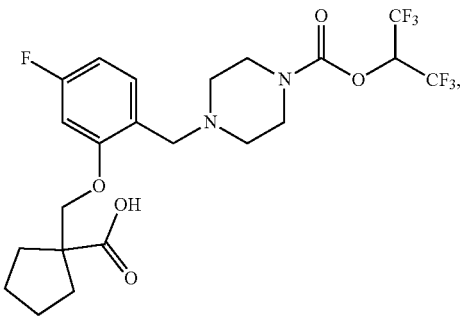
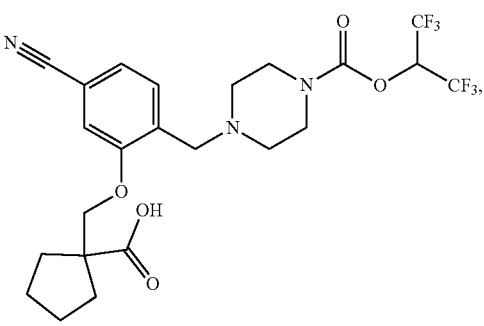
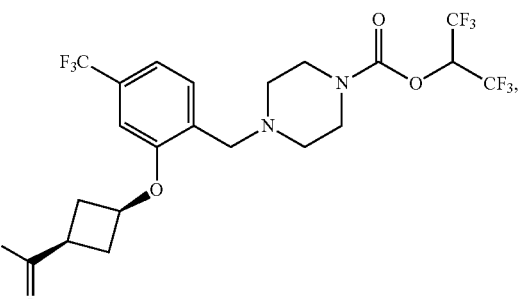
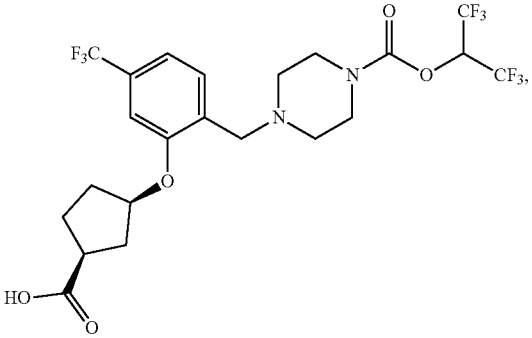

201
-continued
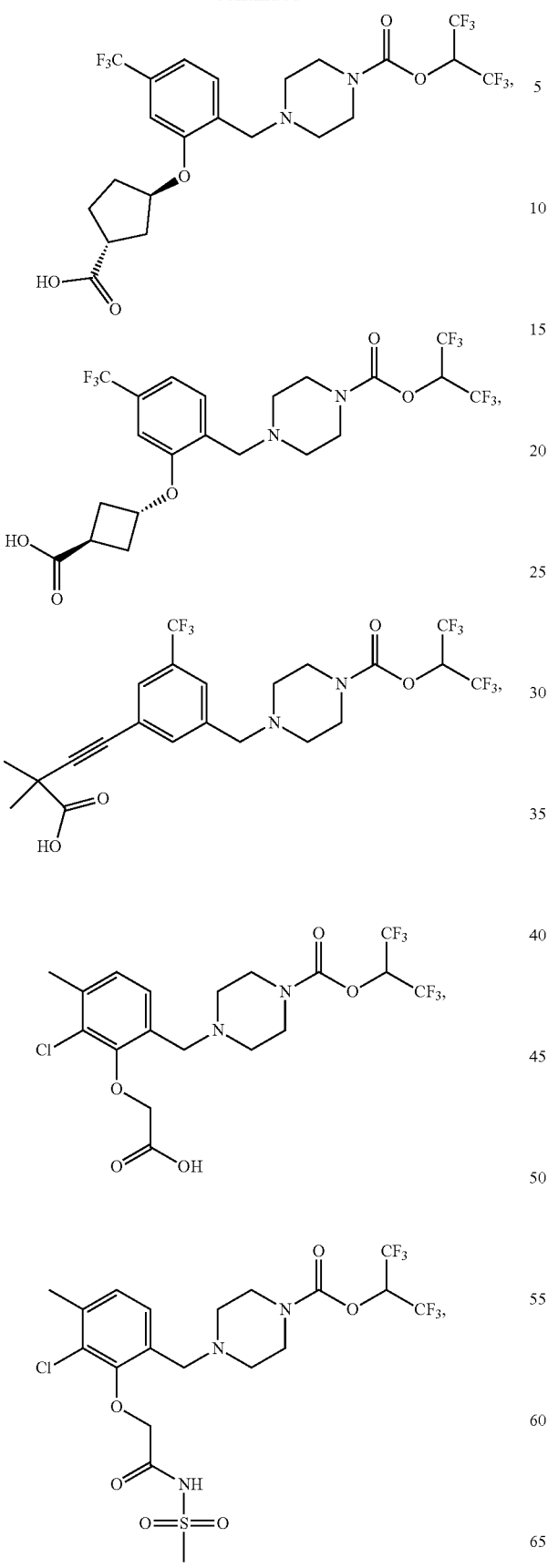
202
-continued
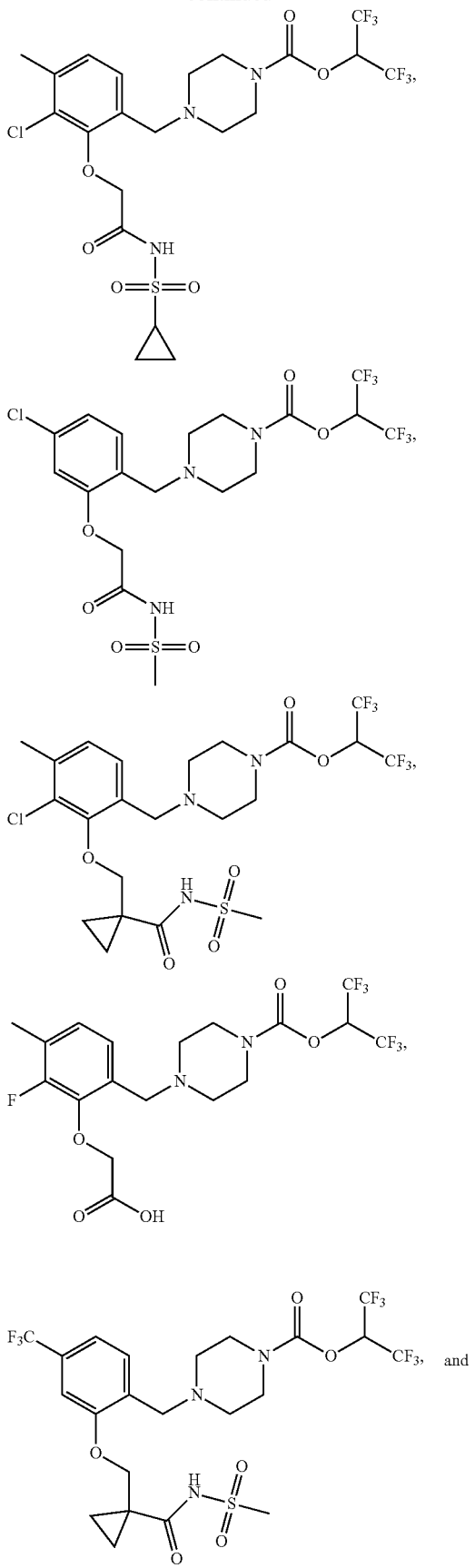

-continued

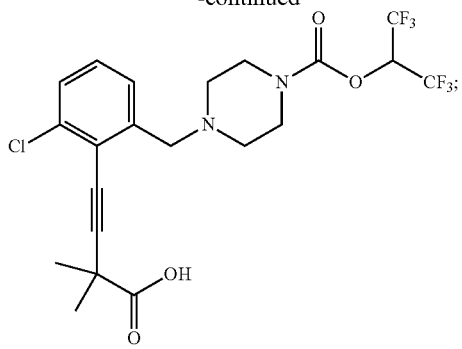

or a pharmaceutically acceptable salt or solvate thereof.

17. A pharmaceutical composition comprising a compound of claim 1, or a pharmaceutically acceptable salt or solvate thereof, and at least one pharmaceutically acceptable excipient.

18. A pharmaceutical composition comprising a compound of claim 16, or a pharmaceutically acceptable salt or solvate thereof, and at least one pharmaceutically acceptable excipient.

* * * * *